(12) United States Patent
Fox et al.

(10) Patent No.: US 7,138,251 B1
(45) Date of Patent: Nov. 21, 2006

(54) POLYNUCLEOTIDES ENCODING A NEUROTROPHIC FACTOR RECEPTOR

(75) Inventors: Gary M. Fox, Newbury Park, CA (US); Shuqian Jing, Thousand Oaks, CA (US); Duanzhi Wen, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 08/866,354

(22) Filed: May 30, 1997

Related U.S. Application Data

(63) Continuation-in-part of application No. 08/837,199, filed on Apr. 14, 1997, now Pat. No. 6,455,277.

(60) Provisional application No. 60/017,221, filed on May 9, 1996, and provisional application No. 60/015,907, filed on Apr. 22, 1996.

(51) Int. Cl.
*C12N 15/12* (2006.01)
*C12N 15/63* (2006.01)
*C12N 15/70* (2006.01)
*C12N 15/85* (2006.01)

(52) U.S. Cl. .................. 435/69.1; 435/325; 435/252.3; 435/320.1; 536/23.5

(58) Field of Classification Search .............. 435/69.1, 435/325, 320.1, 252.3; 536/23.5
See application file for complete search history.

(56) References Cited

U.S. PATENT DOCUMENTS

| | | | | |
|---|---|---|---|---|
| 4,518,584 | A | 5/1985 | Mark et al. | 424/85 |
| 4,892,538 | A | 1/1990 | Aebischer et al. | 604/891.1 |
| 5,011,472 | A | 4/1991 | Aebischer et al. | 604/50 |
| 5,106,627 | A | 4/1992 | Aebischer et al. | 424/424 |
| 5,437,981 | A | 8/1995 | Deger et al. | 435/7.1 |
| 5,792,606 | A | 8/1998 | Deger et al. | 436/6 |
| 6,372,453 | B1 * | 4/2002 | Klein et al. | 435/69.1 |

FOREIGN PATENT DOCUMENTS

| | | |
|---|---|---|
| EP | 398753 | 5/1990 |
| EP | 401384 | 12/1990 |
| EP | 0 444 561 | 9/1991 |
| WO | WO 90/14363 | 5/1990 |
| WO | WO 93/06116 | 9/1992 |
| WO | WO 95/05452 | 2/1995 |
| WO | WO 95/34670 | 12/1995 |

OTHER PUBLICATIONS

Watalie, Gen Bank Accession No. AB000800, Jan. 1997.*
Wartiovaara et al., Gen Bank Accession No. 2193703 and 05316, Mar. 1997.*
Rudinger In "Peptide Hormones" (Jun. 1976) ed. J.A. Parsons, University Park Press, Baltimore, pp 1–7.*
Baloh et al. (1997) 'TrnR2, a Novel Receptor That Mediates Neurturin and GDNF Signaling through Ret', *Neuron* 18:793–802.
Angrist et al. (1995) 'Mutation analysis of the RET receptor tyrosine kinase in Hirschsprung disease', *Human Mol. Gen.* 4:821–830.
Choi–Lundberg et al. (1995), 'Ontegeny and distribution of glial cell line–derived neurotrophic factor (GDNF) mRNA in rat', *Dev Brain Res* 85:80–88.
Cunningham and Wells (1989), 'High–Resolution Epitope Mapping of hGH–Receptor Interactions by Alanine–scanning Mutagenesis', *Science* 244:1081–1085.
Davis, et al. (1993), 'LIFRβ and gp130 as Heterodimerizing Signal Transducers of the Tripartite CNTF Receptor', *Science* 270:1805–1807.
Economides, et al. (1995), 'Designer cytokines: targeting actions to cells of choice', *Science* 270:1351–1353.
Edery, et al. (1994), 'Mutations of the RET proto–oncogene in Hirschsprung's disease', *Nature* 367:378–380.
Hefti (1994), 'Neurotrophic Factor Therapy for Nervous System Degenerative Diseases', *J. Neurobiol.* 25: 1418–1435.
Henderson et al. (1994), 'GNDF: A Potent Survival Factor for Motoneurons Present in Peripheral Nerve and Muscle', *Science* 266:1062–1064.
Ikeda, et al. (1990), 'Specific expression of the ret proto–oncogene in human neuroblastoma cell lines', *Oncogene* 5:1291–1296.
Iwamoto, et al. (1993), 'cDNA cloning of mouse ret proto–oncogene and its sequence similarity to the cadherin superfamily', *Oncogene* 8:1087–1091.
Jing, et al. (1990), 'Role of the human transferrin receptor cytoplasmic domain in endocytosis: localization of a specific signal sequence for internalization', *J. Cell Bio.* 100:283–294.

(Continued)

Primary Examiner—Gary Kunz
Assistant Examiner—Robert C. Hayes
(74) *Attorney, Agent, or Firm*—Robert L. Sharp; Ron K. Levy; Stuart L. Watt

(57) ABSTRACT

The present invention relates to glial cell line-derived neurotrophic factor (GDNF), a potent neurotrophin that exhibits a broad spectrum of biological activities on a variety of cell types from both the central and peripheral nervous systems. The present invention involves the cloning and characterization of receptors for GDNF. Nucleic acid and amino acid sequences are described for GDNFR protein products. A hydrophobic domain with the features of a signal peptide is found at the amino terminus, while a second hydrophobic domain at the carboxy terminus is involved in the linkage of the receptor to the cell membrane. The lack of a transmembrane domain and cytoplasmic region indicates that GDNFR requires one or more accessory molecules in order to mediate transmembrane signaling. GDNFR mRNA is widely distributed in both nervous system and non-neural tissues, consistent with the similar distribution found for GDNF.

11 Claims, 118 Drawing Sheets

OTHER PUBLICATIONS

Kohler, et al. (1975) 'Continuous cultures of fused cells secreting antibody of predefined specificity', *Nature* 256:495–497.

Li et al. (1995), 'Rescue of adult mouse motoneurons from injury–induced cell death by glial cell line–derived neurotrophic factor', *Proc. Natl. Acad. Sci.* 92:9771–9775.

Lin et al. (1993), 'GNDF: A Glial Cell Line–Derived Neurotrophic Factor for Midbrain Dopaminergic Neurons', *Science* 260:1130–1132.

Malik et al. (1992), 'Polyethylene Glycol (PEG)–modified Granulocyte–Macrophage Colony–stimulating Factor (GM–CSF) with Conserved Biological Activity', *Exp. Hematol.* 20:1028–1035.

Oppenheim et al. (1995), 'Developing motor neurons rescued from programmed and axotomy–induced cell death by GDNF', *Nature* 373:344–346.

Pachnis et al. (1993), 'Expression of the c–ret proto–oncogene during mouse embrogenesis', *Development* 119:1005–1017.

Romeo et al. (1994), 'Point mutations affecting the tyrosine kinase domain of the RET proto–oncogene in Hirschsprung's disease', *Nature* 367:377–378.

Schlessinger et al. (1992), 'Growth Factor Signaling by Receptor Tyrosine Kinases', *Neuron* 9:383–391.

Schuchardt et al. (1994), 'Defects in the kidney and enteric nervous system of mice lacking tyrosine kinase receptor Ret', *Nature* 367:380–383.

Takebe et al. (1988), 'SRα Promoter: an Efficient and Versatile Mammalian cDNA Expression System Composed of the Simian Virus 40 Early Promoter and the R–U5 Segment of Human T–Cell Leukemia Virus Type 1 Long Terminal Repeat', *Mol and Cell Bio* 8:466–472.

Urlaub et al. (1980), 'Isolation of Chinese hamster cell mutants deficient in dihydrofolate reductase activity', *Proc. Natl. Acad. Sci* 77:4216–4220.

Van Heyningen (1994), 'One gene—four syndromes', *Nature* 367:319–320.

Von Heijne (1987), 'SIGPEP: a sequence data base for secretory signal peptides', *Protein Seq Data Anal* 1:41–42.

Von Heijne (1986), 'A new method for predicting signal sequence cleavage sites', *Nucleic Acids Res.* 14:4683–4690.

Wells et al. (1985), 'Cassette mutagenesis: an efficient method for generation of multiple mutations at defined sites', *Gene* 34:315–323.

Yan et al. (1995), 'In vivo neurotrophic effects of GNDF on neonatal and adult facial motor neurons', *Nature* 373:341–344.

Zurn et al. (1994), 'Glial cell line–derived neurotrophic factor (GDNF), a new neurotrophic factor for motoneurones', *NeuroReport* 6:113–118.

Bunone, et al. (1995) 'Induction of RET Proto–Oncogene Expression in Neuroblastoma Cells Precedes Neuronal Differentiation and Is Not Mediated by Protein Synthesis' *Exp Cell Res.* 217:92–99.

Culouscou, et al. (1995) 'HER4 Receptor Activation and Phosphorylation of Shc Proteins by Recombinant Heregulin–Fc Fusion Proteins' *J Bio Chem* 270:12857–12863.

Hudson, et al. (1995) 'Glial Cell Line–derived Neurotrophic Factor Augments Midbrain Dopaminergic Circuits In Vivo' *Brain Res Bul* 36(5): 425–432.

Jing, et al. (1996) 'GDNF–Induced Activation of the Ret Protein Tyrosine Kinase Is Mediated by GDNFR–α, a Novel Receptor for GDNF' *Cell* 85:1113–1124.

Kotzbauer, et al. (1996) 'Neurturin, a relative of glial–cell–line–derived neurotrophic factor' *Nature* 384:467–470.

Moore, et al. (1996) 'Renal and Neuronal Abnormalities in Mice Lacking GDNF' *Nature* 382:76–79.

Pickel, et al. (1996) 'Defects in enteric innervation and kidney development in mice lacking GDNF' *Nature* 382:73–76.

Sanchez, et al. (1996) 'Renal agenesis and the absence of enteric neurons in mice lacking GDNF' *Nature* 382:70–73.

Sonnenfeld, et al. (1982) 'Nerve Growth Factor Effects and Receptors in Cultured Human Neuroblastoma Cell Lines' *J Neuro Res* 8:375–391.

Treanor, et al. (1996) 'Characterization of a multicomponent receptor for GDNF' *Nature* 382:80–83.

Zhou, et al. (1994) 'Isolation and Characterization of Bsk, a Growth Factor Receptor–Like Tyrosine Kinase Associated With the Limbic System' *J Neuro Res* 37:129–143.

\* cited by examiner

FIG. 1A

Human Glial Cell Line-Derived
Neurotrophic Factor Receptor Protein 10                    30                    50
AATCTGGCCTCGGAACACGCCATTCTCCGCGCCTTCCAATAACCACTAACATCCCTA 70                    90                   110
ACGAGCATCCGAGCCCGAGGGCTCTGCTCGGAAATCGTCCTGGCCCAACTCGGCCCCTTCGA 130                   150                   170
GCTCTCGAAGATTACCGCATCTATTTTTTTTTTCTTTTCTTTTCCTAGCGGCAGATA

FIG.1B 190  210  230
AAGTGAGCCCGGAAAGGAAGGGGGGCGGGGACACCATTGCCCTGAAAGAATAAATAA 250  270  290
GTAAATAAACAAAACTGGGCTCCTCGCCCGCAGCTGGACGCGGTCGGTTGAGTCCAGGTTGGG 310  330  350
TCGGACCCTGAACCCCTAAAAGCGGAACCGCTCCCCGCCCCTCGCCATCCCGGAGCTGAGTC 370  390  410
GCCGGGCGGTGGCTGCTGCCAGACCCGGAGTTCCTCTTTCACTGGGATGGAGCTGAAC

FIG. 1C

```
                                    430                         450                           470
TTTGGGGGGCCAGAGCAGCACAGCTGTCCGGGATCGCTGCACGCTGAGCTCCCTCGGCA 490                         510                           530
AGACCCAGCGGCGGCTCGGGGATTTTTTTGGGGGCGGGACCAGCCCCGGCACC 550                         570                           590
ATGTTCCTGGCGACCCTGTACTTCGCGCTGCCGCTCTTGGACTTGCTCCTGTCGGCCGAA
 M  F  L  A  T  L  Y  F  A  L  P  L  L  D  L  L  L  S  A  E
```

FIG.1D

```
         610         630              650
GTGAGCGGGGAGACCGCCTGGATTGCCGTGAAAGCCAGTGATCAGTGCCTGAAGGAGCAG
 V  S  G  G  D  R  L  D  C  V  K  A  S  D  Q  C  L  K  E  Q 670         690              710
AGCTGCAGCACCAAGTACCGCACGCTAAGGCAGTGCGTGGGGCAAGGAGACCAACTTC
 S  C  S  T  K  Y  R  T  L  R  Q  C  V  A  G  K  E  T  N  F 730         750              770
AGCCTGGCATCCGGCCTGGAGGCCAAGGATGAGTGCCGCAGCGCCATGGAGGCCCTGAAG
 S  L  A  S  G  L  E  A  K  D  E  C  R  S  A  M  E  A  L  K
```

FIG.1E

```
                        790                         810                         830
CAGAAGTCGCTCTACAACTGCCCGCTGCAAGCGGGGTATGAAGAAGAAGAACTGCCTG
 Q  K  S  L  Y  N  C  R  C  K  R  G  M  K  K  E  K  N  C  L 850                         870                         890
CGCATTTACTGGAGCATGTACCAGAGCCTGCAGGAAATGATCTGCTGGAGGATTCCCA
 R  I  Y  W  S  M  Y  Q  S  L  Q  G  N  D  L  L  E  D  S  P 910                         930                         950
TATGAACCAGTTAACAGCAGATTGTCAGATATATTCCGGGTGGTCCCATTCATATCAGAT
 Y  E  P  V  N  S  R  L  S  D  I  F  R  V  V  P  F  I  S  D
```

FIG.1F

```
                     970                     990                    1010
GTTTTTCAGCAAGTGGAGCACATTCCCAAAGGGAACAACTGCCTGGATGCAGCCGAAGGCC
 V  F  Q  Q  V  E  H  I  P  K  G  N  N  C  L  D  A  A  K  A 1030                    1050                    1070
TGCAACCTCGACGACATTTGCAAGAAGTACAGGTCGGCGTACATCACCCCGTGCACCACC
 C  N  L  D  D  I  C  K  K  Y  R  S  A  Y  I  T  P  C  T  T 1090                    1110                    1130
AGCGTGTCCAACGATGTCTGCAACCGGCGCAAGTGCCACAAGGCCCTCCGGCAGTTCTTT
 S  V  S  N  D  V  C  N  R  R  K  C  H  K  A  L  R  Q  F  F
```

FIG.1G

```
                    1170                               1190
1150
GACAAGGTCCCGGCCAAGCACAGCTACGGAATGCTCTTCTGCTCCTGCCGGGACATCGCC
 D   K   V   P   A   K   H   S   Y   G   M   L   F   C   S   C   R   D   I   A 1230                               1250
1210
TGCACAGAGCGGAGGCGACAGACCATCGTGCCTGTGTGCTCCTATGAAGAGAGGGAGAAG
 C   T   E   R   R   R   Q   T   I   V   P   V   C   S   Y   E   E   R   E   K 1290                               1310
1270
CCCAACTGTTTGAATTTGCAGGACTCCTGCAAGACGAATTACATCTGCAGATCTCGCCTT
 P   N   C   L   N   L   Q   D   S   C   K   T   N   Y   I   C   R   S   R   L
```

FIG.1H

```
              1330                          1350                          1370
GCGGATTTTTTTACCAACTGCCAGCCAGAGTCAAGGTCTGTCAGCAGTGTCTAAAGGAA
 A  D  F  F  T  N  C  Q  P  E  S  R  S  V  S  S  C  L  K  E 1390                          1410                          1430
AACTACGCTGACTGCCTCCTCGCCTACTCGGGGCTTATTGGCACAGTCATGACCCCCAAC
 N  Y  A  D  C  L  L  A  Y  S  G  L  I  G  T  V  M  T  P  N 1450                          1470                          1490
TACATAGACTCCAGTAGCCTCAGTGTGGCCCCATGGTGTGACTGCAGCAACAGTGGGAAC
 Y  I  D  S  S  S  L  S  V  A  P  W  C  D  C  S  N  S  G  N
```

FIG.1I

```
            1510                  1530                  1550
GACCTAGAAGAGTGCTTGAAATTTTGAATTTCTTCAAGGACAATACATGTCTTAAAAAT
 D   L   E   E   C   L   K   F   L   N   F   F   K   D   N   T   C   L   K   N 1570                  1590                  1610
GCAATTCAAGCCTTTGGCAATGGCTCCGATGTGACCGTGTGGCAGCCTTCCCAGTA
 A   I   Q   A   F   G   N   G   S   D   V   T   V   W   Q   P   A   F   P   V 1630                  1650                  1670
CAGAGACCACCACTGCCACTACCACCACTGCCCTCCGGGTTAAGAACAAGCCCCTGGGGCCA
 Q   T   T   T   T   T   A   L   R   V   K   N   K   P   L   G   P
```

FIG. 1J

```
                 1690                    1710                      1730
GCAGGGTCTGAGAATGAAATTCCCACTCATGTTTTGCCACCGTGTGCAAATTTACAGGCA
 A  G  S  E  N  E  I  P  T  H  V  L  P  P  C  A  N  L  Q  A 1750                    1770                      1790
CAGAAGCTGAAATCCAATGTGTCGGGCAATACACACCTCTGTATTTCCAATGGTAATTAT
 Q  K  L  K  S  N  V  S  G  N  T  H  L  C  I  S  N  G  N  Y 1810                    1830                      1850
GAAAAGAAGGTCTCGGTGCTTCCAGCCACATAACCACAAAATCAATGGCTGCTCCTCCA
 E  K  E  G  L  G  A  S  S  H  I  T  T  K  S  M  A  A  P  P
```

FIG.1K

```
                            1870                                     1890                              1910
AGCTGTGGTCTGAGCCCACTGCTGGTCCTGGTGGTAACCGCTCTGTCCACCCTATTATCT
 S   C   G   L   S   P   L   L   V   L   V   V   T   A   L   S   T   L   L   S 1930                                     1950                              1970
TTAACAGAAACATCATAGCTGCATTAAAAAATACAATATGGACATGTAAAAAGACAAAA
 L   T   E   T   S   *

1990                                     2010                              2030
ACCAAGTTATCTGTTTCCCTGTTCTCTCTTGTATAGCTGAAATTCCAGTTTAGGAGCTCAGTT 2050                                     2070                              2090
GAGAAACAGTTTCCATTCAACTGGAACATTTTTTTTTT.CCTTTAAGAAAGCTTCTTGT
```

FIG. 1L

```
         2110              2130              2150
GATCCTT.GGGGCTTCTGTGAAAAACCTGATGCAGCTCCATCCAAACTCAGAAGGCTT 2170              2190              2210
TGGGATATGCTCTGTATTTAAAGGGACAGTTTGTAACTTGGGCTGTAAAGCAAACTGGGGC 2230              2250              2270
TGTGTTTCGATGATGATGAT.ATCATGAT.ATGAT...........

2290              2310              2330
........GATTTAACAGTTTTACTTCTGGCCTTCCTAGCTAGAGAAGGAG
```

FIG. 1M

```
        2350                2370                2390
TTAATATTTCTAAGGTAACTCCCATATCTCCTTTAATGACATTGATTTCTAATGATATAA 2410                2430                2450
ATTTCAGCCTACATTGATGCCAAGCTTTTTTGCCACAAAGAAGATTCTTACCAAGAGTGG 2470                2490                2510
GCTTTGTGGAAACAGCTGGTACTGATGTTCACCTTTATATATGTACTAGCATTTTCCACG 2530                2550
CTGATGTTTATGTACTGTAAACAGTTCTGCACTCTTGTACAAAAGAAAA
```

FIG.2A
Human Glial Cell Line-Derived Neurotrophic Factor Receptor Protein

```
240  K E R E Y S C V P I T Q R R E T C T N P
260  L R S R C I Y N K P S D Q L L N C F C N
280  E L S V S G L R E S P Q C N T F D A Y E (partial)
300  N P T V G D C H G L S K A S C D Y H L I
320  N G S C T K D F V S L K N S E A D E Q T
340  N K L F T C N Q K V T N G F A T E Q L I
360  V P A F L P W K T R V D W G T E A T S L
380  P G P L P V R L V K N T E N S K E T G
400  A Q N A S I C P V H G T N V A S L E K G
420  Y N G A M S K C T H G S H I V T K K C
440  P P A L M S K T T H S A S L G P L E C S
460  S L L T A L A * (465)
```

FIG.3A

Rat Glial Cell Line-Derived Neurotrophic Factor Receptor Protein

```
           10                  30                  50
AGCTCGCTCTCCCGGGGCAGTGGTGTGGATGCACCGGAGTTCGGGCGCTGGGCAAGTTGG 70                  90                 110
GTCGGGAACTGAACCCCTGAAAGCGGGTCCGCTCCCGCCCTCGCCCTCGCCCGGATCTGA 130                 150                 170
GTCGCTGGGCGGGGTGGGCAGAGCCGACGGGGAGTCTGCTCTCACCCTGGATGGAGCT
```

FIG.3B

```
                            190                       210                        230
GAACTTTGAGTGTGGCCAGAGAGGCGCAGTCGCCCGGGATCGCTGCACGCTGAGCTCTCTC 250                       270                        290
CCCGAGACCGGGCGGGCTTTGGATTTTGGGGGCGGGGACCAGCTGCGCGGGGGCAC 310                       330                        350
CATGTTCCTAGCCACTCTGTACTTCGCGCTGCCACTCCTGGATTTGCTGATGTCCGCCGA
 M   F   L   A   T   L   Y   F   A   L   P   L   L   D   D   L   L   M   S   A   E 370                       390                        410
GGTGAGTGGTGGAGACCGTCTGGACTGTGTGAAAGCCAGCGATCAGTGCCTGAAGGAACA
 V   S   G   G   D   R   L   D   C   V   K   A   S   D   Q   C   L   K   E   Q
```

FIG.3C

```
                          430                              450                               470
             GAGCTGCAGCACCAAGTACCGCACACTAAGGCAGTGCCGTGGGGCAAGGAAACCAACTT
              E  L  Q  H  Q  V  P  H  T  K  A  V  P  W  G  K  E  T  N  F
              S  C  S  T  K  Y  R  T  L  R  Q  C  V  A  G  K  E  T  N  F 490                              510                               530
             CAGCCCTGACATCCGGCCTTGAGGCCAAGGATGAGTGCCGTAGCGCCATGGAGGCCTTGAA
              S  L  T  S  G  L  E  A  K  D  E  C  R  S  A  M  E  A  L  K
```

(Note: amino acid letters as shown: S C S T K Y R T L R Q C V A G K E T N F / S L T S G L E A K D E C R S A M E A L K)

FIG.3D

```
         550                    570                     590
GCAGAAGTCTCTGTACAACTGCCAAGCGGCTGCAAGAGAAGAATTGTCT
 Q   K   S   L   Y   N   C   R   C   K   R   G   M   K   K   E   K   N   C   L 610                    630                     650
GCGTATCTACTGGAGCATGTACCAGAGCCTGCAGGGAAATGACCTCCTGGAAGATTCCCC
 R   I   Y   W   S   M   Y   Q   S   L   Q   G   N   D   L   L   E   D   S   P 670                    690                     710
GTATGAGCCGGTTAACAGCAGGTTGTCAGATATATTCCGGGCAGTCCCGTTCATATCAGA
 Y   E   P   V   N   S   R   L   S   D   I   F   R   A   V   P   F   I   S   D
```

FIG. 3E

```
              730                         750                            770
TGTTTCCAGCAAGTGGAACACATTTCCAAAGGGAACAACTGCCTGGACGCAGCCAAGGC
 V  F  Q  Q  V  E  H  I  S  K  G  N  N  C  L  D  A  A  K  A 790                         810                            830
CTGCAACCTGGACGACACCTGTAAGAAGTACAGGTCGGCCTACATCACCCCTGCACCAC
 C  N  L  D  D  T  C  K  K  Y  R  S  A  Y  I  T  P  C  T  T 850                         870                            890
CAGCATGTCCAACGAGGTCTGCAACCGCCGTAAGTGCCACAAGGCCCTCAGGCAGTTCTT
 S  M  S  N  E  V  C  N  R  R  K  C  H  K  A  L  R  Q  F  F
```

FIG.3F

```
           910                   930                   950
CGACAAGGTTCCGGCCAAGCACAGCTACGGGATGCTCTTCTGCTCCTGCCGGGACATCGC
 D  K  V  P  A  K  H  S  Y  G  M  L  F  C  S  C  R  D  I  A 970                   990                  1010
CTGCACCGAGCGGCGGCGACAGACTATCGTCCCCGTGTGCTCCTATGAAGAACGAGAGAG
 C  T  E  R  R  R  Q  T  I  V  P  V  C  S  Y  E  E  R  E  R 1030                  1050                  1070
GCCCAACTGCCTGAGTCTGCAAGACTCCTGCAAGACCAATTACATCTGCAGATCTCGCCT
 P  N  C  L  S  L  Q  D  S  C  K  T  N  Y  I  C  R  S  R  L
```

FIG. 3G

```
                              1090                                    1110                                    1130
TGCAGATTTTTTTACCAACTGCCAGAGTCAAGGTCTGTCAGCAACTGTCTTAAGGA
 A  D  F  F  T  N  C  Q  P  E  S  R  S  V  S  N  C  L  K  E 1150                                    1170                                    1190
GAACTACGCAGACTGCCTCCTGGCCTACTCGGGACTGATTGGCACAGTCATGACTCCCAA
 N  Y  A  D  C  L  L  A  Y  S  G  L  I  G  T  V  M  T  P  N 1210                                    1230                                    1250
CTACGTAGACTCCAGCAGCCTCAGCGTGGCACCATGGTGTGACTGCAGCAACAGCGGCAA
 Y  V  D  S  S  S  L  S  V  A  P  W  C  D  C  S  N  S  G  N
```

FIG. 3H

```
                              1270                                  1290                                  1310
TGACCTGGAAGACTGCTTGAAATTTCTGAATTTTTTTAAGGACAATACTTGTCTCAAAAA
 D   L   E   D   C   L   K   F   L   N   F   F   K   D   N   T   C   L   K   N 1330                                  1350                                  1370
TGCAATTCAAGCCTTTGGCAATGGCTCAGATGTGACCATGTGGCAGCCAGCCCCTCCAGT
 A   I   Q   A   F   G   N   G   S   D   V   T   M   W   Q   P   A   P   P   V 1390                                  1410                                  1430
CCAGACCACCACTGCCACCACTACCACTGCCTTCCGGGTCAAGAACAAGCCTCTGGGGCC
 Q   T   T   T   A   T   T   T   T   A   F   R   V   K   N   K   P   L   G   P
```

FIG. 31

```
                    1450                      1470                      1490
AGCAGGGTCTGAGAATGAGATCCCCACACGTTTTACCACCCTGTGCGAATTTGCAGGC
 A  G  S  E  N  E  I  P  T  H  V  L  P  P  C  A  N  L  Q  A 1510                      1530                      1550
TCAGAAGCTGAAATCCAATGTGTCGGGTAGCACACACCTCTGTCTTTCTGATAGTGATTT
 Q  K  L  K  S  N  V  S  G  S  T  H  L  C  L  S  D  S  D  F 1570                      1590                      1610
CGGAAAGGATGGTCTCGCTGGTGCCTCCAGCCACATAACCACAAATCAATGGCTGCTCC
 G  K  D  G  L  A  G  A  S  S  H  I  T  T  K  S  M  A  A  P
```

FIG. 3J

```
1630                   1650                   1670
TCCCAGCTGCAGTCTGAGCTCACTGCCGGTGCTGATGCTCACCGCCCTTGCTGCCCTGTT
 P   S   Q   L   Q   S   E   L   T   A   V   L   M   L   T   A   L   A   A   L 1690                   1710                   1730
ATCTGTATCGTTGGCAGAAACGTCGTAGCTGCATCCGGGAAAACAGTATGAAAAGACAAA
 S   V   S   L   A   E   T   S   *

1750                   1770                   1790
AGAGAACCAAGTATTCTGTCCCTGTCCTCTTGTATATCTGAAAATCCAGTTTAAAAGCT 1810                   1830                   1850
CCGTTGAGAAGCAGTTTCACCCAACTGGAACTCTTTCCTTGTTTTAAGAAAGCTTGTGG
```

FIG.3K

```
1870                                                          1890                                                          1910
CCCTCAGGGGCTTCTGTTGAAGAACTGCTACAGGGCTAATTCCAAACCCATAAGGCTCTG 1930                                                          1950                                                          1970
GGGCGTGGTGCGGCTTAAGGGGACCATTTGCACCATGTAAAGCAAGCTGGGGCTTATCATG 1990                                                          2010                                                          2030
TGTTTGATGGTGAGGATGGTAGTGGTGATGATGGTAATTTTAACAGCTTGAACCCTG 2050                                                          2070                                                          2090
TTCTCTCTACTGGTTAGGAACAGGAGATACTATTGATAAAGATTCTTCCATGTCTTACTC 2110                                                          2130
AGCAGCATTGCCTTCTGAAGACAGGCCCGCAGCCCGTCG
```

FIG.4A

Rat Glial Cell Line-Derived Neurotrophic Factor Receptor Protein

```
  1  M F L A T L Y F A L P L L D L L M S A E   20
 21  V S G D R L D C V K A S D Q C L K E        40
 41  S C S T K Y R T L R Q C V A G K E T N F    60
 61  S L T S G L E A K C R D C K M E A L K      80
 81  Q K S L Y N M Y Q S R L H I K K S A M E L  100
101  R Y W S N V D K L D I F R A V P L L K P
121  Y E P V Q D D R K G N C L D      140
141  N M S N P V D D E A A K T H      160
161  D K V P A K R S H K C A L R Q F      180
181  K T C H Y M F G M F R V S Y E R      200
201  D K T R R C H I Q T V Q S Y E E R      240
```

(Amino acid sequence figure — position markers at every 20 residues: E 20, Q 40, F 60, K 80, L 100, P 120, D 140, A 160, T 180, F 200, A 220, R 240)

Human GDNF receptor Clones -- Alignment to generate consensus sequence

```
                                       -237                                                          -188
(SEQ ID NO:45)    Gdnfr      AATCTGGCCT CGGAACACGC CATTCTCCGC GCCGCTTCCA ATAACCACTA
(SEQ ID NO:46)    Hsgr-21af             TCTGGCCT CGGAACACGC CATTCTCCGC GCCGCTTCCA ATAACCACTA
(SEQ ID NO:47)    Hsgr-21bf  AATCTGGCCT CGGAACACGC CATTCTCCGC GCCGCTTCCA ATAACCACTA
(SEQ ID NO:48)    21acon              TCTGGCCT CGGAACACGC CATTCTCCGC GCCGCTTCCA ATAACCACTA
(SEQ ID NO:49)    21bcon     AATCTGGCCT CGGAACACGC CATTCTCCGC GCCGCTTCCA ATAACCACTA -187                                                          -138
(SEQ ID NO:45)    Gdnfr      ACATCCCTAA CGAGCATCCG AGCCGAGGGC TCTGCTCGGA AATCGTCCTG
(SEQ ID NO:46)    Hsgr-21af  ACATCCCTAA CGAGCATCCG AGCCGAGGGC TCTGCTCGGA AATCGTCCTG
(SEQ ID NO:47)    Hsgr-21bf  ACATCCCTAA CGAGCATCCG AGCCGAGGGC TCTGCTCGGA AATCGTCCTG
(SEQ ID NO:48)    21acon     ACATCCCTAA CGAGCATCCG AGCCGAGGGC TCTGCTCGGA AATCGTCCTG
(SEQ ID NO:49)    21bcon     ACATCCCTAA CGAGCATCCG AGCCGAGGGC TCTGCTCGGA AATCGTCCTG -137                                                          -88
(SEQ ID NO:45)    Gdnfr      GCCCAACTCG GCCCTTCGAG CTCTCGAAGA TTACCGCATC TATTTTTTTT
(SEQ ID NO:46)    Hsgr-21af  GCCCAACTCG GCCCTTCGAG CTCTCGAAGA TTACCGCATC TATTTTTTTT
(SEQ ID NO:47)    Hsgr-21bf  GCCCAACTCG GCCCTTCGAG CTCTCGAAGA TTACCGCATC TATTTTTTTT
(SEQ ID NO:48)    21acon     GCCCAACTCG GCCCTTCGAG CTCTCGAAGA TTACCGCATC TATTTTTTTT
(SEQ ID NO:49)    21bcon     GCCCAACTCG GCCCTTCGAG CTCTCGAAGA TTACCGCATC TATTTTTTTT
```

FIG. 5B

```
                              -87                                                              -38
(SEQ ID NO:45)      Gdnfr    TTCTTTTTTT  TCTTTTCCTA  GCGCAGATAA  AGTGAGCCCG  GAAAGGGAAG
(SEQ ID NO:46)     Hsgr-21af TTCTTTTTTT  TCTTTTCCTA  GCGCAGATAA  AGTGAGCCCG  GAAAGGGAAG
(SEQ ID NO:47)     Hsgr-21bf TTCTTTTTTT  TCTTTTCCTA  GCGCAGATAA  AGTGAGCCCG  GAAAGGGAAG
(SEQ ID NO:48)     21acon    TTCTTTTTTT  TCTTTTCCTA  GCGCAGATAA  AGTGAGCCCG  GAAAGGGAAG
(SEQ ID NO:49)     21bcon    TTCTTTTTTT  TCTTTTCCTA  GCGCAGATAA  AGTGAGCCCG  GAAAGGGAAG -37                                                               12
(SEQ ID NO:45)      Gdnfr    GAGGGGGCGG  GGACACCATT  GCCCTGAAAG  AATAAATAAG  TAAATAAACA
(SEQ ID NO:46)     Hsgr-21af GAGGGGGCGG  GGACACCATT  GCCCTGAAAG  AATAAATAAG  TAAATAAACA
(SEQ ID NO:47)     Hsgr-21bf GAGGGGGCGG  GGACACCATT  GCCCTGAAAG  AATAAATAAG  TAAATAAACA
(SEQ ID NO:48)     21acon    GAGGGGGCGG  GGACACCATT  GCCCTGAAAG  AATAAATAAG  TAAATAAACA
(SEQ ID NO:49)     21bcon    GAGGGGGCGG  GGACACCATT  GCCCTGAAAG  AATAAATAAG  TAAATAAACA 13                                                               62
(SEQ ID NO:45)      Gdnfr    AACTGGCTCC  TCGCCGCAGC  TGGACGCGGT  CGGTTGAGTC  CAGGTTGGGT
(SEQ ID NO:46)     Hsgr-21af AACTGGCTCC  TCGCCGCAGC  TGGACGCGGT  CGGTTGAGTC  CAGGTTGGGT
(SEQ ID NO:47)     Hsgr-21bf AACTGGCTCC  TCGCCGCAGC  TGGACGCGGT  CGGTTGAGTC  CAGGTTGGGT
(SEQ ID NO:48)     21acon    AACTGGCTCC  TCGCCGCAGC  TGGACGCGGT  CGGTTGAGTC  CAGGTTGGGT
(SEQ ID NO:49)     21bcon    AACTGGCTCC  TCGCCGCAGC  TGGACGCGGT  CGGTTGAGTC  CAGGTTGGGT 63                                                              112
(SEQ ID NO:45)      Gdnfr    CGGACCTGAA  CCCCTAAAAG  CGGAACCGCC  TCCCGCCCTC  GCCATCCCGG
(SEQ ID NO:46)     Hsgr-21af CGGACCTGAA  CCCCTAAAAG  CGGAACCGCC  TCCCGCCCTC  GCCATCCCGG
(SEQ ID NO:47)     Hsgr-21bf CGGACCTGAA  CCCCTAAAAG  CGGAACCGCC  TCCCGCCCTC  GCCATCCCGG
(SEQ ID NO:48)     21acon    CGGACCTGAA  CCCCTAAAAG  CGGAACCGCC  TCCCGCCCTC  GCCATCCCGG
(SEQ ID NO:49)     21bcon    CGGACCTGAA  CCCCTAAAAG  CGGAACCGCC  TCCCGCCCTC  GCCATCCCGG
```

FIG. 5C

```
                                    113                                                                          162
(SEQ ID NO:45)    Gdnfr       AGCTGAGTCG CCGGCGGGGG TGGCTGCTGC CAGACCCGGA GTTTCCTCTT
(SEQ ID NO:46)    Hsgr-21af   AGCTGAGTCG CCGGCGGGGG TGGCTGCTGC CAGACCCGGA GTTTCCTCTT
(SEQ ID NO:47)    Hsgr-21bf   AGCTGAGTCG CCGGCGGGGG TGGCTGCTGC CAGACCCGGA GTTTCCTCTT
(SEQ ID NO:48)    21acon      AGCTGAGTCG CCGGCGGGGG TGGCTGCTGC CAGACCCGGA GTTTCCTCTT
(SEQ ID NO:49)    21bcon      AGCTGAGTCG CCGGCGGGGG TGGCTGCTGC CAGACCCGGA GTTTCCTCTT 163                                                                          212
(SEQ ID NO:45)    Gdnfr       TCACTGGATG GAGCTGAACT TTGGGCGGCC AGAGCAGCAC AGCTGTCCGG
(SEQ ID NO:46)    Hsgr-21af   TCACTGGATG GAGCTGAACT TTGGGCGGCC AGAGCAGCAC AGCTGTCCGG
(SEQ ID NO:47)    Hsgr-21bf   TCACTGGATG GAGCTGAACT TTGGGCGGCC AGAGCAGCAC AGCTGTCCGG
(SEQ ID NO:48)    21acon      TCACTGGATG GAGCTGAACT TTGGGCGGCC AGAGCAGCAC AGCTGTCCGG
(SEQ ID NO:49)    21bcon      TCACTGGATG GAGCTGAACT TTGGGCGGCC AGAGCAGCAC AGCTGTCCGG 213                                                                          262
(SEQ ID NO:45)    Gdnfr       GGATCGCTGC ACGCTGAGCT CCCTCGGCAA GACCCAGCGG CGGCTCGGGA
(SEQ ID NO:46)    Hsgr-21af   GGATCGCTGC ACGCTGAGCT CCCTCGGCAA GACCCAGCGG CGGCTCGGGA
(SEQ ID NO:47)    Hsgr-21bf   GGATCGCTGC ACGCTGAGCT CCCTCGGCAA GACCCAGCGG CGGCTCGGGA
(SEQ ID NO:48)    21acon      GGATCGCTGC ACGCTGAGCT CCCTCGGCAA GACCCAGCGG CGGCTCGGGA
(SEQ ID NO:49)    21bcon      GGATCGCTGC ACGCTGAGCT CCCTCGGCAA GACCCAGCGG CGGCTCGGGA 263                                                                          312
(SEQ ID NO:45)    Gdnfr       TTTTTTTGGG GGGGCGGGGA CCAGCCCCGC GCCGGCACCA TGTTCCTGGC
(SEQ ID NO:46)    Hsgr-21af   TTTTTTTGGG
(SEQ ID NO:47)    Hsgr-21bf   TTTTTTTGGG
(SEQ ID NO:48)    21acon      TTTTTTTGGG GGGGCGGGGA CCAGCCCCGC GCCGGCACCA TGTTCCTGGC
(SEQ ID NO:49)    21bcon      TTTTTTTGGG GGGGCGGGGA CCAGCCCCGC GCCGGCACCA TGTTCCTGGC
```

FIG. 5D

```
                                313
Gdnfr   (SEQ ID NO:45)   GACCCTGTAC TTCGCGCTGC CGCTCTTGGA CTTGCTCCTG TCGGCCGAAG
21acon  (SEQ ID NO:48)   GNCCCTGTAC TTCGCGCTGC CGCTCTTGGA CTTGCTCCTG TCGGCCGAAG
21bcon  (SEQ ID NO:49)   GACCCTGTAC TTCGCGCTGC CGCTCTTGGA CTTGCTCCTG TCGGCCGAAG
                                                                           362

363
Gdnfr   (SEQ ID NO:45)   TGAGCGGGCGG AGACCGCCTG GATTGCGTGA AAGCCAGTGA TCAGTGCCTG
21acon  (SEQ ID NO:48)   TGAGCGGGCGG AGACCGCCTG GATTGCGTGA AAGCCAGTGA TCAGTGCCTG
21bcon  (SEQ ID NO:49)   TGAGCGGGCGG AGACCGCCTG GATTGCGTGA AAGCCAGTGA TCAGTGCCTG
                                                                           412

413
Gdnfr   (SEQ ID NO:45)   AAGGAGCAGA GCTGCAGCAC CAAGTACCGC ACGCTAAGGC AGTGCGTGGC
21acon  (SEQ ID NO:48)   AAGGAGCAGA GCTGCAGCAC CAAGTACCGC ACGCTAAGGC AGTGCGTGGC
21bcon  (SEQ ID NO:49)   AAGGAGCAGA GCTGCAGCAC CAAGTACCGC ACGCTAAGGC AGTGCGTGGC
                                                                           462

463
Gdnfr   (SEQ ID NO:45)   GGGCAAGGAG ACCAACTTCA GCCTGGCATC CGGCCTGGAG GCCAAGGATG
21acon  (SEQ ID NO:48)   GGGCAAGGAG ACCAACTTCA GCCTGGCATC CGGCCTGGAG GCCAAGGATG
21bcon  (SEQ ID NO:49)   GGGCAAGGAG ACCAACTTCA GCCTGGCATC CGGCCTGGAG GCCAAGGATG
                                                                           512

513
Gdnfr   (SEQ ID NO:45)   AGTGCCGCAG CGCCATGGAG GCCCTGAAGC AGAAGTCGCT CTACAACTGC
21acon  (SEQ ID NO:48)   AGTGCCGCAG CGCCATGGAG GCCCTGAAGC AGAAGTCGCT CTACAACTGC
21bcon  (SEQ ID NO:49)   AGTGCCGCAG CGCCATGGAG GCCCTGAAGC AGAAGTCGCT CTACAACTGC
                                                                           562
```

FIG. 5E

```
                          563                                                              612
(SEQ ID NO:45) Gdnfr    CGCTGCAAGC GGGGTATGAA GAAGGAGAAG AACTGCCTGC GCATTTACTG
(SEQ ID NO:48) 21acon   CGCTGCAAGC GGGGTATGAA GAAGGAGAAG AACTGCCTGC GCATTTACTG
(SEQ ID NO:49) 21bcon   CGCTGCAAGC GGGGTATGAA GAAGGAGAAG AACTGCCTGC GCATTTACTG 613                                                              662
(SEQ ID NO:45) Gdnfr    GAGCATGTAC CAGAGCCTGC AGGGAAATGA TCTGCTGGAG GATTCCCCAT
(SEQ ID NO:48) 21acon   GAGCATGTAC CAGAGCCTGC AGGGAAATGA TCTGCTGGAG GATTCCCCAT
(SEQ ID NO:49) 21bcon   GAGCATGTAC CAGAGCCTGC AGGGAAATGA TCTGCTGGAG GATTCCCCAT 663                                                              712
(SEQ ID NO:45) Gdnfr    ATGAACCAGT TAACAGCAGA TTGTCAGATA TATTCCGGGT GGTCCCATTC
(SEQ ID NO:48) 21acon   ATGAACCAGT TAACAGCAGA TTGTCAGATA TATTCCGGGT GGTCCCATTC
(SEQ ID NO:49) 21bcon   ATGAACCAGT TAACAGCAGA TTGTCAGATA TATTCCGGGT GGTCCCATTC 713                                                              762
(SEQ ID NO:45) Gdnfr    ATATCAGATG TTTTTCAGCA AGTGGAGCAC ATTCCCAAAG GGAACAACTG
(SEQ ID NO:48) 21acon   ATATCAGATG TTTTTCAGCA AGTGGAGCAC ATTCCCAAAG GGAACAACTG
(SEQ ID NO:49) 21bcon   ATATCAGATG TTTTTCAGCA AGTGGAGCAC ATTCCCAAAG GGAACAACTG 763                                                              812
(SEQ ID NO:45) Gdnfr    CCTGGATGCA GCGAAGGCCT GCAACCTCGA CGACATTTGC AAGAAGTACA
(SEQ ID NO:48) 21acon   CCTGGATGCA GCGAAGGCCT GCAACCTCGA CGACATTTGC AAGAAGTACA
(SEQ ID NO:49) 21bcon   CCTGGATGCA GCGAAGGCCT GCAACCTCGA CGACATTTGC AAGAAGTACA
```

FIG. 5F

```
                                813
Gdnfr     (SEQ ID NO:45)    GGTCGGCGTA  CATCACCCCG  TGCACCACCA  GCGTGTCCAA  .GATGTCTGC
Hsgr-29a  (SEQ ID NO:50)     GTCGGCGTA  CATCACCCCG  TGCACCACCA  GCGTGTCCAA  TGATGTCTGC
21acon    (SEQ ID NO:48)    GGTCGGCGTA  CATCACCCCG  TGCACCACCA  GCGTGTCCAA  CGATGTCTGC
21bcon    (SEQ ID NO:49)    GGTCGGCGTA  CATCACCCCG  TGCACCACCA  GCGTGTCCAA  CGATGTCTGC
29brc     (SEQ ID NO:51)     GTCGGCGTA  CATCACCCCG  TGCACCACCA  GCGTGTCCAA  TGATGTCTGC
                                                                              862

863
Gdnfr     (SEQ ID NO:45)    AACCGCCGCA  AGTGCCACAA  GGCCCTCCGG  CAGTTCTTTG  ACAAGGTCCC
Hsgr-29a  (SEQ ID NO:50)    AACCGCCGCA  AGTGCCACAA  GGCCCTCCGG  CAGTTCTTTG  ACAAGGTCCC
21acon    (SEQ ID NO:48)    AACCGCCGCA  AGTGCCACAA  GGCCCTCCGG  CAGTTCTTTG  ACAAGGTCCC
21bcon    (SEQ ID NO:49)    AACCGCCGCA  AGTGCCACAA  GGCCCTCCGG  CAGTTCTTTG  ACAAGGTCCC
29brc     (SEQ ID NO:51)    AACCGCCGCA  AGTGCCACAA  GGCCCTCCGG  CAGTTCTTTG  ACAAGGTCCC
                                                                              912

913
Gdnfr     (SEQ ID NO:45)    GGCCAAGCAC  AGCTACGGAA  TGCTCTTCTG  CTCCTGCCGG  GACATCGCCT
Hsgr-29a  (SEQ ID NO:50)    GGCCAAGCAC  AGCTACGGAA  TGCTCTTCTG  CTCCTGCCGG  GACATCGCCT
21acon    (SEQ ID NO:48)    GGCCAAGCAC  AGCTACGGAA  TGCTCTTTCTG CTCCTGCCGG  GACATCGCCT
21bcon    (SEQ ID NO:49)    GGCCAAGCAC  AGCTACGGAA  TGCTCTCTCTG CTCCTGCCGG  GACATCGCCT
29brc     (SEQ ID NO:51)    GGCCAAGCAC  AGCTACGGAA  TGCTCTTCTG  CTCCTGCCGG  GACATCGCCT
                                                                              962

963
Gdnfr     (SEQ ID NO:45)    GCACAGAGCG  GAGGCGACAG  ACCATCGTGC  CTGTGTGCTC  CTATGAAGAG
Hsgr-29a  (SEQ ID NO:50)    GCACAGAGCG  GAGGCGACAG  ACCATCGTGC  CTGTGTGCTC  CTATGAAGAG
21acon    (SEQ ID NO:48)    GCACAGAGCG  GAGGCGACAG  ACCATCGTGC  CTGTGTGCTC  CTATGAAGAG
21bcon    (SEQ ID NO:49)    GCACAGAGCG  GAGGCGACAG  ACCATCGTGC  CTGTGTGCTC  CTATGAAGAG
29brc     (SEQ ID NO:51)    GCACAGAGCG  GAGGCGACAG  ACCATCGTGC  CTGTGTGCTC  CTATGAAGAG
                                                                              1012
```

FIG. 5G

```
                                                                                           1062
(SEQ ID NO:45)    Gdnfr    AGGGAGAAGC CCAACTGTTT GAATTTGCAG GACTCCTGCA AGACGAATTA
(SEQ ID NO:52)    Hsgr-21ar                                 GACTCCTGCA AGACGAATTA
(SEQ ID NO:53)    Hsgr-21br                                                      A
(SEQ ID NO:50)    Hsgr-29a AGGGAGAAGC CCAACTGTTT GAATTTGCAG GACTCCTGCA AGACGAATTA
(SEQ ID NO:48)    21acon   AGGGAGAAGC CCAACTGTTT GAATTTGCAG GACTCCTGCA AGACGAATTA
(SEQ ID NO:49)    21bcon   AGGGAGAAGC CCAACTGTTT GAATTTGCAG GACTCCTGCA AGACGAATTA
(SEQ ID NO:51)    29brc    AGGGAGAAGC CCAACTGTTT GAATTTGCAG GACTCCTGCA AGACGAATTA 1112
(SEQ ID NO:45)    Gdnfr    CATCTGCAGA TCTCGCCTTG CGGATTTTTT TACCAACTGC CAGCCAGAGT
(SEQ ID NO:52)    Hsgr-21ar CATCTGCAGA TCTCGCCTTG CGGATTTTTT TACCAACTGC CAGCCAGAGT
(SEQ ID NO:53)    Hsgr-21br CATCTGCAGA TCTCGCCTTG CGGATTTTTT TACCAACTGC CAGCCAGAGT
(SEQ ID NO:50)    Hsgr-29a CATCTGCAGA TCTCGCCTTG CGGATTTTTT TACCAACTGC CAGCCAGAGT
(SEQ ID NO:48)    21acon   CATCTGCAGA TCTCGCCTTG CGGATTTTTT TACCAACTGC CAGCCAGAGT
(SEQ ID NO:49)    21bcon   CATCTGCAGA TCTCGCCTTG CGGATTTTTT TACCAACTGC CAGCCAGAGT
(SEQ ID NO:51)    29brc    CATCTGCAGA TCTCGCCTTG CGGATTTTTT TACCAACTGC CAGCCAGAGT 1162
(SEQ ID NO:45)    Gdnfr    CAAGGTCTGT CAGCAGCTGT CTAAAGGAAA ACTACGCTGA CTGCCTCCTC
(SEQ ID NO:52)    Hsgr-21ar CAAGGTCTGT CAGCAGCTGT CTAAAGGAAA ACTACGCTGA CTGCCTCCTC
(SEQ ID NO:53)    Hsgr-21br CAAGGTCTGT CAGCAGCTGT CTAAAGGAAA ACTACGCTGA CTGCCTCCTC
(SEQ ID NO:50)    Hsgr-29a CAAGGTCTGT CAGCAGCTGT CTAAAGGAAA ACTACGCTGA CTGCCTCCTC
(SEQ ID NO:48)    21acon   CAAGGTCTGT CAGCAGCTGT CTAAAGGAAA ACTACGCTGA CTGCCTCCTC
(SEQ ID NO:49)    21bcon   CAAGGTCTGT CAGCAGCTGT CTAAAGGAAA ACTACGCTGA CTGCCTCCTC
(SEQ ID NO:51)    29brc    CAAGGTCTGT CAGCAGCTGT CTAAAGGAAA ACTACGCTGA CTGCCTCCTC
```

FIG. 5H

```
                             1163                                                                    1212
     Gdnfr  (SEQ ID NO:45)   GCCTACTCGG GGCTTATTGG CACAGTCATG ACCCCCAACT ACATAGACTC
  Hsgr-21ar  (SEQ ID NO:52)  GCCTACTCGG GGCTTATTGG CACAGTCATG ACCCCCAACT ACATAGACTC
  Hsgr-21br  (SEQ ID NO:53)  GCCTACTCGG GGCTTATTGG CACAGTCATG ACCCCCAACT ACATAGACTC
   Hsgr-29a  (SEQ ID NO:50)  GCCTACTCGG GGCTTATTGG CACAGTCATG ACCCCCAACT ACATAGACTC
     21acon  (SEQ ID NO:48)  GCCTACTCGG GGCTTATTGG CACAGTCATG ACCCCCAACT ACATAGACTC
     21bcon  (SEQ ID NO:49)  GCCTACTCGG GGCTTATTGG CACAGTCATG ACCCCCAACT ACATAGACTC
      29brc  (SEQ ID NO:51)  GCCTACTCGG GGCTTATTGG CACAGTCATG ACCCCCAACT ACATAGACTC
                             1213                                                                    1262
     Gdnfr  (SEQ ID NO:45)   CAGTAGCCTC AGTGTGGCCC CATGGTGTGA CTGCAGCAAC AGTGGGAACG
    Hsgr-2  (SEQ ID NO:54)                                                TGGAACG
  Hsgr-21ar (SEQ ID NO:52)   CAGTAGCCTC AGTGTGGCCC CATGGTGTGA CTGCAGCAAC AGTGGGAACG
  Hsgr-21br (SEQ ID NO:53)   CAGTAGCCTC AGTGTGGCCC CATGGTGTGA CTGCAGCAAC AGTGGGAACG
   Hsgr-29a (SEQ ID NO:50)   CAGTAGCCTC AGTGTGGCCC CATGGTGTGA CTGCAGCAAC AGTGGGAACG
     21acon (SEQ ID NO:48)   CAGTAGCCTC AGTGTGGCCC CATGGTGTGA CTGCAGCAAC AGTGGGAACG
     21bcon (SEQ ID NO:49)   CAGTAGCCTC AGTGTGGCCC CATGGTGTGA CTGCAGCAAC AGTGGGAACG
      29brc (SEQ ID NO:51)   CAGTAGCCTC AGTGTGGCCC CATGGTGTGA CTGCAGCAAC AGTGGGAACG
```

FIG. 51

```
                              1263                                                    1312
(SEQ ID NO:45)      Gdnfr     ACCTAGAAGA  GTGCTTGAAA  TTTTTGAATT  TCTTCAAGGA  CAATACATGT
(SEQ ID NO:54)      Hsgr-2    ACCTAGAAGA  GTGCTTGAAA  TTTTTGAATT  TCTTCAAGGA  CAATACATGT
(SEQ ID NO:55)      Hsgr-9             A  GTGCTTGAAA  TTTTTGAATT  TCTTCAAGGA  CAATACATGT
(SEQ ID NO:52)      Hsgr-21ar  ACCTAGAAGA  GTGCTTGAAA  TTTTTGAATT  TCTTCAAGGA  CAATACATGT
(SEQ ID NO:53)      Hsgr-21br  ACCTAGAAGA  GTGCTTGAAA  TTTTTGAATT  TCTTCAAGGA  CAATACATGT
(SEQ ID NO:50)      Hsgr-29a   ACCTAGAAGA  GTGCTTGAAA  TTTTTGAATT  TCTTCAAGGA  CAATACATGT
(SEQ ID NO:48)      21acon     ACCTAGAAGA  GTGCTTGAAA  TTTTTGAATT  TCTTCAAGGA  CAATACATGT
(SEQ ID NO:49)      21bcon     ACCTAGAAGA  GTGCTTGAAA  TTTTTGAATT  TCTTCAAGGA  CAATACATGT
(SEQ ID NO:51)      29brc      ACCTAGAAGA  GTGCTTGAAA  TTTTTGAATT  TCTTCAAGGA  CAATACATGT 1313                                                    1362
(SEQ ID NO:45)      Gdnfr     CTTAAAAATG  CAATTCAAGC  CTTTGGCAAT  GGCTCCGATG  TGACCGTGTG
(SEQ ID NO:54)      Hsgr-2    CTTAAAAATG  CAATTCAAGC  CTTTGGCAAT  GGCTCCGATG  TGACCGTGTG
(SEQ ID NO:55)      Hsgr-9    CTTAAAAATG  CAATTCAAGC  CTTTGGCAAT  GGCTCCGATG  TGACCGTGTG
(SEQ ID NO:52)      Hsgr-21ar CTTAAAAATG  CAATTCAAGC  CTTTGGCAAT  GGCTCCGATG  TGACCGTGTG
(SEQ ID NO:53)      Hsgr-21br CTTAAAAATG  CAATTCAAGC  CTTTGGCAAT  GGCTCCGATG  TGACCGTGTG
(SEQ ID NO:50)      Hsgr-29a  CTTAAAAATG  CAATTCAAGC  CTTTGGCAAT  GGCTCCGATG  TGACCGTGTG
(SEQ ID NO:48)      21acon    CTTAAAAATG  CAATTCAAGC  CTTTGGCAAT  GGCTCCGATG  TGACCGTGTG
(SEQ ID NO:49)      21bcon    CTTAAAAATG  CAATTCAAGC  CTTTGGCAAT  GGCTCCGATG  TGACCGTGTG
(SEQ ID NO:51)      29brc     CTTAAAAATG  CAATTCAAGC  CTTTGGCAAT  GGCTCCGATG  TGACCGTGTG
```

FIG. 5J

```
                       1363                                                                              1412
(SEQ ID NO:45) Gdnfr    GCAGCCAGCC TTCCCAGTAC AGACCACCAC TGCCacTACC ACCACTGCCC
(SEQ ID NO:54) Hsgr-2   GCAGCCAGCC TTCCCAGTAC AGACCACCAC TGCCACTACC ACCACTGCCC
(SEQ ID NO:55) Hsgr-9   GCAGCCAGCC TTCCCAGTAC AGACCACCAC TGCCACTACC ACCACTGCCC
(SEQ ID NO:52) Hsgr-21ar GCAGCCAGCC TTCCCAGTAC AGACCACCAC TGCCACTACC ACCACTGCCC
(SEQ ID NO:53) Hsgr-21br GCAGCCAGCC TTCCCAGTAC AGACCACCAC TGCCACTACC ACCACTGCCC
(SEQ ID NO:50) Hsgr-29a  GCAGCCAGCC TTCCCAGTAC AGACCACCAC TGCCACTACC ACCACTGCCC
(SEQ ID NO:48) 21acon    GCAGCCAGCC TTCCCAGTAC AGACCACCAC TGCCACTACC ACCACTGCCC
(SEQ ID NO:49) 21bcon    GCAGCCAGCC TTCCCAGTAC AGACCACCAC TGCCACTACC ACCACTGCCC
(SEQ ID NO:51) 29brc     GCAGCCAGCC TTCCCAGTAC AGACCACCAC TGCCGCTACC ACCACTGCCC 1413                                                                              1462
(SEQ ID NO:45) Gdnfr    TCCGGGTTAA GAACAAGCCC CTGGGGCCAG CAGGGTCTGA GAATGAAATT
(SEQ ID NO:54) Hsgr-2   TCCGGGTTAA GAACAAGCCC CTGGGGCCAG CAGGGTCTGA GAATGAAATT
(SEQ ID NO:55) Hsgr-9   TCCGGGTTAA GAACAAGCCC CTGGGGCCAG CAGGGTCTGA GAATGAAATT
(SEQ ID NO:52) Hsgr-21ar TCCGGGTTAA GAACAAGCCC CTGGGGCCAG CAGGGTCTGA GAATGAAATT
(SEQ ID NO:53) Hsgr-21br TCCGGGTTAA GAACAAGCCC CTGGGGCCAG CAGGGTCTGA GAATGAAATT
(SEQ ID NO:50) Hsgr-29a  TCCGGGTTAA GAACAAGCCC CTGGGGCCAG CAGGGTCTGA GAATGAAATT
(SEQ ID NO:48) 21acon    TCCGGGTTAA GAACAAGCCC CTGGGGCCAG CAGGGTCTGA GAATGAAATT
(SEQ ID NO:49) 21bcon    TCCGGGTTAA GAACAAGCCC CTGGGGCCAG CAGGGTCTGA GAATGAAATT
(SEQ ID NO:51) 29brc     TCCGGGTTAA GAACAAGCCC CTGGGGCCAG CAGGGTCTGA GAATGAAATT
```

FIG. 5K

```
                                1463                                                                    1512
Gdnfr      (SEQ ID NO:45)   CCCACTCATG  TTTTGCCACC  GTGTGCAAAT  TTACAGGCAC  AGAAGCTGAA
Hsgr-2     (SEQ ID NO:54)   CCCACTCATG  TTTTGCCACC  GTGTGCAAAT  TTACAGGCAC  AGAAGCTGAA
Hsgr-9     (SEQ ID NO:55)   CCCACTCATG  TTTTGCCACC  GTGTGCAAAT  TTACAGGCAC  AGAAGCTGAA
Hsgr-21ar  (SEQ ID NO:52)   CCCACTCATG  TTTTGCCACC  GTGTGCAAAT  TTACAGGCAC  AGAAGCTGAA
Hsgr-21br  (SEQ ID NO:53)   CCCACTCATG  TTTTGCCACC  GTGTGCAAAT  TTACAGGCAC  AGAAGCTGAA
Hsgr-29a   (SEQ ID NO:50)   CCCACTCATG  TTTTGCCACC  GTGTGCAAAT  TTACAGGCAC  AGAAGCTGAA
21acon     (SEQ ID NO:48)   CCCACTCATG  TTTTGCCACC  GTGTGCAAAT  TTACAGGCAC  AGAAGCTGAA
21bcon     (SEQ ID NO:49)   CCCACTCATG  TTTTGCCACC  GTGTGCAAAT  TTACAGGCAC  AGAAGCTGAA
29brc      (SEQ ID NO:51)   CCCACTCATG  TTTTGCCACC  GTGTGCAAAT  TTACAGGCAC  AGAAGCTGAA 1513                                                                    1562
Gdnfr      (SEQ ID NO:45)   ATCCAATGTG  TCGGGCAATA  CACACCTCTG  TATTTCCAAT  GGTAATTATG
Hsgr-2     (SEQ ID NO:54)   ATCCAATGTG  TCGGGCAATA  CACACCTCTG  TATTTCCAAT  GGTAATTATG
Hsgr-9     (SEQ ID NO:55)   ATCCAATGTG  TCGGGCAATA  CACACCTCTG  TATTTCCAAT  GGTAATTATG
Hsgr-21ar  (SEQ ID NO:52)   ATCCAATGTG  TCGGGCAATA  CACACCTCTG  TATTTCCAAT  GGTAATTATG
Hsgr-21br  (SEQ ID NO:53)   ATCCAATGTG  TCGGGCAATA  CACACCTCTG  TATTTCCAAT  GGTAATTATG
Hsgr-29a   (SEQ ID NO:50)   ATCCAATGTG  TCGGGCAATA  CACACCTCTG  TATTTCCAAT  GGTAATTATG
21acon     (SEQ ID NO:48)   ATCCAATGTG  TCGGGCAATA  CACACCTCTG  TATTTCCAAT  GGTAATTATG
21bcon     (SEQ ID NO:49)   ATCCAATGTG  TCGGGCAATA  CACACCTCTG  TATTTCCAAT  GGTAATTATG
29brc      (SEQ ID NO:51)   ATCCAATGTG  TCGGGCAATA  CACACCTCTG  TATTTCCAAT  GGTAATTATG
```

FIG. 5L

```
                    1563
(SEQ ID NO:45)  Gdnfr     AAAAAGAAGG TCTCGGTGCT TCCAGCCACA TAACCACAAA ATCAATGGCT
(SEQ ID NO:54)  Hsgr-2    AAAAAGAAGG TCTCGGTGCT TCCAGCCACA TAACCACAAA ATCAATGGCT
(SEQ ID NO:55)  Hsgr-9    AAAAAGAAGG TCTCGGTGCT TCCAGCCACA TAACCACAAA ATCAATGGCT
(SEQ ID NO:52)  Hsgr-21ar AAAAAGAAGG TCTCGGTGCT TCCAGCCACA TAACCACAAA ATCAATGGCT
(SEQ ID NO:53)  Hsgr-21br AAAAAGAAGG TCTCGGTGCT TCCAGCCACA TAACCACAAA ATCAATGGCT
(SEQ ID NO:48)  21acon    AAAAAGAAGG TCTCGGTGCT TCCAGCCACA TAACCACAAA ATCAATGGCT
(SEQ ID NO:49)  21bcon    AAAAAGAAGG TCTCGGTGCT TCCAGCCACA TAACCACAAA ATCAATGGCT
(SEQ ID NO:51)  29brc     AAAAAGAAGG TCTCGGTGCT TCCAGCCACA TAACCACAAA ATCAATGGCT
                                                                              1612

1613
(SEQ ID NO:45)  Gdnfr     GCTCCTCCAA GCTGTGGTCT GAGCCCACTG CTGGTCCTGG TGGTAACCGC
(SEQ ID NO:54)  Hsgr-2    GCTCCTCCAA GCTGTGGTCT GAGCCCACTG CTGGTCCTGG TGGTAACCGC
(SEQ ID NO:55)  Hsgr-9    GCTCCTCCAA GCTGTGGTCT GAGCCCACTG CTGGTCCTGG TGGTAACCGC
(SEQ ID NO:52)  Hsgr-21ar GCTCCTCCAA GCTGTGGTCT GAGCCCACTG CTGGTCCTGG TGGTAACCGC
(SEQ ID NO:53)  Hsgr-21br GCTCCTCCAA GCTGTGGTCT GAGCCCACTG CTGGTCCTGG TGGTAACCGC
(SEQ ID NO:48)  21acon    GCTCCTCCAA GCTGTGGTCT GAGCCCACTG CTGGTCCTGG TGGTAACCGC
(SEQ ID NO:49)  21bcon    GCTCCTCCAA GCTGTGGTCT GAGCCCACTG CTGGTCCTGG TGGTAACCGC
(SEQ ID NO:51)  29brc     GCTCCTCCAA GCTGTGGTCT GAGCCCACTG CTGGTCCTGG TGGTAACCGC
                                                                              1662
```

FIG. 5M

```
                           1663                                                              1712
(SEQ ID NO:45)    Gdnfr    TCTGTCCACC CTATTATCTT TAACAGAAAC ATCATAGCTG CATTAAAAAA
(SEQ ID NO:54)    Hsgr-2   TCTGTCCACC CTATTATCTT TAACAGAAAC ATCATAGCTG CATTAAAAAA
(SEQ ID NO:55)    Hsgr-9   TCTGTCCACC CTATTATCTT TAACAGAAAC ATCATAGCTG CATTAAAAAA
(SEQ ID NO:52)    Hsgr-21ar TCTGTCCACC CTATTATCTT TAACAGAAA
(SEQ ID NO:53)    Hsgr-21br TCTGTCCACC CTATTATCTT TAACAGAAA
(SEQ ID NO:48)    21acon   TCTGTCCACC CTATTATCTT TAACAGAAA
(SEQ ID NO:49)    21bcon   TCTGTCCACC CTATTATCTT TAACAGAAA
(SEQ ID NO:51)    29brc    TCTGTCCACC CTATTATCTT TAACAGAAAC ATCATAGCTG CATTAAAAAA 1713                                                              1762
(SEQ ID NO:45)    Gdnfr    ATACAATATG GACATGTAAA AAGACAAAAA CCAAGTTATC TGTTTCCTGT
(SEQ ID NO:54)    Hsgr-2   ATACAATATG GACATGTAAA AAGACAAAAA CCAAGTTATC TGTTTCCTGT
(SEQ ID NO:55)    Hsgr-9   ATACAATATG GACATGTAAA AAGACAAAAA CCAAGTTATC TGTTTCCTGT
(SEQ ID NO:51)    29brc    ATACAATATG GACATGTAAA AAGACAAAAA CCAAGTTATC TGTTTCCTGT 1763                                                              1812
(SEQ ID NO:45)    Gdnfr    TCTCTTGTAT AGCTGAAATT CCAGTTTAGG AGCTCAGTTG AGAAACAGTT
(SEQ ID NO:54)    Hsgr-2   TCTCTTGTAT AGCTGAAATT CCAGTTTAGG AGCTCAGTTG AGAAACAGTT
(SEQ ID NO:55)    Hsgr-9   TCTCTTGTAT AGCTGAAATT CCAGTTTAGG AGCTCAGTTG AGAAACAGTT
(SEQ ID NO:51)    29brc    TCTCTTGTAT AGCTGAAATT CCAGTTTAGG AGCTCAGTTG AGAAACAGTT 1813                                                              1862
(SEQ ID NO:45)    Gdnfr    CCATTCAACT GGAACATTTT TTTTTTT.CC TTTTAAGAAA GCTTCTTGTG
(SEQ ID NO:54)    Hsgr-2   CCATTCAACT GGAACATTTT TTTTTTT.CC TTTTAAGAAA GCTTCTTGTG
(SEQ ID NO:55)    Hsgr-9   CCATTCAACT GGAACATTTT TTTTTTTTCC TTTTAAGAAA GCTTCTTGTG
(SEQ ID NO:51)    29brc    CCATTCAACT GGAACATTTT TTTTTTT.CC TTTTAAGAAA GCTTCTTGTG
```

FIG. 5N

```
                                1863                                                              1912
(SEQ ID NO:45)  Gdnfr   ATCCTTCGGG GCTTCTGTGA AAAACCTGAT GCAGTGCTCC ATCCAAACTC
(SEQ ID NO:54)  Hsgr-2  ATCCTTCGGG GCTTCTGTGA AAAACCTGAT GCAGTGCTCC ATCCAAACTC
(SEQ ID NO:55)  Hsgr-9  ATCCTTTGGG GCTTCTGTGA AAAACCTGAT GCAGTGCTCC ATCCAAACTC
(SEQ ID NO:51)  29brc   ATCCTTCGGG GCTTCTGTGA AAAACCTGAT GCAGTGCTCC ATCCAAACTC 1913                                                              1962
(SEQ ID NO:45)  Gdnfr   AGAAGGCTTT GGGATATGCT GTATTTTAAA GGGACAGTTT GTAACTTGGG
(SEQ ID NO:54)  Hsgr-2  AGAAGGCTTT GGGATATGCT GTATTTTAAA GGGACAGTTT GTAACTTGGG
(SEQ ID NO:55)  Hsgr-9  AGAAGGCTTT GGGATATGCT GTATTTTAAA GGGACAGTTT GTAACTTGGG
(SEQ ID NO:51)  29brc   AGAAGGCTTT GGGATATGCT GTATTTTAAA GGGACAGTTT GTAACTTGGG 1963                                                              2012
(SEQ ID NO:45)  Gdnfr   CTGTAAAGCA AACTGGGGCT GTGTTTTCGA GGGACAGTTT TGATGATGAT CATCATGATC
(SEQ ID NO:54)  Hsgr-2  CTGTAAAGCA AACTGGGGCT GTGTTTTCGA                      CATCATGATC
(SEQ ID NO:55)  Hsgr-9  CTGTAAAGCA AACTGGGGCT GTGTTTTCGA                      GATCATGATG
(SEQ ID NO:51)  29brc   CTGTAAAGCA AACTGGGGCT GTGTTTTCGA                      CATCATGATC 2013                                                              2062
(SEQ ID NO:45)  Gdnfr   ATGAT.....                                            .....GATTT
(SEQ ID NO:54)  Hsgr-2  ATGAT.....                                            .....GATTT
(SEQ ID NO:55)  Hsgr-9  ATGATCATCA TGATCATGAT GATGATCATC ATGATCATGA TGATGATTTT
(SEQ ID NO:51)  29brc   ATGAT.....                                            .....GATTT
```

FIG. 50

```
                                                2063                                                          2112
(SEQ ID NO: 45)  Gdnfr    AACAGTTTTA CTTCTGGCCT TTCCTAGCTA GAGAAGGAGT TAATATTTCT
(SEQ ID NO: 54)  Hsgr-2   AACAGTTTTA CTTCTGGCCT TTCCTAGCTA GAGAAGGAGT TAATATTTCT
(SEQ ID NO: 55)  Hsgr-9   AACAGTTTTA CTTCTGGCCT TTCCTAGCTA GAGAAGGAGT TAATATTTCT
(SEQ ID NO: 51)  29brc    AACAGTTTTA CTTCTGGCCT TTCCTAGCTA GAGAAGGAGT TAATATTTCT 2113                                                          2162
(SEQ ID NO: 45)  Gdnfr    AAGGTAACTC CCATATCTCC TTTAATGACA TTGATTTCTA ATGATATAAA
(SEQ ID NO: 54)  Hsgr-2   AAGGTAACTC CCATATCTCC TTTAATGACA TTGATTTCTA ATGATATAAA
(SEQ ID NO: 55)  Hsgr-9   AAGGTAACTC CCATATCTCC TTTAATGACA TTGATTTCTA ATGATATAAA
(SEQ ID NO: 51)  29brc    AAGGTAACTC CCATATCTCC TTTAATGACA TTGATTTCTA ATGATATAAA 2163                                                          2212
(SEQ ID NO: 45)  Gdnfr    TTTCAGCCTA CATTGATGCC AAGCTTTTTT GCCACAAAGA AGATTCTTAC
(SEQ ID NO: 54)  Hsgr-2   TTTCAGCCTA CATTGATGCC AAGCTTTTTT GCCACAAAGA AGATTCTTAC
(SEQ ID NO: 55)  Hsgr-9   TTTCAGCCTA CATTGATGCC AAGCTTTTTT GCCACAAAGA AGATTCTTAC
(SEQ ID NO: 51)  29brc    TTTCAGCCTA CATTGATGCC AAGCTTTTTT GCCACAAAGA AGATTCTTAC 2213                                                          2262
(SEQ ID NO: 45)  Gdnfr    CAAGAGTGGG CTTTGTGGAA ACAGCTGGTA CTGATGTTCA CCTTTATATA
(SEQ ID NO: 54)  Hsgr-2   CAAGAGTGGG CTTTGTGGAA ACAGCTGGTA CTGATGTTCA CCTTTATATA
(SEQ ID NO: 55)  Hsgr-9   CAAGAGTGGG CTTTGTGGAA ACAGCTGGTA CTGATGTTCA CCTTTATATA
(SEQ ID NO: 51)  29brc    CAAGAGTGGG CTTTGTGGAA ACAGCTGGTA CTGATGTTCA CCTTTATATA
```

FIG. 5P

```
                                                                                        2312
(SEQ ID NO:45) Gdnfr   2263 TGTACTAGCA TTTTCCACGC TGATGTTTAT GTACTGTAAA CAGTTCTGCA
(SEQ ID NO:54) Hsgr-2       TGTACTAGCA TTTTCCACGC TGATGTTTAT GTACTGTAAA CAGTTCTGCA
(SEQ ID NO:55) Hsgr-9       TGTACTAGCA TTTTCCACGC TGATGTTTAT GTACTGTAAA CAGTTCTGCA
(SEQ ID NO:51) 29brc        TGTACTAGCA TTTTCCACGC TGATGTTTAT GTACTGTAAA CAGTTCTGCA 2362
(SEQ ID NO:45) Gdnfr   2313 CTCTTGTACA AAAGAAAAAA CACCTGTCAC ATCCAAATAT AGTATCTGTC
(SEQ ID NO:54) Hsgr-2       CTCTTGTACA AAAGAAAA
(SEQ ID NO:55) Hsgr-9       CTCTTGTACA AAAGAAAAA
(SEQ ID NO:51) 29brc        CTCTTGTACA AAAGAAAAAA CACCTGTCAC ATCCAAATAT AGTATCTGTC 2412
(SEQ ID NO:45) Gdnfr   2363 TTTTCGTCAA AATAGAGAGT GGGGAATGAG TGTGCCGATT CAATACCTCA
(SEQ ID NO:51) 29brc        TTTTCGTCAA AATAGAGAGT GGGGAATGAG TGTGCCGATT CAATACCTCA 2462
(SEQ ID NO:45) Gdnfr   2413 ATCCCTGAAC GACACTCTCC TAATCCTAAG CCTTACCTGA GTGAGAAGCC
(SEQ ID NO:51) 29brc        ATCCCTGAAC GACACTCTCC TAATCCTAAG CCTTACCTGA GTGAGAAGCC 2512
(SEQ ID NO:45) Gdnfr   2463 CTTTACCTAA CAAAGTCCA ATATAGCTGA AATGTCGCTC TAATACTCTT
(SEQ ID NO:51) 29brc        CTTTACCTAA CAAAGTCCA ATATAGCTGA AATGTCGCTC TAATACTCTT 2562
(SEQ ID NO:45) Gdnfr   2513 TACACATATG AGGTTATATG TAGAAAAAAA TTTTACTACT AAATGATTTC
(SEQ ID NO:51) 29brc        TACACATATG AGGTTATATG TAGAAAAAAA TTTTACTACT AAATGATTTC
```

FIG. 5Q

```
              2563                                                            2612
Gdnfr  (SEQ ID NO:45)  AACTATTGGC TTTCTATATT TTGAAAGTAA TGATATTGTC TCATTTTTTT
29brc  (SEQ ID NO:51)  AACTATTGGC TTTCTATATT TTGAAAGTAA TGATATTGTC TCATTTTTTT 2613                                                            2662
Gdnfr  (SEQ ID NO:45)  ACTGATGGTT TAATACAAAA TACACAGAGC TTGTTTCCCC TCATAAGTAG
29brc  (SEQ ID NO:51)  ACTGATGGTT TAATACAAAA TACACAGAGC TTGTTTCCCC TCATAAGTAG 2663                                                            2712
Gdnfr  (SEQ ID NO:45)  TGTTCGCTCT GATATGAACT TCACAAATAC AGCTCATCAA AAGCAGACTC
29brc  (SEQ ID NO:51)  TGTTCGCTCT GATATGAACT TCACAAATAC AGCTCATCAA AAGCAGACTC 2713                                                            2762
Gdnfr  (SEQ ID NO:45)  TGAGAAGCCT CGTGCTGTAG CAGAAAGTTC TGCATCATGT GACTGTGGAC
29brc  (SEQ ID NO:51)  TGAGAAGCCT CGTGCTGTAG CAGAAAGTTC TGCATCATGT GACTGTGGAC 2763                                                            2812
Gdnfr  (SEQ ID NO:45)  AGGCAGGAGG AAACAGAACA GACAAGCATT GTCTTTTGTC ATTGCTCGAA
29brc  (SEQ ID NO:51)  AGGCAGGAGG AAACAGAACA GACAAGCATT GTCTTTTGTC ATTGCTCGAA 2813                                                            2862
Gdnfr  (SEQ ID NO:45)  GTGCAAGCGT GCATACCTGT GGAGGGAACT GGTGGCTGCT TGTAAATGTT
29brc  (SEQ ID NO:51)  GTGCAAGCGT GCATACCTGT GGAGGGAACT GGTGGCTGCT TGTAAATGTT 2863                                                            2912
Gdnfr  (SEQ ID NO:45)  CTGCAGCATC TCTTGACACA CTTGTCATGA CACAATCCAG TACCTTGGTT
29brc  (SEQ ID NO:51)  CTGCAGCATC TCTTGACACA CTTGTCATGA CACAATCCAG TACCTTGGTT
```

FIG. 5R

```
              2913
Gdnfr   TTCAGGTTAT CTGACAAAGG CAGCTTTGAT TGGGACATGG AGGCATGGGC
29brc   TTCAGGTTAT CTGACAAAGG CAGCTTTGAT TGGGACATGG AGGCATGGGC
                                                           2962

2963
Gdnfr   AGGCCGGAA
29brc   AGGCCGGAA
```

(SEQ ID NO:45)
(SEQ ID NO:51)

(SEQ ID NO:45)
(SEQ ID NO:51)

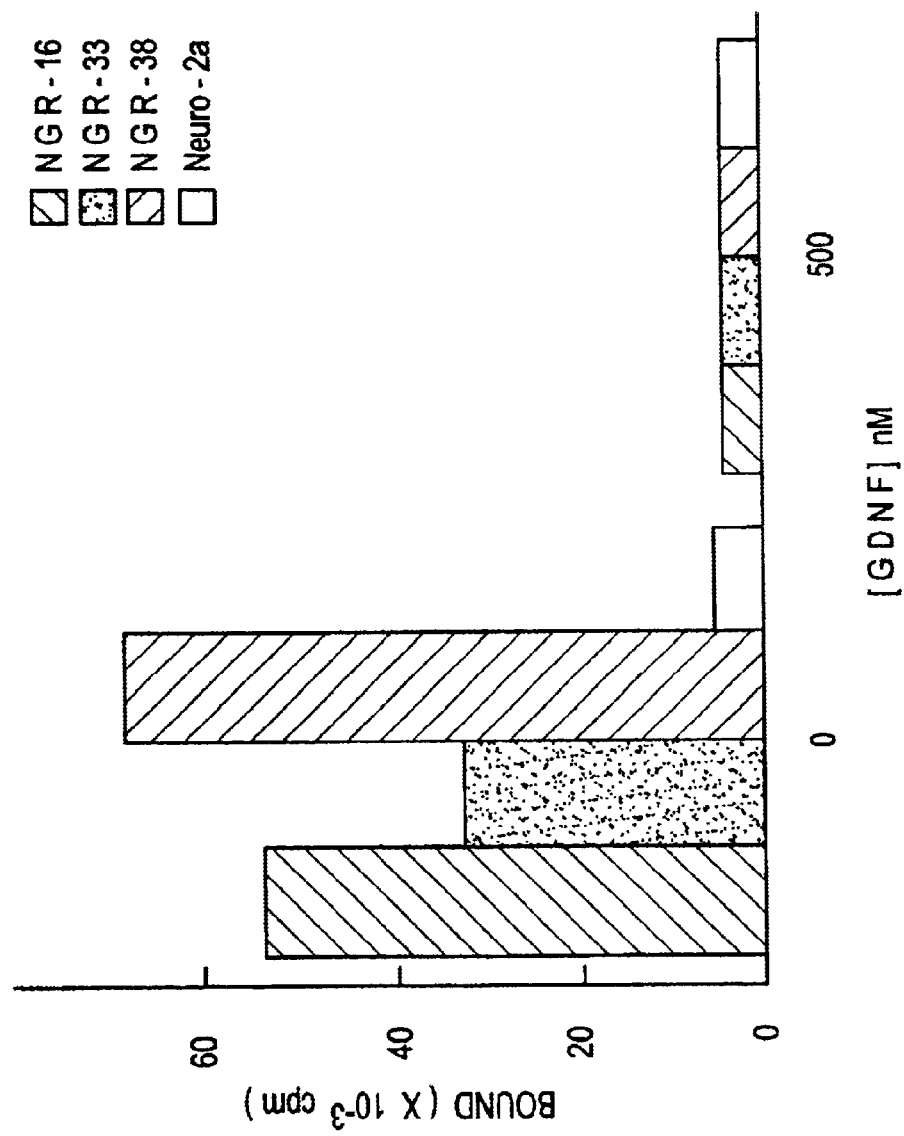

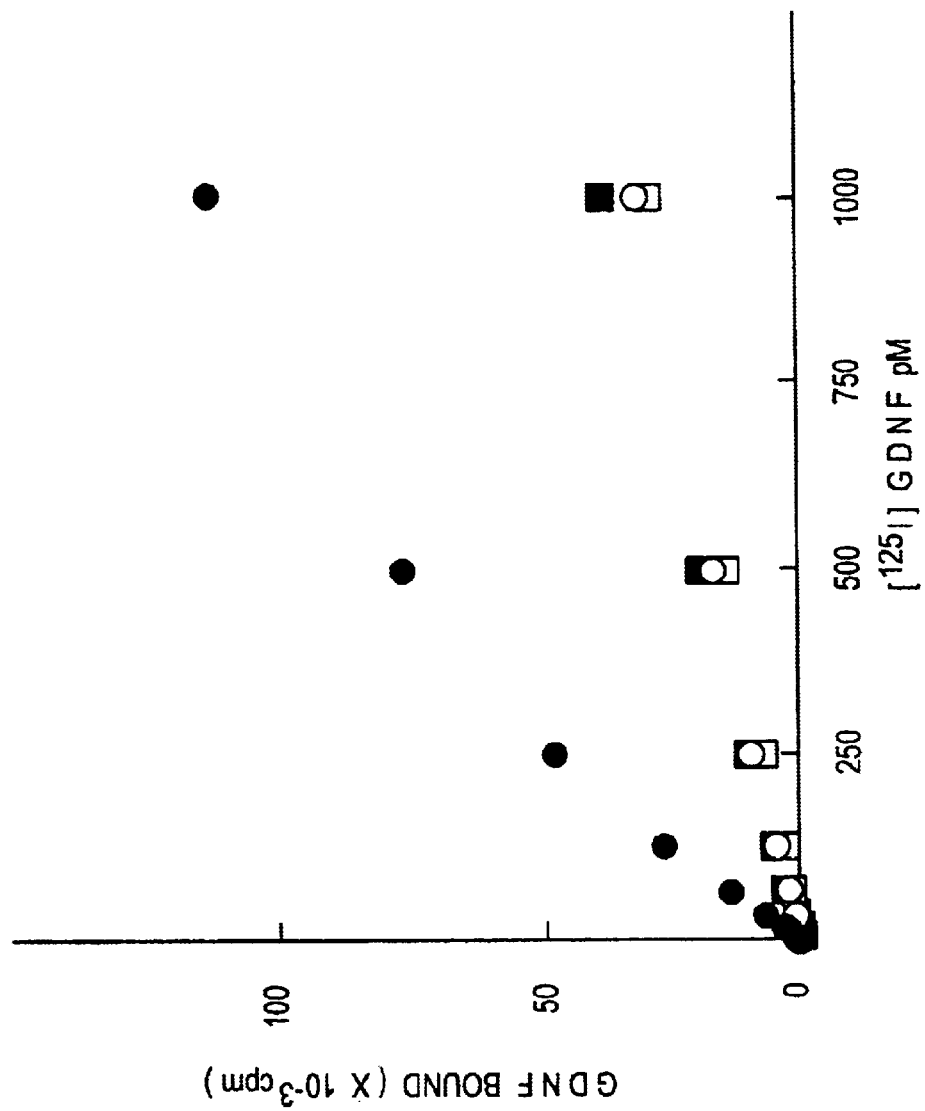

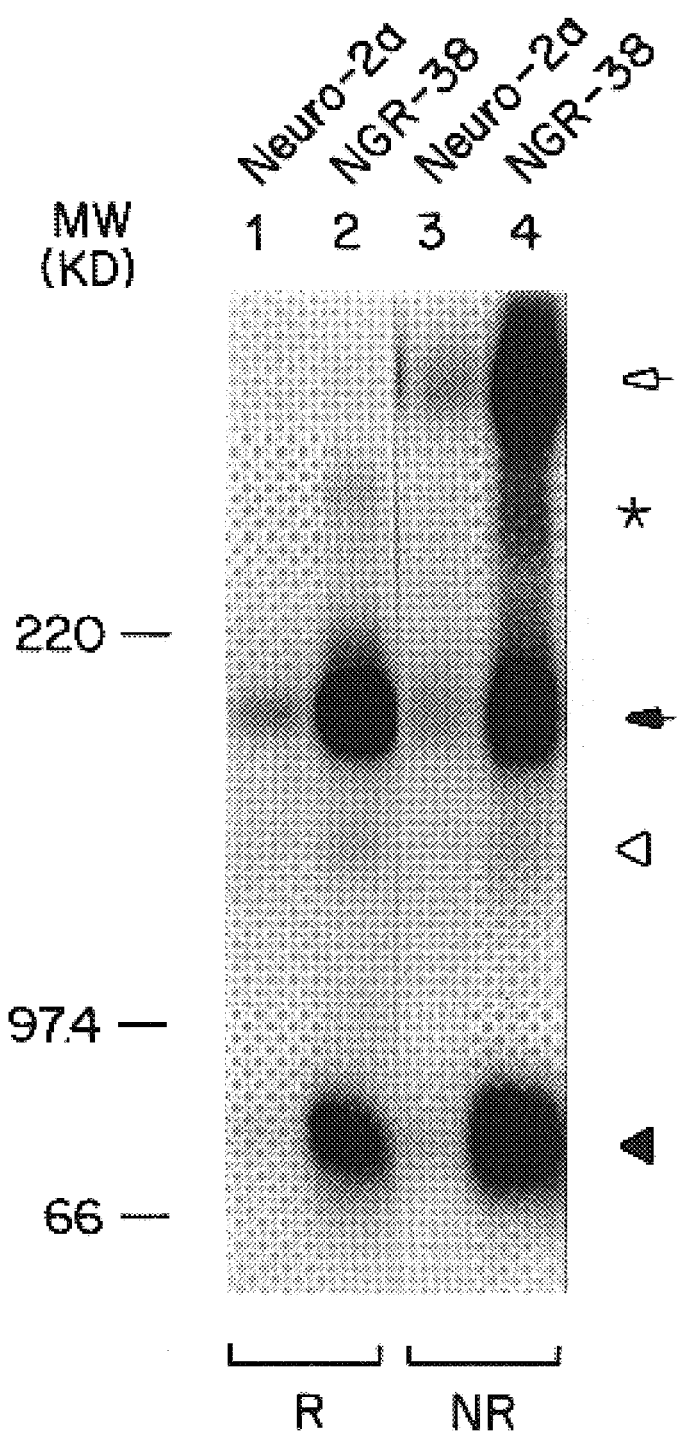

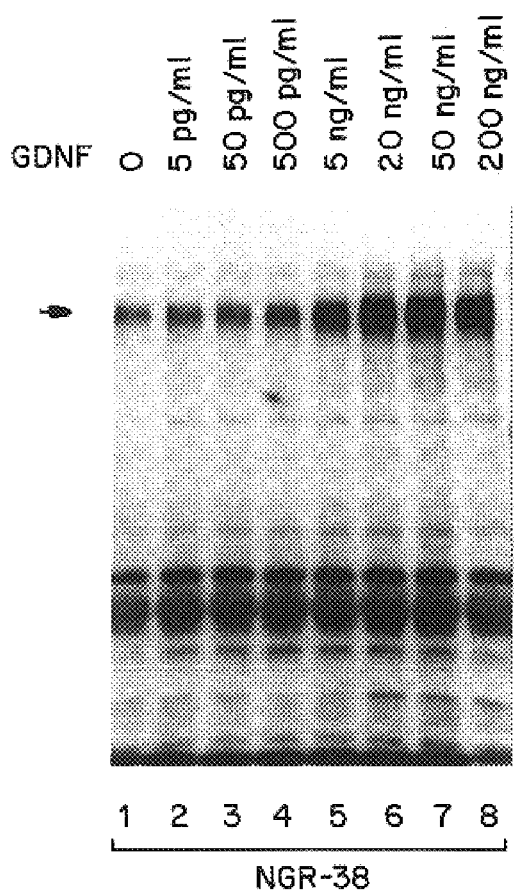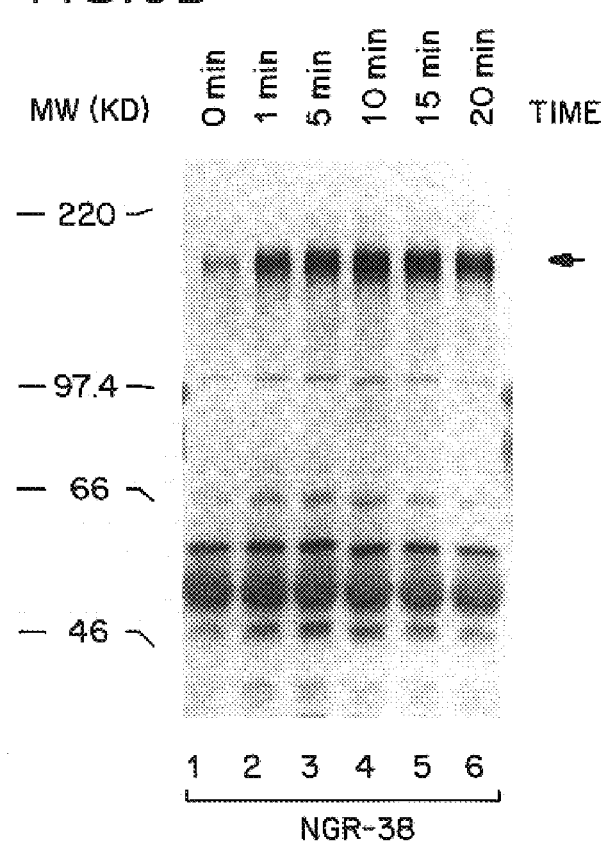
FIG. 9B

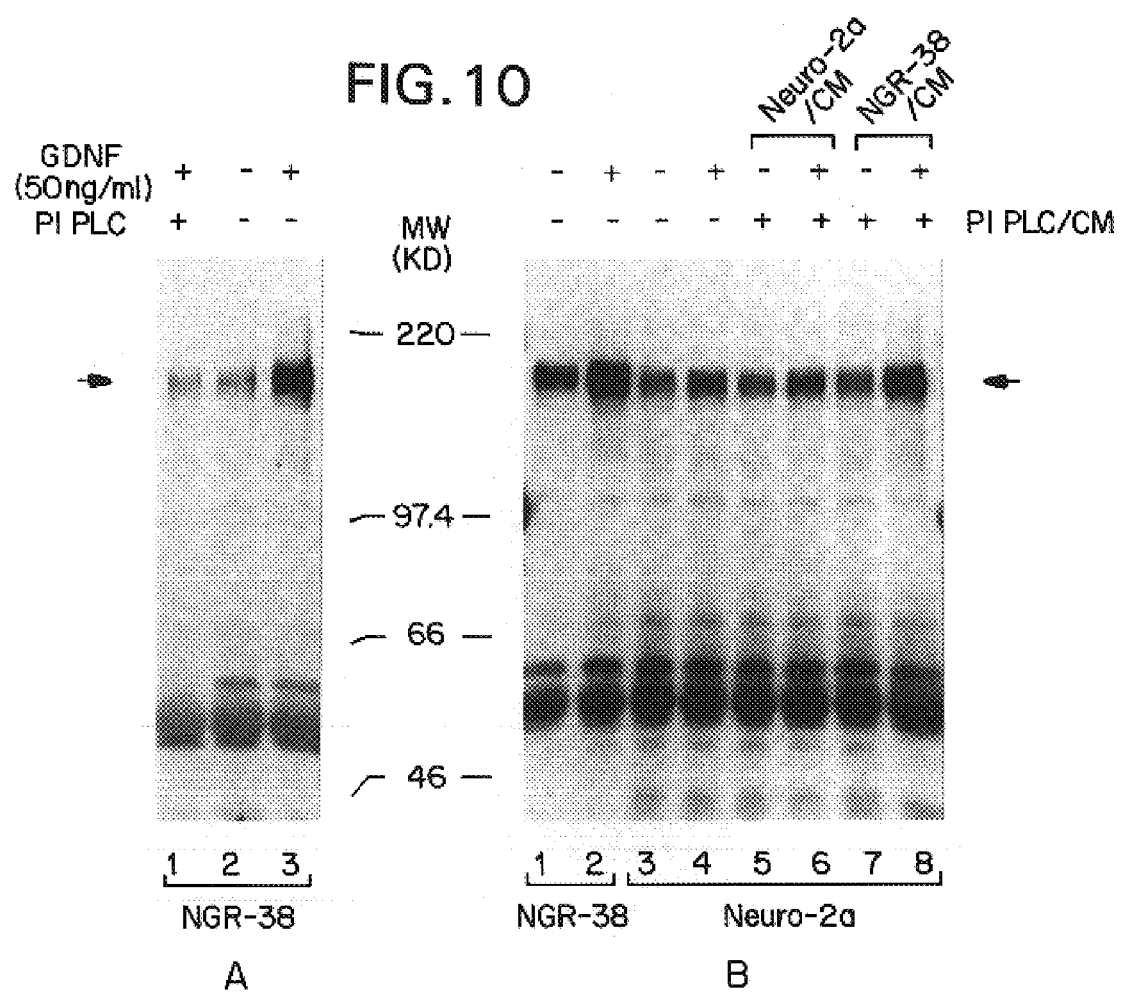

FIG. 14A

Human GRR2

```
1    CATGAAGAAACCTCAGTAAGTCTCAGACTTGGCCCAAGGAGCCCAACTAGTTACTCCCT     60
61   GGTCTGTGTTACAGAGGATCTGGCTATTACACTCAACAGCAAAAATTCAATTCCCGCT    120
121  AAAGATATAAGAATCACTAGGAAKAATAAGCCAGAGAACTCAAGACAGAAAATAGCATTAAGT  180
181  AGTTCCCTTCAGTACAGTGAGCAGAAGCTGGCCACTCTACGACTCTAWAAGACTCAGAAAA   240
241  GCTTACTAGGGACCWCTGGGCATWCCGGTGTCCTATGTGGGATTTCGTAACGTCTTTGA    300
```

FIG. 14B

```
301  GTCAGAAGCTGCCCTCAAAATAGTTTCTCAAAACGGTTTCAGGCTTTGTTAGAAAGG   360
361  GAAGACTTCACTGCCACTTTACCCAGATCATCTACCCCATCCTTGGAATGAATGGGAAG   420
421  CTTCAGCCCACCCTACCAGGCTCCCTAAAATCACCAACTTGAGAGAAAAACTATAACGTTGC   480
481  TCTACCAGTACTTCAGGAGGTTAAAGAAAGTCACAGAAGAAAAGAACTCTGGGAAAACA   540
541  GTCAAATTCGGGCTATTAAGACATTAGTTACACAGGCCCCTGTACCTCTCCTAGAAACCCT   600
601  GGGAGTACACCCGCAGAGGAGAGAGCCCAAGCCACCAAGCAAAGTCAACCAATCTGGC   660
661  AAAGGGGCGTCCCACTGCGGCTTTCAGTCCCAAGAAGTGGATCCTGCTGGTTCGCAGTCTC   720
```

FIG. 14C

```
721   TCTTCTCTATCTCCTCACTTCCTATTTACCCTTTGAAGTGGGTACTGAATAGCCCGTTCCCA   780
781   AGCAGAGGCCCTTTGTATACGGGGTGCTACAGTCGCCTGGTGGAAACACCTTGGCAGAGT     840
841   TGTTTGGTGCCAGGATGGGCCACTGAAGGCATCTGCTGTGACACACACACACACACA        900
901   CACACACACACACAGAGAGAGAGAGAAAGACACGCACGCAGAGACACAC                960
961   GGTCACTGGAATTCCATTAGAAAAAAGTGAGCCGAGCAAGGGTTAGCGGGAGAAGATTTT     1020
1021  TTTGAATCTTGTCTTCGTCTTGGTGCGAAAGAAGCGACTCCAGTCTCTCGTCCTCGAAGC    1080
1081  TCCGACTGGATTGTTCTTGGGCGCTGACACCGTCTGTGGATTTCTTTTTCTATTTGCATT    1140
```

FIG. 14D

```
1141  TTATTCCGACCCCCTCCCTGCGCTTCCTTCCAGCCCTTCACTCGCAAATCGCCTCTCT  1200
1201  CCCCACCTCCCCAGGCCCCTCCTGGGAATTGGACCCGCGGGACTCACG            1260
1261  CCTTCCCGACGATTGGAGGGGCTGACCCCAGGACTGGGCTGTGTTGGCTTAGAAAGC  1320
1321  CGATACACAGATACGCGTATATTTGATTGTAGCGGGCAAGGGGCGTCGAGAGCAGCA   1380
1381  GCCCATCGCCCCGCCCTCTCACCCCCCTCCAGCCAGAGGCGAGAATCGCAGGACTCGG  1440
1441  GATCTTCATCGGGTGGACTAGCTCCGCATTGGATTTGGGGCTGATTACCACTG       1500
```

FIG. 14E

```
1501 CTTGGCTATTATTATTGTTGTTGTACTACTATTATTTTTTTACCAAGGAGAAAGA    1560

1561 CAAAAAAACGGTGGGATTTATTAACATGATCTTGGCAAACGTCTTCTGCCTCTTCT    1620
   1                         M  I  L  A  N  V  F  C  L  F  F     12

1621 TTCTAGACGACACCCTCCGCTCTTGGCAGCCCTCCCCTGCAGGGCCCCGAGCTCC    1680
  13  F  L  D  D  T  L  R  S  L  A  S  P  S  S  L  Q  G  P  E  L  H    32

1681 ACGGCTGGCGCCCCCCAGTGGACTGTGTCCGGGCCAATGAGCTGTGTGCCGCCGAATCCA    1740
  33  G  W  R  P  P  V  D  C  V  R  A  N  E  L  C  A  A  E  S  N    52

1741 ACTGCAGCTCTCGCTACCGCAAGACTCTGCGGCAGTGCCTGGCCGGACCGCAACACCA    1800
  53  C  S  S  R  Y  R  K  T  L  R  Q  C  L  A  G  R  D  R  N  T  M    72
```

FIG. 14F

```
1801  TGCTGGCCAACAAGGAGTGCCAGGCGGCCGCCCTGGAGGTCTTGCAGGAGAGCCCGCTGTACG  1860
 73    L  A  N  K  E  C  Q  A  A  A  L  E  V  L  Q  E  S  P  L  Y  D    92

1861  ACTGCCGCTGCAAGCGGGGCATGAAGAAGAAGGAGCTGCAGTGTCTGCAGATCTACTGGAGCA  1920
 93    C  R  C  K  R  G  M  K  K  K  E  L  Q  C  L  Q  I  Y  W  S  I   112

1921  TCCACCTGGGGCTGACCGAGGGTGAGGAGTTCTACGAAGCCTCCCCCTATGAGCCGGTGA     1980
113    H  L  G  L  T  E  G  E  E  F  Y  E  A  S  P  Y  E  P  V  T   132

1981  CCTCCCCGCCTCTCGGACATCTTCAGGCTTGCTTCAATCTTCAGTGGCACAGGGCAGACC    2040
133    S  R  L  S  D  I  F  R  L  A  S  I  F  S  G  T  G  A  D  P   152

2041  CGGTGGTCAGCGCCAAGAGCAACCATTGCCTGGATGCTGCCAAGGCCTGCAACCTGAATG    2100
153    V  V  S  A  K  S  N  H  C  L  D  A  A  K  A  C  N  L  N  D   172

2101  ACAACTGCAAGAAGCTGCGCTCCTCCTACATCTCCATCTGCAACCGCGAGATCTCGCCCA    2160
173    N  C  K  K  L  R  S  S  Y  I  S  I  C  N  R  E  I  S  P  T   192
```

FIG. 14G

```
2161  CCGAGCGCTGCAACCGCCGCAAGTGCCACAAGGCCCTGCGCCAGTTCTTCGACCGGGTGC  2220
 193   E  R  C  N  R  R  K  C  H  K  A  L  R  Q  F  F  D  R  V  P   212

2221  CCAGCGAGTACACCTACCGCATGCTCTTCTGCTCTTGCCAAGACCAGGCGTGCGCTGAGC  2280
 213   S  E  Y  T  Y  R  M  L  F  C  S  C  Q  D  Q  A  C  A  E  R   232

2281  GCCGCCGGCAAACCATCCTGCCCAGCTGTTGCTCCTATGAGGACAAGGAGAAGCCCAACTGCC  2340
 233   R  R  Q  T  I  L  P  S  C  S  Y  E  D  K  E  K  P  N  C  L   252

2341  TGGACCTGCGCTGGTGTGCCGGGACTGACCACCTGTGTCGGTCCCGGCTGGCCGACTTCC  2400
 253   D  L  R  G  V  C  R  T  D  H  L  C  R  S  R  L  A  D  F  H   272

2401  ATGCCAATTGTCGAGCCTCCTACCAGACGGTTACCAGCTGCCCTGCGGACAATTACCAGG  2460
 273   A  N  C  R  A  S  Y  Q  T  V  T  S  C  P  A  D  N  Y  Q  A   292
```

FIG.14H

```
2461  CGTGTCTGGGCTCTTATGCTGGCATGATTGGTTTGACATGACACCTAACTATGTGGACT  2520
293    C  L  G  S  Y  A  G  M  I  G  F  D  M  T  P  N  Y  V  D  S   312

2521  CCAGCCCCACTGGCATCGTGGTGTCCCCTGTGTGCAGCTGTGTGGCAGCGGGAACATGG  2580
313    S  P  T  G  I  V  V  S  P  W  C  S  C  R  G  S  G  N  M  E   332

2581  AGGAGGAGTGTGAGAAGTTCCTCAGGGACTTCACCGAGAACCCATGCCTCCGGAACGCCA  2640
333    E  E  C  E  K  F  L  R  D  F  T  E  N  P  C  L  R  N  A  I   352

2641  TCCAGGCCCTTTGGCAACGGCACGAACGTGAACGTGTCCCCAAAAGGCCCCTCGTTCCAGG  2700
353    Q  A  F  G  N  G  T  N  V  N  V  S  P  K  G  P  S  F  Q  A   372

2701  CCACCCCAGGCCCCCTCGGGTGGAGAAGACGCCTTCTTTGCCAGATGACCTCAGTGACAGTA  2760
373    T  Q  A  P  R  V  E  K  T  P  S  L  P  D  D  L  S  D  S  T   392
```

FIG. 14I

```
2761  CCAGCTTGGGGACCAGTGTCATCACCACCTGCAGTCTGTCCAGGAGCAGGGGCTGAAGG   2820
393        S  L  G  T  S  V  I  T  T  C  T  S  V  Q  E  Q  G  L  K  A     412

2821  CCAACAACTCCAAAGAGTTAAGCATGTGCTTCACAGAGCTCACGACAAATATCATCCCAG   2880
413        N  N  S  K  E  L  S  M  C  F  T  E  L  T  T  N  I  I  P  G     432

2881  GGAGTAACAAGGTGATCAAACCTAACTCAGGCCCCAGCAGACCAGCCGTCGGCTGCCT     2940
433        S  N  K  V  I  K  P  N  S  G  P  S  R  A  R  P  S  A  A  L     452

2941  TGACCGTGCTGTCTGTCCTGATGCTGAAACTGGCCTTGTAGGCGTGTGGGAACCGAGTCAG   3000
453        T  V  L  S  V  L  M  L  K  L  A  L  *                          464

3001  AAGATTTTTGAAAGCTACGCAGACAAGAACAGCCGCCTGACGAAATGGAAACACACACAG   3060
```

FIG. 14J

```
3061  ACACACACACCTTGCAAAAAAATTGTTTTCCCACCTTGTCGCTGAACCTGTCTC  3120
3121  CTCCCAGGTTTCTTCTCTGGAGAAGTTTTTGTAAACCAAACAGACAAGCAGGCAGGCAGC  3180
3181  CTGAGAGCTGGCCCAGGGGTCCCCTGGCCAGGGGAAACTCTGGTGCCGGGGAGGGCACGAG  3240
3241  GCTCTAGAAATGCCCTTCACTTTCTCTCCTGGTGTTTTCTCTGACCCTTCTGAAGCAG  3300
3301  AGACCGGACAAGAGCTGCAGCGGAAGGACTCTGGGCTGTGCCTGAGGCTGGGGG  3360
3361  CAGGACAACACAGCTGCTCCCCAGGCTGCCCACTCTGGGACCCGCTGGCAG  3420
3421  AGGGCATCGGTCAGCGGGGCAGCTGGCCATGAGGGTCCACCTTCAGCCCCTTTGGC  3480
```

FIG. 14K

```
3481  TTCAAGGAGGATGGAGATGGTTTTGCCCTCTCTGCCCTCTCTGCCCCTCTCTGCCCTGGGGTGGGGCTGGTGGGTCTG   3540
3541  CAGCTGGTGTGGGAACTTCCCCACGGATGGCGGTGGAGGGGTTCGCACCGTGCTGGGCT                      3600
3601  CCCCCTGACTGTAGCACGGAGTGTTGGGGGCTGGGGCCAGCTCCAGGAGGCTTGAGAGC                     3660
3661  TCAGCCTGCCTGGGAGAGCCCTTGTGGGAGGCATTAAAAACTTGGGCACCAGCTTCTTTC                    3720
3721  TCGGTGGCAGAAATTTGAAGTCAGAGAGAAACGTCCTTTGTTGGCTTCTTTGCTTTCT                      3780
3781  CGTGGGTCCTTTGGGCAGGCCCTCCCCTTTGGGGAGAGGGAGAGACCACAGCCGGGTG                      3840
3841  TGTGTCTGCAGCACCGTGGGCCCTCAAGCTTTCCCTGCTGTCTTCCCTCCCTCCTCCTTT                    3900
```

FIG.14L

```
3901  CCCCTTTCTCTTCCTCATTTCCTAGACGTACGTCAACTGTATGTACATACCGGGGCTCC  3960
3961  TCTCCTAACATATATGTATATACACATCCATATACATATATTGTGTGGTTTCCCCTTTCT  4020
4021  TTCCTTTTTTAAGCAACAAAACTATGGAAATAATACCCCAACAGATGAGCGAAAATGTA  4080
4081  TTATTGTAAAGTTTATTTTTTTTAATACTGTGTGTCTATAATGGGGAAAAAGGACATTGGC  4140
4141  CCCGCAGTGCCCTGCCCCCAGTCAGCCTGGCTCGGTGGGGCTCCTGATCCGCAT  4200
4201  CCAAGCTTAACCAAGGCTCCAATAAACGTGCG  4232
```

FIG. 15A

Human GRR3

```
  1   CAAGTCAAAGGTTTAATCATGATCCAAGAGCCCAGAGAGACTTTAGGACAATAATAGGAA    60
 61   TAAAGCAAGGCCCACAGCTCCAGCTCCTGATGCCCAGATGTTCGGCAGGATCCGGGGAC   120
121   AGGGCAGTGCAGGCAGTAGTTTTCCATCCTCCATCCAGGGGAGGGAGCGGAGGAGCGCGG   180
181   AGCCCGGCCGCCTACAGCTCGCCATGGTGCGCCCCCTGAACCCGAGGCCGCTGCCGCCGT   240
  1                                    M  V  R  P  L  N  P  R  P  L  P  P  V    13
241   AGTCCTGATGTTGCTGCTGCTCCTGCCGCCGTCGCCGCTCCTGCCTCTGCAGCCGGAGACCC   300
 14    V  L  M  L  L  L  L  L  P  P  S  P  L  P  L  A  A  G  D  P    33
```

FIG. 15B

```
301  CCTTCCCACAGAAAGCCGACTCATGAACAGCTGTCTCCAGGCCAGGAGGAAGTGCCAGGC   360
 34   L  P  T  E  S  R  L  M  N  S  C  L  Q  A  R  R  K  C  Q  A    53

361  TGATCCCACCTGCAGTGCTGCCTACCACCACCTGGATTCCTGCACTCTAGCATAAGCAC   420
 54   D  P  T  C  S  A  A  Y  H  H  L  D  S  C  T  S  S  I  S  T    73

421  CCCACTGCCCTCAGAGGAGCCTTCGGTCCCGGTGCCTGACTGCCTGGAGGCAGCACAGCAACT   480
 74   P  L  P  S  E  E  P  S  V  P  A  D  C  L  E  A  A  Q  Q  L    93

481  CAGGAACAGCTCTCTGATAGGCTGCATGTGCCACCGGCGCATGAAGAACCAGGTTGCCTG   540
 94   R  N  S  S  L  I  G  C  M  C  H  R  R  M  K  N  Q  V  A  C   113

541  CTTGGACATCTATTGGACCGTTCACCGTGCCCGCAGCCTTGGTAACTATGAGCTGGATGT   600
114   L  D  I  Y  W  T  V  H  R  A  R  S  L  G  N  Y  E  L  D  V   133
```

FIG.15C

```
601  CTCCCCCTATGAAGACACAGTGACCAGCAAACCCTGGAAAATGAATCTCAGCAAACTGAA  660
134   S  P  Y  E  D  T  V  T  S  K  P  W  K  M  N  L  S  K  L  N   153

661  CATGCTCAAACCAGACTCAGACCTCTGCCTCAAGTTTGCCATGCTGTGTACTCTCAATGA  720
154   M  L  K  P  D  S  D  L  C  L  K  F  A  M  L  C  T  L  N  D   173

721  CAAGTGTGACCGGCTGCGCAAGGCCTACGGGGAGGCGTGCTCCGGCCCCACTGCCAGCG   780
174   K  C  D  R  L  R  K  A  Y  G  E  A  C  S  G  P  H  C  Q  R   193

781  CCACGTCTGCCTGCGCCAGCTGCTCACTTTCTTCGAGAAGGCCGAGCCCCACGCGCA    840
194   H  V  C  L  R  Q  L  L  T  F  F  E  K  A  A  E  P  H  A  Q   213

841  GGGCCTGCTACTGTGCCCCATGCGCCCCAACGACCGGGGCTGCGGGGAGCGCCGGCGCAA  900
214   G  L  L  L  C  P  C  A  P  N  D  R  G  C  G  E  R  R  R  N   233
```

FIG. 15D

```
901  CACCATGCCCCCCAACTGCGCGCCTGTGGCCCTGTGGGCGCCTGGAGCTGCGGCG   960
234   T  I  A  P  N  C  A  L  P  P  V  A  P  N  C  L  E  L  R  R   253

961  CCTCTGCTTCTCCGACCCGCTTTGCAGATCACGCGCCTGGTGGATTTCCAGACCCACTGCCA   1020
254   L  C  F  S  D  P  L  C  R  S  R  L  V  D  F  Q  T  H  C  H   273

1021 TCCCATGGACATCCTAGGAACTGTGCAACAGAGCAGTCCAGATGTCTACGAGCATACCT   1080
274   P  M  D  I  L  G  T  C  A  T  E  Q  S  R  C  L  R  A  Y  L   293

1081 GGGGCTGATTGGGACTGCCATGACCCCCAACTTTGCCAGCAATGTCAACACCAGTGTTGC   1140
294   G  L  I  G  T  A  M  T  P  N  F  A  S  N  V  N  T  S  V  A   313

1141 CTTAAGCTGCACCTGCCGAGGCAGTGGCAACCTGCAGGAGGAGTGTGAAATGCTGGAAGG   1200
314   L  S  C  T  C  R  G  S  G  N  L  Q  E  E  C  E  M  L  E  G   333
```

FIG.15E

```
1201  GTTCTTCTCCCACAACCCCTGCCTCACGGAGGCCATTGCAGCTAAGATGCGTTTTCACAG    1260
 334   F  F  S  H  N  P  C  L  T  E  A  I  A  A  K  M  R  F  H  S      353

1261  CCAACTCTCTCCCAGGACTGGCCACACCCTACCTTTGCTGTGATGGCACACCAGAATGA     1320
 354   Q  L  F  S  Q  D  W  P  H  P  T  F  A  V  M  A  H  Q  N  E      373

1321  AAACCCTGCTGTGAGGCCACAGCCCTGGGTGCCCTCTCTTTTCTCCTGCACGCTTCCCTT   1380
 374   N  P  A  V  R  P  Q  P  W  V  P  S  L  F  S  C  T  L  P  L      393

1381  GATTCTGCTCCTGAGCCTATGGTAGCTGGACTTCCCCAGGGCCCTCTTCCCCTCCACCAC   1440
 394   I  L  L  L  S  L  W  *                                           400

1441  ACCCAGGTGGACTTGCAGCCCCACAAGGGGGTGAGGAGAAAGGACAGCAGCAGGAAGGAGGTGC  1500
```

FIG. 15F

```
1501  AGTGCGCAGATGAGGGCACAGGAGAAGCTAAGGGTTATGACCTCCAGATCCTTACTGGTC   1560
1561  CAGTCCTCCATTCCCTCCACCCCATCTCCACTTCTGATTCATGCTGCCCCTCCTTGGTGGC   1620
1621  CACAATTTAGCCATGTCATCTGGTGGTGACCAGCTCCACCAAGCCCCTTTGTGAGCCCTT   1680
1681  CCTCTTGACTACCAGGATCACCAGAATCTAATAAGTTAGCCTTTCTCTATTGCATTCCAG   1740
1741  ATTAGGGTTAGGGTAGGGAGGACTGGGTGTTCTGAGGCAGCCTAGAAAGTCATTCTCCTT   1800
1801  TGTGAAGAAGGCTCCTGCCCCTCCTCCTCCTCTGAGTGGAGGATGGAAAACTACTGC   1860
1861  CTGCACTGCCCGTCCCCGGATCCTGCCGAACATCTGGGCATCAGGAGCTGGAGCCTGTG   1920
```

FIG.15G

```
1921 GGCCTTGCTTTATTCCTATTATTGTCCTAAAGTCTCTCTGGGCTCTCTTGGATCATGATTAA    1980
1981 ACCTTTGACTG  1991
```

FIG.16A
Rat GRF2

```
1    GCGGCCGGCGTCGACCCTGACCATGCAGACACTTTTCAGGCCTCTGTCTGGTGTGAAGTT    60
61   GGCAGATACAAGCAAGGCCCGAAAGGGGGTCTCAGCTCTTCTCTCCTGGGCCCTCCTGACT  120
121  GAGTTAGGCTTGCTTCTGGTTGTCTTCTAAAGGCACGGTGATACAGAATGATGAGACTAG  180
181  GCTGGAGGGGCTTTCTCTGCTTCTCCTGTGTGTGACCTTGAGTTATCTCCCTTCGTTGGATC  240
241  CGAGCTTTCCTGGAATATGAATGTTGAATATGAGTTCTGCCTAAGGTCCAGACAG       300
```

FIG. 16B

```
301  GCTCTGAGGGTTAACTGACTTTTGGAGCCTTCAAATCAATACCTTGGATGGAGTGGGGGT    360
361  TTGTCCAATGGGAGTTGAGGCAAGATCCCTTTGCATAAGCCTTGCCACATCATGTTGAAG    420
421  CCATGCCATTCTGTCTGGACTATTGGCATCTTACCTTTCCAGCAGTTTCAGTGAAGGCCT    480
481  TCCTGGATTTATCATTCTGTGTTCCACTGCCTAGGATTGTGCTCAAGAGGAAATGAATGT    540
541  GAACCATGGTTGTAGGGGAGTATGGCCAACCAGGTTGGGTGTGTTGACCTTGGTCTTG      600
  1   M  V  V  G  E  Y  G  Q  P  G  W  V  C  V  D  L  G  L  G        19
601  GTGTTCTTTTGTGTAAAGTGGGTGAGAAGTTCCTTCAAACCTTAGGCCTACATTGGGGTC    660
 20  V  L  C  K  V  G  E  K  F  L  Q  T  L  G  L  H  W  G  Q        39
```

FIG. 16C

```
661  AGAGACTGTGGTGGCCCTCATTCATGCTTGTCCTTCCCACTACCCAGACGAAACCC    720
40    R  L  W  W  P  S  F  M  L  V  F  P  S  H  Y  P  D  E  T  L     59

721  TCCGCTCTCTTTGGCCAGCCCCTTCCCCTGCAGGGCTCTGAGCTCCACGGCTGGCGCCCC    780
60    R  S  L  A  S  P  S  S  L  Q  G  S  E  L  H  G  W  R  P  Q     79

781  AAGTGGACTGTGTCCCGGGCCAATGAGCTGTGTGCGGCTGAATCCAACTGCAGCTCCAGGT    840
80    V  D  C  V  R  A  N  E  L  C  A  A  E  S  N  C  S  S  R  Y     99

841  ACCGCACCCTTCGGCAGTGCCTGGCAGGCCGGGATCGCAATACCATGCTGGCCAATAAGG    900
100   R  T  L  R  Q  C  L  A  G  R  D  R  N  T  M  L  A  N  K  E    119

901  AGTGCCAGGCAGCCCTGGAGGTCTTGCAGGAAAGCCCACTGTATGACTGCCGCTGCAAGC    960
120   C  Q  A  A  L  E  V  L  Q  E  S  P  L  Y  D  C  R  C  K  R    139
```

FIG. 16D

```
 961 GGGGCATGAAGAAGGAGCTGCAGTGTCTGCAGATCTACTGGAGCATCCATCTGGGGCTGA 1020
 140  G  M  K  K  E  L  Q  C  L  Q  I  Y  W  S  I  H  L  G  L  T  159
1021 CAGAGGGTGAGGAGTTCTATGAAGCTTCCCCTATGAGCCTGTGACCTCGCCTCTCGG     1080
 160  E  G  E  E  F  Y  E  A  S  P  Y  E  P  V  T  S  R  L  S  D  179
1081 ACATCTTCAGGCTCGCTTCAATCTTCTCAGGGACACAGGGACAGACCCGGGTCAGTACCA 1140
 180  I  F  R  L  A  S  I  F  S  G  T  D  P  A  V  S  T  K  199
1141 AAAGCAACCACTGCCTGGATGCCGCCAAGGCCTGCAACCTGAATGACAACTGCAAGAAGC 1200
 200  S  N  H  C  L  D  A  A  K  A  C  N  L  N  D  N  C  K  K  L  219
1201 TTCGCTCCTCTTATATCTCCATCTGCAACCGTGAGATCTCTCCCACCGAACGCTGCAACC 1260
 220  R  S  S  Y  I  S  I  C  N  R  E  I  S  P  T  E  R  C  N  R  239
```

FIG.16E

```
1261 GCCGCAAGTGCCACAAGGCTCTGCGCCAGTTCTTTGACCGTGTGCCCAGCGAGTATACCT   1320
 240   R   K   C   H   K   A   L   R   Q   F   F   D   R   V   P   S   E   Y   T   Y    259

1321 ACCGGATGCTCTTCTGCTCTTGTCAGGACCAGGCATGTGCTGAGCGTGCCGCAAACCA     1380
 260   R   M   L   F   C   S   C   Q   D   Q   A   C   A   E   R   R   R   Q   T   I    279

1381 TCCTGCCCCAGTTGCTCCTATGAGGACAAGGAGAAGCCCAACTGCCTGGACCTGCGCAGCC  1440
 280   L   P   S   C   S   Y   E   D   K   E   K   P   N   C   L   D   L   R   S   L    299

1441 TGTGTGTACAGAACCACCTGCCCCGGTCCCGACTGGCCAGATTTCCACGCCAACTGTCGAG  1500
 300   C   R   T   D   H   L   C   R   S   R   L   A   D   F   H   A   N   C   R   A    319

1501 CCTCCTACCGGACAATCACCAGCTGTCCTGCGGACAACTACCAGGCATGTCTGGGCTCCT   1560
 320   S   Y   R   T   I   T   S   C   P   A   D   N   Y   Q   A   C   L   G   S   Y    339
```

FIG. 16F

```
1561  ATGCTGGCATGATTGGGTTTGATATGACACCCAACTATGTGGACTCCAACCCCACGGGCA  1620
 340   A  G  M  I  G  F  D  M  T  P  N  Y  V  D  S  N  P  T  G  I   359

1621  TCGTGGTGTCTCCCTGGTGTGCAATTGTCGTGGCAGTGGGAACATGGAAGAAGAGTGTGAGA  1680
 360   V  V  S  P  W  C  N  C  R  G  S  G  N  M  E  E  E  C  E  K   379

1681  AGTTCCTCAGGGACTTCACGGAAAACCCATGCCTCCGGAATGCCATTCAGGCCTTTGGTA  1740
 380   F  L  R  D  F  T  E  N  P  C  L  R  N  A  I  Q  A  F  G  N   399

1741  ATGGCACAGATGTGAACATGTCTCCCAAAGGCCCCTCACTCCCAGCTACCCAGGCCCCTC  1800
 400   G  T  D  V  N  M  S  P  K  G  P  S  L  P  A  T  Q  A  P  R   419

1801  GGGTGGAGAAGACTCCCTTCACTGCCAGATGACCTCAGTGACAGCACCAGCCTGGGGACCA  1860
 420   V  E  K  T  P  S  L  P  D  D  D  L  S  D  S  T  S  L  G  T  S   439

1861  GTGTCATCACCACCTGCACATCTATCCAGGAGCAAGGCTGAAGGCCAACAACTCCAAAG  1920
```

FIG. 16G

```
440        V  I  T  T  C  T  S  I  Q  E  Q  G  L  K  A  N  N  S  K  E              459
1921   AGTTAAGCATGTGCTTCACAGAGCTCACGACAAACATCAGTCCAGGGAGTAAAAAGGTGA                  1980
460        L  S  M  C  F  T  E  L  T  T  N  I  S  P  G  S  K  K  V  I              479
1981   TCAAACTTAACTCAGGCTCCAGCAGAGCCAGACTGTCGGCCTTGACTGCCCTCCCAC                    2040
480        K  L  N  S  G  S  S  R  A  R  L  S  A  A  L  T  A  L  P  L              499
2041   TCCTGATGCTGACCTTGGCCTTGTAGGCCTTTGGAACCCAGCACAAAAGTTCTTCAAGCA                 2100
500        L  M  L  T  L  A  L  *                                                  506
2101   ACCCAGATATGAACTCCCGCCTGACAAAATGGAAACACGCATACACACATGCCACACA                   2160
2161   CAGACACACACAGACACACACACACACACAGACACACATACAGACGTCGACGCGGCCGC       2215
```

FIG. 17A

Rat GRR3

```
1    GCGGCCGCGTCGACCGAGCACAGGCAGAGCCCAGAGCCTGCCGGGCTCCGGGTGTCCAGA    60

61   CCCGGCCATGGGGCTCTCCCGGAGCCCGCGCCCGCCGCCTAGTGATCCTGCTACTGGTG   120
1     M  G  L  S  R  S  P  R  P  P  P  L  V  I  L  L  L  V      18

121  CTGTCGCTGTGGCTACCCCTTGGAACAGGAAACTCCCTTCCCACAGAGAACAGGCTTGTG   180
19    L  S  L  W  L  P  L  G  T  G  N  S  L  P  T  E  N  R  L  V   38

181  AACAGCTGTACCCAGGCCAGAAAAAAATGCGAGGCTAATCCCGCTTGCAAGGCTGCCTAC   240
39    N  S  C  T  Q  A  R  K  K  C  E  A  N  P  A  C  K  A  A  Y   58
```

FIG. 17B

```
241  CAGCACCTGGACTCCTGCACCCCCAGTCTCAGCAGTCCACTGCCCCTCAGGGGAGTCTGCC   300
 59   Q  H  L  D  S  C  T  P  S  L  S  S  P  L  P  S  G  E  S  A    78

301  ACATCTGCAGCGGTGCCTTGAAGCAGCACAGCAACTCAGGAACAGCTCTCATAGACTGC    360
 79   T  S  A  A  C  L  E  A  A  Q  Q  L  R  N  S  S  L  I  D  C    98

361  AGGTGCCACGGGCGCATGAAGCACCAAGCACCAAGCTACCTGTCTGGACATTTATTGGACCGTTCAC  420
 99   R  C  H  R  R  M  K  H  Q  A  T  C  L  D  I  Y  W  T  V  H   118

421  CCTGTCCGAAGCCTTGGTGACTACGAGTTGGACGTCTCACCCTATGAAGACACAGTGACC   480
119   P  V  R  S  L  G  D  Y  E  L  D  V  S  P  Y  E  D  T  V  T   138

481  AGCAAACCCTGGAAAATGAATCTCAGCAAGCTGAGCATGCTCAAACCAGACTCCGACCTC   540
139   S  K  P  W  K  M  N  L  S  K  L  S  M  L  K  P  D  S  D  L   158
```

FIG. 17C

```
541  TGCCTCAAATTGCTATGCTGTGTACTCTTAACGACAAGTGCGACCGCCTCCGAAAGGCC  600
159   C   L   K   F   A   M   L   C   T   L   N   D   K   C   D   R   L   R   K   A    178

601  TACGGGGAGGCGTGCTCAGGGATCCGCTGCCAGCTCTGCCTAGCTCAGCTGCGC        660
179   Y   G   E   A   C   S   G   I   R   C   Q   R   H   L   C   L   A   Q   L   R    198

661  TCCTTCTTCGAGAAGGCGGCAGAGTCCCACGCTCAGGGCCTCCTGTGTCCCTGTGCA    720
199   S   F   F   E   K   A   A   E   S   H   A   Q   G   L   L   L   C   P   C   A    218

721  CCCGAAGATGCGGGCTGTGGGAGCGGCAACACCATCGCCCCCAGTTGCGCCCTC       780
219   P   E   D   A   G   C   G   E   R   R   R   N   T   I   A   P   S   C   A   L    238

781  CCGTCTGTGGCCCCAACTGCCTAGATCTTCGGAGCTTCTGCCGTGCGGGACCCTCTGTGC 840
239   P   S   V   A   P   N   C   L   D   L   R   S   F   C   R   A   D   P   L   C    258
```

FIG. 17D

```
841   AGATCACGCCTGATGGACTTCCAGACTTCCACCTGCCACCCTATGGACATCCTCGGACTTGT   900
259   R  S  R  L  M  D  F  Q  T  H  C  H  P  M  D  I  L  G  T  C     278

901   GCAACTGAGCAGTCCAGATGTCTGCGGGCATACCTGGGCTAATTGGGACTGCCATGACC      960
279   A  T  E  Q  S  R  C  L  R  A  Y  L  G  L  I  G  T  A  M  T     298

961   CCAAACTTCATCAGCAAGGTCAACACTACTGTTGCCTTAGGCTGTACCTGCCAGGCAGT     1020
299   P  N  F  I  S  K  V  N  T  T  V  A  L  G  C  T  C  R  G  S     318

1021  GGCAACCTGCAGGACGAGTGTGAACAGCTGGAAAAGTCCTTCTCCCAGAACCCCTGCCTC    1080
319   G  N  L  Q  D  E  C  E  Q  L  E  K  S  F  S  Q  N  P  C  L     338

1081  ATGGAGGCCATTGCGGCTAAAATGCGTTTCCACAGACAACTCTTCTCCCAGGACTGGGCG    1140
339   M  E  A  I  A  A  K  M  R  F  H  R  Q  L  F  S  Q  D  W  A     358
```

FIG. 17E

```
1141  GACTCTACTTTTCTGTGATGCAGCAGAACAGCAGCCCTGCTCTGAGGCCCAGCTC  1200
359    D  S  T  F  S  V  M  Q  Q  Q  N  S  S  P  A  L  R  P  Q  L   378

1201  AGGCTACCCGTTCTGTCTTTCTTCATCCTTACCTTGATTCTGCTGCAGACCCTCTGGTAA  1260
379    R  L  P  V  L  S  F  F  I  L  T  L  I  L  L  Q  T  L  W  *   397

1261  CTGGGCTCCCTCAGGGTCCTTGTCCTCTCCACCACACCCAGACCGACTTGCAGCCTGTG  1320

1321  ATGGGAGAGAAAATGCTGGCCCTCTGGAAGAAGATGCAACCAGGCTCACTGCACATCCTGT  1380

1381  CTGCTCCAGATGAGGTCTTGGAAGAAGCGAGGGCTGTGACCGTTCAGAATCCTGAGCGGC  1440

1441  CAGCTTTCAAACCCTCTCCTACTACTCCCTGCTCCTCCCTAGGACCTTGTAC  1500
```

FIG. 17F

```
1501 TCCAGTTTGGCTGTATATTGTGGTGGTGATTAGCTTCCCACCTCCAGCCCTTCTTCCTGT 1560
1561 TTCCCAGGACCACCCAGGGCTAATGACTCACTCATTCCTGGTTGCCTTCTCCAGGAAGGC 1620
1621 AGGCTGAGGGTTCTGAGGCAGCTGAGAAAGATGGTCCCTTTGTGAGGAAGGCTGGTGGTC 1680
1681 CAACCGTCGACGCGGCCGC 1699
```

FIG. 18A

Alignment of the Amino Acid Sequeces of GDNFRs

```
                                                              50
Mgdnfr  ----------  ----------  -----MFLATL YFVLPLLDLL MSAEVSG.GD RLDCVKASDQ
Rgdnfr  ----------  ----------  -----MFLATL YFALPLLDLL MSAEVSG.GD RLDCVKASDQ
Hgdnfr  ----------  ----------  -----MFLATL YFALPLLDLL LSAEVSG.GD RLDCVKASDQ
Hgrr2   ----------  -----MILANV FCLFFFLDDT LRSLASPSSL QGPELHGWRP PVDCVRANEL
Rgrr2   ----------  --------ML  VFPSHYPDET LRSLASPSSL QGSELHGWRP QVDCVRANEL
Hgrr3   MVRPLNPRPL  PPVVLMLLLL  LPPSPLPLAA GDPLPTESRL MNSCLQARRK
Rgrr3   MGLSRSPRPP  PLVILLIVLS  L...WLPLGT GNSLPTENRL VNSCTQARKK
1
```

FIG. 18B

```
        51                                                            100
Mgdnfr  CLKEQSCSTK YRTLRQCVAG KETNFSLTSG LEAKDECRSA MEALKQKSLY
Rgdnfr  CLKEQSCSTK YRTLRQCVAG KETNFSLTSG LEAKDECRSA MEALKQKSLY
Hgdnfr  CLKEQSCSTK YRTLRQCVAG KETNFSLASG LEAKDECRSA MEALKQKSLY
Hgrr2   CAAESNCSSR YRTLRQCLAG RDRNTML... ..ANKECQAA LEVLQESPLY
Rgrr2   CAAESNCSSR YRTLRQCLAG RDRNTML... ..ANKECQAA LEVLQESPLY
Hgrr3   CQADPTCSAA YHHLDSCTSS ISTPLP.SEE PSVPADCLEA AQQLRNSSLI
Rgrr3   CEANPACKAA YQHLDSCTPS LSSPLP.SGE SATSAACLEA AQQLRNSSLI
```

FIG.18C

```
        101                                                      150
Mgdnfr  NCRCKRGMKK  EKNCLRIYWS  MYQSL.QGND  LLEDSPYEPV  NSRLSDIFRA
Rgdnfr  NCRCKRGMKK  EKNCLRIYWS  MYQSL.QGND  LLEDSPYEPV  NSRLSDIFRA
Hgdnfr  NCRCKRGMKK  EKNCLRIYWS  MYQSL.QGND  LLEDSPYEPV  NSRLSDIFRV
Hgrr2   DCRCKRGMKK  ELQCLQIYWS  IHLGLTEGEE  FYEASPYEPV  TSRLSDIFRL
Rgrr2   DCRCKRGMKK  ELQCLQIYWS  IHLGLTEGEE  FYEASPYEPV  TSRLSDIFRL
Hgrr3   GCMCHRRMKN  QVACLDIYWT  VHRARSLGNY  ELDVSPYE..  ......DTVTS
Rgrr3   DCRCHRRMKH  QATCLDIYWT  VHPVRSLGDY  ELDVSPYE..  ......DTVTS
```

FIG.18D

```
       151                                                   200
Mgdnfr VPFISDVFQQ VEHISKGNNC LDAAKACNLD DTCKKYRSAY ITPCTTSMS.
Rgdnfr VPFISDVFQQ VEHISKGNNC LDAAKACNLD DTCKKYRSAY ITPCTTSMS.
Hgdnfr VPFISDVFQQ VEHIPKGNNC LDAAKACNLD DICKKYRSAY ITPCTTSVS.
Hgrr2  ASIFSGTGAD PVVSAKSNHC LDAAKACNLN DNCKKLRSSY ISICNREISP
Rgrr2  ASIFSGTGTD PAVSTKSNHC LDAAKACNLN DNCKKLRSSY ISICNREISP
Hgrr3  KPWKMNLSKL NMLKPDSDLC LKFAMLCTLN DKCDRLRKAY GEACS.....
```

FIG. 18E

```
Rgrr3   KPWKMNLSKL SMLKPDSDLC LKFAMLCTLN DKCDRLRKAY GEACS.....
        201                                                  250
Mgdnfr  NEVCNRRKCH KALRQFFDKV PAKHSYGMLF CSC..RDVAC TERRRQTIVP
Rgdnfr  NEVCNRRKCH KALRQFFDKV PAKHSYGMLF CSC..RDIAC TERRRQTIVP
Hgdnfr  NDVCNRRKCH KALRQFFDKV PAKHSYGMLF CSC..RDIAC TERRRQTIVP
Hgrr2   TERCNRRKCH KALRQFFDRV PSEYTYRMLF CSC..QDQAC AERRRQTILP
Rgrr2   TERCNRRKCH KALRQFFDRV PSEYTYRMLF CSC..QDQAC AERRRQTILP
Hgrr3   GPHCQRHVCL RQLLTFFEKA AEPHAQGLLL CPCAPNDRGC GERRRNTIAP
Rgrr3   GIRCQRHLCL AQLRSFFEKA AESHAQGLLL CPCAPEDAGC GERRRNTIAP
```

FIG.18F

```
        251                                              300
Mgdnfr  VCSYEERERP  NCLNLQDSCK  TNYICRSRLA  DFFTNCQPES  RSVSNCLKEN
Rgdnfr  VCSYEERERP  NCLSLQDSCK  TNYICRSRLA  DFFTNCQPES  RSVSNCLKEN
Hgdnfr  VCSYEEREKP  NCLNLQDSCK  TNYICRSRLA  DFFTNCQPES  RSVSSCLKEN
Hgrr2   SCSYEDKEKP  NCLDLRGVCR  TDHLCRSRLA  DFHANCRASY  QTVTSCPADN
Rgrr2   SCSYEDKEKP  NCLDLRSLCR  TDHLCRSRLA  DFHANCRASY  RTITSCPADN
Hgrr3   NCALPP.VAP  NCLELRRLCF  SDPLCRSRLV  DFQTHCHP..  MDILGTCATE
Rgrr3   SCALPS.VAP  NCLDLRSFCR  ADPLCRSRLM  DFQTHCHP..  MDILGTCATE
```

FIG. 18G

```
       301                                                         350
Mgdnfr YADCLLAYSG LIGTVMTPNY VDSS..SLSV APWCDCSNSG NDLEDCLKFL
Rgdnfr YADCLLAYSG LIGTVMTPNY VDSS..SLSV APWCDCSNSG NDLEDCLKFL
Hgdnfr YADCLLAYSG LIGTVMTPNY IDSS..SLSV APWCDCSNSG NDLEECLKFL
Hgrr2  YQACLGSYAG MIGFDMTPNY VDSSPTGIVV SPWCSCRGSG NMEEECEKFL
Rgrr2  YQACLGSYAG MIGFDMTPNY VDSNPTGIVV SPWCNCRGSG NMEEECEKFL
Hgrr3  QSRCLRAYLG LIGTAMTPNF ASNVNTSVAL S..CTCRGSG NLQEECEMLE
Rgrr3  QSRCLRAYLG LIGTAMTPNF ISKVNTTVAL G..CTCRGSG NLQDECEQLE
```

FIG. 18H

```
        351                                                                400
Mgdnfr  NFFKDNTCLK  NAIQAFGNGS  DVTMWQPAP.  PVQTTTATTT  TAFRIKNKPS
Rgdnfr  NFFKDNTCLK  NAIQAFGNGS  DVTMWQPAP.  PVQTTTATTT  TAFRVKNKPL
Hgdnfr  NFFKDNTCLK  NAIQAFGNGS  DVTVWQPAF.  PVQTTTATTT  TALRVKNKPL
Hgrr2   RDFTENPCLR  NAIQAFGNGT  NVNVSPKGP.  SFQATQAPRV  EKTPSLPDDL
Rgrr2   RDFTENPCLR  NAIQAFGNGT  DVNMSPKGP.  SLPATQAPRV  EKTPSLPDDL
Hgrr3   GFFSHNPCLT  EAIAAKMRFH  SQLFSQDWPH  PTFAVMAHQN  ENPAVRPQPW
Rgrr3   KSFSQNPCLM  EAIAAKMRFH  RQLFSQDWAD  STFSVMQQN   SSPALRPQLR
```

FIG. 18I

```
       401                                                        450
Mgdnfr GPACSENEIP THVLPPCANL QAQKLKSNVS GSTHLCLSDN DYGKDGLAGA
Rgdnfr GPAGSENEIP THVLPPCANL QAQKLKSNVS GSTHLCLSDS DFGKDGLAGA
Hgdnfr GPAGSENEIP THVLPPCANL QAQKLKSNVS GNTHLCISNG NYEKEGL.GA
Hgrr2  SDSTS...LG TSVITTCTSV QEQGLKANNS KELSMCFTEL TTNIIPGSNK
Rgrr2  SDSTS...LG TSVITTCTSI QEQGLKANNS KELSMCFTEL TTNISPGSKK
Hgrr3  VPSLFSCTLP LILLLSLW~~ ~~~~~~~~~~ ~~~~~~~~~~ ~~~~~~~~~~
Rgrr3  LPVLSFFILT LILLQTLW*~ ~~~~~~~~~~ ~~~~~~~~~~ ~~~~~~~~~~
```

FIG. 18J

```
       451                                           490
Mgdnfr SSHITTKSMA APPSCGLSSL PVMVFTALAA LLSVSLAETS
Rgdnfr SSHITTKSMA APPSCSLSSL PVLMLTALAA LLSVSLAETS
Hgdnfr SSHITTKSMA APPSCGLSPL LVLVVTALST LLSLTETS--
Hgrr2  VIKPNSGPSR ARPSAALTVL SVLMLKLAL* ----------
Rgrr2  VIKLNSGSSR ARLSAALTAL PLLMLTLAL* ----------
Hgrr3  ---------- ---------- ---------- ----------
Rgrr3  ---------- ---------- ---------- ----------
```

FIG. 19A

GDNFR Family of Receptors

```
              1                                                    50
Consensus   MV..l...p .pp...m.l llslalPl.. .lqgael.g. .Rl..dCv.A.
Hgdnfr                  MFLAT LYFALPLLDL LLSAEVSGGD RL..DCVKAS
Rgdnfr                  MFLAT LYFALPLLDL LMSAEVSGGD RL..DCVKAS
Hgrr2       MILANVF CLFFFLDDTL RSLASPSS.. LQGPELHGW. RPPVDCVRAN
Rgrr2           MLV FPSHYPDETL RSLASPSS.. LQGSELHGW. RPQVDCVRAN
Hgrr3       MVRPLNPRPL PPVVLMLLLL LPPS.PLP.L AAGDPLPTES RLMNSCLQAR
Rgrr3       MGLSRSPR PPPLVILLLV LSLWLPLG.. .TGNSLPTEN RLVNSCTQAR
```

FIG. 19B

```
             51                                                          100
Consensus    ..C.ae..Cs  ..YrtLrgC.  ag...nt.La  sg.E......  C..A.e.L..

Hgdnfr       DQCLKEQSCS  TKYRTLRQCV  AGKETNFSLA  SGLEAKDE..  CRSAMEALKQ
Rgdnfr       DQCLKEQSCS  TKYRTLRQCV  AGKETNFSLT  SGLEAKDE..  CRSAMEALKQ
Hgrr2        ELCAAESNCS  SRYRTLRQCL  AGRDRNTMLA  NK.E......  CQAALEVLQE
Rgrr2        ELCAAESNCS  SRYRTLRQCL  AGRDRNTMLA  NK.E......  CQAALEVLQE
Hgrr3        RKCQADPTCS  AAYHHLDSCT  ..SSISTPLP  SE.EPSVPAD  CLEAAQQLRN
Rgrr3        KKCEANPACK  AAYQHLDSCT  ..PSLSSPLP  SG.ESATSAA  CLEAAQQLRN
```

FIG. 19C

```
              101                                                      150
Consensus     ssLydCrCkR  gMKke..CL.  IYWs.h..l.  .Gn..le.SP  YEp.VtSrls
Hgdnfr        KSLYNCRCKR  GMKKEKNCLR  IYWSMYQSLQ  .GNDLLEDSP  YEP.VNSRLS
Rgdnfr        KSLYNCRCKR  GMKKEKNCLR  IYWSMYQSLQ  .GNDLLEDSP  YEP.VNSRLS
Hgrr2         SPLYDCRCKR  GMKKELQCLQ  IYWSIHLGLT  EGEEFYEASP  YEP.VTSRLS
Rgrr2         SPLYDCRCKR  GMKKELQCLQ  IYWSIHLGLT  EGEEFYEASP  YEP.VTSRLS
Hgrr3         SSLIGCMCHR  RMKNQVACLD  IYWTVHRARS  LGNYELDVSP  YEDTVTSKPW
Rgrr3         SSLIDCRCHR  RMKHQATCLD  IYWTVHPVRS  LGDYELDVSP  YEDTVTSKPW
```

FIG.19D

```
           151                                                            200
Consensus  difr..s..s  ....d......  ksn.CLdaAk  aCnLnD.Ckk  lRsaYi..C.

Hgdnfr     DIFRVVPFIS  DVFQQVEHIP   KGNNCLDAAK  ACNLDDICKK  YRSAYITPCT
Rgdnfr     DIFRAVPFIS  DVFQQVEHIS   KGNNCLDAAK  ACNLDDTCKK  YRSAYITPCT
Hgrr2      DIFRLASIFS  GTGADPVVSA   KSNHCLDAAK  ACNLNDNCKK  LRSSYISICN
Rgrr2      DIFRLASIFS  GTGTDPAVST   KSNHCLDAAK  ACNLNDNCKK  LRSSYISICN
Hgrr3      KMNL..SKLN  MLKPD......  .SDLCLKFAM  LCTLNDKCDR  LRKAYGEAC.
Rgrr3      KMNL..SKLS  MLKPD......  .SDLCLKFAM  LCTLNDKCDR  LRKAYGEAC.
```

FIG. 19E

```
          201                                                          250
Consensus ...S..erCn RrkChkaLrq FFdkvp..h. ygmLfCsC.. .D.aC.ERRR
Hgdnfr    TSVS.NDVCN RRKCHKALRQ FFDKVPAKHS YGMLFCSC.. RDIACTERRR
Rgdnfr    TSMS.NEVCN RRKCHKALRQ FFDKVPAKHS YGMLFCSC.. RDIACTERRR
Hgrr2     REISPTERCN RRKCHKALRQ FFDRVPSEYT YRMLFCSC.. QDQACAERRR
Rgrr2     REISPTERCN RRKCHKALRQ FFDRVPSEYT YRMLFCSC.. QDQACAERRR
Hgrr3     ...SG.PHCQ RHVCLRQLLT FFEKAAEPHA QGLLLCPCAP NDRGGERRR
Rgrr3     ...SG.IRCQ RHLCLAQLRS FFEKAAESHA QGLLLCPCAP EDAGGGERRR
```

FIG. 19F

```
           251                                                    300
Consensus  qTI.PsCsye  ..ekPNCLdL  r..Crtd.lC  RSRLaDF.tn  C...r.v.s
Hgdnfr     QTIVPVCSYE  EREKPNCLNL  QDSCKTNYIC  RSRLADFFTN  CQPESRSVSS
Rgdnfr     QTIVPVCSYE  ERERPNCLSL  QDSCKTNYIC  RSRLADFFTN  CQPESRSVSN
Hgrr2      QTILPSCSYE  DKEKPNCLDL  RGVCRTDHLC  RSRLADFHAN  CRASYQTVTS
Rgrr2      QTILPSCSYE  DKEKPNCLDL  RSLCRTDHLC  RSRLADFHAN  CRASYRTITS
Hgrr3      NTIAPNC.AL  PPVAPNCLEL  RRLCFSDPLC  RSRLVDFQTH  C.HPMDILGT
Rgrr3      NTIAPSC.AL  PSVAPNCLDL  RSFCRADPLC  RSRLMDFQTH  C.HPMDILGT
```

FIG. 19G

```
           301                                                              350
Consensus  C.a.ny..CL  .aY.GlIGt.  MTPNyvdss.  t...VapwC.  CrgSGN..ee
Hgdnfr     CLKENYADCL  LAYSGLIGTV  MTPNYIDSSS  ..LSVAPWCD  CSNSGNDLEE
Rgdnfr     CLKENYADCL  LAYSGLIGTV  MTPNYVDSSS  ..LSVAPWCD  CSNSGNDLED
Hgrr2      CPADNYQACL  GSYAGMIGFD  MTPNYVDSSP  TGIVVSPWCS  CRGSGNMEEE
Rgrr2      CPADNYQACL  GSYAGMIGFD  MTPNYVDSNP  TGIVVSPWCN  CRGSGNMEEE
Hgrr3      C.ATEQSRCL  RAYLGLIGTA  MTPNFASNVN  TS..VALSCT  CRGSGNLQEE
Rgrr3      C.ATEQSRCL  RAYLGLIGTA  MTPNFISKVN  TT..VALGCT  CRGSGNLQDE
```

FIG. 19H

```
              351                                                    400
Consensus     Cekfl.fF..  NpCL.nAIqA  fgng......  ......p.fsv  .....t.t.a Hgdnfr        CLKFLNFFKD  NTCLKNAIQA  FGNGS.....D  VTVWQPAFPV   QTTATTTTA
Rgdnfr        CLKFLNFFKD  NTCLKNAIQA  FGNGS.....D  VTMWQPAPPV   QTTATTTTA
Hgrr2         CEKFLRDFTE  NPCLRNAIQA  FGNGTNV...  ......NVSP   KGPSFQATQA
Rgrr2         CEKFLRDFTE  NPCLRNAIQA  FGNGTDV...  ......NMSP   KGPSLPATQA
Hgrr3         CEMLEGFFSH  NPCLTEAIAA  KMRFHSQLFS  QDWPHPTFAV   MAHQNENPAV
Rgrr3         CEQLEKSFSQ  NPCLMEAIAA  KMRFHRQLFS  QDWADSTFSV   MQQQNSSPAL
```

FIG. 19I

```
                401                                                          450
Consensus       .rv...PsL.  ...s....l.  t.v...C..l  Q.Q.LK.N.S  .e...Cf.el
Hgdnfr          LRVKNKP.LG  PAGSENEIP.  THVLPPCANL  QAQKLKSNVS  GNTHLCISNG
Rgdnfr          FRVKNKP.LG  PAGSENEIP.  THVLPPCANL  QAQKLKSNVS  GSTHLCLSDS
Hgrr2           PRVEKTPSLP  DDLSDSTSLG  TSVITTCTSV  QEQGLKANNS  KELSMCFTEL
Rgrr2           PRVEKTPSLP  DDLSDSTSLG  TSVITTCTSI  QEQGLKANNS  KELSMCFTEL
Hgrr3           RPQPWVPSLF  SCTLPLILLL  SLW
Rgrr3           RPQLRLPVLS  FFILTLILLQ  TLW 451                                                499
Consensus       ttn....sg.  ...i...s..  A.pS.aL..L  pvlmltala.  LLS.....S
Hgdnfr          NYEKEGL.GA  SSHITTKSMA  APPSCGLSPL  LVRVVTALST  LLSLTETS
Rgdnfr          DFGKDGLAGA  SSHITTKSMA  APPSCSLSSL  PVLMLTALAA  LLSVSLA
Hgrr2           TTNIIPGSNK  VIKPNSGPSR  ARPSAALTVL  SVLMLK.LAL
Rgrr2           TTNISPGSKK  VIKLNSGSSR  ARLSAALTAL  PLLMLTLAL
```

FIG. 20A

```
Human GDNFRα                                  MFLATLYFALPLLDLLLSAEVSGGDRLDCVKASDQCLKE
Rat   GDNFRα                                  MFLATLYFALPLLDLLLMSAEVSGGDRLDCVKASDQCLKE
Human GRR2     MILANVECLFFLEDTLRSLASPSSLQGPELHGWREPVDCVRANELCAAE
Rat   GRR2     MLVFPSFYPDETLRSLASPSSLQGSELHGWRPCVDCVRANELCAAE Human GDNFRα   QSCSTKYRTLRQCVAGKETNFSLASGLEAKDECRSAMEAIKQKSLYNCRC
Rat   GDNFRα   QSCSTKVRTLRQCVAGKETNESITSGLEAKDECRSAMEAIKQKSLYNCRC
Human GRR2     SNCSSRYRTLRQCIAGRDRN......TMIANKECQAALEVLQESPLYDCRC
Rat   GRR2     SNCSSRVRTLRQCIAGRDRN......TMIANKECQAALEVTQESPLYDCRC Human GDNFRα   KRGMKKEKNCLRIYWSMYQSL.QGNDLLEDSPYEPVNSRLSDIFRVVPFI
Rat   GDNFRα   KRGMKKEKNCLRIYWSMYQSLQGNDLLEDSPYEPVNSRLSDIFRAVPFI
Human GRR2     KRGMKKELQCLQIYWSIHLGLTEGEEFYEASPYEPVTSRLSDIFRLASIF
Rat   GRR2     KRGMKKELQCIQIYWSIHLGLTEGEEFYEASPYEPVTSRLSDIFRLASTF
```

FIG. 20B

```
Human GDNFRα   SDVFQQVEHIPKCNNCLDAAKACNLDDICKKYRSAYITPCTTSVS.NCV
Rat   GDNFRα   SDVFQQVEHISKCNNCLDAAKACNLDDICKKYRSAYITPCTTSMSNEVC
Human GRR2     SGTGADFWSAKSNHCLDAAKACNINDNCKKLRSSYISICNREISPTERC
Rat   GRR2     SGTGTDEAVSTKSNHCLDAAKACNINDNCKKLRSSYISICNREISPTERC Human GDNFRα   NRRKCHKALRQFFDKVPAKHSVGMLFCSCRDIACTERRRQTIVPVCSYEE
Rat   GDNFRα   NRRKCHKALRQFFDKVPAKHSVGMLFCSCRDIACTERRRQTIVPVCSYEE
Human GRR2     NRRKCHKALRQFFDRVPSEYTMRMLFCSCQDQACAERRRQTILPSCSYED
Rat   GRR2     NRRKCHKALRQFFDRVPSEYTMRMLFCSCQDQACAERRRQTILPSCSYED Human GDNFRα   REKPNCLNLQDSCKTNYICRSRLADFFTNCQPESRSVSSCLKENYADCLL
Rat   GDNFRα   RERPNCLSIQDSCKTNYICRSRLADFFTNCQPESRSVSNCLKENYADCLL
Human GRR2     KEKPNCLDLRGVCRTDHLCRSRLADFHANCRASYQTVTSCPADNYQACLG
Rat   GRR2     KEKPNCLDIRSLCRTDHLCRSRLADFHANCRASYRITSCPADNYQACLG Human GDNFRα   AVSGLIGTVMTPNYIDSS..SLSVAPWCDCSNSGNDLEECLKFLNFFKDN
Rat   GDNFRα   AVSGLIGTVMTPNYVDSS..SLSVAPWCDCSNSGNDLEDCLKFINFFKDN
Human GRR2     SYAGMIGFDMTPNYVDSSPTGIVVSPWCSCRGSGNMEEECKFLRDFTEN
Rat   GRR2     SYAGMIGFDMTPNYVDSNPTGIVVSPWCNCRGSGNMEEECKFLRDFTEN
```

FIG. 20C

```
Human GDNFRα    TCLKNAIQAFGNGSDVTVWQPAFPVQTTTATTTALRVKNKPLGPAGSEN
Rat GDNFRα     TCLKNAIQAFGNGSDVTVWQPAPPVQTTTATTTAFRVKNKDFGPAGSEN
Human GRR2     PCLRNAIQAFGNGTNVSPKGPSFQATCAPRVEKTPSLPDDLSDSTS..
Rat GRR2       PCLRNAIQAFGNGIDVNMSPKGPSLPATCAPRVEKTPSLPDDLSDSTS..

Human GDNFRα   EIPTHVLPECANLQAQKLKSNVSGNTHLCISNGNYEKEGL.GASSHITTK
Rat GDNFRα    EIPTHVLPECANLQAQKLKSNVSGSTHLCTSDSDFGKDGLAGASSHTTTK
Human GRR2    .LGTSVITTSVQEQGLKANNSKELSMCFTELTTNIIPGSNKVIKPNSG
Rat GRR2      .LGTSVITTSIQEQGLKANNSKELSMCFTELTTNISPGSKKVIKLNSG Human GDNFRα  SMAAPPSCGLSPLLIVLVVT.ALSTLI..SLNETS
Rat GDNFRα    SMAAPPSCSISSLPVLMLT.ALAALLISVSLAETS
Human GRR2    PSRARPSAAITVLSVLMLKLAL
Rat GRR2      SSRARLSAAITALPLLMITIAL
```

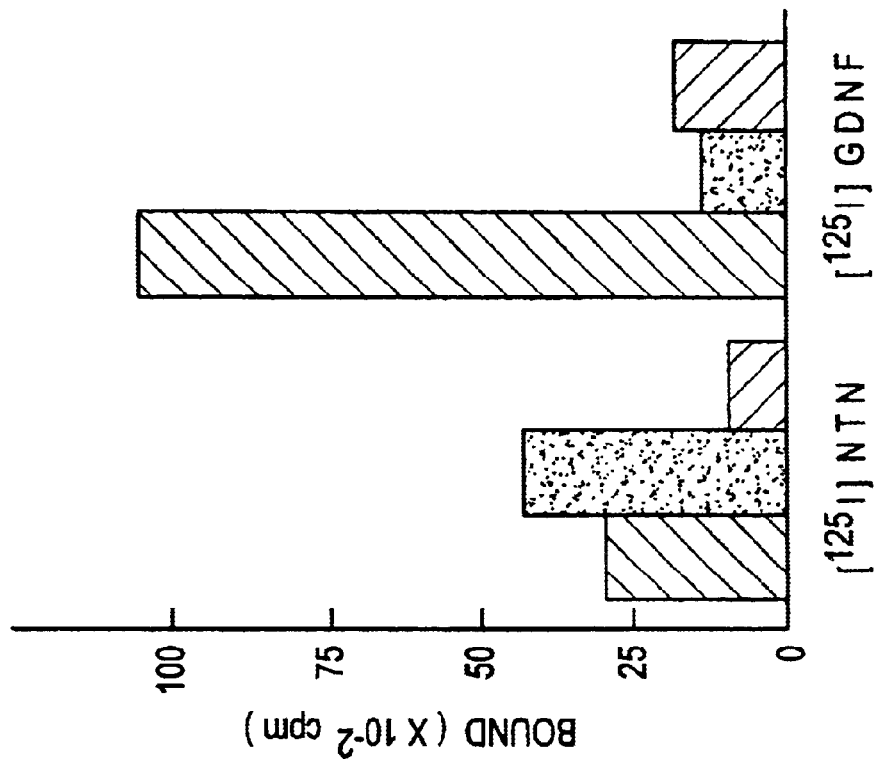
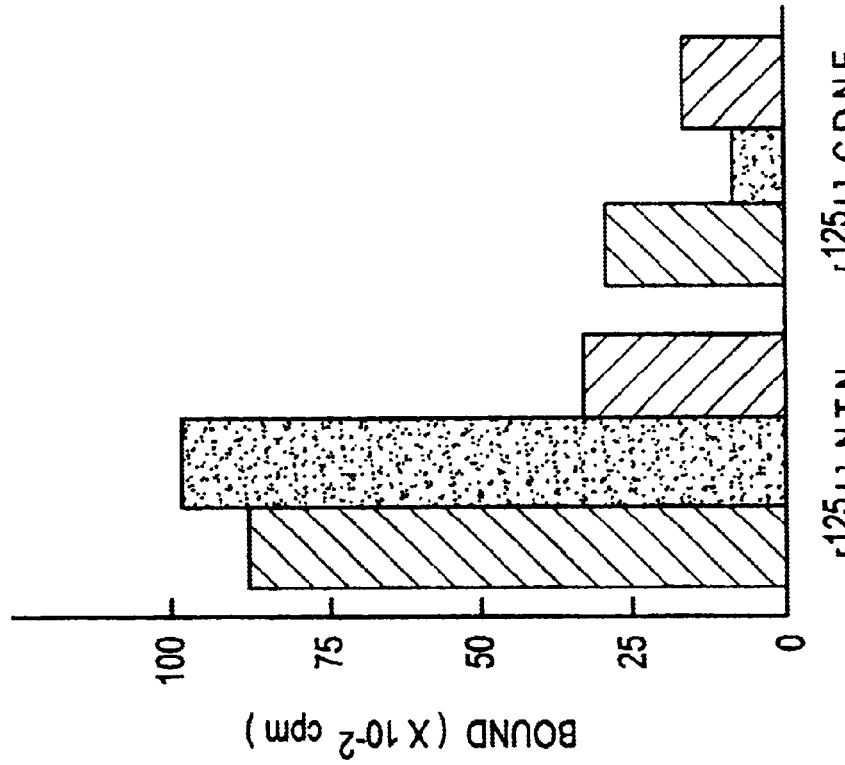
FIG. 21A
FIG. 21B

FIG. 26A

```
                                                                           50
CONSENSUS  ..........?  ....l.tl.s  l..pl.l..s  ..........  Cv.A....C.a
GDNFR      ..........   ..MELATLVP  ALPLDLLMS.  AEVSGGDRLD  CVKASDQCLK
GRR2       ....MLVFP.   SHYPDETLRS  LASPSSLQGS  ELEGWRPQVD  CVRANELCAA
GRR3       MGLSRSPRPP   PLVILLVLS.  LWLPLGTGNS  LPTENRLVNS  CTQARKKCEA

100
CONSENSUS  e..Cs.Yr.    LrgC.ag...  n.........  ..eC..A.e.  L..ssLydCCR
GDNFR      EQSCSTKYRT   LRCCVAGKET  NFSLITSGLEA KDECRSAMEA  LKQKSLYNCR
GRR2       ESNCSSRVRT   LRCCLAGRDR  N....TMLA.  NKECQAALEV  LQESPLYDCR
GRR3       NPACKRAYQH   LDSCTPSLSS  PLPSGES.AT  SAACLEAAQQ  LRNSSLIDCR 101                                                            150
CONSENSUS  CkRgMKke..   CL.IYws.h.  .l..G...le  .SPYE.pVtS  rlsdIf...s
GDNFR      CKRGMKKEKN   CLRIYWSMYQ  SL.QGNDLLE  DSPYE.PVNS  RLSDIFRAVP
GRR2       CKRGMKKELQ   CLQIYWSIHL  GLTEGEEFYE  ASPYE.PVTS  RLSDIFRLAS
GRR3       CHRRMKECAT   CLDIYWTVFP  VRSLGDYELD  VSPYEDTVTS  ..KPWKMNLS
```

FIG. 26.B

```
           151                                                                              200
CONSENSUS  ..s....d..  ...ksn.Cld  aAkaChlnD.  Ckkirsayi.  .C....s..e
GDNFR      FISDVFQQVE  HISKGNNCLD  AAKACNLDDT  CKKVRSAYIT  PCTTSMS.NE
GRR2       IFSGTGTDPA  VSTKSNECLD  AAKACNLNDN  CKKLRSSYIS  ECNREISPTE
GRR3       KLSMLKPD..  ....SDLCTK  FAMLCTLNDK  CDRLRKAYGE  AC....SG.I 201                                                                              250
CONSENSUS  rCnrrkChka  LRqFfdkvp.  .h.ygmLfCs  C....D.aC.E  RRRqTi.PsC
GDNFR      VCNRRKCHKA  LRQFFDKVPA  KHSYGMLFCS  C....RDIACTE  RRRQTIVPVC
GRR2       RCNRRKCHKA  LRQFFDRVPS  EVTYRMLFCS  C....QDQACAE  RRRQTILPSC
GRR3       RCQRHLCLAQ  LRSFFEKARE  SHAQGLLLCP  CAPEDAGCGE  RRRNTIAPSC 251                                                                              300
CONSENSUS  sve..e.PNC  LdIrs.Crtd  .lCRSRLadF  s..t...Vap  .tnC.p..r.  .t.C.a.ny.
SYEERERPNC  SYEDKEKPNC  ALPSVA.PNC  LDLRSLCRTD  LDLRSLCRTD  LDLRSFCRAD  LDLRSRLMDF  SSSL.SVAP  SNPTGIVVSP  VAL  FTNCQPESRS  HANCRASYRT  QTHCHPMDIL  VSNCLKENYA  ITSCPADNYQ  GT.C.ATEQS
GDNFR      SYEERERPNC  YICRSRLADF  SSSL.SVAP  FTNCQPESRS  VSNCLKENYA
GRR2       SYEDKEKPNC  HLCRSRLADF  SNPTGIVVSP  HANCRASYRT  ITSCPADNYQ
GRR3       ALPSVA.PNC  PLCRSRLMDF  KVNTI..VAL  QTHCHPMDIL  GT.C.ATEQS 301                                                                              350
CONSENSUS  .Cl.av.Gl.  Gt.MTPNyvd  wC.CrgSGN.  .eeCekfl..  LEDCLKFLNF
GDNFR      DCLLAYSGLI  GTVMTPNYVD  WCDCSNSGND  LEDCLKFLNF  EEECEKFLRD
GRR2       ACLGSYAGMI  GFDMTPNYVD  WCNCRGSGNM  EEECEKFLRD  QDECEQLEKS
GRR3       RCLRAVLGLI  GTAMTPNFIS  GCTCRGSGNL  QDECEQLEKS
```

FIG. 26C

```
          351                                                           400
CONSENSUS  f..NpCl.nA  iqAfgng.dv  .msg.p...  .t.a......  rv...p.l..
GDNFR      FKDNTCLKNA  IQAFGNGSDV  TMWQPAPPVQ  TTTATTTAF   RVKNKP.LGP
GRR2       FTENPCLRVA  IQAFGNGTDV  NMSPKGPSLP  ATQAP.....  RVEKTPSLPD
GRR3       FSQNPCLMEA  IAAKMRFHRQ  LFSQDWADST  FSVMCQQNSS  PALRPQ....

401                                                           450
CONSENSUS  ..s......  .v...c...  .q.lk.n.s.  ....c.....  ..........
GDNFR      AGS.ENEIT   HVLPPCANLQ  AQKLKSNVSG  STELCLSDSD  FGKDGLAGAS
GRR2       DLSDSTSLGF  SVITTCTSIQ  EQGLKENNSK  ELSMCFTELT  TNISPGSKKV
GRR3       ..........  ..........  ..........  ..........  ..........

451                                                 489
CONSENSUS  ......s.a  ..s.l..LP  vLmlt.l...  l...l.ets
GDNFR      SHITTKSMAA  PPSCSLSSLP  VLMLTALAAL  LSVSLAETS
GRR2       IKLNSGSSRA  RLSAALTALP  LLMLTLAL    .........
GRR3       ..........  .......LRLP VLSFFILTLI  LLQTLW
```

POLYNUCLEOTIDES ENCODING A NEUROTROPHIC FACTOR RECEPTOR

This application is a continuation-in-part of U.S. patent application Ser. No. 08/837,199, Apr. 14, 1997, now U.S. Pat. No. 6,455,277, which claims the benefit of U.S. provisional patent applications Ser. Nos. 60/017,221 filed May 9, 1996 and 60/015,907 filed Apr. 22, 1996, which are, in their entirety, hereby incorporated by reference herein.

FIELD OF THE INVENTION

The present invention relates to receptors for neurotrophic factors. In particular, the invention relates to receptors for glial cell line-derived neurotrophic factor (GDNF) and neurturin and provides nucleic acid and amino acid sequences encoding the receptors. The present invention also relates to therapeutic techniques for the treatment of neurotrophic factors-responsive conditions.

BACKGROUND OF THE INVENTION
Glial Cell Line-derived Neurotrophic Factor

Glial cell line-derived neurotophic factor (GDNF) was initially isolated and cloned from rat B49 cells as a potent neurotrophic factor that enhances survival of midbrain dopaminergic neurons (Lin et al., Science, 260, 1130–1132, 1993). Recent studies have indicated that this molecule exhibits a variety of other biological activities, having effects on several types of neurons from both the central and peripheral nervous systems. In the central nervous system (CNS), GDNF has been shown to prevent the axotomy-induced death of mammalian facial and spinal cord motor neurons (Li et al., Proceedings Of The National Academy Of Sciences, U.S.A., 92, 9771–9775, 1995; Oppenheim et al., Nature, 373, 344–346, 1995; Yan et al., Nature, 373, 341–344, 1995; Henderson et al., Science, 266, 1062–1064, 1994; Zurn et al., Neuroreport, 6, 113–118, 1994), and to rescue developing avian motor neurons from natural programmed cell death (Oppenheim et al., 1995 supra). Local administration of GDNF has been shown to protect nigral dopaminergic neurons from axotomy-induced (Kearns and Gash, Brain Research, 672, 104–111, 1995; Beck et al., Nature, 373, 339–341, 1995) or neurotoxin-induced degeneration (Sauer et al., Proceedings Of The National Academy Of Sciences U.S.A., 92, 8935–8939, 1995; Tomac et al., Nature, 373, 335–339, 1995). In addition, local administration of GDNF has been shown to induce sprouting from dopaminergic neurons, increase levels of dopamine, noradrenaline, and serotonin, and improve motor behavior (Tomac et al., 1995 supra).

More recently, GDNF has been reported to be a potential trophic factor for brain noradrenergic neurons and Purkinje cells. Grafting of fibroblasts ectopically expressing GDNF prevented 6-hydroxydopamine-induced degeneration and promoted the phenotype of adult noradrenergic neurons in vivo (Arenas et al., Neuron, 15, 1465–1473, 1995), while exogeneously applied GDNF effectively promoted survival and morphological differentiation of embryonic Purkinje cells in vitro (Mount et al., Proceedings Of The National Academy Of Sciences U.S.A., 92, 9092–9096, 1995). In the peripheral nervous system, GDNF has been shown to promote the survival of neurons in nodose, ciliary, and sympathetic ganglia, as well as small populations of embryonic sensory neurons in dorsal root ganglia (DRG) and trigeminal ganglia (Trupp et al., Journal Of Cell Biology, 130, 137–148, 1995; Ebendal et al., Journal Of Neuroscience Research, 40, 276–284, 1995; Oppenheim et al., 1995 supra; Yan et al., 1995 supra; Henderson et al., 1994 supra). GDNF has also been reported to enhance the expression of vasoactive intestinal peptide and preprotachykinin-A mRNA in cultured superior cervical ganglion (SCG) neurons, and thus effects the phenotype of SCG neurons and induces bundle-like sprouting (Trupp et al., 1995 supra).

Expression of GDNF has been observed in a number of different cell types and structures of the nervous system. In the CNS, GDNF mRNA expression has been observed by reverse transcriptase polymerase chain reaction (RT-PCR) in both developing and adult rat striatum, the major target of nigral dopaminergic innervation, and widely in other regions, including hippocampus, cortex, thalamus, septum, cerebellum, spinal cord, and medulla oblongata (Arenas et al., supra 1995; Poulsen et al., Neuron, 13, 1245–1252, 1994; Springer et al., Experimental Neurology, 127, 167–170, 1994; Stroemberg et al., Experimental Neurology, 124, 401–412, 1993; Schaar et al., Experimental Neurology, 124, 368–371, 1993). In human, GDNF transcripts have also been detected in striatum, with highest level in the caudate and lower levels in the putamen. Detectable levels are also found in hippocampus, cortex, and spinal cord, but not in cerebellum (Schaar et al., Experimental Neurology, 130, 387–393, 1994; Springer et al., 1994 supra). In the periphery, GDNF mRNA expression has been reported in DRG and SCG of postnatal day I rats, sciatic nerve, and primary cultures of neonatal Schwann cells (Trupp et al., 1995 supra; Hoffer et al., Neuroscience Letters, 182, 107–111, 1994; Henderson et al., 1994 supra; Springer et al., 1994 supra). In addition, recent studies have shown that GDNF transcripts are also widely expressed in peripheral non-neuronal organs, including postnatal testis and kidney, embryonic whisker pad, stomach, and skin. Expression can be detected at lower levels in embryonic muscle, adrenal gland and limb bud, and in postnatal lung, liver and ovary (Trupp et al., 1995 supra; Henderson et al., 1994 supra). So far, however, the biological significance of the non-neuronal expression of GDNF is not clear.

A neurotrophic factor refered to as "neurturin" is described in Nature 384(5):467–470, 1996. Detailed descriptions of the preparation and characterization of GDNF protein products may be found in U.S. patent application Ser. No. 08/182,183 filed May 23, 1994, now abandoned, and its parent applications (also see PCT/US92/07888, WO 93/06116 filed Sep. 17, 1992 and European Patent Application No. 92921022.7, Publication No. EP 610 254) the disclosures of which are hereby incorporated by reference. Additional GDNF protein products are described in U.S. patent application Ser. No. 08/535,681 filed Sep. 28, 1995, now U.S. Pat. No. 6,184,200, the disclosure of which is hereby incorporated by reference. As used herein, the term "GDNF protein product" includes biologically active synthetic or recombinant GDNF proteins and analogs, as well as chemically modified derivatives thereof. GDNF analogs include deletion variants such as truncated GDNF proteins, as well as insertion and substitution variants of GDNF. Also included are GDNF proteins that are substantially homologous to the human GDNF protein.

GDNF Therapy

GDNF therapy is helpful in the treatment of nerve damage caused by conditions that compromise the survival and/or proper function of one or more types of nerve cells. Such nerve damage may occur from a wide variety of different causes. Nerve damage may occur to one or more types of nerve cells by: (1) physical injury, which causes the degeneration of the axonal processes and/or nerve cell bodies near the site of injury; (2) temporary or permanent cessation of blood flow to parts of the nervous system, as in stroke; (3)

intentional or accidental exposure to neurotoxins, such as chemotherapeutic agents (e.g., cisplatinum) for the treatment of cancer or dideoxycytidine (ddC) for the treatment of AIDS; (4) chronic metabolic diseases, such as diabetes or renal dysfunction; or (5) neurodegenerative diseases such as Parkinson's disease, Alzheimer's disease, and amyotrophic lateral sclerosis (ALS), which result from the degeneration of specific neuronal populations.

Several studies indicate that GDNF therapy is particularly helpful in the treatment of neurodegenerative conditions such as the degeneration of the dopaminergic neurons of the substantia nigra in Parkinson's disease. The only current treatments for Parkinson's disease are palliative, aiming at increasing dopamine levels in the striatum. The expected impact of GDNF therapy is not simply to produce an increase in the dopaminergic neurotransmission at the dopaminergic nerve terminals in the striatum (which will result in a relief of the symptoms), but also to slow down, or even stop, the progression of the degenerative processes and to repair the damaged nigrostriatal pathway and restore its function. GDNF may also be used in treating other forms of damage to or improper function of dopaminergic nerve cells in human patients. Such damage or malfunction may occur in schizophrenia and other forms of psychosis. The only current treatments for such conditions are symptomatic and require drugs which act upon dopamine receptors or dopamine uptake sites, consistent with the view that the improper functioning of the dopaminergic neurons which innervate these receptor-bearing neuronal populations may be involved in the disease process.

Receptor

A number of receptors which mediate binding and response to protein factors have been characterized and molecularly cloned, including receptors for insulin, platelet derived growth factor, epidermal growth factor and its relatives, the fibroblast growth factors, various interleukins, hematopoietic growth factors and ciliary neurotrophic factor (U.S. Pat. No. 5,426,177). Study results indicate that some receptors can bind to multiple (related) growth factors, while in other cases the same factor can bind and activate multiple (related) receptors (e.g., Lupu et al., Science, 249:1552–1555, 1990; Dionne et al., EMBO J., 9:2685–2692, 1990; Miki et al., Science, 251:72–75, 1991). Most receptors can broadly be characterized as having an extracellular portion or domain responsible for specifically binding a protein factor, a transmembrane domain which spans the cell membrane, and an intracellular domain that is often involved in initiating signal transduction upon binding of the protein factor to the receptor's extracellular portion. Although many receptors are comprised of a single polypeptide chain, other receptors apparently require two or more separate subunits in order to bind to their protein factor with high-affinity and to allow functional response following binding (e.g., Hempstead et al., Science, 243:373–375, 1989; Hibi et al., Cell, 63:1149–1157, 1990).

The extracellular and intracellular portions of a given receptor may share common structural motifs with the corresponding regions of other receptors, suggesting evolutionary and functional relationships between different receptors. These relationships can often be quite distant and may simply reflect the repeated use of certain general domain structures. For example, a variety of different receptors that bind unrelated factors make use of "immunoglobulin" domains in their extracellular portions, while other receptors utilize "cytokine receptor" domains in their factor-binding regions (e.g., Akira et al., The FASEB J., 4:2860–2867, 1990). A large number of receptors with distinct extracellular binding domains (which thus bind different factors) contain related intracytoplasmnic domains encoding tyrosine-specific protein kinases that are activated in response to factor binding (e.g., Ullrich and Schlessinger, Cell, 61:203–212, 1990). The mechanisms by which factor-binding "activates" the signal transduction process is poorly understood, even in the case of receptor tyrosine kinases. For other receptors, in which the intracellular domain encodes a domain of unknown function or in which the binding component associates with a second protein of unknown function (e.g., Hibi et al., Cell, 63:1149–1157, 1990), activation of signal transduction is not well characterized.

The mode of action of GDNF in vivo is not clearly elucidated in the art, in part due to the absence of information on a receptor for GDNF. Two groups have independently found that striatum injected $[^{125}I]$-labeled GDNF can be retrogradely transported by dopaminergic neurons in the substantia nigra (Tomac et al., Proceedings Of The National Academy Of Sciences Of The United States Of America. 92, 8274–8278, 1995; Yan et al., 1995 supra). Retrograde transport of $[^{125}I]$-GDNF by spinal cord motor neurons, DRG sensory neurons and neurons in the B layer of retina ganglia was also been observed. These retrograde transport phenomena can all be specifically inhibited by 100-fold or higher concentrations of unlabeled GDNF, suggesting a saturable, receptor-mediated transport process. In vitro, recombinant GDNF has been shown to enhance the survival and promote dopamine uptake of cultured dopaminergic neurons at very low concentrations. The observed half-maximal effective concentration ($EC_{50}$) of GDNF on these neurons is 0.2 to 1.6 pM (Lin et al., 1993 supra). GDNF has also been shown to support the survival of dissociated motor neurons at low concentrations. The reported $EC_{50}$ of GDNF on motor neurons, in a 5 to 10 fM range, is even lower than that on dopaminergic neurons (Henderson et al., 1994 supra).

Taken together, these observations indicate that receptor(s) for GDNF expressed in these cells have very high ligand binding affinities. Similar to members of the TGF-β family, the widely diversified tissue distribution and varied biological function of GDNF on different populations of cells suggest that different types of receptor(s) for GDNF or receptor complexes may exist. Saturation steady-state and competitive binding of $[^{125}I]$-GDNF to E10 chick sympathetic neurons has shown that these neurons express GDNF binding sites differing from those observed in dopaminergic and motor neurons. The half maximal saturation concentration and the half-maximal inhibition concentration of GDNF on these binding sites is in the range of 1 to 5 nM (Trupp et al., 1995 supra). Similarly, the $EC_{50}$ of GDNF in supporting the survival of sympathetic neurons from P1 rat SCG has also been reported to be in the nanomolar range (Trupp et al., 1995 supra).

To better understand the mechanism by which GDNF activates signal transduction to exert its affects on cells, it would be beneficial to identify the receptor(s) which mediate binding and response to this protein factor. It would also be beneficial for GDNF therapy to identify and make possible the production of accessory molecules which provide for or enhance GDNF signal transduction. Moreover, the identification of a protein receptor for GDNF would provide powerful applications in diagnostic uses, for example, as an aid in determining if individuals would benefit from GDNF protein therapy. Furthermore, the protein receptor for GDNF could be a key component in an assay for identifying additional molecules which bind to the receptor and result in desired biological activity.

SUMMARY OF THE INVENTION

The present invention provides nucleic acid sequences which encode neurotrophic factor receptor proteins having amino acid sequences as depicted in the Figures as well as biologically equivalent analogs. The neurotrophic factor receptor protein and protein products of the present invention are designated herein as glial cell line-derived neurotrophic factor receptor (GDNFR) protein and protein products. Particular receptor proteins refered to herein include GDNFR-α, and glial cell line-derived neurotrophic factor receptor-α-related receptor proteins 2 and 3 (GRR2 and GRR3). The novel proteins are functionally characterized by the ability to bind GDNF and/or neurturin specifically, and to act as part of a molecular complex which mediates or enhances the signal transduction affects of GDNF and/or neurturin. GDNFR protein products are typically provided as a soluble receptor protein and in a substantially purified form.

In one aspect, the present invention provides for the production of GDNFR protein products by recombinant genetic engineering techniques. In an alternative embodiment, the GDNFR proteins are synthesized by chemical techniques, or a combination of the recombinant and chemical techniques.

In another aspect of the present invention, the GDNFR proteins may be made in glycosylated or non-glycosylated forms. Derivatives of GDNFR protein typically involve attaching the GDNFR protein to a water soluble polymer. For example, the GDNFR protein may be conjugated to one or more polyethylene glycol molecules to decrease the precipitation of the GDNFR protein product in an aqueous environment.

Yet another aspect of the present invention includes the various polynucleotides encoding GDNFR proteins. These nucleic acid sequences are used in the expression of GDNFR in a eukaryotic or prokaryotic host cell, wherein the expression product or a derivative thereof is characterized by the ability to bind to GDNF and thereby form a complex capable of mediating GDNF activity, such as increasing dopamine uptake by dopaminergic cells. The polynucleotides may also be used in cell therapy or gene therapy applications. Suitable nucleic acid sequences include those specifically depicted in the Figures as well as degenerate sequences, naturally occurring allelic variations and modified sequences based on the present invention.

Exemplary nucleic acid sequences include sequences encoding a neurotrophic factor receptor protein comprising an amino acid sequence as depicted in the Figures capable of complexing with glial cell line-derived neurotrophic factor (GDNF) and/or neurturin and mediating cell response to GDNF and/or neurturin, and biologically equivalent analogs thereof. Such sequences include: (a) a sequence set forth in FIG. 1 (SEQ ID NO. 1) comprising nucleotides encoding $Met^1$ through $Ser^{465}$ or FIG. 3 (SEQ ID NO. 3) comprising nucleotides encoding $Met^1$ through $Ser^{468}$ encoding a neurotrophic factor receptor (GDNFR-α) capable of complexing with glial cell line-derived neurotrophic factor (GDNF) and mediating cell response to GDNF, as well as GRR2 and GRR3; (b) a nucleic acid sequence which (1) hybridizes to a complementary sequence of (a) and (2) encodes an amino acid sequence with GDNFR activity; and (c) a nucleic acid sequence which but for the degeneracy of the genetic code would hybridize to a complementary sequence of (a) and (2) encodes an amino acid sequence with GDNFR activity. Also disclosed herein are vectors such nucleic acid sequences wherein the sequences typically are operatively linked to one or more operational elements capable of effecting the amplification or expression of the nucleic acid sequence. Host cells containing such vectors are also contemplated. Typically, the host cell is selected from mammalian cells and bacterial cells, such as a COS-7 cell or *E. coli*, respectively.

A further aspect of the present invention involves vectors containing the polynucleotides encoding GDNFR proteins operatively linked to amplification and/or expression control sequences. Both prokaryotic and eukaryotic host cells may be stably transformed or transfected with such vectors to express GDNFR proteins. The present invention further includes the recombinant production of a GDNFR protein wherein such transformed or transfected host cells are grown in a suitable nutrient medium, and the GDNFR protein expressed by the cells is, optionally, isolated from the host cells and/or the nutrient medium. The present invention further includes the use of polynucleotides encoding GDNFR protein and vectors containing such polynucleotides in gene therapy or cell therapy.

The host cell may also be selected for its suitability to human implantation, wherein the implanted cell expresses and secretes a neurotrophic factor receptor of the present invention. The host cell also may be enclosed in a semipermeable membrane suitable for human implantation. The host cell may be transformed or transfected ex vivo. An exemplary device for treating nerve damage involves: (a) a semipermeable membrane suitable for implantation; and (b) cells encapsulated within the membrane, wherein the cells express and secrete a neurotrophic factor receptor as disclosed herein. The membrane is selected from a material that is permeable to the neurotrophic factor receptor protein but impermeable to materials detrimental to the encapsulated cells.

Methods for the recombinant production of a neurotrophic factor receptor of the present invention are also disclosed. An exemplary method involves: (a) culturing a host cell containing a nucleic acid sequence encoding a GDNFR protein of the present invention, such as an amino acid sequence depicted in the Figures capable of complexing with glial cell line-derived neurotrophic factor and/or neurturin and mediating cell response to GDNF and/or neurturin, or biologically equivalent analogs thereof; (b) maintaining said host cell under conditions suitable for the expression of said neurotrophic factor receptor by said host cell; and (c) optionally, isolating said neurotrophic factor receptor expressed by said host cell. The host cell may be a prokaryotic cell or a eukaryotic cell. If bacterial expression is involved, the method may further include the step of refolding the neurotrophic factor receptor.

The present invention includes an isolated and purified protein comprising an amino acid sequence as depicted in the Figures capable of complexing with glial cell line-derived neurotrophic factor and/or neurturin and mediating cell response to GDNF and/or neurturin, and biologically equivalent analogs thereof. Exemplary analogs include, but are not limited to, proteins comprising the amino acid sequence $Ser^{18}$ through $Pro^{446}$, $Asp^{25}$ through $Leu^{447}$ and $Cys^{29}$ through $Cys^{442}$ as depicted in FIG. 2 (SEQ ID NO:2) as well as proteins comprising the amino acid sequence $Met^{17}$ through $Pro^{449}$ and $Cys^{29}$ through $Cys^{443}$ as depicted in FIG. 4 (SEQ ID NO:4). The proteins of the present invention may be glycosylated or non-glycosylated and may be produced by recombinant technology or chemical synthesis. The present invention further includes nucleic acid sequences encoding a receptor protein comprising such amino acid sequences.

Also disclosed herein are pharmaceutical compositions comprising a GDNFR protein of the present invention in combination with a pharmaceutically acceptable carrier. A variety of other formulation materials may be used to facilitate manufacture, storage, handling, delivery and/or efficacy.

Another aspect of the present invention includes the therapeutic use of GDNFR genes and proteins. For example, a circulating or soluble GDNFR protein product may be used alone or in conjunction with GDNF and/or neurturin in treating disease of or injury to the nervous system by enhancing the activity of transmembrane signaling of GDNF and/or neurturin. Thus, the proteins and pharmaceutical compositions of the present invention may be used in treating improperly functioning dopaminergic nerve cells, Parkinson's disease, Alzheimer's disease and amyotrophic lateral sclerosis. Alternatively, a recombinant GDNFR gene may be inserted in the cells of tissues which would benefit from increased sensitivity to GDNF or neurturin, such as motor neurons in patients suffering from amyotrophic lateral sclerosis. In yet another embodiment, GDNFR may be used to block GDNF or neurturin activity in cases where the GDNF or neurturin activity is thought to be detrimental. The GDNFR protein may be used to verify that observed effects of GDNF or neurturin are due to the GDNFR protein.

In another aspect of the invention, GDNFR probes may be used to identify cells and tissues which are responsive to GDNF or neurturin in normal or diseased states. Alternatively, the probes may be used to detect an aberrancy of GDNFR protein expression in a patient suffering from a GDNF- or neurturin-related disorder.

In a further aspect of the invention, GDNFR probes, including nucleic acid as well as antibody probes, may be used to identify GDNFR-related molecules. For example, the present invention provides for such molecules which form a complex with GDNFR protein and thereby participate in GDNFR protein function. As another example, the present invention provides for receptor molecules which are homologous or cross-reactive antigenically, but not identical to GDNFR-α GRR2 or GRR3, including consensus sequence molecules as depicted in the Figures.

The present invention also provides for the development of both binding and functional assays for GDNF or neurturin based on the receptor. For example, assay systems for detecting GDNF activity may involve cells which express high levels of GDNFR-α, and which are therefore extremely sensitive to even very low concentrations of GDNF or GDNF-like molecules. Similar assays may involve neurturin and GRR2. In yet another embodiment, soluble GDNFR may be used to bind or detect the presence of GDNF or GDNF-like molecules.

In addition, the present invention provides for experimental model systems for studying the physiological role of GDNF or neurturin. Such systems include assays involving anti-GDNFR antibodies or oligonucleotide probes as well as animal models, such as transgenic animals which express high levels of GDNFR and therefore are hypersensitive to GDNF and/or neurturin or animals derived using embryonic stem cell technology in which the endogenous GDNFR genes were deleted from the genome. An anti-GDNFR antibody will binds a peptide portion of the neurotrophic factor receptor proteins. Antibodies include monoclonal and polyclonal antibodies. Alternatively, immunological tags for which antibodies already exist may be attached to the GDNFR protein to aid in detection. Such tags include but are not limited to Flag (IBI/Eastman Kodak) and myc sequences. Other tag sequences such as polyhistidine have also been used for detection and purification on metal chelating columns.

Yet another aspect of the present invention involves the use of GDNFRs to identify ligands which activate receptors as described in the following detailed description and examples. Proteins as well as small molecule neurotrophic factor mimetics may be identified and studied following the binding studies described herein.

Additional aspects and advantages of the invention will be apparent to those skilled in the art upon consideration of the following description, which details the practice of the present invention.

BRIEF DESCRIPTION OF THE FIGURES

FIG. 1 depicts a nucleic acid sequence (SEQ ID NO:1) encoding human glial cell line-derived neurotrophic factor receptor (GDNFR-α; SEQ ID NO:2). The amino acid sequence of the full length GDNFR protein is encoded by nucleic acids 540 to 1934 of SEQ ID NO:1.

FIG. 2 depicts the amino acid sequence (SEQ ID NO:2) of the full length human GDNFR-α protein.

FIG. 3 depicts a nucleic acid sequence (SEQ ID NO:3) encoding rat GDNFR-α (SEQ ID NO:4). The amino acid sequence of the full length GDNFR-α protein is encoded by nucleic acids 302 to 1705 of SEQ ID NO:3.

FIG. 4 depicts the amino acid sequence (SEQ ID NO:4) of the full length rat GDNFR-α protein FIGS. 5(A)–(R) depict the alignment and comparison of portions of GDNFR-α cDNAsequences (SEQ ID NOS: 46–55) produced in various clones as well as the consensus sequence for human GDNFR-α (SEQ ID NO:45).

FIG. 6 depicts the identification of Neuro-2A derived cell lines expressing GDNFR-α.

FIGS. 7A and 7B depict the results of the equilibrium binding of [$^{125}$I]GDNF to cells expressing GDNFR-α.

FIG. 8 depicts the results of the chemical cross-linking of [$^{125}$I]GDNF to GDNFR-α and Ret Expressed in cells expressing GDNFR-α.

FIGS. 9A–C depicts the results of the induction of c-Ret autophosphorylation by GDNF in cells expressing GDNFR-α.

FIGS. 10A–B depicts the results of the induction of c-Ret autophosphorylation by GDNF and soluble GDNFR-α.

FIGS. 14A–D depicts a nucleic acid sequence (SEQ ID NO:35) encoding human glial cell line-derived neurotrophic factor receptor-α-related protein 2 (GRR2). The amino acid sequence (SEQ ID NO:36) of the full length GRR2 protein is encoded by nucleic acids 1587 to 2978.

FIGS. 15A–C depicts a nucleic acid sequence (SEQ ID NO:37) encoding human glial cell line-derived neurotrophic factor receptor-α-related protein 3 (SEQ ID NO:38).

FIGS. 16A–C depicts a nucleic acid sequence (SEQ ID NO:39) encoding rat glial cell line-derived neurotrophic factor receptor-α-related protein 2 (SEQ ID NO:40).

FIGS. 17A–B depicts a nucleic acid sequence (SEQ ID NO:41) encoding rat glial cell line-derived neurotrophic factor receptor-α-related protein 3 (SEQ ID NO:42).

FIG. 18 depicts the alignment and comparison of various human, rat and mouse GDNFR amino acid sequences (SEQ ID NOS:2, 4, and 56, respectively).

FIG. 19 depicts the alignment and comparison of human GDNFR-α, rat, GDNFR-α, human GRR2, rat GRR2 human GRR3 and rat GRR3 amino acid sequences ((SEQ ID NOS:2, 4, 36, 40, 38, and 42, respectively) and an exemplary consensus GDNFR sequence (SEQ ID NO:43).

FIG. 20 depicts the alignment and comparison of human GDNFR-α (SEQ ID NO:2), rat GDNFR-α (SEQ ID NO:4), human GRR2 (SEQ ID NO:36) and rat GRR2 peptide sequences (SEQ ID NO:40).

FIG. 21 (Panels A and B) depicts the binding of neurturin and GDNF to LA-N-% and NGR-38 cells. LA-N-5 (Panel A) and NGR-38 (Panel B) cells were incubated with 50 pM of either [$^{125}$I]NTN or [$^{125}$I]GDNF in the absence (light gray bars) or presence of unlabeled GDNF (dark gray bars) or neurturin (black bars) at 4° C. for two hours.

FIG. 26 depicts the amino acid sequences of rat GDNFR-α, rat GRR2 and rat GRR3 (SEQ ID NOS:4, 40, and 42, respectively) are aligned and a consensus sequence (SEQ ID NO:44) is shown above the three receptor sequences. Upper case letters in the consensus sequence indicate amino acids that are conserved in all three receptors, lower case letters indicate that two of the three receptors share that amino acid, and dots indicate all three receptors have a different amino acid at that position. Predicted signal peptide sequences are underlined in GDNFR-α and GRR3; no signal peptide is predicted for GRR2. The hydrophobic C-terminal regions of all three putative receptors are underlined. Potential N-glycosylation sites are shown in boldface and sites conserved between two receptors are outlined by boxes.

DETAILED DESCRIPTION OF THE INVENTION

Figure 7B:
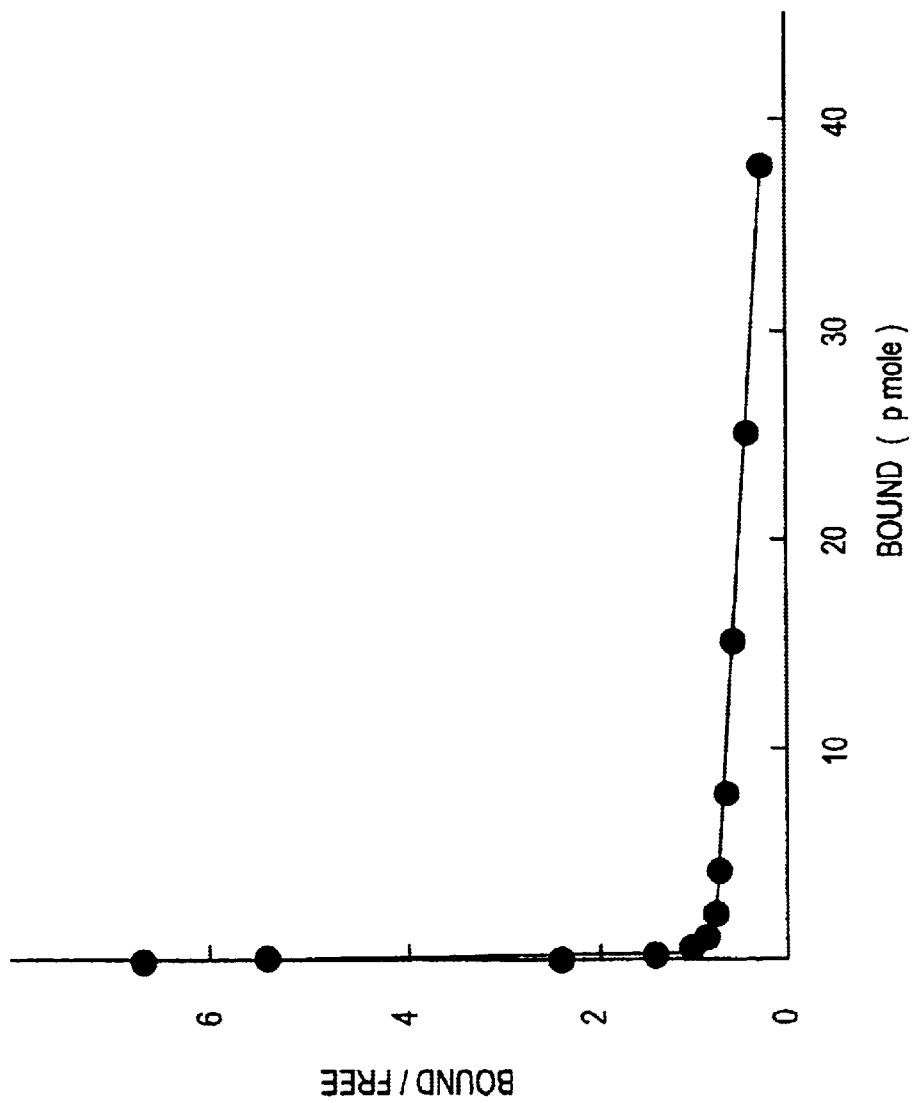

Glial cell line-derived neurotrophic factor (GDNF) is a potent neurotrophic factor which exhibits a broad spectrum of biological activities on a variety of cell types from both the central and peripheral nervous systems. It is a glycosylated, disulfide-linked dimer which is distantly related (less than 20% homology) to the transforming growth factor-β (TGF-β) superfamily. GDNFs ability to enhance the survival of dopaminergic neurons and other neuron populations demonstrates its therapeutic potential for the treatment of Parkinson's disease as well as other forms of nerve damage or malfunction.

The described biological activities of the neurturin neurotrophic factor (Nature 384(5):467–470, 1996) include promoting the survival of nodose ganglia sensory neurons and a small population of dorsal root ganglia sensory neurons, in addition to superior cervical ganglion sympathetic neurons. The activity suggests the possibility of a common or similar signaling pathway. In addition, the biological activities of neurturin may extend to motor neurons and dopaminergic neurons. Thus, neurturin may be useful in the treatment of diseases for which the use of GDNF may be indicated.

The present invention is based upon the discovery of a high affinity receptor first found on the surface of cultured retinal cells from postnatal rats. These receptors possess an estimated GDNF binding affinity comparable to that of the receptors found in dopaminergic and motor neurons; midbrain dopaminergic neurons (Lin et al., 1993 supra; Sauer et al., 1995 supra; Kearns and Gash, 1995 supra; Beck et al., 1995 supra; Tomac et al., 1995a supra), facial and spinal cord motor neurons (Li et al., 1995 supra; Oppenheim et al., 1995 supra; Yan et al., 1995 supra; Zurn et al., 1994 supra; Henderson et al., 1994 supra). The receptor molecule has been named GDNF receptor-alpha (GDNFR-α) since it is the first known component of a receptor system for GDNF. The present invention also provides the first description of the expression cloning and characterization of GDNFR-α protein. Cells modified to express the recombinant receptor bind GDNF with high affinity. Additional receptor proteins include glial cell line-derived neurotrophic factor receptor-α related receptor proteins 2 and 3 (GRR2 and GRR3).

Using a dopamine uptake assay and [$^{125}$I]-GDNF binding on cultured cells, high affinity receptors to GDNF were detected on the surface of rat photoreceptor cells. As further described in the Examples, the study of photoreceptor cells lead to the isolation of a cDNA clone by expression cloning for GDNFR-α. The nucleic acid sequence for GDNFR-α encodes a protein of 468 amino acids with 31 cysteine residues and three potential N-glycosylation sites. Next, a nucleic acid sequence from the rat cDNA clone was used to isolate its human homolog which was found to be nearly identical to the rat receptor at the amino acid level. The human GDNFR-α cDNA sequence encodes a protein of 465 amino acids with the positions of all cysteine residues and potential N-glycosylation sites conserved relative to the rat receptor. This high degree of primary sequence conservation indicated an important role for this receptor in the biological function of GDNF.

As discussed above, many receptors have three main domains: an extracellular or cell surface domain responsible for specifically binding a protein factor; a transmembrane domain which spans the cell's membrane; and an intracellular or cytoplasmic domain that is typically involved in initiating signal transduction when a protein factor binds to the extracellular domain. It was determined, however, that GDNFR-α is unrelated in sequence or structural characteristics to any known protein (such as the consensus sequences found in either receptor kinases or cytokine receptors), lacks a cytoplasmic domain, lacks the C-terminal charged residues characteristic of a transmembrane domain and is anchored to the cell membrane by is glycosyl-phosphatidylinositol (GPI) linkage, as described in greater detail below. Although the absence of an intracellular catalytic domain precluded a direct role in transmembrane signaling, the high binding affinity and strong evolutionary sequence conservation further suggested that this receptor was important for GDNF function.

Because GDNFR-α lacks a cytoplasmic domain, it was thought that this receptor must act in conjunction with one or more accessory molecules which play a role in transmembrane signaling. It was then discovered that transgenic mice which lack the gene for GDNF die and have no kidneys. Transgenic mice which lack the gene for c-ret proto-oncogene (Schuchardt, et al., Nature, 367, 380–383, 1994) were found to have a similar phenotype. The c-ret proto-oncogene encodes a receptor tyrosine kinase (RTK) whose normal function had not yet been determined. All RTKs have a similar topology: they possess an extracellular ligand-binding domain, a transmembrane domain and a cytoplasmic segment containing the catalytic protein-tyrosine kinase domain. Binding of a ligand leads to the activation of the kinase domain and phosphorylation of specific substrates in the cell that mediate intracellular signaling. The present invention involves the discovery that a soluble form of GDNFR-α may be used to mediate the binding of GDNF to the c-ret proto-oncogene and thereby elicit a cellular response to GDNF as well as modify its cell-type specificity.

Similar species, called "receptor alpha" components, provide ligand binding specificity but do not have the capacity to transduce signal on their own. Such components are found in the ciliary neurotrophic factor (CNTF) and interleukin-6 (IL-6) receptor systems. Like GDNFR-α, and in contrast to IL-6 receptor, CNTF receptor binds its ligand with high affinity, has a hydrophobic C-terminus, no cytoplasmic domain, and is anchored to the cell membrane by GPI linkage (Davis et al., 1991). In order to mediate signal transduction, CNTF binds first to CNTF receptor, creating a complex which is able to bind gp130. This inactive complex then binds to LIF receptor to form the active signaling complex (Davis, et al., Science, 260, 1805–1807, 1993). As with the present invention, CNTF receptor (the ligand specific binding component) must be present for signaling to occur but it need not be membrane bound (Economides et al., Science, 270, 1351–1353, 1995).

As further described below, the GDNFR protein may be anchored to a cell surface, or it may be provided in a soluble form. In either case, the GDNFR protein forms a ligand complex with GDNF and/or neurturin, and the ligand complex binds to cell surface receptor to effectuate intracellular signaling. Thus, a soluble form of GDNFR protein may be used to potentiate the action of a neurotrophic factor that binds thereto and/or modify its cell-type specificity.

The GDNFR proteins are unrelated to previously known receptors. There are no apparent matches in the GenBank and Washington University-Merck databases for related sequences. An expressed sequence tag (EST) found in the Washington University-Merck EST database shows 75% homology to a small portion of the coding region of GDNFR-α (approximately 340 nucleotides of the 521 nucleotides of sequence generated from the 5' end of the clone). This clone (GenBank accession #H12981) was isolated from an oligo-dT primed human infant brain library and cloned directionally into the Lafmid BA vector (Hillier, L. et al, unpublished data). The 3' end of the #H12981 clone has been sequenced, but it exhibits no homology to any part of GDNFR-α. The appearance of homology between this #H12981 clone and GDNFR-α over a short region, which homology then disappears, suggests that the #H12981 clone represents an unspliced transcript, or cloning artifact rather than a bona fide cDNA transcript.

Thus, the present invention enables the cloning of a GDNFR protein by providing a method for selecting target cells which express GDNFR protein. By providing a means of enriching for GDNFR protein-encoding sequences, the present invention further provides for the purification of GDNFR protein and the direct cloning of GDNFR-encoding DNA. The present description of the GDNFR nucleic acid and amino acid sequences provides the information needed to reproduce these entities as well as a variety of GDNFR analogs. With this information, GDNFR protein products may be isolated or generated by any means known to those skilled in the art. A variety of means for the recombinant or synthetic production of GDNFR protein are disclosed.

As used herein, the term "GDNFR protein product" includes biologically active purified natural, synthetic or recombinant GDNFR-α, GRR2 and GRR3 (jointly referred to as glial cell line derived neurotrophic factor receptors, GDNFR, GDNFR protein), GDNFR analogs (i.e., GDNFR homologs and variants involving insertion, substitution and deletion variations, such as based on the consensus sequences depicted in the Figures), and chemically modified derivatives thereof. GDNFR analogs are substantially homologous to the GDNFR amino acid sequences set forth in the Figures.

The term "biologically active", as used herein, means that the GDNFR protein product demonstrates high affinity binding to GDNF and/or neurturin and mediates or enhances GDNF-induced or neurturin-induced signal transduction. Using the present disclosure, it is well within the ability of those of ordinary skill in the art to determine whether a GDNFR protein analog has substantially the same biological activity as the GDNFR protein products set forth in the Figures.

The term "substantially homologous" amino acid sequence, as used herein, refers to an amino acid sequence sharing a degree of "similarity" or homology to the GDNFR amino acid sequences set forth in the Figures such that the homologous sequence has a biological activity or function similar to that described for these GDNFR amino acid sequences. It will be appreciated by those skilled in the art, that a relatively large number of individual or grouped amino acid residues can be changed, positionally exchanged (e.g.s, reverse ordered or reordered) or deleted entirely in an amino acid sequence without affecting the three dimensional configuration or activity of the molecule. Such modifications are well within the ability of one skilled in the art following the present disclosure. The identification and means of providing such modified sequences are described in greater detail below. It is preferable that the degree of homology of a substantially homologous protein (peptide) is equal to or in excess of 70% (i.e., a range of from 70% to 100% homology). Thus, a preferable "substantially homologous" GDNFR amino acid sequence may have a degree of homology greater than or equal to 70% of the amino acid sequences set forth for GDNFR-α, GRR2, GRR3 and consensus sequences thereof as depicted in the Figures. More preferably the degree of homology may be equal to or in excess of 80% or 85%. Even more preferably it is equal to or in excess of 90%, or most preferably it is equal to or in excess of 95%.

The percentage of homology as described herein is calculated as the percentage of amino acid residues found in one protein sequence which align with identical or similar amino acid residues in the second protein sequence. Thus, in the case of GDNFR protein homology, the degree of sequence homology may be determined by optimally aligning the amino acid residues of the comparison molecule to those of a reference GDNFR polypeptide, such as depicted in the Figures or those encoded by the nucleic acid sequences depicted in the Figures, to maximize matches of residues between the two sequences. It will be appreciated by those skilled in the art that such alignment may include appropriate conservative residue substitutions and will disregard truncations and internal deletions or insertions of the comparison sequence by introducing gaps as required; see, for example Dayhoff, Adas of Protein Sequence and Structure Vol. 5, wherein an average of three or four gaps in a length of 100 amino acids may be introduced to assist in alignment (p. 124, National Biochemical Research Foundation, Washington, D.C., 1972; the disclosure of which is hereby incorporated by reference). Once so aligned, the percentage is determined by the number of aligned residues in the comparison polypeptide divided by the total number of residues in the comparison polypeptide. It is further contemplated that the GDNFR protein sequences of the present invention may be used to form a portion of a fusion protein or chimeric protein which has, at least in part, GDNFR protein activity. The alignment and homology of such a protein would be determined using that portion of the fusion protein or chimeric protein which is related to GDNFR protein activity.

The sources of such substantially homologous GDNFR proteins include the GDNFR proteins of other mammals (such as depicted in the Figures) which are expected to have a high degree of homology to the human GDNFR protein. For example, the degree of homology between the rat and human GDNFR proteins disclosed herein is about 93%. Substantially homologous GDNFR proteins may be isolated from such mammals by virtue of cross-reactivity with antibodies to the GDNFR amino acid sequences depicted in the Figures. Alternatively, they may be expressed by nucleic acid sequences which are isolated through hybridization with the gene or with segments of the gene encoding the GDNFR proteins or which hybridize to a complementary sequence of the nucleic acid sequences illustrated in the Figures. Suitable hybridization conditions are described in further detail below.

The novel GDNFR protein products are typically isolated and purified to form GDNFR protein products which are substantially free of unwanted substances that would detract from the use of the present polypeptides for an intended purpose. For example, preferred GDNFR protein products may be substantially free from the presence of other human (e.g., non-GDNFR) proteinaceous materials or pathological agents. Preferably, the GDNFR protein products are about 80% free of other proteins which may be present due to the production technique used in the manufacture of the GDNFR protein product. More preferably, the GDNFR protein products are about 90% free of other proteins, particularly preferably, about 95% free of other proteins, and most preferably about >98% free of other proteins. In addition, the present invention furnishes the unique advantage of providing polynucleotide sequences for the manufacture of homogeneous GDNFR proteins.

Figure 2A:
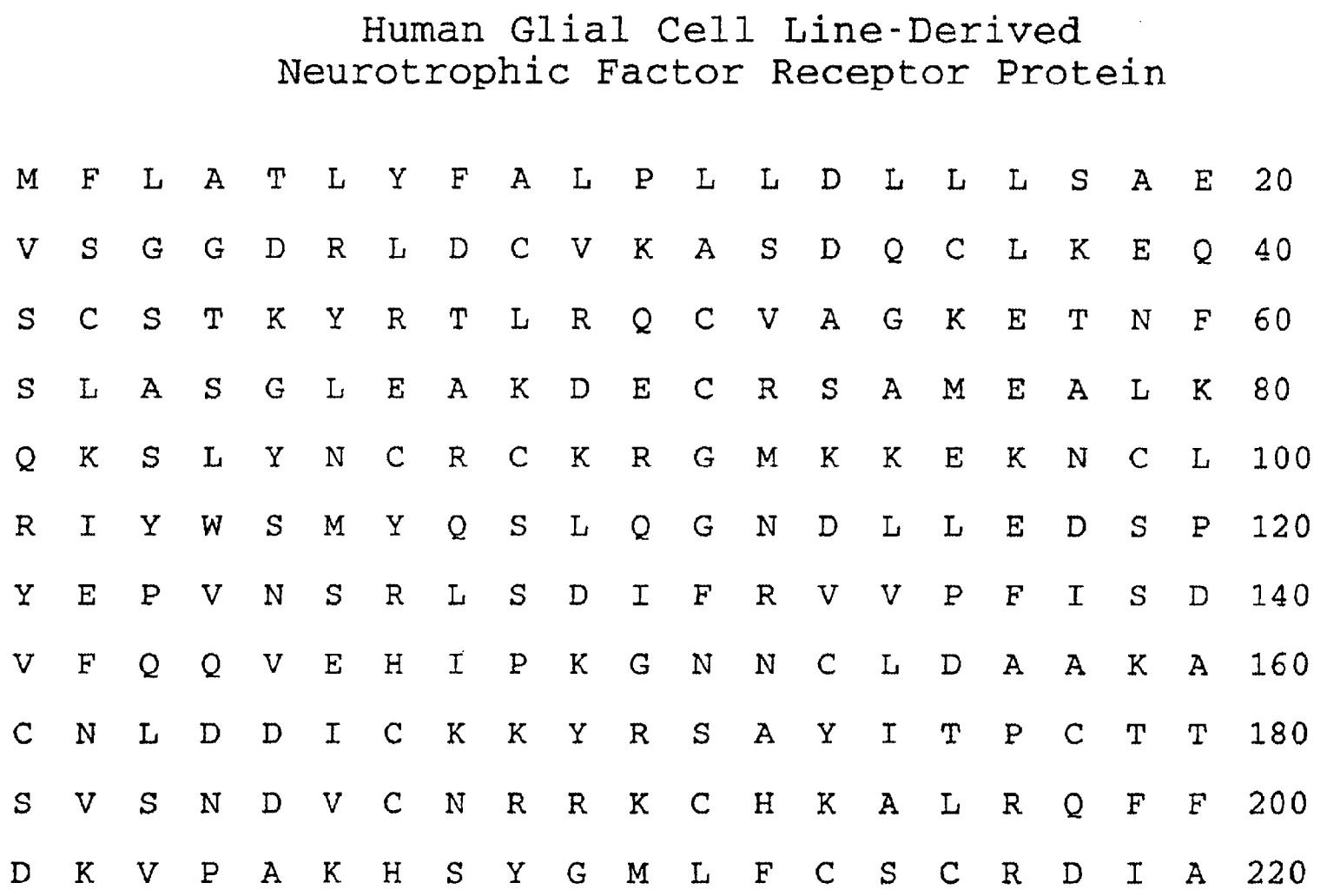
Figure 4B:
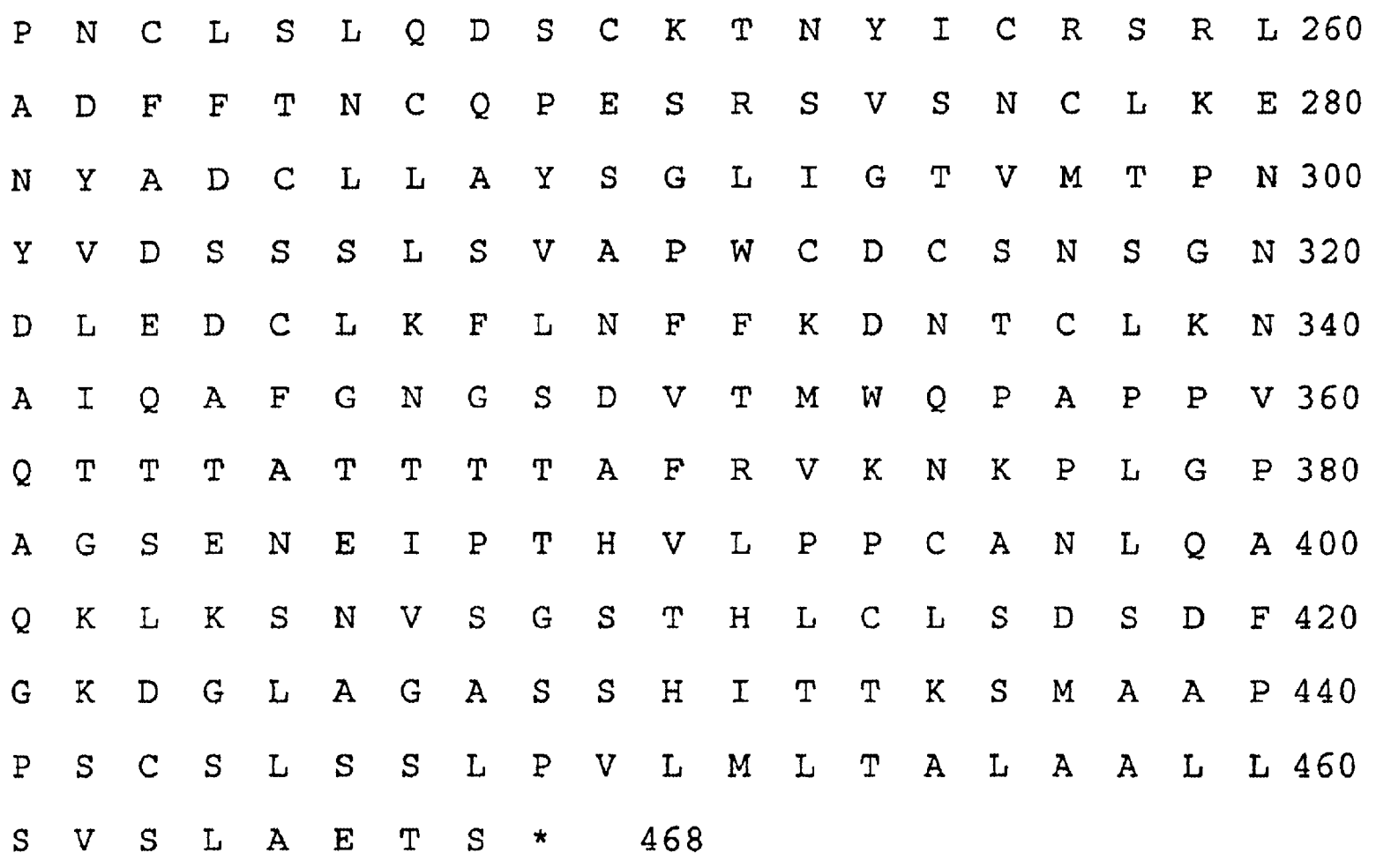

A variety of GDNFR variants are contemplated, including addition, deletion and substitution variants. For example, a series of deletion variants may be made by removing one or more amino acid residues from the amino and/or carboxy termini of the GDNFR protein. Using rules for the prediction of signal peptide cleavage as described by von Heijne (von Heijne, Nucleic Acids Research, 14, 4683–4690, 1986), the first amino acid residue of the GDNFR-α protein which might be involved in GDNF binding is $Ser^{18}$, as depicted in the full length amino acid sequence of human GDNFR-α in FIG. 2 (SEQ ID NO:2). Amino acid residues $Met^1$ through $Ser^{18}$ are in the amino-terminal hydrophobic region that is likely to be part of a signal peptide sequence, and therefore, not be included in the mature form of the receptor protein. Similarly, the last amino acid residue of the GDNFR-α protein which is likely to be necessary for GDNF binding is $Ser^{446}$. Amino acid residues $Leu^{447}$ through $Ser^{465}$ are in the carboxy-terminal hydrophobic region that is involved in the GPI linkage of the protein to the cell surface. Thus, it is contemplated that any or all of the residues from $Met^1$ through $Ser^{18}$ and/or $Leu^{447}$ through $Ser^{465}$ (as depicted in FIG. 2 (SEQ ID NO:2) may be removed from the protein without affecting GDNF binding to the GDNFR-α protein, thereby leaving a "core" sequence of $Ala^{19}$ through $Pro^{446}$. Using known analysis techniques, it is further contemplated that N-terminal truncations may include the removal of one or more amino acid residues up to and including $Gly^{24}$. Thus, GDNFR-α truncation analogs also may include the deletion of one or more amino acid residues from either or both termini such that an amino acid sequence of $Asp^{25}$ through $Pro^{446}$ or $Leu^{447}$ forms the basis for a core molecule. Additional GDNFR-α analogs are contemplated as involving amino acid residues $Ser^{18}$ through $Pro^{449}$ as depicted in the GDNFR-α amino acid sequence of FIG. 4 (SEQ ID NO:4), i.e., deleting one or more amino acid residues from either or both termini involving the hydrophobic regions depicted as amino acid residues $Met^1$ through $Ser^{18}$ and/or $Pro^{449}$ through $Ser^{468}$. Similar analogs may be designed using the amino acid sequences for GRR2 and GRR3, as well as consensus sequences, as depicted in the Figures.

In addition, it is contemplated that one or more amino acid residues may be removed from either or both of the amino and carboxy termini of the GDNFR protein until the first and last cysteine residues in the full length sequence are reached. It is advantageous to retain the cysteine residues for the proper intramolecular binding of the GDNFR protein. As depicted in the full length amino acid sequence of human GDNFR-α in FIG. 2 (SEQ ID NO:2), any or all of amino acid residues from $Met^1$ to $Asp^{28}$ may be removed from the amino terminal without removing the first cysteine residue which appears as $Cys^{29}$. Similarly, any or all of amino acid residues from $Gly^{443}$ to $Ser^{465}$ may be removed from the carboxy terminal without removing the last cysteine residue which appears as $Cys^{442}$. Other GDNFR-α analogs may be made using amino acid residues $Cys^{29}$ through $Cys^{443}$ as depicted in the GDNFR-α amino acid sequence of FIG. 4 (SEQ ID NO:4), i.e., deleting all or part of the terminal regions depicted as amino acid residues $Met^1$ through $Asp^{28}$ and/or $Ser^{444}$ through $Ser^{468}$. Similar analogs may be designed using the amino acid sequences for GRR2 and GRR3, as well as consensus sequences, as depicted in the Figures.

It will be appreciated by those skilled in the art that, for the same reasons, it is contemplated that these identified amino acid residues may be replaced, rather than deleted, without affecting the function of the GDNFR protein. Alternatively, these identified amino acid residues may be modified by intra-residue insertions or terminal additions without affecting the function of the GDNFR protein. In yet another embodiment, a combination of one or more deletions, substitutions or additions may be made.

The present GDNFR proteins or nucleic acids may be used for methods of treatment, or for methods of manufacturing medicaments for treatment. Such treatment includes conditions characterized by excessive production of GDNF or neurturin, wherein the present GDNFRs, particularly in soluble form, may be used to complex to and therefore inactivate such excessive GDNF or neurturin. This treatment may be accomplished by preparing a soluble receptor (e.g., use of the GDNF or neurturin binding domain) or by preparation of a population of cells containing such GDNFR, and transplanting such cells into the individual in need thereof. The present GDNFR protein products may also be used for treatment of those having defective GDNF and/or neurturin receptors. For example, one may treat an individual having defective GDNFRs by preparation and delivery of a soluble receptor, or by preparation of a population of cells containing such non-defective GDNFR and transplanting such cells into an individual. Or, an individual may have an inadequate number of GDNF or neurturin receptors, and cells containing such receptors may be transplanted in order to increase the number of GDNF or neurturin receptors available to an individual. Such compositions may be used in conjunction with the delivery of GDNF or neurturin. It is also contemplated GDNFR protein products may be used in the treatment of conditions responsive to the activation of the c-ret receptor tyrosine kinase.

In yet another aspect of the present invention, a further advantage to the novel compositions is the use of GDNFR to stabilize GDNF protein or neurturin pharmaceutical compositions. In another aspect of the present invention, a GDNFR may be used to screen compounds for antagonist activity.

Other aspects and advantages of the present invention will be apparent to those skilled in the art. For example, additional uses include new assay systems, transgenic animals and antibody production.

Study Models

The present invention provides for assay systems in which GDNF or neurturin activity or activities similar to GDNF or neurturin activity resulting from exposure to a peptide or non-peptide compound may be detected by measuring an elicited physiological response in a cell or cell line which expresses the GDNFR molecules of the present invention. A physiological response may comprise any of the biological effects of GDNF or neurturin, including but not limited to, dopamine uptake, extension of neurites, increased cell survival or growth, as well as the transcriptional activation of certain nucleic acid sequences (e.g. promoter/enhancer elements as well as structural genes), GDNF-related processing, translation, or phosphorylation, and the induction of secondary processes in response to processes directly or indirectly induced by GDNF, to name but a few.

For example, a model system may be created which may be used to study the effects of excess GDNF activity. In such a system, the response of a cell to GDNF may be increased by engineering an increased number of suitable GDNFRs on the cells of the model system relative to cells which have not been so modified. A system may also be developed to selectively provide an increased number of such GDNFRs on cells which normally express GDNFRs. In order to ensure expression of GDNFR, the GDNFR gene may be placed under the control of a suitable promoter sequence. It may be desirable to put the GDNFR gene under the control of a constitutive and/or tissue specific promoter (including but not limited to the CNS neuron specific enolase, neurofilament, and tyrosine hydroxylase promoter), an inducible promoter (such as the metallothionein promoter), the UV activated promoter in the human immunodeficiency virus long terminal repeat (Valeri et al., 1988, Nature 333:78–81), or the CMV promoter (as contained in pCMX, infra) or a developmentally regulated promoter.

By increasing the number of cellular GDNFRs, the response to endogenous GDNF may be increased. If the model system contains little or no GDNF, GDNF may be added to the system. It may also be desirable to add additional GDNF to the model system in order to evaluate the effects of excess GDNF activity. Over expressing GDNF (or secreted GDNF) may be one method for studying the effects of elevated levels of GDNF on cells already expressing GDNFR.

GDNFR Therapies

In another aspect, certain conditions may benefit from an increase in GDNF and/or neurturin responsiveness. It may, therefore, be beneficial to increase the number or binding affinity of GDNFRs in patients suffering from conditions responsive to GDNF and/or neurturin therapy. This could be achieved through gene therapy, whereby selective expression of recombinant GDNFR in appropriate cells is achieved, for example, by using GDNFR genes controlled by tissue specific or inducible promoters or by producing localized infection with replication defective viruses carrying a recombinant GDNFR gene.

It is envisioned that conditions which will benefit from GDNFR or combined GDNF or neurturin/GDNFR delivery include, but are not limited to, motor neuron disorders including amyotrophic lateral sclerosis, neurological disorders associated with diabetes, Parkinson's disease, Alzheimer's disease, and Huntington's chorea. Additional indications for the use of GDNFR or combined GDNF or neurturin/GDNFR delivery are described above and further include the treatment of: glaucoma or other diseases and conditions involving retinal ganglion cell degeneration; sensory neuropathy caused by injury to, insults to, or degeneration of, sensory neurons; pathological conditions, such as inherited retinal degenerations and age, disease or injury-related retinopathies, in which photoreceptor degeneration occurs and is responsible for vision loss; and injury or degeneration of inner ear sensory cells, such as hair cells and auditory neurons for preventing and/or treating hearing loss due to variety of causes.

Transgenic Animals

In yet another aspect, a recombinant GDNFR gene may be used to inactivate or "knock out" the endogenous gene (e.g., by homologous recombination) and thereby create a GDNFR deficient cell, tissue, or animal. For example, a recombinant GDNFR-α gene may be engineered to contain an insertional mutation which inactivates GDNFR-α Such a construct, under the control of a suitable promoter, may be introduced into a cell, such as an embryonic stem cell, by any conventional technique including transfection, transduction, injection, etc. Cells containing the construct may then be selected, for example by G418 resistance. Cells which lack an intact GDNFR-α gene are then identified (e.g., by Southern blotting or Northern blotting or assay of expression). Cells lacking an intact GDNFR-α gene may then be fused to early embryo cells to generate transgenic animals deficient in GDNFR. A comparison of such an animal with an animal not expressing endogenous GDNF would reveal that either the two phenotypes match completely or that they do not, implying the presence of additional GDNF-like factors or receptors. Such an animal may be used to define specific neuronal populations, or other in vivo processes, normally dependent upon GDNF. Thus, these populations or processes may be expected to be effected if the animal did not express GDNFR-α, and therefore, could not respond to GDNF. Similar constructs may be made and procedures followed for GRR2 and GRR3.

Diagnostic Applications

According to the present invention, GDNFR probes may be used to identify cells and tissues which are responsive to GDNF or neurturin in normal or diseased states. The present invention provides for methods for identifying cells which are responsive to GDNF or neurturin by detecting GDNFR expression in such cells. GDNFR expression may be evidenced by transcription of GDNFR mRNA or production of GDNFR protein. GDNFR expression may be detected using probes which identify GDNFR nucleic acid or protein or by detecting "tag" sequences artificially added to the GDNFR protein.

One variety of probe which may be used to detect GDNFR expression is a nucleic acid probe, which may be used to detect GDNFR-encoding RNA by any method known in the art, including, but not limited to, in situ hybridization, Northern blot analysis, or PCR related techniques. Nucleic acid products of the invention may be labeled with detectable markers (such as radiolabels and non-isotopic labels such as biotin) and employed in hybridization processes to locate the human GDNFR gene position and/or the position of any related gene family in a chromosomal map. They may also be used for identifying human GDNFR gene disorders at the DNA level and used as gene markers for identifying neighboring genes and their disorders. Contemplated herein are kits containing such labeled materials.

Polypeptide products of the invention may be "labeled" by association with a detectable marker substance or label (e.g., a radioactive isotope, a fluorescent or chemiluminescent chemical, an enzyme or other label available to one skilled in the art) to provide reagents useful in detection and quantification of GDNF or neurturin in solid tissue and fluid samples such as blood or urine. Such products may also be used in detecting cells and tissues which are responsive to GDNF or neurturin in normal or diseased states.

Another possible assay for detecting the presence of GDNF or neurturin in a test sample or screening for the presence of a GDNF-like molecule involves contacting the test sample with a GDNFR protein, suitable for binding GDNF or neurturin, immobilized on a solid phase, thereby producing GDNFR-bound GDNF or neurturin protein. The GDNFR-bound GDNF or neurturin may optionally be contacted with a detection reagent, such as a labeled antibody specific for GDNF or neurturin, thereby forming a detectable product. Such assays may be developed in the form of assay devices for analyzing a test sample. In a basic form, such devices include a solid phase containing or coated with an appropriate GDNFR protein. A method for analyzing a test sample for the presence of GDNF-like protein may involve contacting the sample to an assay reagent comprising GDNFR protein, wherein said GDNFR protein reacts with the GDNF-like protein present in the test sample and produces a detectable reaction product indicative of the presence of GDNF.

The assay reagents provided herein may also be embodied as part of a kit or article of manufacture. Contemplated is an article of manufacture comprising a packaging material and one or more preparations of the presently provided nucleic acid or amino acid sequences. Such packaging material will comprise a label indicating that the preparation is useful for detecting GDNF, neurturin, GDNFR or GDNFR defects in a biological sample. As such, the kit may optionally include materials to carry out such testing, such as reagents useful for performing protein analysis, DNA or RNA hybridization analysis, or PCR analysis on blood, urine, or tissue samples.

Anti-GDNFR Antibody

According to the present invention, GDNFR protein, or fragments or derivatives thereof, may be used as an immunogen to generate anti-GDNFR antibodies. To further improve the likelihood of producing an anti-GDNFR immune response, the amino acid sequence of GDNFR may be analyzed in order to identify portions of the molecule which may be associated with increased immunogenicity. For example, the amino acid sequence may be subjected to computer analysis to identify surface epitopes which present computer-generated plots of hydrophilicity, surface probability, flexibility, antigenic index, amphiphilic helix, amphiphilic sheet, and secondary structure of GDNFR. Alternatively, the amino acid sequences of GDNFR from different species could be compared, and relatively non-homologous regions identified; these non-homologous regions would be more likely to be immunogenic across various species.

Also comprehended are polypeptide fragments duplicating only a part of the continuous amino acid sequence or secondary conformations within GDNFR, which fragments may possess one activity of mammalian GDNFR (e.g., immunological activity) and not others (e.g., GDNF protein binding activity). Thus, the production of antibodies can include the production of anti-peptide antibodies. The following exemplary peptides were synthesized using GDNFR sequences:

TABLE 1

| GDNFR-α Peptides | | |
|---|---|---|
| SJP-6 | H$_2$N-QSCSTKYRTL-COOH | human GDNFR-α, AA 40–49 (SEQ ID NO:25) |
| SJP-7 | H$_2$N-CKRGMKKEKN-COOH | human GDNFR-α, AA 89–98 (SEQ ID NO:26) |
| SJP-8 | H$_2$N-LLEDSPYEPV-COOH | human GDNFR-α, AA 115–124 (SEQ ID NO:27) |
| SJP-9 | H$_2$N-CSYEERERPN-COOH | rat GDNFR-α, AA 233–242 (SEQ ID NO:28) |
| SJP-10 | H$_2$N-PAPPVQTTTATTTT-COOH | rat GDNFR-α, AA 356–369 (SEQ ID NO:29) |

Peptides SJP-6, 7, and 8 are identical in rat and human GDNFR-α. Peptides SJP-9 and 10 are derived from the rat sequence and are each one amino acid different from human. Both polyclonal and monoclonal antibodies may be made by methods known in the art using these peptides or other portions of GDNFR.

Monoclonal antibodies directed against GDNFR may be prepared by any known technique which provides for the production of antibody molecules by continuous cell lines in culture. For example, the hybridoma technique originally developed by Kohler and Milstein to produce monoclonal antibodies (Nature, 256:495–497, 1975), as well as the trioma technique, the human B-cell hybridoma technique (Kozbor et al., Immunology Today 4:72, 1983), the EBV-hybridoma technique (Cole et al., in "Monoclonal Antibodies and Cancer Therapy," Alan R. Liss, Inc. pp. 77–96, 1985), and the like, may be used.

Human monoclonal antibodies or chimeric human-mouse (or other species) monoclonal antibodies also may be prepared for therapeutic use and may be made by any of numerous techniques known in the art (e.g., Teng et al., Proc. Natl. Acad. Sci. U.S.A., 80:7308–7312, 1983; Kozbor et al., Immunology Today, 4:72–79, 1983; Olsson et al., Meth. Enzymol., 92:3–16, 1982). Chimeric antibody molecules may be prepared containing a mouse antigen-binding domain with human constant regions (Morrison et al., Proc. Natl. Acad. Sci. U.S.A., 81:6851, 1984; Takeda et al., Nature, 314:452, 1985).

Various procedures known in the art also may be used for the production of polyclonal antibodies. For the production of antibody, various host animals including, but not limited to, rabbits, mice, rats, etc., can be immunized by injection with GDNFR protein, or a fragment or derivative thereof. Various adjuvants may be used to increase the immunological response, depending on the host species selected. Useful adjuvants include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and human adjuvants such as BCG (Bacille Calmette-Guerin) and Corynebacterium parvum.

A molecular clone of an antibody to a GDNFR epitope also may be prepared by known techniques. Recombinant DNA methodology (see e.g., Maniatis et al., Molecular Cloning, A Laboratory Manual, Cold Spring Harbor Laboratory, Cold Spring Harbor, N.Y., 1982) may be used to construct nucleic acid sequences which encode a monoclonal antibody molecule, or antigen binding region thereof.

Antibody molecules may be purified by known techniques, e.g., immunoabsorption or immunoaffinity chromatography, chromatographic methods such as high performance liquid chromatography, or a combination thereof, etc. The present invention provides for antibody molecules as well as fragments of such antibody molecules. Antibody fragments which contain the idiotype of the molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent.

Such selective binding molecules may themselves be alternatives to GDNFR protein, and may be formulated as a pharmaceutical composition.

Recombinant Expression of GDNFR Protein

The present invention provides various polynucleotides encoding GDNFR proteins. The expression product or a derivative thereof is characterized by the ability to bind to GDNF or neurturin so that further interactions with signaling molecules can occur, thereby providing or enhancing GDNF or neurturin activity such as increasing dopamine uptake by dopaminergic cells. The polynucleotides may also be used in cell therapy or gene therapy applications.

According to the present invention, novel GDNFR protein and DNA sequences coding for all or part of such receptors are provided. Novel nucleic acid sequences of the invention are useful in securing expression in procaryotic or eucaryotic host cells of polypeptide products having at least a part of the primary structural conformation and one or more of the biological properties of recombinant human GDNFR. The nucleic acids may be purified and isolated, so that the desired coding region is useful to produce the present polypeptides. Alternatively, the nucleic acid sequence may be used for diagnostic purposes, as described more fully below. Exemplary DNA sequences of the present invention comprise nucleic acid sequences encoding the GDNFR-α amino acid sequences depicted in FIGS. 2 and 4 and set forth in SEQ. ID NOS:2 and 4. In addition, DNA sequences disclosed by the present invention include: (a) the GDNFR DNA sequences depicted in the Figures (and complementary strands); (b) a DNA sequence which hybridizes (under hybridization conditions disclosed in the cDNA library screening section below, or equivalent conditions or more stringent conditions) to the DNA sequence in subpart (a) or to fragments thereof; and (c) a DNA sequence which, but for the degeneracy of the genetic code, would hybridize to the DNA sequence in subpart (a). Specifically comprehended in parts (b) and (c) are genomic DNA sequences encoding allelic variant forms of human GDNFR and/or encoding GDNFR from other mammalian species, and manufactured DNA sequences encoding GDNFR, fragments of GDNFR, and analogs of GDNFR which DNA sequences may incorporate codons facilitating transcription and translation of messenger RNA in microbial hosts. Such manufactured sequences may readily be constructed according to the methods known in the art as well as the methods described herein.

Recombinant expression techniques, conducted in accordance with the descriptions set forth herein or other known methods, may be used to produce these polynucleotides and express the various GDNFR proteins. For example, by inserting a nucleic acid sequence which encodes a GDNFR protein into an appropriate vector, one skilled in the art can readily produce large quantities of the desired nucleotide sequence. The sequences can then be used to generate detection probes or amplification primers. Alternatively, a polynucleotide encoding a GDNFR protein can be inserted into an expression vector. By introducing the expression vector into an appropriate host, the desired GDNFR protein may be produced in large amounts.

As further described herein, there are numerous host/vector systems available for the propagation of nucleic acid sequences and/or the production of GDNFR proteins. These include, but are not limited to, plasmid, viral and insertional vectors, and prokaryotic and eukaryotic hosts. One skilled in the art can adapt a host/vector system which is capable of propagating or expressing heterologous DNA to produce or express the sequences of the present invention.

By means of such recombinant techniques, the GDNFR proteins of the present invention are readily produced in commercial quantities with greater purity. Furthermore, it will be appreciated by those skilled in the art that, in view of the present disclosure, the novel nucleic acid sequences include degenerate nucleic acid sequences encoding the GDNFR proteins specifically set forth in the Figures, sequences encoding variants of GDNFR proteins, and those nucleic acid sequences which hybridize, preferably under stringent hybridization conditions, to complements of these nucleic acid sequences (see, Maniatis et. al., Molecular Cloning (A Laboratory Manual); Cold Spring Harbor Laboratory, pages 387 to 389, 1982.) Exemplary stringent hybridization conditions are hybridization in 4×SSC at 62–67° C., followed by washing in 0.1×SSC at 62–67° C. for approximately an hour. Alternatively, exemplary stringent hybridization conditions are hybridization in 45–55% formamide, 4×SSC at 40–45° C. DNA sequences which hybridize to the complementary sequences for GDNFR protein under relaxed hybridization conditions and which encode a GDNFR protein of the present invention are also included herein. Examples of such relaxed stringency hybridization conditions are 4×SSC at 45–55° C. or hybridization with 30–40% formamide at 40–45° C.

Preparation of Polynucleotides Encoding GDNFR

Based upon the disclosure of the present invention, a nucleic acid sequence encoding a full length GDNFR protein or a fragment thereof may readily be prepared or obtained by a variety of means, including, without limitation, chemical synthesis, cDNA or genomic library screening, expression library screening, and/or PCR amplification of cDNA. These methods and others useful for preparing nucleic acid sequences are known in the art and are set forth, for example, by Sambrook et al. (Molecular Cloning: A Laboratory Manual, Cold Spring Harbor Laboratory Press, Cold Spring Harbor, N.Y., 1989), by Ausubel et al., eds (Current Protocols in Molecular Biology, Current Protocols Press, 1994), and by Berger and Kimmel (Methods in Enzymology: Guide to Molecular Cloning Techniques, vol. 152, Academic Press, Inc., San Diego, Calif., 1987). Preferred nucleic acid sequences encoding GDNFR are mammalian sequences.

Chemical synthesis of a nucleic acid sequence which encodes a GDNFR protein can also be accomplished using methods known in the art, such as those set forth by Engels et al. (Angew. Chem. Intl. Ed., 28:716–734, 1989). These methods include, inter alia, the phosphotriester, phosphoramidite and H-phosphonate methods of nucleic acid sequence synthesis. A preferred method for such chemical synthesis is polymer-supported synthesis using standard phosphoramidite chemistry. Typically, the DNA encoding the desired polypeptide will be several hundred base pairs (bp) or nucleotides in length. Nucleic acid sequences larger than about 100 nucleotides can be synthesized as several fragments using these methods. The fragments can then be ligated together to form a sequence for the expression of a full length GDNFR protein or a portion thereof.

Alternatively, a suitable nucleic acid sequence may be obtained by screening an appropriate cDNA library (i.e., a library prepared from one or more tissue source(s) believed to express the protein) or a genomic library (a library prepared from total genomic DNA). The source of the cDNA library is typically a tissue that is believed to express GDNFR in reasonable quantities. Typically, the source of the genomic library is any tissue or tissues from a mammalian species believed to harbor a gene encoding GDNFR. The library can be screened for the presence of the GDNFR cDNA/gene using one or more nucleic acid probes (such as oligonucleotides, cDNA or genomic DNA fragments based upon the presently disclosed sequences) that will hybridize selectively with GDNFR cDNA(s) or gene(s) present in the library. The probes typically used for such library screening usually encode a small region of the GDNFR nucleic acid sequence from the same or a similar species as the species from which the library was prepared. Alternatively, the probes may be degenerate, as discussed herein.

Library screening is typically accomplished by annealing the oligonucleotide probe or cDNA to the clones in the library under conditions of stringency that prevent non-specific binding but permit binding (hybridization) of those clones that have a significant level of homology with the probe or primer. Typical hybridization and washing stringency conditions depend in part on the size (i.e., number of nucleotides in length) of the cDNA or oligonucleotide probe, and whether the probe is degenerate. The probability of obtaining a clone(s) is also considered in designing the hybridization solution (e.g., whether a cDNA or genomic library is being screened; if it is a cDNA library, the probability that the cDNA of interest is present at a high level).

Where DNA fragments (such as cDNAs) are used as probes, typical hybridization conditions include those as set forth in Ausubel et al., eds., supra. After hybridization, the blot containing the library is washed at a suitable stringency, depending on several factors such as probe size, expected homology of probe to clone, type of library being screened, number of clones being screened, and the like. Examples of stringent washing solutions (which are usually low in ionic strength and are used at relatively high temperatures) are as follows. One such stringent wash is 0.015 M NaCl, 0.005 M NaCitrate and 0.1% SDS at 55–65° C. Another such stringent buffer is 1 mM $Na_2EDTA$, 40 mM $NaHPO_4$, pH 7.2, and 1% SDS at about 40–50° C. One other stringent wash is 0.2×SSC and 0.1% SDS at about 50–65° C.

There are also exemplary protocols for stringent washing conditions where oligonucleotide probes are used to screen cDNA or genomic libraries. For example, a first protocol uses 6×SSC with 0.05 percent sodium pyrophosphate at a temperature of between about 35 and 62° C., depending on the length of the probe. For example, 14 base probes are washed at 35–40° C., 17 base probes at 45–50° C., 20 base probes at 52–57° C., and 23 base probes at 57–63° C. The temperature can be increased 2–3° C. where the background non-specific binding appears high. A second protocol uses tetramethylammonium chloride (TMAC) for washing. One such stringent washing solution is 3 M TMAC, 50 mM Tris-HCl, pH 8.0, and 0.2% SDS.

Another suitable method for obtaining a nucleic acid sequence encoding a GDNFR protein is by polymerase chain reaction (PCR). In this method, poly(A)+RNA or total RNA is extracted from a tissue that expresses GDNFR. A cDNA is then prepared from the RNA using the enzyme reverse transcriptase (i.e., RT-PCR). Two primers, typically complementary to two separate regions of the GDNFR cDNA (oligonucleotides), are then added to the cDNA along with a polymerase such as Taq polymerase, and the polymerase amplifies the cDNA region between the two primers.

Where the method of choice for preparing the nucleic acid sequence encoding the desired GDNFR protein requires the use of oligonucleotide primers or probes (e.g., PCR, cDNA or genomic library screening), the oligonucleotide sequences selected as probes or primers should be of adequate length and sufficiently unambiguous so as to mninimize the amount of non-specific binding that will occur during library screening or PCR amplification. The actual sequence of the probes or primers is usually based on conserved or highly homologous sequences or regions from the same or a similar gene from another organism, such as the rat nucleic acid sequence involved in the present invention. Optionally, the probes or primers can be fully or partially degenerate, i.e., contain a mixture of probes/primers, all encoding the same amino acid sequence, but using different codons to do so. An alternative to preparing degenerate probes is to place an inosine in some or all of those codon positions that vary by species. The oligonucleotide probes or primers may be prepared by chemical synthesis methods for DNA as described above.

GDNFR proteins based on these nucleic acid sequences encoding GDNFR, as well as mutant or variant sequences thereof, are also contemplated as within the scope of the present invention. Mutant or variant sequences include those sequences containing one or more nucleotide substitutions, deletions, and/or insertions as compared to the wild type sequence and that results in the expression of amino acid sequence variations as compared to the wild type amino acid sequence. In some cases, naturally occurring GDNFR amino acid mutants or variants may exist, due to the existence of natural allelic variation. GDNFR proteins based on such naturally occurring mutants or variants are also within the scope of the present invention. Preparation of synthetic mutant sequences is also well known in the art, and is described for example in Wells et al. (Gene, 34:315, 1985) and in Sambrook et al., supra.

In some cases, it may be desirable to prepare nucleic acid and/or amino acid variants of naturally occurring GDNFR. Nucleic acid variants (wherein one or more nucleotides are designed to differ from the wild-type or naturally occurring GDNFR) may be produced using site directed mutagenesis or PCR amplification where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well. Preferred nucleic acid variants are those containing nucleotide substitutions accounting for codon preference in the host cell that is to be used to recombinantly produce GDNFR. Other preferred variants are those encoding conservative amino acid changes (e.g., wherein the charge or polarity of the naturally occurring amino acid side chain is not altered substantially by substitution with a different amino acid) as compared to wild type, and/or those designed to either generate a novel glycosylation and/or phosphorylation site(s) on GDNFR, or those designed to delete an existing glycosylation and/or phosphorylation site(s) on GDNFR. Yet other preferred variants are those encoding a GDNFR based upon a GDNFR consensus sequence as depicted in the Figures.

Vectors

The cDNA or genomic DNA encoding the desired GDNFR protein is inserted into a vector for further cloning (amplification of the DNA) or for expression. Suitable vectors are commercially available, or the vector may be specially constructed. Possible vectors include, but are not limited to, cosmids, plasmids or modified viruses, but the vector system must be compatible with the selected host cell. Such vectors include, but are not limited to, bacteriophages such as lambda derivatives, or plasmids such as pBR322, pUC, or Bluescript® plasmid derivatives (Stratagene, La Jolla Calif.). The recombinant molecules can be introduced into host cells via transformation, transfection, infection, electroporation, or other known techniques.

For example, the GDNFR-encoding nucleic acid sequence is inserted into a cloning vector which is used to transform, transfect, or infect appropriate host cells so that many copies of the nucleic acid sequence are generated. This can be accomplished by ligating a DNA fragment into a cloning vector which has complementary cohesive termini. If the complementary restriction sites used to fragment the DNA are not present in the cloning vector, the ends of the DNA molecules may be enzymatically modified. It also may prove advantageous to incorporate restriction endonuclease cleavage sites into the oligonucleotide primers used in polymerase chain reaction to facilitate insertion of the resulting nucleic acid sequence into vectors. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and GDNFR-encoding nucleic acid sequence may be modified by homopolymeric tailing. In specific embodiments, transformation of host cells with recombinant DNA molecules that incorporate an isolated GDNFR gene, cDNA, or synthesized DNA sequence enables generation of multiple copies of the gene. Thus, the GDNFR-encoding nucleic acid sequence may be obtained in large quantities by growing transformants, isolating the recombinant DNA molecules from the transformants and, when necessary, retrieving the inserted gene from the isolated recombinant DNA.

The selection or construction of the appropriate vector will depend on 1) whether it is to be used for DNA amplification or for DNA expression, 2) the size of the DNA to be inserted into the vector, and 3) the host cell (e.g., mammalian, insect, yeast, fungal, plant or bacterial cells) to be transformed with the vector. Each vector contains various components depending on its function (amplification of DNA or expression of DNA) and its compatibility with the intended host cell. For DNA expression, the vector components may include, but are not limited to, one or more of the following: a signal sequence, an origin of replication, one or more selection or marker genes, enhancer elements, promoters, a transcription termination sequence, and the like. These components may be obtained from natural sources or synthesized by known procedures. The vectors of the present invention involve a nucleic acid sequence which encodes the GDNFR protein of interest operatively linked to one or more amplification, expression control, regulatory or similar operational elements capable of directing, controlling or otherwise effecting the amplification or expression of the GDNFR-encoding nucleic acid sequence in the selected host cell.

Expression vectors containing GDNFR nucleic acid sequence inserts can be identified by three general approaches: (a) DNA-DNA hybridization; (b) the presence or absence of "marker" gene functions, and (c) the expression of inserted sequences. In the first approach, the presence of a foreign nucleic acid sequence inserted in an expression vector can be detected by DNA-DNA hybridization using probes comprising sequences that are homologous to an inserted GDNFR-encoding nucleic acid sequence. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a foreign nucleic acid sequence into the vector. For example, if a GDNFR-encoding nucleic acid sequence is inserted within the marker gene sequence of the vector, recombinants containing the GDNFR insert can be identified by the absence of the marker gene function. In the third approach, recombinant expression vectors can be identified by detecting the foreign protein product expressed by the recombinant nucleic acid sequence. Such assays can be based on the physical or functional properties of the expressed GDNFR protein product, for example, by binding of the GDNFR-α protein to GDNF or to an antibody which directly recognizes GDNFR-α.

Signal Sequence

The signal sequence may be a component of the vector, or it may be a part of GDNFR DNA that is inserted into the vector. The native GDNFR DNA encodes a signal sequence at the amino terminus of the protein that is cleaved during post-translational processing of the protein to form the mature GDNFR protein. Included within the scope of this invention are GDNFR polynucleotides with the native signal sequence as well as GDNFR polynucleotides wherein the native signal sequence is deleted and replaced with a heterologous signal sequence. The heterologous signal sequence selected should be one that is recognized and processed, i.e., cleaved by a signal peptidase, by the host cell. For prokaryotic host cells that do not recognize and process the native GDNFR signal sequence, the signal sequence is substituted by a prokaryotic signal sequence selected, for example, from the group of the alkaline phosphatase, penicillinase, or heat-stable enterotoxin II leaders. For yeast secretion, the native GDNFR signal sequence may be substituted by the yeast invertase, alpha factor, or acid phosphatase leaders. In mammalian cell expression the native signal sequence is satisfactory, although other mammalian signal sequences may be suitable.

Origin of Replication

Expression and cloning vectors generally include a nucleic acid sequence that enables the vector to replicate in one or more selected host cells. In cloning vectors, this sequence is typically one that enables the vector to replicate independently of the host chromosomal DNA, and includes origins of replication or autonomously replicating sequences. Such sequences are well known for a variety of bacteria, yeasts, and viruses. The origin of replication from the plasmid pBR322 is suitable for most Gram-negative bacteria and various origins (e.g., SV40, polyoma, adenovirus, VSV or BPV) are useful for cloning vectors in mammalian cells. Generally, the origin of replication component is not needed for mammalian expression vectors (for example, the SV40 origin is often used only because it contains the early promoter).

Selection Gene

The expression and cloning vectors may contain a selection gene. This gene encodes a "marker" protein necessary for the survival or growth of the transformed host cells when grown in a selective culture medium. Host cells that were not transformed with the vector will not contain the selection gene, and therefore, they will not survive in the culture medium. Typical selection genes encode proteins that (a) confer resistance to antibiotics or other toxins, e.g., ampicillin, neomycin, methotrexate, or tetracycline; (b) complement auxotrophic deficiencies; or (c) supply critical nutrients not available from the culture medium.

Other selection genes may be used to amplify the gene which will be expressed. Amplification is the process wherein genes which are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure which only the transformants are uniquely adapted to survive by virtue of the marker present in the vector. Selection pressure is imposed by culturing the transformed cells under conditions in which the concentration of selection agent in the medium is successively changed, thereby leading to amplification of both the selection gene and the DNA that encodes GDNFR. As a result, increased quantities of GDNFR are synthesized from the amplified DNA.

For example, cells transformed with the DHFR selection gene are first identified by culturing all of the transformants in a culture medium that contains methotrexate, a competitive antagonist of DHFR. An appropriate host cell when wild-type DHFR is used is the Chinese hamster ovary cell line deficient in DHFR activity (see, for example, Urlaub and Chasin, Proc. Natl. Acad. Sci., U.S.A., 77(7): 4216–4220, 1980). The transformed cells are then exposed to increased levels of methotrexate. This leads to the synthesis of multiple copies of the DHFR gene, and, concomitantly, multiple copies of other DNA present in the expression vector, such as the DNA encoding a GDNFR protein.

Promoter

The expression and cloning vectors of the present invention will typically contain a promoter that is recognized by the host organism and operably linked to the nucleic acid sequence encoding the GDNFR protein. Promoters are untranslated sequences located upstream (5') to the start codon of a structural gene (generally within about 100 to 1000 bp) that control the transcription and translation of a particular nucleic acid sequence, such as that encoding GDNFR. Promoters are conventionally grouped into one of two classes, inducible promoters and constitutive promoters. Inducible promoters initiate increased levels of transcription from DNA under their control in response to some change in culture conditions, such as the presence or absence of a nutrient or a change in temperature. A large number of promoters, recognized by a variety of potential host cells, are well known. These promoters are operably linked to the DNA encoding GDNFR by removing the promoter from the source DNA by restriction enzyme digestion and inserting the desired promoter sequence into the vector. The native GDNFR promoter sequence may be used to direct amplification and/or expression of GDNFR DNA. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase, a tryptophan (trp) promoter system; and hybrid promoters such as the tac promoter. Other known bacterial promoters are also suitable. Their nucleotide sequences have been published, thereby enabling one skilled in the art to ligate them to the desired DNA sequence(s), using linkers or adaptors as needed to supply any required restriction sites.

Suitable promoting sequences for use with yeast hosts are also well known in the art. Yeast enhancers are advantageously used with yeast promoters. Suitable promoters for use with mammalian host cells are well known and include those obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40). Other suitable mammalian promoters include heterologous mammalian promoters, e.g., heat-shock promoters and the actin promoter. A promoter for possible use in the production of GDNFR proteins in CHO cells is SRa (see Takebe et al., Mol. Cell. Biol., 8(1): 466–472, 1988). A suitable expression vector is pDSRa2. The pDSRa2 plasmid constructs containing the appropriate GDNFR cDNA may be prepared substantially in accordance with the process described in the co-owned and copending U.S. patent application Ser. No. 501,904 filed Mar. 29, 1990 (also see, European Patent Application No. 90305433, Publication No. EP 398 753, filed May 18, 1990 and WO 90/14363 (1990), the disclosures of which are hereby incorporated by reference.

Additional promoters which may be of interest in controlling GDNFR expression include, but are not limited to: the SV40 early promoter region (Bemoist and Chambon, Nature, 290:304–310, 1981); the CMV promoter, the promoter contained in the 3' long terminal repeat of Rous sarcoma virus (Yamamoto, et al., Cell, 22:787–797, 1980); the herpes thymidine kinase promoter (Wagner et al., Proc. Natl. Acad. Sci. U.S.A., 78:144–1445, 1981); the regulatory sequences of the metallothionine gene (Brinster et al., Nature, 296:39–42, 1982); prokaryotic expression vectors such as the beta-lactamase promoter (Villa-Kamaroff, et al., Proc. Natl. Acad. Sci. U.S.A., 75:3727–3731, 1978); or the tac promoter (DeBoer, et al., Proc. Natl. Acad. Sci. U.S.A., 80:21–25, 1983). Also of interest are the following animal transcriptional control regions, which exhibit tissue specificity and have been utilized in transgenic animals: the elastase I gene control region which is active in pancreatic acinar cells (Swift et al., Cell, 38:639–646, 1984; Omitz et al., Cold Spring Harbor Symp. Quant. Biol. 50:399–409, 1986; MacDonald, Hepatology, 7:425–515, 1987); the insulin gene control region which is active in pancreatic beta cells (Hanahan, Nature, 315:115–122, 1985); the immunoglobulin gene control region which is active in lymphoid cells (Grosschedl et al., Cell, 38:647–658, 1984; Adames et al., Nature, 318:533–538, 1985; Alexander et al., Mol. Cell. Biol., 7:1436–1444, 1987); the mouse mammary tumor virus control region which is active in testicular, breast, lymphoid and mast cells (Leder et al., Cell, 45:485–495, 1986), albumin gene control region which is active in liver (Pinkert et al., Genes and Devel., 1:268–276, 1987); the alpha-fetoprotein gene control region which is active in liver (Knumlauf et al., Mol. Cell. Biol., 5:1639–1648, 1985; Hammer et al., Science, 235:53–58, 1987); the alpha 1-antitrypsin gene control region which is active in the liver (Kelsey et al., Genes and Devel., 1:161–171, 1987); the beta-globin gene control region which is active in myeloid cells (Mogram et al., Nature, 315:338–340, 1985; Kollias et al., Cell, 46:89–94, 1986); the myelin basic protein gene control region which is active in oligodendrocyte cells in the brain (Readhead et al., Cell, 48:703–712, 1987); the myosin light chain-2 gene control region which is active in skeletal muscle (Sani, Nature, 314:283–286, 1985); and the gonadotropic releasing hormone gene control region which is active in the hypothalamus (Mason et al., Science, 234:1372–1378, 1986).

Enhancer Element

An enhancer sequence may be inserted into the vector to increase the transcription of a DNA sequence encoding a GDNFR protein of the present invention by higher eukaryotes. Enhancers are cis-acting elements of DNA, usually about 10–300 bp in length, that act on the promoter to increase its transcription. Enhancers are relatively orientation and position independent. They have been found 5' and 3' to the transcription unit. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to GDNFR DNA, it is typically located at a site 5' from the promoter.

Transcription Termination

Expression vectors used in eukaryotic host cells (yeast, fungi, insect, plant, animal, human, or nucleated cells from other multicellular organisms) will also contain sequences necessary for terminating transcription and stabilizing the mRNA. Such sequences are commonly available from the 5' and occasionally 3' untranslated regions of eukaryotic DNAs or cDNAs. These regions contain nucleotide segments transcribed as polyadenylated fragments in the untranslated portion of the mRNA encoding GDNFR.

The construction of suitable vectors containing one or more of the above-listed components together with the desired GDNFR-encoding sequence is accomplished by standard ligation techniques. Isolated plasmids or DNA fragments are cleaved, tailored, and religated in the desired order to generate the plasmids required. To confirm that the correct sequences have been constructed, the ligation mixtures may be used to transform E. coli, and successful transformants may be selected by known techniques, such as ampicillin or tetracycline resistance as described above. Plasmids from the transformants may then be prepared, analyzed by restriction endonuclease digestion, and/or sequenced to confirm the presence of the desired construct.

Vectors that provide for the transient expression of DNA encoding GDNFR in mammalian cells may also be used. In general, transient expression involves the use of an expression vector that is able to replicate efficiently in a host cell, such that the host cell accumulates many copies of the expression vector and, in turn, synthesizes high levels of the desired protein encoded by the expression vector. Transient expression systems, comprising a suitable expression vector and a host cell, allow for the convenient positive identification of proteins encoded by cloned DNAs, as well as for the rapid screening of such proteins for desired biological or physiological properties. Thus, transient expression systems are particularly useful in identifying variants of the protein.

Selection and Transformation of Host Cells

Host cells (e.g., bacterial, mammalian, insect, yeast, or plant cells) transformed with nucleic acid sequences for use in expressing a recombinant GDNFR protein are also provided by the present invention. The transformed host cell is cultured under appropriate conditions permitting the expression of the nucleic acid sequence. The selection of suitable host cells and methods for transformation, culture, amplification, screening and product production and purification are well known in the art. See for example, Gething and Sambrook, Nature, 293: 620–625 (1981), or alternatively, Kaufman et al., Mol. Cell. Biol., 5 (7): 1750–1759 (1985) or Howley et al., U.S. Pat. No. 4,419,446. Additional exemplary materials and methods are discussed herein. The transformed host cell is cultured in a suitable medium, and the expressed GDNFR protein is then optionally recovered, isolated and purified from the culture medium (or from the cell, if expressed intracellularly) by an appropriate means known to those skilled in the art.

Different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed. For example, expression in a bacterial system can be used to produce an unglycosylated core protein product. Expression in yeast may be used to produce a glycosylated product. Expression in mammalian cells can be used to ensure "native" glycosylation of the heterologous GDNFR protein. Furthermore, different vector/host expression systems may effect processing reactions such as proteolytic cleavages to different extents.

Suitable host cells for cloning or expressing the vectors disclosed herein are prokaryote, yeast, or higher eukaryote cells. Eukaryotic microbes such as filamentous fungi or yeast may be suitable hosts for the expression of GDNFR proteins. *Saccharomyces cerevisiae*, or common baker's yeast, is the most commonly used among lower eukaryotic host microorganisms, but a number of other genera, species, and strains are well known and commonly available.

Host cells to be used for the expression of glycosylated GDNFR protein are also derived from multicellular organisms. Such host cells are capable of complex processing and glycosylation activities. In principle, any higher eukaryotic cell culture might be used, whether such culture involves vertebrate or invertebrate cells, including plant and insect cells. The propagation of vertebrate cells in culture (tissue culture) is a well known procedure. Examples of useful mammalian host cell lines include, but are not limited to, monkey kidney CV1 line transformed by SV40 (COS7), human embryonic kidney line (293 or 293 cells subcloned for growth in suspension culture), baby hamster kidney cells, and Chinese hamster ovary cells. Other suitable mammalian cell lines include but are not limited to, HeLa, mouse L-929 cells, 3T3 lines derived from Swiss, Balb-c or NIH mice, BHK or HaK hamster cell lines.

Suitable host cells also include prokaryotic cells. Prokaryotic host cells include, but are not limited to, bacterial cells, such as Gram-negative or Gram-positive organisms, for example, *E. coli*, Bacilli such as *B. subtilis*, Pseudomonas species such as *P. aeruginosa, Salmonella typhimurium*, or *Serratia marcescans*. For example, the various strains of *E. coli* (e.g., HB101, DH5a, DH10, and MC1061) are well-known as host cells in the field of biotechnology. Various strains of Streptomyces spp. and the like may also be employed. Presently preferred host cells for producing GDNFR proteins are bacterial cells (e.g., *Escherichia coli*) and mammalian cells (such as Chinese hamster ovary cells, COS cells, etc.)

The host cells are transfected and preferably transformed with the above-described expression or cloning vectors and cultured in a conventional nutrient medium. The medium may be modified as appropriate for inducing promoters, selecting transformants, or amplifying the genes encoding the desired sequences. Transfection and transformation are performed using standard techniques which are well known to those skilled in the art and which are selected as appropriate to the host cell involved. For example, for mammalian cells without cell walls, the calcium phosphate precipitation method may be used. Electroporation, micro injection and other known techniques may also be used.

Culturing the Host Cells

Transformed cells used to produce GDNFR proteins of the present invention are cultured in suitable media The media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamicin), trace elements (defined as inorganic compounds usually present at final concentrations in the micromolar range), and glucose or other energy source. Other supplements may also be included, at appropriate concentrations, as will be appreciated by those skilled in the art. Suitable culture conditions, such as temperature, pH, and the like, are also well known to those skilled in the art for use with the selected host cells.

Once the GDNFR protein is produced, it may be isolated and purified by standard methods including chromatography (e.g., ion exchange, affinity, and sizing column chromatography), centrifugation, differential solubility, or by any other standard technique for the purification of proteins. For example, GDNFR-α protein may be isolated by binding to an affinity column comprising GDNF or anti-GDNFR-α antibody bound to a stationary support. Similarly, GRR2 protein may be isolated by binding to an affinity column comprising neurturin or anti-GRR2 antibody bound to a stationary support.

Homologous Recombination

It is further envisioned that GDNFR proteins may be produced by homologous recombination, or with recombinant production methods utilizing control elements introduced into cells already containing DNA encoding GDNFR. For example, homologous recombination methods may be used to modify a cell that contains a normally transcriptionally silent GDNFR gene or under expressed gene and thereby produce a cell which expresses GDNFR. Homologous recombination is a technique originally developed for targeting genes to induce or correct mutations in transcriptionally active genes (Kucherlapati, Prog. in Nucl. Acid Res. and Mol. Biol., 36:301, 1989). The basic technique was developed as a method for introducing specific mutations into specific regions of the mammalian genome (Thomas et al., Cell, 44:419–428, 1986; Thomas and Capecchi, Cell, 51:503–512, 1987; Doetschman et al., Proc. Natl. Acad. Sci., 85:8583–8587, 1988) or to correct specific mutations within defective genes (Doetschman et al., Nature, 330:576–578, 1987). Exemplary homologous recombination techniques are described in U.S. Pat. No. 5,272,071 (EP 91 90 3051, EP Publication No. 505 500; PCT/US90/07642, International Publication No. WO 91/09955) the disclosure of which is hereby incorporated by reference.

Through homologous recombination, the DNA sequence to be inserted into the genome can be directed to a specific region of the gene of interest by attaching it to targeting DNA. The targeting DNA is DNA that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence of DNA, it too is incorporated into the newly synthesized strand as a result of the recombination. As a result of the proofreading function, it is possible for the new sequence of DNA to serve as the template. Thus, the transferred DNA is incorporated into the genome.

If the sequence of a particular gene is known, such as the nucleic acid sequence, the pre-pro sequence or expression control sequence of GDNFR presented herein, a piece of DNA that is complementary to a selected region of the gene can be synthesized or otherwise obtained, such as by appropriate restriction of the native DNA at specific recognition sites bounding the region of interest. This piece serves as a targeting sequence upon insertion into the cell and will hybridize to its homologous region within the genome. If this hybridization occurs during DNA replication, this piece of DNA, and any additional sequence attached thereto, will act as an Okazaki fragment and will be backstitched into the newly synthesized daughter strand of DNA.

Attached to these pieces of targeting DNA are regions of DNA which may interact with the expression of a GDNFR protein. For example, a promoter/enhancer element, a suppresser, or an exogenous transcription modulatory element is inserted in the genome of the intended host cell in proximity and orientation sufficient to influence the transcription of DNA encoding the desired GDNFR protein. The control element does not encode GDNFR, but instead controls a portion of the DNA present in the host cell genome. Thus, the expression of GDNFR proteins may be achieved not by transfection of DNA that encodes the GDNFR gene itself, but rather by the use of targeting DNA (containing regions of homology with the endogenous gene of interest) coupled with DNA regulatory segments that provide the endogenous gene sequence with recognizable signals for transcription of a GDNFR protein.

A. GDNFR Variants

As discussed above, the terms "GDNFR analogs" as used herein include polypeptides in which amino acids have been deleted from ("deletion variants"), inserted into ("addition variants"), or substituted for ("substitution variants") residues within the amino acid sequence of naturally-occurring GDNFR polypeptides including those depicted in the Figures. Such variants are prepared by introducing appropriate nucleotide changes into the DNA encoding the polypeptide or by in vitro chemical synthesis of the desired polypeptide. It will be appreciated by those skilled in the art that many combinations of deletions, insertions, and substitutions can be made to an amino acid sequence such as mature human GDNFR provided that the final molecule possesses GDNFR activity.

Based upon the present description of particular GDNFR-α, GRR2 and GRR3 amino acid sequences from multiple species, as well as the consensus sequences derived therefrom, one can readily design and manufacture a variety of nucleic acid sequences suitable for use in the recombinant (e.g., microbial) expression of polypeptides having primary conformations which differ from those depicted in the Figures in terms of the identity or location of one or more residues. Mutagenesis techniques for the replacement, insertion or deletion of one or more selected amino acid residues encoded by the nucleic acid sequences depicted in FIGS. 2 and 4 are well known to one skilled in the art (e.g., U.S. Pat. No. 4,518,584, the disclosure of which is hereby incorporated by reference.) There are two principal variables in the construction of substitution variants: the location of the mutation site and the nature of the mutation. In designing GDNFR substitution variants, the selection of the mutation site and nature of the mutation will depend on the GDNFR characteristic(s) to be modified. The sites for mutation can be modified individually or in series, e.g., by (1) substituting first with conservative amino acid modifications and then with more radical selections depending upon the results achieved, (2) deleting the target amino acid residue, or (3) inserting amino acid residues adjacent to the located site. Conservative changes in from 1 to 30 contiguous amino acids are preferred. N-terminal and C-terminal deletion GDNFR protein variants may also be generated by proteolytic enzymes.

For GDNFR deletion variants, deletions generally range from about 1 to 30 contiguous residues, more usually from about 1 to 10 contiguous residues, and typically from about 1 to 5 contiguous residues. N-terminal, C-terminal and internal intrasequence deletions are contemplated. Deletions may be introduced into regions of the molecule which have low homology with non-human GDNFR to modify the activity of GDNFR. Deletions in areas of substantial homology with non-human GDNFR sequences will be more likely to significantly modify GDNFR biological activity. The number of consecutive deletions typically will be selected so as to preserve the tertiary structure of the GDNFR protein product in the affected domain, e.g., cysteine crosslinking. Non-limiting examples of deletion variants include truncated GDNFR protein products lacking N-terminal or C-terminal amino acid residues. For example, one may prepare a soluble receptor by elimination of the peptide region involved in a glycosyl-phosphatidylinositol (GPI) anchorage of GDNFR receptor to the cytoplasmic membrane.

For GDNFR addition variants, amino acid sequence additions typically include N-and/or C-terminal fusions or terminal additions ranging in length from one residue to polypeptides containing a hundred or more residues, as well as internal or medial additions of single or multiple amino acid residues. Polypeptides of the invention may also include an initial methionine amino acid residue (at position −1 with respect to the first amino acid residue of the desired polypeptide). Internal additions may range generally from about 1 to 10 contiguous residues, more typically from about 1 to 5 residues, and usually from about 1 to 3 amino acid residues. Examples of N-terminal addition variants include GDNFR with the inclusion of a heterologous N-terminal signal sequence to the N-terminus of GDNFR to facilitate the secretion of mature GDNFR from recombinant host cells and thereby facilitate harvesting or bioavailability. Such signal sequences generally will be obtained from, and thus be homologous to, the intended host cell species. Additions may also include amino acid sequences derived from the sequence of other neurotrophic factors. For example, it is contemplated that a fusion protein of GDNF and GDNFR-α, or neurturin and GRR2, may be produced, with or without a linking sequence, thereby forming a single molecule therapeutic entity.

GDNFR substitution variants have one or more amino acid residues of the GDNFR amino acid sequence removed and a different residue(s) inserted in its place. Such substitution variants include allelic variants, which are characterized by naturally-occurring nucleotide sequence changes in the species population that may or may not result in an amino acid change. As with the other variant forms, substitution variants may involve the replacement of single or contiguous amino acid residues at one or more different locations.

Specific mutations of the GDNFR amino acid sequence may involve modifications to a glycosylation site (e.g., serine, threonine, or asparagine). The absence of glycosylation or only partial glycosylation results from amino acid substitution or deletion at any asparagine-linked glycosylation recognition site or at any site of the molecule that is modified by addition of an O-linked carbohydrate. An asparagine-linked glycosylation recognition site comprises a tripeptide sequence which is specifically recognized by appropriate cellular glycosylation enzymes. These tripeptide sequences are either Asn-Xaa-Thr or Asn-Xaa-Ser, where Xaa can be any amino acid other than Pro. A variety of amino acid substitutions or deletions at one or both of the first or third amino acid positions of a glycosylation recognition site (and/or amino acid deletion at the second position) result in non-glycosylation at the modified tripeptide sequence. Thus, the expression of appropriate altered nucleotide sequences produces variants which are not glycosylated at that site. Alternatively, the GDNFR amino acid sequence may be modified to add glycosylation sites.

One method for identifying GDNFR amino acid residues or regions for mutagenesis is called "alanine scanning mutagenesis" as described by Cunningham and Wells (Science, 244: 1081–1085, 1989). In this method, an amino acid residue or group of target residues are identified (e.g., charged residues such as Arg, Asp, His, Lys, and Glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions may then be refined by introducing additional or alternate residues at the sites of substitution. Thus, the target site for introducing an amino acid sequence variation is determined, alanine scanning or random mutagenesis is conducted on the corresponding target codon or region of the DNA sequence, and the expressed GDNFR variants are screened for the optimal combination of desired activity and degree of activity.

The sites of greatest interest for substitutional mutagenesis include sites where the amino acids found in GDNFR proteins from various species are substantially different in terms of side-chain bulk, charge, and/or hydrophobicity. Other sites of interest are those in which particular residues of GDNFR-like proteins, obtained from various species, are identical. Such positions are generally important for the biological activity of a protein. Initially, these sites are substituted in a relatively conservative manner. Such conservative substitutions are shown in Table 2 under the heading of preferred substitutions. If such substitutions result in a change in biological activity, then more substantial changes (exemplary substitutions) may be introduced, and/or other additions or deletions may be made, and the resulting products are screened for activity.

TABLE 2

Amino Acid Substitutions

| Original Residue | Preferred Substitutions | Exemplary Substitutions |
| --- | --- | --- |
| Ala (A) | Val | Val; Leu; Ile |
| Arg (R) | Lys | Lys; Gln; Asn |
| Asn (N) | Gln | Gln; His; Lys; Arg |

TABLE 2-continued

Amino Acid Substitutions

| Original Residue | Preferred Substitutions | Exemplary Substitutions |
|---|---|---|
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Arg | Asn; Gln; Lys; Arg |
| Ile (I) | Leu | Leu; Val; Met; Ala; Phe; norleucine |
| Leu (L) | Ile | norleucine; Ile; Val; Met; Ala; Phe |
| Lys (K) | Arg | Arg; Gln; Asn |
| Met (M) | Leu | Leu; Phe; Ile |
| Phe (F) | Leu | Leu; Val; Ile; Ala |
| Pro (P) | Gly | Gly |
| Ser (S) | Thr | Thr |
| Thr (T) | Ser | Ser |
| Trp (W) | Tyr | Tyr |
| Tyr (Y) | Phe | Trp; Phe; Thr; Ser |
| Val (V) | Leu | Ile; Leu; Met; Phe; Ala; norleucine |

Conservative modifications to the amino acid sequence (and the corresponding modifications to the encoding nucleic acid sequences) are expected to produce GDNFR protein products having functional and chemical characteristics similar to those of naturally occurring GDNFR. In contrast, substantial modifications in the functional and/or chemical characteristics of GDNFR protein products may be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues may be divided into groups based on common side chain properties:

1) hydrophobic: norleucine, Met, Ala, Val, Leu, Iie;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

Non-conservative substitutions may involve the exchange of a member of one of these classes for a member from another class. Such substituted residues may be introduced into regions of the human GDNFR protein that are homologous with non-human GDNFR proteins, or into the non-homologous regions of the molecule.

Thus, GDNFR proteins include those biologically active molecules containing all or part of the amino acid sequences as depicted in the Figures, as well as consensus and modified sequences in which biologically equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. It is also contemplated that the GDNFR proteins, analogs, or fragments or derivatives thereof may be differentially modified during or after translation, e.g., by phosphorylation, glycosylation, crosslinking, acylation, proteolytic cleavage, linkage to an antibody molecule, membrane molecule or other ligand.

B. GDNFR Derivatives

Chemically modified derivatives of GDNFR or GDNFR analogs may be prepared by one of skill in the art based upon the present disclosure. The chemical moieties most suitable for derivatization include water soluble polymers. A water soluble polymer is desirable because the protein to which it is attached does not precipitate in an aqueous environment, such as a physiological environment. Preferably, the polymer will be pharmaceutically acceptable for the preparation of a therapeutic product or composition. One skilled in the art will be able to select the desired polymer based on such considerations as whether the polymer/protein conjugate will be used therapeutically, and if so, the desired dosage, circulation time, resistance to proteolysis, and other considerations. The effectiveness of the derivatization may be ascertained by administering the derivative, in the desired form (e.g., by osmotic pump, or, more preferably, by injection or infusion, or, further formulated for oral, pulmonary or other delivery routes), and determining its effectiveness.

Suitable water soluble polymers include, but are not limited to, polyethylene glycol, copolymers of ethylene glycol/propylene glycol, carboxymethylcellulose, dextan, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water.

The polymer may be of any molecular weight, and may be branched or unbranched. For polyethylene glycol, the preferred molecular weight is between about 2 kDa and about 100 kDa for ease in handling and manufacturing (the term "about" indicating that in preparations of polyethylene glycol, some molecules will weigh more, some less, than the stated molecular weight). Other sizes may be used, depending on the desired therapeutic profile (e.g., the duration of sustained release desired; the effects, if any, on biological activity; the ease in handling; the degree or lack of antigenicity and other known effects of polyethylene glycol on a therapeutic protein or variant).

The number of polymer molecules so attached may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules to protein (or peptide) molecules will vary, as will their concentrations in the reaction mixture. In general, the optimum ratio (in terms of efficiency of reaction in that there is no excess unreacted protein or polymer) will be determined by factors such as the desired degree of derivatization (e.g., mono, di-, tri-, etc.), the molecular weight of the polymer selected, whether the polymer is branched or unbranched, and the reaction conditions.

The polyethylene glycol molecules (or other chemical moieties) should be attached to the protein with consideration of effects on functional or antigenic domains of the protein. There are a number of attachment methods available to those skilled in the art. See for example, EP 0 401 384, the disclosure of which is hereby incorporated by reference (coupling PEG to G-CSF), see also Malik et al., Exp. Hematol., 20: 1028–1035, 1992 (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residue. Those having a free carboxyl group may include aspartic acid residues, glutamic acid residues, and the C-terminal amino acid residue. Sulfhydrl groups may also be used as a reactive group for attaching the polyethylene glycol molecule(s). For therapeutic purposes, attachment at an amino group, such as attachment at the N-terminus or lysine group is preferred. Attachment at residues important for receptor binding should be avoided if receptor binding is desired.

One may specifically desire an N-terminal chemically modified protein. Using polyethylene glycol as an illustration of the present compositions, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one may selectively N-terminally pegylate the protein by performing the reaction at a pH which allows one to take advantage of the pKa differences between the e-amino group of the lysine residues and that of the a-amino group of the N-terminal residue of the protein. By such selective derivatization, attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer may be of the type described above, and should have a single reactive aldehyde for coupling to the protein. Polyethylene glycol propionaldehyde, containing a single reactive aldehyde, may be used.

The present invention contemplates use of derivatives which are prokaryote-expressed GDNFR proteins, or variants thereof, linked to at least one polyethylene glycol molecule, as well as use of GDNFR proteins, or variants thereof, attached to one or more polyethylene glycol molecules via an acyl or alkyl linkage.

Pegylation may be carried out by any of the pegylation reactions known in the art. See, for example: Focus on Growth Factors, 3 (2): 4–10, 1992; EP 0 154 316, the disclosure of which is hereby incorporated by reference; EP 0 401 384; and the other publications cited herein that relate to pegylation. The pegylation may be carried out via an acylation reaction or an alkylation reaction with a reactive polyethylene glycol molecule (or an analogous reactive water-soluble polymer).

Pegylation by acylation generally involves reacting an active ester derivative of polyethylene glycol (PEG) with the GDNFR protein or variant. Any known or subsequently discovered reactive PEG molecule may be used to carry out the pegylation of GDNFR protein or variant A preferred activated PEG ester is PEG esterified to N-hydroxysuccinimide (NHS). As used herein, "acylation" is contemplated to include without limitation the following types of linkages between the therapeutic protein and a water soluble polymer such as PEG: amide, carbamate, urethane, and the like. See Bioconjugate Chem., 5: 133–140, 1994. Reaction conditions may be selected from any of those known in the pegylation art or those subsequently developed, but should avoid conditions such as temperature, solvent, and pH that would inactivate the GDNFR or variant to be modified.

Pegylation by acylation will generally result in a poly-pegylated GDNFR protein or variant. Preferably, the connecting linkage will be an amide. Also preferably, the resulting product will be substantially only (e.g., >95%) mono-, di- or tri-pegylated. However, some species with higher degrees of pegylation may be formed in amounts depending on the specific reaction conditions used. If desired, more purified pegylated species may be separated from the mixture, particularly unreacted species, by standard purification techniques, including, among others, dialysis, salting-out, ultrafiltration, ion-exchange chromatography, gel filtration chromatography and electrophoresis.

Pegylation by alkylation generally involves reacting a terminal aldehyde derivative of PEG with the GDNFR protein or variant in the presence of a reducing agent. Pegylation by alkylation can also result in poly-pegylated GDNFR protein or variant. In addition, one can manipulate the reaction conditions to favor pegylation substantially only at the a-amino group of the N-terminus of the GDNFR protein or variant (i.e., a mono-pegylated protein). In either case of monopegylation or polypegylation, the PEG groups are preferably attached to the protein via a —$CH_2$—NH— group. With particular reference to the —$CH_2$— group, this type of linkage is referred to herein as an "alkyl" linkage.

Derivatization via reductive alkylation to produce a monopegylated product exploits differential reactivity of different types of primary amino groups (lysine versus the N-terminal) available for derivatization. The reaction is performed at a pH which allows one to take advantage of the pKa differences between the e-amino groups of the lysine residues and that of the a-amino group of the N-terminal residue of the protein. By such selective derivatization, attachment of a water soluble polymer that contains a reactive group such as an aldehyde, to a protein is controlled: the conjugation with the polymer takes place predominantly at the N-terminus of the protein and no significant modification of other reactive groups, such as the lysine side chain amino groups, occurs. In one important aspect, the present invention contemplates use of a substantially homogeneous preparation of monopolymer/GDNFR protein (or variant) conjugate molecules (meaning GDNFR protein or variant to which a polymer molecule has been attached substantially only (i.e., >95%) in a single location). More specifically, if polyethylene glycol is used, the present invention also encompasses use of pegylated GDNFR protein or variant lacking possibly antigenic linking groups, and having the polyethylene glycol molecule directly coupled to the GDNFR protein or variant.

Thus, GDNFR protein products according to the present invention include pegylated GDNFR protein or variants, wherein the PEG group(s) is (are) attached via acyl or alkyl groups. As discussed above, such products may be mono-pegylated or poly-pegylated (e.g., containing 2–6, and preferably 2–5, PEG groups). The PEG groups are generally attached to the protein at the a- or e-amino groups of amino acids, but it is also contemplated that the PEG groups could be attached to any amino group co attached to the protein, which is sufficiently reactive to become attached to a PEG group under suitable reaction conditions.

The polymer molecules used in both the acylation and alkylation approaches may be selected from among water soluble polymers as described above. The polymer selected should be modified to have a single reactive group, such as an active ester for acylation or an aldehyde for alkylation, preferably, so that the degree of polymerization may be controlled as provided for in the present methods. An exemplary reactive PEG aldehyde is polyethylene glycol propionaldehyde, which is water stable, or mono C1–C10 alkoxy or aryloxy derivatives thereof (see, U.S. Pat. No. 5,252,714). The polymer may be branched or unbranched. For the acylation reactions, the polymer(s) selected should have a single reactive ester group. For the present reductive alkylation, the polymer(s) selected should have a single reactive aldehyde group. Generally, the water soluble polymer will not be selected from naturally-occurring glycosyl residues since these are usually made more conveniently by mammalian recombinant expression systems. The polymer may be of any molecular weight, and may be branched or unbranched.

An exemplary water-soluble polymer for use herein is polyethylene glycol. As used herein, polyethylene glycol is meant to encompass any of the forms of PEG that have been used to derivatize other proteins, such as mono-(C1–-C10) alkoxy- or aryloxy-polyethylene glycol.

In general, chemical derivatization may be performed under any suitable condition used to react a biologically active substance with an activated polymer molecule. Methods for preparing a pegylated GDNFR protein product will generally comprise the steps of (a) reacting a GDNFR protein product with polyethylene glycol (such as a reactive ester or aldehyde derivative of PEG) under conditions whereby the protein becomes attached to one or more PEG groups, and (b) obtaining the reaction product(s). In general, the optimal reaction conditions for the acylation reactions will be determined case-by-case based on known parameters and the desired result. For example, the larger the ratio of PEG:protein, the greater the percentage of poly-pegylated product.

Reductive alkylation to produce a substantially homogeneous population of mono-polymer/GDNFR protein product will generally comprise the steps of: (a) reacting a GDNFR protein or variant with a reactive PEG molecule under reductive alkylation conditions, at a pH suitable to permit selective modification of the a-amino group at the amino terminus of said GDNFR protein or variant; and (b) obtaining the reaction product(s).

For a substantially homogeneous population of mono-polymer/GDNFR protein product, the reductive alkylation reaction conditions are those which permit the selective attachment of the water soluble polymer moiety to the N-terminus of GDNFR protein or variant. Such reaction conditions generally provide for pKa differences between the lysine amino groups and the a-amino group at the N-terminus (the pKa being the pH at which 50% of the amino groups are protonated and 50% are not). The pH also affects the ratio of polymer to protein to be used. In general, if the pH is lower, a larger excess of polymer to protein will be desired (i.e., the less reactive the N-terminal a-amino group, the more polymer needed to achieve optimal conditions). If the pH is higher, the polymer:protein ratio need not be as large (i.e., more reactive groups are available, so fewer polymer molecules are needed). For purposes of the present invention, the pH will generally fall within the range of 3–9, preferably 3–6.

Another important consideration is the molecular weight of the polymer. In general, the higher the molecular weight of the polymer, the fewer polymer molecules may be attached to the protein. Similarly, branching of the polymer should be taken into account when optimizing these parameters. Generally, the higher the molecular weight (or the more branches) the higher the polymer:protein ratio. In general, for the pegylation reactions contemplated herein, the preferred average molecular weight is about 2 kDa to about 100 kDa. The preferred average molecular weight is about 5 kDa to about 50 kDa, particularly preferably about 12 kDa to about 25 kDa. The ratio of water-soluble polymer to GDNF protein or variant will generally range from 1:1 to 100:1, preferably (for polypegylation) 1:1 to 20:1 and (for monopegylation) 1:1 to 5:1.

Using the conditions indicated above, reductive alkylation will provide for selective attachment of the polymer to any GDNFR protein or variant having an a-amino group at the amino terminus, and provide for a substantially homogenous preparation of monopolymer/GDNFR protein (or variant) conjugate. The term "monopolymer/GDNFR protein (or variant) conjugate" is used here to mean a composition comprised of a single polymer molecule attached to a molecule of GDNFR protein or GDNFR variant protein. The monopolymer/GDNFR protein (or variant) conjugate typically will have a polymer molecule located at the N-terminus, but not on lysine amino side groups. The preparation will generally be greater than 90% monopolymer/GDNFR protein (or variant) conjugate, and more usually greater than 95% monopolymer/GDNFR protein (or variant) conjugate, with the remainder of observable molecules being unreacted (i.e., protein lacking the polymer moiety). It is also envisioned that the GDNFR protein product may involve the preparation of a pegylated molecule involving a fusion protein or linked GDNFR and neurotrophic factor, such as GDNFR-α and GDNF molecules or GRR2 and neurturin molecules.

For the present reductive alkylation, the reducing agent should be stable in aqueous solution and preferably be able to reduce only the Schiff base formed in the initial process of reductive alkylation. Suitable reducing agents may be selected from at sodium borohydride, sodium cyanoborohydride, dimethylamine borane, trimethylamine borane and pyridine borane. A particularly suitable reducing agent is sodium cyanoborohydride. Other reaction parameters, such as solvent, reaction times, temperatures, etc., and means of purification of products, can be determined case-by-case based on the published information relating to derivatization of proteins with water soluble polymers (see the publications cited herein).

C. GDNFR Protein Product Pharmaceutical Compositions

GDNFR protein product pharmaceutical compositions typically include a therapeutically or prophylactically effective amount of GDNFR protein product in admixture with one or more pharmaceutically and physiologically acceptable formulation materials selected for suitability with the mode of administration. Suitable formulation materials include, but are not limited to, antioxidants, preservatives, coloring, flavoring and diluting agents, emulsifying agents, suspending agents, solvents, fillers, bulking agents, buffers, delivery vehicles, diluents, excipients and/or pharmaceutical adjuvants. For example, a suitable vehicle may be water for injection, physiological saline solution, or artificial cerebrospinal fluid, possibly supplemented with other materials common in compositions for parenteral administration. Neutral buffered saline or saline mixed with serum albumin are further exemplary vehicles. The term "pharmaceutically acceptable carrier" or "physiologically acceptable carrier" as used herein refers to a formulation material(s) suitable for accomplishing or enhancing the delivery of the GDNFR protein product as a pharmaceutical composition.

The primary solvent in a vehicle may be either aqueous or non-aqueous in nature. In addition, the vehicle may contain other formulation materials for modifying or maintaining the pH, osmolarity, viscosity, clarity, color, sterility, stability, rate of dissolution, or odor of the formulation. Similarly, the vehicle may contain additional formulation materials for modifying or maintaining the rate of release of GDNFR protein product, or for promoting the absorption or penetration of GDNFR protein product across the blood-brain barrier.

Once the therapeutic pharmaceutical composition has been formulated, it may be stored in sterile vials as a solution, suspension, gel, emulsion, solid, or dehydrated or lyophilized powder. Such formulations may be stored either in a ready to use form or in a form (e.g., lyophilized) requiring reconstitution prior to administration.

The optimal pharmaceutical formulation will be determined by one skilled in the art depending upon the intended route of administration and desired dosage. See for example, Remington's Pharmaceutical Sciences, 18th Ed. (1990, Mack Publishing Co., Easton, Pa. 18042) pages 1435–1712, the disclosure of which is hereby incorporated by reference. Such compositions may influence the physical state, stability, rate of in vivo release, and rate of in vivo clearance of the present proteins and derivatives.

Effective administration forms, such as (1) slow-release formulations, (2) inhalant mists, or (3) orally active formulations are envisioned. The GDNFR protein product pharmaceutical composition also may be formulated for parenteral administration. Such parenterally administered therapeutic compositions are typically in the form of a pyrogen-free, parenterally acceptable aqueous solution comprising the GDNFR protein product in a pharmaceutically acceptable vehicle. One preferred vehicle is physiological saline. The GDNFR protein product pharmaceutical compositions also may include particulate preparations of polymeric compounds such as polylactic acid, polyglycolic acid, etc. or into liposomes. Hyaluronic acid may also be used, and this may have the effect of promoting sustained duration in the circulation.

A particularly suitable vehicle for parenteral injection is sterile distilled water in which the GDNFR protein product is formulated as a sterile, isotonic solution, properly preserved. Yet another preparation may involve the formulation of the GDNFR protein product with an agent, such as injectable microspheres or liposomes, that provides for the slow or sustained release of the protein which may then be delivered as a depot injection. Other suitable means for the introduction of GDNFR protein product include implantable drug delivery devices which contain the GDNFR protein product.

The preparations of the present invention may include other components, for example parenterally acceptable preservatives, tonicity agents, cosolvents, wetting agents, complexing agents, buffering agents, antimicrobials, antioxidants and surfactants, as are well known in the art. For example, suitable tonicity enhancing agents include alkali metal halides (preferably sodium or potassium chloride), mannitol, sorbitol and the like. Suitable preservatives include, but are not limited to, benzalkonium chloride, thimerosal, phenethyl alcohol, methylparaben, propylparaben, chlorhexidine, sorbic acid and the like. Hydrogen peroxide may also be used as preservative. Suitable cosolvents are for example glycerin, propylene glycol and polyethylene glycol. Suitable complexing agents are for example caffeine, polyvinylpyrrolidone, beta-cyclodextrin or hydroxypropyl-beta-cyclodextrin. Suitable surfactants or wetting agents include sorbitan esters, polysorbates such as polysorbate 80, tromethamine, lecithin, cholesterol, tyloxapal and the like. The buffers can be conventional buffers such as borate, citrate, phosphate, bicarbonate, or Tris-HCl.

The formulation components are present in concentration that are acceptable to the site of administration. For example, buffers are used to maintain the composition at physiological pH or at slightly lower pH, typically within a pH range of from about 5 to about 8.

A pharmaceutical composition may be formulated for inhalation. For example, the GDNFR protein product may be formulated as a dry powder for inhalation. GDNFR protein product inhalation solutions may also be formulated in a liquefied propellant for aerosol delivery. In yet another formulation, solutions may be nebulized.

It is also contemplated that certain formulations containing GDNFR protein product are to be administered orally. GDNFR protein product which is administered in this fashion may be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional formulation materials may be included to facilitate absorption of GDNFR protein product. Diluents, flavorings, low melting point waxes, vegetable oils, lubricants, suspending agents, tablet disintegrating agents, and binders may also be employed.

Another preparation may involve an effective quantity of GDNFR protein product in a mixture with non-toxic excipients which are suitable for the manufacture of tablets. By dissolving the tablets in sterile water, or other appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional GDNFR protein product formulations will be evident to those skilled in the art, including formulations involving GDNFR protein product in combination with GDNF protein product. Techniques for formulating a variety of other sustained- or controlled-delivery means, such as liposome carriers, bio-erodible microparticles or porous beads and depot injections, are also known to those skilled in the art. See, for example, Supersaxo et al. description of controlled release porous polymeric microparticles for the delivery of pharmaceutical compositions (International Publication No. WO 93/15722; International Application No. PCT/US93/00829) the disclosure of which is hereby incorporated by reference.

D. Administration of GDNFR Protein Product

The GDNFR protein product may be administered parenterally via a variety of routes, including subcutaneous, intramuscular, intravenous, transpulmonary, transdermal, intrathecal and intracerebral delivery. In addition, protein factors that do not readily cross the blood-brain barrier may be given directly intracerebrally or otherwise in association with other elements that will transport them across the barrier. For example, the GDNFR protein product may be administered intracerebroventricularly or into the brain or spinal cord subarachnoid space. GDNFR protein product may also be administered intracerebrally directly into the brain parenchyma. GDNFR protein product may be administered extracerebrally in a form that has been modified chemically or packaged so that it passes the blood-brain barrier, or with one or more agents capable of promoting penetration of GDNFR protein product across the barrier. For example, a conjugate of NGF and monoclonal anti-transferrin receptor antibodies has been shown to be transported to the brain via binding to transferrin receptors.

To achieve the desired level of GDNFR protein product, repeated daily or less frequent injections may be administered, or GDNFR protein product may be infused continuously or periodically from a constant- or programmable-flow implanted pump. Slow-releasing implants containing the neurotrophic factor embedded in a biodegradable polymer matrix can also deliver GDNFR protein product. The frequency of dosing will depend on the pharmacokinetic parameters of the GDNFR protein product as formulated, and the route and site of administration.

Regardless of the manner of administration, the specific dose may be calculated according to body weight, body surface area or organ size. Further refinement of the calculations necessary to determine the appropriate dosage for treatment involving each of the above mentioned formulations is routinely made by those of ordinary skill in the art and is within the ambit of tasks routinely performed by them. Appropriate dosages may be ascertained through use of appropriate dose-response data.

The final dosage regimen involved in a method for treating a specific injury or condition will be determined by the attending physician. Generally, an effective amount of the GDNFR protein product will be determined by considering various factors which modify the action of drugs, e.g., the age, condition, body weight, sex and diet of the patient, the severity of any infection, time of administration and other clinical factors. See, Remington's Pharmaceutical Sciences, supra, at pages 697–773, herein incorporated by reference. For example, it is contemplated that if GDNFR-α is used to enhance GDNF action, then the GDNFR-α dose is selected to be similar to that required for GDNF therapy; if GDNFR-α is used to antagonize GDNF action, then the GDNFR-α dose would be several times the GDNF dose. Dosing may be one or more times daily, or less frequently, and may be in conjunction with other compositions as described herein. It should be noted that the present invention is not limited to the dosages recited herein.

It is envisioned that the continuous administration or sustained delivery of GDNFR protein products may be advantageous for a given treatment. While continuous administration may be accomplished via a mechanical means, such as with an infusion pump, it is contemplated that other modes of continuous or near continuous administration may be practiced. For example, chemical derivatization or encapsulation may result in sustained release forms of the protein which have the effect of continuous presence in the bloodstream, in predictable amounts, based on a determined dosage regimen. Thus, GDNFR protein products include proteins derivatized or otherwise formulated to effectuate such continuous administration. Sustained release forms of the GDNFR protein products will be formulated to provide the desired daily or weekly effective dosage.

It is further contemplated that the GDNFR protein product may be administered in a combined form with GDNF and/or neurturin. Alternatively, the GDNFR protein product may be administered separately form a neurotrophic factor, either sequentially or simultaneously.

GDNFR protein product of the present invention may also be employed, alone or in combination with other growth factors in the treatment of nerve disease. In addition, other factors or other molecules, including chemical compositions, may be employed together with a GDNFR protein product. For example, in the treatment of Parkinson's Disease, it is contemplated that GDNFR protein product be used by itself or in conjunction with the administration of Levodopa, wherein the GDNFR would enhance the activity of endogenous GDNF and thereby enhance the neuronal uptake of the increased concentration of dopamine.

As stated above, it is also contemplated that additional neurotrophic or neuron nurturing factors will be useful or necessary to treat some neuronal cell populations or some types of injury or disease. Other factors that may be used in conjunction with GDNFR or a combination of GDNFR and a neurotrophic factor such as GDNF or neurturin include, but are not limited to: mitogens such as insulin, insulin-like growth factors, epidermal growth factor, vasoactive growth factor, pituitary adenylate cyclase activating polypeptide, interferon and somatostatin; neurotrophic factors such as nerve growth factor, brain derived neurotrophic factor, neurotrophin-3, neurotrophin-4/5, neurotrophin-6, insulin-like growth factor, ciliary neurotrophic factor, acidic and basic fibroblast growth factors, fibroblast growth factor-5, transforming growth factor, cocaine-amphetamine regulated transcript (CART); and other growth factors such as epidermal growth factor, leukemia inhibitory factor, interleukins, interferons, and colony stimulating factors; as well as molecules and materials which are the functional equivalents to these factors.

GDNFR Protein Product Cell Therapy and Gene Therapy

GDNFR protein product cell therapy, e.g., intracerebral implantation of cells producing GDNFR protein product, is also contemplated. This embodiment would involve implanting into patients cells capable of synthesizing and secreting a biologically active form of GDNFR protein product Such GDNFR protein product-producing cells may be cells that are natural producers of GDNFR protein product or may be recombinant cells whose ability to produce GDNFR protein product has been augmented by transformation with a gene encoding the desired GDNFR protein product. Such a modification may be accomplished by means of a vector suitable for delivering the gene as well as promoting its expression and secretion. In order to minimize a potential immunological reaction in patients being administered a GDNFR protein product of a foreign species, it is preferred that the natural cells producing GDNFR protein product be of human origin and produce human GDNFR protein product. Likewise, it is preferred that the recombinant cells producing GDNFR protein product be transformed with an expression vector containing a gene encoding a human GDNFR protein product.

Implanted cells may be encapsulated to avoid infiltration of surrounding tissue. Human or non-human animal cells may be implanted in patients in biocompatible, semipermeable polymeric enclosures or membranes that allow release of GDNFR protein product, but that prevent destruction of the cells by the patient's immune system or by other detrimental factors from the surrounding tissue. Alternatively, the patient's own cells, transformed to produce GDNFR protein product ex vivo, could be implanted directly into the patient without such encapsulation.

Techniques for the encapsulation of living cells are familiar to those of ordinary skill in the art, and the preparation of the encapsulated cells and their implantation in patients may be accomplished without undue experimentation. For example, Baetge et al. (International Publication No. WO 95/05452; International Application No. PCT/US94/09299 the disclosure of which is hereby incorporated by reference) describe biocompatible capsules containing genetically engineered cells for the effective delivery of biologically active molecules. In addition, see U.S. Pat. No. 4,892,538, 5,011,472, and 5,106,627, each of which is specifically incorporated herein by reference. A system for encapsulating living cells is described in PCT Application WO 91/10425 of Aebischer et al., specifically incorporated herein by reference. See also, PCT Application WO 91/10470 of Aebischer et al., Winn et al., Exper. Neurol., 113:322–329, 1991, Aebischer et al., Exper. Neurol., 111:269–275, 1991; Tresco et al., ASAIO, 38:17–23, 1992, each of which is specifically incorporated herein by reference.

In vivo and in vitro gene therapy delivery of GDNFR protein product is also envisioned. In vitro gene therapy may be accomplished by introducing the gene coding for GDNFR protein product into targeted cells via local injection of a nucleic acid construct or other appropriate delivery vectors. (Hefti, J. Neurobiol,. 25:1418–1435, 1994). For example, a nucleic acid sequence encoding a GDNFR protein product may be contained in an adeno-associated virus vector for delivery into the targeted cells (e.g., Johnson, International Publication No. WO 95/34670; International Application No. PCT/US95/07178 the disclosure of which is hereby incorporated by reference). Alternative viral vectors include, but are not limited to, retrovirus, adenovirus, herpes simplex virus and papilloma virus vectors. Physical transfer, either in vivo or ex vivo as appropriate, may also be achieved by liposome-mediated transfer, direct injection (naked DNA), receptor-mediated transfer (ligand-DNA complex), electroporation, calcium phosphate precipitation or microparticle bombardment (gene gun).

It is also contemplated that GDNFR protein product gene therapy or cell therapy can further include the delivery of GDNF protein product. For example, the host cell may be modified to express and release both GDNFR protein product and GDNF, or GRR2 and neurturin. Alternatively, the GDNFR-α and GDNF protein products, or GRR2 and neurturin, may be expressed in and released from separate cells. Such cells may be separately introduced into the patient or the cells may be contained in a single implantable device, such as the encapsulating membrane described above.

It should be noted that the GDNFR protein product formulations described herein may be used for veterinary as well as human applications and that the term "patient" should not be construed in a limiting manner. In the case of veterinary applications, the dosage ranges may be determined as described above.

EXAMPLES

Example 1

Identification of Cells Expressing High Affinity GDNF Binding Sites

Expression cloning involved the selection of a source of mRNA which is likely to contain significant levels of the target transcript. Retina photoreceptor cells were identified as responsive to GDNF at very low concentrations, suggesting the existence of a functional, high affinity receptor. To confirm that rat photoreceptor cells did express a high affinity receptor for GDNF, [$^{125}$I]GDNF binding and photographic emulsion analysis were carried out.

Rat Retinal Cell Cultures

The neural retinas of 5-day-old C57B1/6 mouse pups or 3-day-old Sprague-Dawley rat pups (Jackson Laboratories, Bar Harbor, Mass.) were carefully removed and dissected free of the pigment epithelium, cut into 1 mm$^2$ fragments and placed into ice-cold phosphate-buffered saline (PBS). The retinas were then transferred into 10 mL of Hank's balanced salt solution (HBSS) containing 120 units papain and 2000 units DNAase and incubated for 20 minutes at 37° C. on a rotary platform shaker at about 200 rpm. The cells were then dispersed by trituration through fire-polished Pasteur pipettes, sieved through a 20 µm Nitex nylon mesh and centrifuged for five minutes at 200×g. The resulting cell pellet was resuspended into HBSS containing 1% ovalbumin and 500 units DNAase, layered on top of a 4% ovalbumin solution (in HBSS) and centrifuged for 10 minutes at 500×g. The final pellet was resuspended in complete culture medium (see below), adjusted to about 15,000 cells/mL, and seeded in 90 µl aliquots into tissue culture plates coated with polyornithine and laminin as previously described (Louis et al., Journal Of Pharmacology And Experimental Therapeutics, 262, 1274–1283, 1992).

The culture medium consisted of a 1:1 mixture of Dulbecco's Modified Eagle's Medium (DMEM) and F12 medium, and was supplemented with 2.5% heat-inactivated horse serum (Hyclone, Logan, Utah), B27 medium supplement (GIBCO, Grand Island, N.Y.), D-glucose (final concentration: 5 mg/mL), L-glutamine (final concentration: 2 mM), 20 mM HEPES, bovine insulin and human transferrin (final concentrations: 2.5 and 0.1 mg/mL, respectively).

Immunocytochemical Identification of Photoreceptors

Photoreceptors were identified by immunostaining for arrestin, a rod-specific antigen. Cultures of photoreceptors were fixed for 30 minutes at room temperature with 4% paraformaldehyde in PBS, pH 7.4, followed by three washes in PBS. The fixed cultures were then incubated in Superblock blocking buffer (Pierce, Rockford, Ill.), containing 1% Nonidet P-40 to increase the penetration of the antibodies. The anti-arrestin antibodies (polyclonal rabbit antibody against the synthetic peptide sequence of arrestin: Val-Phe-Glu-Glu-Phe-Ala-Arg-Gln-Asn-Leu-Lys-Cys (SEQ ID NO:57)) were then applied at a dilution of between 1:2000 in the same buffer, and the cultures were incubated for one hour at 37° C. on a rotary shaker. After three washes with PBS, the cultures were incubated for one hour at 37° C. with goat-anti-rabbit IgG (Vectastain kit from Vector Laboratories, Burlingame, Calif.) at a 1:500 dilution. After three washes with PBS, the secondary antibodies were then labeled with an avidin-biotin-peroxidase complex diluted at 1:500 (45 minutes at 37° C.). After three more washes with PBS, the labeled cell cultures were reacted for 5–20 minutes in a solution of 0.1 M Tris-HCl, pH 7.4, containing 0.04% 3',3'-diaminobenzidine-(HCl)4, 0.06 percent NiCl$_2$ and 0.02 percent hydrogen peroxide. Based on arrestin-immunoreactivity, about 90% of the cells in the cultures were rod photoreceptors.

The survival of photoreceptors was determined by examination of arrestin-stained cultures with bright-light optics at 200× magnification. The number of arrestin-positive photoreceptors was counted in one diametrical 1×6 mm strip, representing about 20 percent of the total surface area of a 6 mm-well. Viable photoreceptors were characterized as having a regularly-shaped cell body, with a usually short axon-like process. Photoreceptors showing signs of degeneration, such as having irregular, vacuolated perikarya or fragmented neurites, were excluded from the counts (most of the degenerating photoreceptors, however, detached from the culture substratum). Cell numbers were expressed either as cells/6 mm well.

Cultured rat retinal cells enriched for photoreceptors (10,000/6-mm well) were treated with human recombinant GDNF (ten-fold serial dilutions ranging from 10 ng/mL to 1 pg/mL). The cultures were fixed after six days and immunostained for arrestin, a rod photoreceptor-specific antigen. In cultures that were not treated with GDNF, the number of photoreceptors declined steadily over time to reach about 25 percent of the initial number after six days in culture. Treatment of the cultures with GDNF resulted in an about two-fold higher number of viable arrestin-positive photoreceptors after six days in culture. The effect of GDNF was maximal at about 200 pg/mL, with an $ED_{50}$ of about 30 pg/mL. In addition to promoting photoreceptor survival, the addition of the GDNF also stimulated the extension of their axon-like process, thereby demonstrating an effect on the morphological development of the photoreceptors (mean neurite length of photoreceptors in GDNF: 68 μm, compared to 27±18 μm in control cultures).

In order to confirm that rat retinal cells express high affinity GDNF receptors, [$^{125}$I]GDNF binding and photographic emulsion analysis were carried out. Post-natal rat photoreceptor cells were seeded on plastic slide flaskettes (Nunc) at a density of 2800 cells/mm2, three to four days before the experiments. The cells were washed once with ice-cold washing buffer (Dulbecco's Modified Eagle's Medium (DMEM) containing 25 mM N-2-hydroxyethylpiperazine-N'-2-ethanesulfonic acid (HEPES), pH 7.5). For competitive binding, the cells were incubated with various concentrations of [$^{125}$I]GDNF in binding buffer (DMEM containing 25 mM HEPES, pH 7.5, and 2 mg/nL of bovine serum albumin (BSA)) in the presence or absence of 500 nM unlabeled GDNF at 4° C. for four hours, Cells were washed four times with ice-cold washing buffer, lysed in 1 M NaOH and the radioactivity associated with the cells was determined in a gamma counter. A significant amount of [$^{125}$I]GDNF bound to the photoreceptor cells even at low ligand concentrations (as low as 30 pM), and this binding was inhibited completely by the presence of excess unlabeled GDNF.

For photographic emulsion detection, cells were incubated with 50 pM of [$^{125}$I]GDNF in binding buffer in the presence or absence of 500 nM unlabeled GDNF at 4° C. for four hours. Cells were washed six times with ice-cold washing buffer, fixed with 2.5% glutaraldehyde and dehydrated sequentially with 50% and 70% ethanol, and dipped in NTB-2 photographic emulsion (Eastman Kodak, Rochester N.Y.). After five days of exposure, the slides were developed and examined. The photographic emulsion analysis demonstrated the association of [$^{125}$I]GDNF to some of the photoreceptor cells, thereby indicating the presence of a receptor for GDNF. This association, however, was efficiently blocked by the addition of unlabeled GDNF.

Example 2

Expression Cloning of a GDNFR-α from Photoreceptor Cells

Rat photoreceptor cells were selected as a possible source of a high affinity receptor for GDNF based upon their cell surface binding of radiolabeled GDNF and their ability to respond to very low concentrations of the ligand, as described in Example 1. In order to identify the receptor, a size-selected cDNA library of approximately 50,000 independent clones was constructed using a mammalian expression vector (a derivative of pSR, Takebe et al., 1988 supra) and mRNA isolated from cultured post-natal rat photoreceptor cells, by the methods described below. The library was divided into pools of approximately 1,500 to 2,000 independent clones and screened using an established expression cloning approach (Gearing et al., EMBO Journal, 8, 3667–3676, 1989). Plasmid DNA representing each pool of the library was prepared and transfected into COS7 cells grown on plastic microscope slide w flaskettes (Nunc, Naperville, Ill.).

The transfected cells were treated with [$^{125}$I]GDNF, fixed with glutaraldehyde, dehydrated, and dipped in photographic emulsion for autoradiography. Following exposure for five days, the slides were developed and examined for the presence of cells covered by silver grains which indicated the binding of [$^{125}$I]GDNF to the cell surface as a result of the cell's expression of a receptor for GDNF. EGF receptor transfected cells treated with [$^{125}$I]EGF were used as a positive control.

One of the 27 pools (F8-11) screened in this manner exhibited 19 positive cells following transfection. Thus, a single cDNA library pool was identified which contained a cDNA clone that expressed GDNFR-α. This pool was divided into 60 smaller subpools of 100 clones/pool which were rescreened by the same procedure described above. Five of these pools were identified as positive and two of the five pools were further subdivided to yield single clones responsible for the GDNF binding activity. Transfection of plasmid DNA from the single clones into COS7 cells resulted in the binding of [$^{125}$I]GDNF to approximately 15% of the cells. This binding was specifically inhibited by competition with excess unlabeled GDNF.

Construction of Expression cDNA Libraries

Rat retinal cells were harvested from postnatal day 3–7 rats and seeded into culture dishes coated with laminin and polyornithine at a density of approximately 5700 cells/mm$^2$. After 3–4 days in culture, the population was estimated to contain approximately 80% photoreceptor cells. Total RNA was prepared from this culture by standard methods, and Poly A+RNA was purified using a polyA-tract kit (Promega, Madison, Wis.). A cDNA library was constructed from the rat photoreceptor poly A+RNA using the Gibco Superscript Choice System (Gibco/BRL, Gaithersburg, Md.). Two micrograms of poly A+RNA were mixed with 50 ng of random hexamers, heated to 70° C. for 10 minutes and then quick-chilled on ice. First strand synthesis was carried out with 400U Superscript II RT at 37° C. for one hour. Second strand synthesis was performed in the same tube after the addition of dNTPs, 10U of E. coli DNA ligase, 40U of E. coli DNA polymerase I, and 2U of E. coli RNase H. After two hours at 16° C., the cDNA ends were blunted by treatment with 10U of T4 polymerase for an additional five minutes at 16° C. Following isopropanol precipitation, EcoRI cloning sites were added to the cDNA by ligation overnight with 10 μg of unphosphorylated EcoRI adapter oligonucleotides.

The EcoRI adapted cDNA was then phosphorylated and applied to a Sephacryl S-500 HR size fractionation column. Following loading, the column was washed with 100 μl aliquots of TEN buffer (10 mM Tris-HCl pH 7.5, 0.1 mM EDTA, 25 mM NaCl), and 30 μl fractions were collected. Fractions 6 through 8, which contained approximately 34 ng of high molecular weight cDNA, were pooled and precipitated. The recovered EcoRI-adapted cDNA was ligated overnight with 50 ng of EcoRI cut vector pBJ5. Aliquots of the ligation mix containing about 15 ng cDNA each were transformed into competent cells (*E. coli* strain DH10B; GIBCO/BRL, Gaithersburg, Md.) by electroporation. The transformation mixture was titered and then plated on 27 Amp/LB plates at a density of 1500 colonies/plate. Colonies were scraped from each plate and collected into 10 mL of Luria broth (LB) to make 27 pools of 1500 independent clones each. A portion of the cells from each pool was frozen in glycerol and the remainder was used to isolate plasmid DNA using a Qiagen tip-500 kit (Qiagen Inc., Chatsworth, Calif.).

COS Cell Transfection and Photographic Emulsion Analysis

COS7 cells were seeded (220,000 cells/slide) on plastic slide flaskettes (Nunc) coated with ProNectin (10 µg/mL in phosphate buffered saline (PBS)) one day before transfection. For transfection, 700 µl of Opti MEMI (GIBCO/BRL, Gaithersburg, Md.) containing 2 µg cDNA was mixed gently with 35 µl of DEAE Dextran solution (10 mg/mL, Sigma, St. Louis, Mo.) in an Eppendorf tube. Cells were washed twice with PBS and incubated with the transfection mix for 30 minutes at 37° C. in a 5% $CO_2$ atmosphere. Following incubation, 3 mL of DMEM media containing 10% fetal calf serum (FCS) and 80 nM Chloroquine (Sigma, St. Louis, Mo.) were added to each flaskette. Cells were further incubated for 3.5 hours, shocked with 10% dimethylsulfoxide in DMEM at room temperature for two minutes, washed once with PBS, and allowed to grow in DMEM containing 10% FCS. After 48 hours, the transfected COS7 cells were washed once with ice-cold washing buffer (DM containing 25 mM HEPES, pH 7.5) and incubated in ice-cold binding buffer (DMEM containing 25 mM HEPES, pH 7.5 and 2 mg/mL BSA) supplemented with 50 pM [$^{125}$I]GDNF at 4° C. for four hours. Cells were washed six times in ice-cold washing buffer, fixed with 2.5% glutaraldehyde at room temperature for five minutes, dehydrated sequentially with 50% and 70% ethanol, and then dipped in NTB-2 photographic emulsion (Eastman Kodak). After 4–5 day exposure at 4° C. in dark, the slides were developed and screened by bright-field and dark-field microscopy.

Subdivision of Positive Pools

A single pool was identified which contained a putative GDNF receptor clone. Clones from this pool were plated on 60 plates at a density of 100 colonies/plate. Cells were scraped from each plate, collected in LB, and allowed to grow for 4–5 hours at 37° C. Frozen stocks and DNA preparations were made from each pool, as before, to generate 60 subpools containing 100 independent clones each. Two of these 60 subpools were identified as positive by the method described above, and clones from those pools were plated at low density to allow isolation of single colonies. Single colonies (384) were picked from each of the two subpools and grown for six hours in 200 µl LB in 96-well plates. In order to select single clones expressing GDNFR-α, the four 96-well plates were arrayed into a single large matrix consisting of 16 rows and 24 columns. Cells from the wells in each row and in each column were combined to yield a total of 40 mixtures. These mixtures were grown overnight in 10 mL LB/Amp (100 µg/mL), and DNA was prepared using a Qiagen tip-kit. When analyzed for putative GDNF receptor clones, three row mixtures and three column mixtures gave positive signals, suggesting nine potentially positive single clones. DNA from each of the nine potentially positive single clones was prepared and digested with EcoRI and PstI. DNA from three of the nine single clones exhibited identical restriction patterns while the other six were unrelated, suggesting that the three represented the authentic clones containing GDNFR-α.

Example 3

DNA Sequencing and Sequence Analysis

DNA from positive, single clones was prepared and sequenced using an automated ABI373A DNA sequencer (Perkin/Elmer Applied Biosystems, Santa Clara, Calif.) and dideoxy-dye-terminators, according to manufacturer's instructions. Comparison of GDNFR-α sequence with all available public databases was performed using the FASTA (Pearson and Lipman, Proceedings Of The National Academy Of Sciences U.S.A., 85, 2444–2448, 1988) program algorithm as described in the University of Wisconsin Genetics Computer Group package (Program Manual for the Wisconsin Package, Version 8, September 1994, Genetics Computer Group, Madison, Wis.).

Sequence Characterization of the Rat GDNFR-α

Plasmid DNA from the clones described in Example 2, above, was prepared and submitted for DNA sequence analysis. Nucleotide sequence analysis of the cloned 2138 bp rat cDNA revealed a single large open reading frame encoding a translation protein of 468 amino acid residues (FIG. 3).

The coding sequence is flanked by a 5'-untranslated region of 301 bp and a 3'-untranslated region of 430 bp that does not contain a potential polyadenylation site. The presence of an in-frame stop codon upstream of the first ATG at base pair 302 and its surrounding nucleotide context indicate that this methionine codon is the most likely translation initiator site (Kozak, Nucleic Acids Research. 15, 8125–8148, 1987).

No polyadenylation signal is found in the 430 nucleotides of 3' untranslated sequence in the rat cDNA clone. This is not surprising, since the Northern blot data shows the shortest mRNA transcripts to be approximately 3.6 kb.

The GDNFR polypeptide sequence has an N-terminal hydrophobic region of approximately 19 residues (methionine-1 to alanine-19, FIG. 3) with the characteristics of a secretory signal peptide (von Heijne, Protein Sequences And Data Analysis. 1, 41–42, 1987; von Heijne, Nucleic Acids Research. 14, 4683–4690, 1986). No internal hydrophobic domain that could serve as a transmembrane domain was found. Instead, a carboxy-terminal hydrophobic region of 21 residues (leucine-448 to serine-468 in FIG. 3) is present and may be involved in a glycosylphosphatidylinositol (GPI) anchorage of the receptor to the cytoplasmic membrane. Except for the presence of three potential N-linked glycosylation sites, no conserved sequence or structural motifs were found. The protein is extremely rich in cysteine (31 of the 468 amino acid residues) but their spacing is not shared with that of cysteine-rich domains found in the extracellular portions of known receptors.

The GDNFR-α sequence was compared to sequences in available public databases using FASTA. The search did not reveal significant homology to other published sequences. Once the rat cDNA clone was obtained, it was radiolabeled and used to probe a cDNA library prepared from human brain substantia nigra as described below in Example 5.

Example 4

GDNF Binding to Cells Expressing GDNFR-α

A binding assay was performed in accordance with an assay method previously described by Jing et al. (Journal Of Cell Biology, 110, 283–294, 1990). The assay involved the binding of [$^{125}$I]GDNF to rat photoreceptor cells, COS7 cells or 293T cells which had been transfected to express GDNFR-α. Recombinant GDNFR-α expressed on the surface of 293T cells was able to bind GDNF specifically and with an affinity comparable to that observed for GDNF binding sites on rat retinal cells.

Rat photoreceptor cells were prepared as described in Example 1, above, and seeded at a density of 5.7×10$^5$ cells/cm$^2$ two to three days before the assay in 24-well Costar tissue culture plates pre-coated with polyornithine and laminin. COS7 cells were seeded at a density of 2.5×10$^4$ cells/cm$^2$ one day before the assay and transfected with 10–20 μg of plasmid DNA using the DEAE-dextran-chloroquine method (Aruffo and Seed, Proceedings Of The National Academy Of Sciences U.S.A., 84, 8573–8577, 1987). Cells from each dish were removed and reseeded into 30 wells of 24-well Costar tissue culture plates 24 hours following the transfection, and allowed to grow for an additional 48 hours. Cells were then left on ice for 5 to 10 minutes, washed once with ice-cold washing buffer and incubated with 0.2 mL of binding buffer containing various concentrations of [$^{125}$I]GDNF with or without unlabeled GDNF at 4° C. for four hours. Cells were washed four times with 0.5 mL ice-cold washing buffer and lysed with 0.5 mL of 1 M NaOH. The lysates were counted in a 1470 Wizard Automatic Gamma Counter.

For some binding experiments, transiently transfected 293T cells were used (see below for 293T cell transfection). Two days following transfection, cells were removed from dishes by 2× versine. Cells were pelleted, washed once with ice-cold binding buffer and resuspended in ice-cold binding buffer at a density of 3×10$^5$ cells/mL. The cell suspension was divided into aliquots containing 1.5×10$^5$ cell/sample. Cells were then pelleted and incubated with various concentrations of [$^{125}$I]GDNF in the presence or absence of 500 nM of unlabeled GDNF at 4° C. for four hours with gentle agitation. Cells were washed four times with ice-cold washing buffer and resuspended in 0.5 mL washing buffer. Two 0.2 mL aliquots of the suspension were counted in a gamma counter to determine the amount of [$^{125}$I]GDNF associated with the cells.

In all assays, nonspecific binding was determined by using duplicate samples, one of which contained 500 nM of unlabeled GDNF. The level of nonspecific binding varied from 10% to 20% of the specific binding measured in the absence of unlabeled GDNF and was subtracted from the specific binding. The assays demonstrated that cells did not bind GDNF unless the cell had been transfected with the GDNFR-α cDNA clone.

Example 5

Tissue Distribution of GDNFR-α mRNA

The pattern of expression of GDNFR-α mRNA in embryonic mouse, adult mouse, rat, and human tissues was examined by Northern blot analysis. The cloned rat GDNFR-α cDNA was labeled using the Random Primed DNA Labeling Kit (Boehringer Mannheim, Indianapolis, Ind.) according to the manufacturer's procedures. Rat, mouse, and human tissue RNA blots (purchased from Clontech, Palo Alto, Calif.) were hybridized with the probe and washed using the reagents of the ExpressHyb Kit (Clontech) according to the manufacturer's instructions.

Tissue Northern blots prepared from adult rat, mouse, and human tissues indicated that GDNFR-α mRNA is most highly expressed in liver, brain, and kidney. High mRNA expression was also detected in lung, with lower or non-detectable amounts in spleen, intestine, testis, and skeletal muscle. In blots made from mRNA isolated from mouse embryo, expression was undetectable at embryonic day 7, became apparent at day E11, and was very high by day E17. GDNFR-α mRNA was expressed in tissue isolated from several subregions of adult human brain at relatively equal levels. Expression of GDNFR-α mRNA in human adult brain showed little specificity for any particular region.

In most tissues, transcripts of two distinct sizes were present. In mouse and human tissues, transcripts of 8.5 and 4.4 kb were found, while in rat the transcripts were 8.5 and 3.6 kb. The relative amounts of the larger and smaller transcripts varied with tissue type, the smaller transcript being predominant in liver and kidney and the larger being more abundant in brain. The binding of GDNF to 293T cells transfected with a GDNFR-α cDNA clone in the pBKRSV vector was examined by Scatchard analysis. Two classes of binding sites were detected, one with a binding affinity in the low picomolar range and another with an affinity of about 500 pM.

Example 6

Recombinant Human GDNFR-α

An adult human substantia nigra cDNA library (5'-stretch plus cDNA library, Clontech, Palo Alto, Calif.) cloned in bacteriophage gt10 was screened using the rat GDNFR-α cDNA clone of Example 1 as a probe. The probe was labeled with [$^{32}$P]-dNTPs using a Random Primed DNA Labeling Kit (Boehringer Mannheim, Indianapolis, Ind.) according to the manufacturer's instructions. Approximately 1.2×10$^6$ gt10 phage from the human substantia nigra cDNA library were plated on 15 cm agarose plates and replicated on duplicate nitrocellulose filters. The filters were then screened by hybridization with the radiolabeled probe. The filters were prehybridized in 200 mL of 6×SSC, 1×Denhardts, 0.5% SDS, 50 μg/mL salmon sperm DNA at 55° C. for 3.5 hours. Following the addition of 2×10$^8$ cpm of the radiolabeled probe, hybridization was continued for 18 hours. Filters were then washed twice for 30 minutes each in 0.5× SSC, 0.1% SDS at 55° C. and exposed to X-ray film overnight with an intensifying screen.

Five positive plaques were isolated whose cDNA inserts represented portions of the human GDNFR-α cDNA. In comparison to the nucleic acid sequence of rat GDNFR-α depicted in FIG. 3 (bp 0 through 2140), the five human GDNFR-α clones were found to contain the following sequences:

TABLE 3

| Clone 2 | 1247 through 2330 (SEQ ID NO:21) |
| Clone 9 | 1270 through 2330 (SEQ ID NO:23) |
| Clone 21-A | −235 through 1692 (SEQ ID NO:9) |
| Clone 21-B | 237 through 1692 (SEQ ID NO:11) |
| Clone 29 | 805 through 2971 (SEQ ID NO:15) |

An alignment and comparison of the sequences, as depicted in FIG. 5, provided a consensus sequence for human GDNFR-α. The translation product predicted by the human cDNA sequence consists of 465 amino acids and is 93% identical to rat GDNFR-α.

To generate a human cDNA encoding the full length GDNFR-α, portions of clones 21B and 2 were spliced together at an internal BglII site and subcloned into the mammalian expression vector pBKRSV (Stratagene, La Jolla, Calif.).

Recombinant human GDNFR expression vectors may be prepared for expression in mammalian cells. As indicated above, expression may also be in non-mammalian cells, such as bacterial cells. The nucleic acid sequences disclosed herein may be placed into a commercially available mammalian vector (for example, CEP4, Invitrogen) for expression in mammalian cells, including the commercially available human embryonic kidney cell line, "293". For expression in bacterial cells, one would typically eliminate that portion encoding the leader sequence (e.g., nucleic acids 1–590 of FIG. 1). One may add an additional methionyl at the N-terminus for bacterial expression. Additionally, one may substitute the native leader sequence with a different leader sequence, or other sequence for cleavage for ease of expression.

Example 7

Soluble GDNFR Constructs

Soluble human GDNFR protein products were made. The following examples provide four different forms, differing only at the carboxy terminus, indicated by residue numbering as provided in FIG. 2. Two are soluble forms truncated at different points just upstream from the hydrophobic tail and downstream from the last cysteine residue. The other two are the same truncations but with the addition of the "FLAG" sequence, an octapeptide to which a commercial antibody is available (Eastman Kodak). The FLAG sequence is H$_2$N-DYKDDDDK-COOH (SEQ ID NO:58).

Method

Lambda phage clone #21, containing nearly the entire coding region of human GDNFR-α, was digested with EcoRI to excise the cDNA insert. This fragment was purified and ligated into EcoRI cut pBKRSV vector (Stratagene, La Jolla, Calif.) to produce the clone 21-B-3/pBKRSV. Primers 1 and 2 as shown below were used in a PCR reaction with the human GDNFR-α clone 21-B-3/pBKRSV as template. PCR conditions were 94° C., five minutes followed by 25 cycles of 94° C., one minute; 55° C., one minute; 72° C., two minutes and a final extension of five minutes at 72° C. This produced a fragment consisting of nucleotides 1265–1868 of the human GDNFR-α clone plus a termination codon and Hind III restriction site provided by primer 2. This fragment was digested with restriction enzymes Hind III (contained in primer 2) and BglII (position 1304 in human GDNFR-α), and the resulting 572 nucleotide fragment was isolated by gel electrophoresis. This fragment contained the hGDNFR-α-coding region from isoleucine-255 to glycine-443. A similar strategy was used with primers 1 and 3 to produce a fragment with BglII and HindIII ends which coded for isoleucine-255 to proline-446. Primers 4 and 5 were designed to produce fragments coding for the same regions of hGDNFR-α and primers 1 and 3, but with the addition of the Flag peptide coding sequence (IBI/Kodak, New Haven, Conn.). The Flag peptide sequence consists of eight amino acids (H2N-Asp-Tyr-Lys-Asp-Asp-Asp-Asp-Lys-COOH (SEQ ID NO:61) to which antibodies are commercially available. Primers 1 and 4 or 1 and 5 were used in PCR reactions with the same template as before, and digested with HindIII and BglII as before. This procedure produced fragments coding for isoleucine-255 to glycine-443 and isoleucine-255 to proline-446, but with the addition of the Flag peptide at their carboxy termini.

| Primers |
| --- |
| 1) 5'-CTGTTTGGAATTTGCAGGACTC-3' (SEQ ID NO:30) |
| 2) 5'-CTCCTCTCTAAGCTTCTAACCACAGCTTGGAGGAGC-3' (SEQ ID NO:31) |
| 3) 5'-CTCCTCTCTAAGCTTCTATGGGCTCAGACCACAGCTT-3' (SEQ ID NO:32) |
| 4) 5'-CTCCTCTCTAAGCTTCTACTTGTCATCGTCGTCCTTGTA GTCACCACAGCTTGGAGGAGC-3' (SEQ ID NO:33) |
| 5) 5'-CTCCTCTCTAAGCTTCTACTTGTCATCGTCGTCCTTGTAG TCTGGCTCAGACCACAGCTT-3' (SEQ ID NO:34) |

All four fragments, produced as described above, were transferred back into 21B3/pBKRSV. The 21B3/pBKRSV clone was digested with BglII and HindIII, and treated with calf intestinal alkaline phosphatase (CIAP). The large fragment containing the vector and the human GDNFR-α coding region up to the BglII site was gel purified and extracted from gel. Each of the four BglII/HindIII fragments produced as described above were ligated into this vector resulting in the following constructs in the pBKRSV vector:

TABLE 4

| | | |
| --- | --- | --- |
| 1) | GDNFR-α/gly-443/ pBKRSV | hGDNFR-α terminating at glycine 443, followed by stop codon |
| 2) | GDNFR-α/pro-446/ pBKRSV | hGDNFR-α terminating at proline 446, followed by stop codon |
| 3) | GDNF-α/gly-443/Flag/pBKRSV | hGDNFR-α terminating at glycine 443 with C-term Flag tag, followed by stop codon |
| 4) | GDNFR-α/pro-446/Flag/pBKRSV | hGDNFR-α terminating at proline 446 with C-term Flag tag, followed by stop codon |

Correct construction of all clones was confirmed by DNA sequencing. Inserts from the pBKRSV clones were transferred to other expression vectors using enzyme sites present in the pBKRSV polylinker sequence as described below. Soluble GDNFRs (e.g., sGDNFR-α/gly and sGDNFR-α/pro) have also been transferred into vectors for transient expression and into pDSR-2 for stable expression in CHO cells.

pDSRα2+PL Clones:

The appropriate pBKRSV clone is digested with XbaI and SalI. The insert is ligated to pDSRα2+PL cut with the same enzymes and treated with CIAP. This construction may be used for stable expression of GDNFR in CHO cells.

pCEP4 Clones:

The appropriate pBKRSV clone is digested with SpeI and XhoI. The insert is ligated to pCEP4 (Invitrogen, San Diego, Calif.) digested with NheI (SpeI ends) and XhoI, and treated with CIAP. This construction may be used for transient of expression of GDNFR.

The plasmid construct pDSR-2 is prepared substantially in accordance with the process described in the co-owned and U.S. patent application Ser. No. 09/501,904 filed Mar. 29, 1990, now abandoned (also see, European Patent Application No. 90305433, Publication No. EP 398 753, filed May 18, 1990 and WO 90/14363 (1990), the disclosures of which are hereby incorporated by reference. It will be appreciated by those skilled in the art that a variety of nucleic acid sequences encoding GDNFR analogs may be used.

Another construct is pDSRα2; a derivative of the plasmid pCD (Okayamna & Berg, Mol. Cell Biol. 3: 280–289, 1983) with three main modifications: (i) the SV40 polyadenylation signal has been replaced with the signal from the α-subunit of bovine follicular stimulating hormone, α-bFSH (Goodwin et al., Nucleic Acids Res. 11: 6873–6882, 1983); (ii) a mouse dihydrofolate reductase minigene (Gasser et al., Proc. Natl. Acad. Sci. 79: 6522–6526, 1982) has been inserted downstream from the expression cassette to allow selection and amplification of the transformants; and (iii) a 267 bp fragment containing the "R-element" and part of the "U5" sequences of the long terminal repeat (LTR) of human T-cell leukemia virus type I (HTLV-I) has been cloned and inserted between the SV40 promoter and the splice signals as described previously (Takebe et al., Mol. Cell Biol. 8: 466–472, 1988).

The expression of GDNFR-α in CHO cells has been verified by the binding of iodinated GDNF to the cell surface. As discussed above, the recombinantly expressed soluble GDNFR-α protein product may be used to potentiate the activity or cell specificity of GDNF. Soluble GDNFR-α attached to a detectable label also may be used in diagnostic applications as discussed above.

Example 8

Chemical Crosslinking of GDNF with GDNFR-α

In order to study its binding properties and molecular characteristics, GDNFR-α was transiently expressed on the surface of 293T cells by transfection of the rat cDNA clone. Transfection of 293T cells was performed using the Calcium Phosphate Transfection System (GIBCO/BRL, Gaithersburg, Md.) according to the manufacturers instructions. Two days following transfection, cells were removed by 2× versine treatment, washed once with washing buffer, and resuspended in washing buffer at a density of 2×10$^6$ cells/mL. A duplicate set of cells were incubated with 0.5 u/mL PI-PLC at 37° C. for 30 minutes before [$^{125}$I]GDNF binding. These cells were washed three times with ice-cold binding buffer and then incubated with 1 to 3 nM of [$^{125}$I]GDNF along with other cells at 4° C. for four hours. Cells were washed four times with ice-cold washing buffer, resuspended in washing buffer supplemented with 1 mM of Bis suberate for crosslinking (BS$^3$ Pierce, Rockford, Ill.) and incubated at room temperature for 30 minutes. Following three washes with TBS, a duplicate group of samples was treated by 0.5 u/mL of PI-PLC at 37° C. for 30 minutes. These cells were pelleted and the supernatants were collected. The cells were then washed with washing buffer and lysed along with all other cells with 2×SDS-PAGE sample buffer. The cell lysates and the collected supernatants were resolved on a 7.5% SDS-PAGE.

The cell suspension was divided into aliquots containing 1.5×10$^5$ cell/sample. Cells were then pelleted and incubated with various concentrations of [$^{125}$I]GDNF in the presence or absence of 500 nM of unlabeled GDNF at 4° C. for four hours with gentle agitation. Cells were washed four times with ice-cold washing buffer and resuspended in 0.5 mL washing buffer. Two 0.2 mL aliquots of the suspension were counted in a gamma counter to determine the amount of [$^{125}$I]GDNF associated with the cells.

Although mock transfected 293T cells did not exhibit any GDNF binding capacity, GDNFR-α transfected cells bound [$^{125}$I]GDNF strongly even at picomolar concentrations. This binding was almost completely inhibited by 500 nM of unlabeled GDNF, indicating a specific binding of native GDNF to the expressed receptors.

GDNFR-α expressed by the 293T cells can be released from the cells by treatment with phosphatidylinositol-specific phospholipase C (PI-PLC, Boehringer Mannheim, Indianapolis, Ind.). The treatment of transfected cells with PI-PLC prior to ligand binding almost entirely eliminated the GDNF binding capacity of the cell. Additionally, treatment of the transfected cells after cross-linking released the majority of the cross-linked products into the media. These results strongly suggest that GDNFR-α is anchored to the cell membrane through a GPI linkage.

Crosslinking data further indicated that the molecular weight of GDNFR-α is approximately 50–65 kD, suggesting that there is a low level of glycosylation. Although the major cross-linked species has a molecular mass consistent with a monomer of the receptor, a minor species with approximately the mass expected for a dimer has been found.

Example 9

GDNF Signaling is Mediated by a Complex of GDNFR-α and the Ret Receptor Protein Tyrosine Kinase Introduction Mice carrying targeted null mutations in the GDNF gene exhibit various defects in tissues derived from neural crest cells, in the autonomic nervous system, and in trigeminal and spinal cord motor neurons. The most severe defects are the absence of kidneys and complete loss of enteric neurons in digestive tract. The phenotype of GDNF knockout mice is strikingly similar to that of the c-ret knockout animals (Schuchardt et al. 1994), suggesting a possible linkage between the signal transduction pathways of GDNF and c-ret.

The proto-oncogene c-ret was identified using probes derived from an oncogene isolated in gene transfer experiments (Takahashi et al., Cell. 42, 581–588, 1985; Takahashi and Cooper, Mol. Cell. Biol., 7, 1378–1385, 1987). Sequence analysis of the c-ret cDNA revealed a large open reading frame encoding a novel receptor protein tyrosine kinase (PTK). The family of receptor PTKs has been grouped into sub-families according to extracellular domain structure and sequence homology within the intracellular kinase domain (van der Geer et al., 1994). The unique extracellular domain structure of Ret places it outside any other known receptor PTK sub-family; it includes a signal peptide, a cadherin-like motif, and a cysteine-rich region (van Heyningen, Nature, 367, 319–320, 1994; Iwamoto et al., 1993). In situ hybridization and immunohistochemical analysis showed high level expression of ret mRNA and protein in the developing central and peripheral nervous systems and in the excretory system of the mouse embryo (Pachnis et al., 1993; Tsuzuki et al., Oncogene, 10, 191–198, 1995), suggesting a role of the Ret receptor either in the development or in the function of these tissues. A functional ligand of the Ret receptor has not been identified, thereby limiting a further understanding of the molecular mechanism of Ret signaling.

Mutations in the c-ret gene are associated with inherited predisposition to cancer in familial medullary thyroid carcinoma (FMTC), and multiple endocrine neoplasia type 2A (MEN2A) and 2B (MEN2B). These diseases are probably caused by "gain of function" mutations that constitutively activate the Ret kinase (Donis-Keller et al., Hum. Molec. Genet. 2, 851–856, 1993; Hofstra et al., Nature. 367, 375–376, 1994; Mulligan et al., Nature. 363, 458–460, 1993; Santoro et al., Science. 267, 381–383, 1995). They confer a predisposition to malignancy specifically in tissues derived from the neural crest, where ret is normally expressed in early development. Another ret-associated genetic disorder, Hirschsprung's disease (HSCR), is characterized by the congenital absence of parasympathetic innervation in the lower intestinal tract (Edery et al., Nature. 367, 378–380, 1994; Romeo et al., 1994). The most likely causes of HSCR are nonsense mutations that result in the production of truncated Ret protein lacking a kinase domain or missense mutations that inactivate the Ret kinase. As noted above, targeted disruption of the c-ret proto-oncogene in mice results in renal agenesis or severe dysgenesis and lack of enteric neurons throughout the digestive tract (Schuchardt et al., 1994). This phenotype closely resembles that of GDNF knockout mice. Taken together, these data suggest that both Ret and GDNF are involved in signal transduction pathways critical to the development of the kidney and the enteric nervous system. How Ret and GDNF are involved, however, was not known.

The isolation and characterization of cDNA for GDNFR-α by expression cloning, as described above, lead to the expression of GDNFR-α in the transformed human embryonic kidney cell line 293T. Transformation resulted in the appearance of both high ($K_d$ of approximately 2 pM) and low ($K_d$ of approximately 200 pM) affinity binding sites. The high affinity binding sites could be composed of homodimers or homo-oligomers of GDNFR-α alone, or of heterodimers or hetero-oligomers of GDNFR-α with other molecules. As discussed above, because GDNFR-α lacks a cytoplasmic domain, it must function through one or more accessory molecules in order to play a role in GDNF signal transduction. In this study we confirm that, in the presence of GDNFR-α, GDNF associates with the Ret protein tyrosine kinase receptor, and quickly induces Ret autophosphorylation.

Results
Neuro-2a Cells Expressing GDNFR-α Bind GDNF with High Affinity

Neuro-2a is a mouse neuroblastoma cell line that endogenously expresses a high level of Ret protein (Ikeda et al., Oncogene. 5, 1291–1296, 1990; Iwamoto et al., Oncogene. 8, 1087–1091, 1993; Takahashi and Cooper, 1987) but does not express detectable levels of GDNFR-α mRNA as judged by Northern blot. In order to determine if Ret could associate with GDNF in the presence of GDNFR-α, a study was performed to examine the binding of [$^{125}$I]GDNF to Neuro-2a cells engineered to express GDNFR-α. Neuro-2a cells were transfected with a mammalian expression vector containing the rat GDNFR-α cDNA (such as the expression plasmid described above). Three clonal lines, NGR-16, NGR-33, and NGR-38 were tested for their ability to bind [$^{125}$I]GDNF. The unbound [$^{125}$I]GDNF was removed at the end of the incubation and the amount of radioactivity associated with the cells was determined as described in Experimental Procedures. All three lines were able to bind [$^{125}$I]GDNF specifically while parental Neuro-2a cells exhibited little or no [$^{125}$I]GDNF binding (FIG. 6). Binding could be effectively competed by the addition of 500 nM unlabeled GDNF. These results demonstrate that Ret receptor expressed on Neuro-2a cells is unable to bind GDNF in the absence of GDNFR-α and are consistent with the previous observation that GDNFR-α is not expressed at appreciable levels in Neuro-2a cells.

Equilibrium binding of [$^{125}$I]GDNF to NGR-38 cells was examined over a wide range of ligand concentrations (0.5 pM to 1 nM of [$^{125}$I]GDNF in the presence or absence of 500 nM of unlabeled GDNF) (see FIG. 7A). Following incubation, unbound [$^{125}$I]GDNF was removed and the radioactivity associated with the cells was determined as described in Experimental Procedures. Results are depicted in FIG. 7: (A) Equilibrium binding of [$^{125}$I]GDNF to NGR-38 cells (circles) and Neuro-2a cells (squares) in the presence (open circles and open squares) or absence (filled circles and filled squares) of unlabeled GDNF; (B) Scatchard analysis of [$^{125}$I]GDNF binding to NGR-38 cells. Neuro-2a cells exhibited little binding even at a concentration of 1 nM [$^{125}$I]GDNF, and this binding was not affected by the addition of excess unlabeled GDNF. Binding to NGR-38 cells was analyzed by Scatchard plot as shown in FIG. 7B. Two classes of binding sites were detected, one with $K_d$=1.5±0.5 pM and the other with $K_d$=332±53 pM. These dissociation constants are very similar to the values obtained for the high and low affinity binding sites in 293T cells transiently expressing GDNFR-α, as described above.

GDNF Associates with Ret in Neuro-2a Cells Expressing GDNFR-α

In order to determine if the Ret receptor PTK could associate with GDNF in cells expressing GDNFR-α, a cross-linking experiment was carried out using NGR-38 and parental Neuro-2a cells. NGR-38 cells were incubated with [$^{125}$I]GDNF, treated with cross-linking reagent, then lysed either directly in SDS-PAGE sample buffer or in Triton X-100 lysis buffer and further immunoprecipitated with anti-Ret antibody as described in the Experimental Procedures. The immunoprecipitates were analyzed by SDS-PAGE in the absence (NR) or presence (R) of -mercaptoethanol. Lysates were treated with Ret specific antibody, immunoprecipitated, and analyzed by SDS-PAGE under reducing conditions (see FIG. 8, bands are marked as follows: ~75 kD, solid triangle; ~150 kD, open triangle; ~185 kD, solid arrow; ~250 kD, asterisk; ~400 kD, open arrow). The most prominent cross-linked species were at ~75 kD, and ~185 kD, with less intense bands of ~150 kD and ~250 kD. A very faint band of ~400 kD was also visible (FIG. 8, lane 2). When immunoprecipitates were analyzed by non-reducing SDS-PAGE, the ~75 kD, ~150 and ~185 kD bands were present at about the same intensity as in the reducing gel, but the amount of the ~400 kD band increased dramatically (FIG. 8, lane 4). Also becoming more prominent was the band at ~250 kD.

Under both reducing and non-reducing conditions, bands of similar molecular weight but of greatly reduced intensity were observed when parental Neuro-2a cells were used instead of NGR-38 (FIG. 8, lanes 1 and 3). The ~75 kD and ~150 kD species are likely to represent cross-linked complexes of GDNF and GDNFR-α, since species with identical molecular weights are produced by cross-linking in 293T cells that do not express Ret. Furthermore, since the molecular weight of Ret is 170 kD, any complex including Ret must be of at least this size.

The fact that these complexes are immunoprecipitated by anti-Ret antibody indicates they are products of an association between Ret and the GDNF/GDNFR-α complex which was disrupted under the conditions of the gel analysis. It is envisioned that the broad band at ~185 kD probably consists of one molecule of Ret (170 kD) cross-linked with one molecule of monomeric recombinant GDNF (15 kD), although some dimeric GDNF may be included. The presence of Ret in this species was confirmed by a separate experiment in which a band of the same molecular weight was observed when unlabeled GDNF was cross-linked to NGR-38 cells and the products examined by Western blot with anti-Ret antibody (data not shown).

The ~400 kD band was not reliably identified, partly due to the difficulty in estimating its molecular weight. The fact that it is prominent only under non-reducing conditions indicates that it is a disulfide-linked dimer of one or more of the species observed under reducing conditions. The most likely explanation is that it represents a dimer of the 185 kD species, although it may be a mixture of high molecular weight complexes consisting of two Ret, one or two GDNFR-α, and one or two GDNF molecules. The exact identity of the ~250 kD band has not yet been determined. One possibility is that it represents cross-linked heterodimers of the ~75 kD (GDNF+GDNFR-α) and ~185 kD (GDNF+Ret) complexes.

GDNF Stimulates Autophosphorylation of Ret in Neuro-2a Cells Expressing GDNFR-α

Figure 9A:
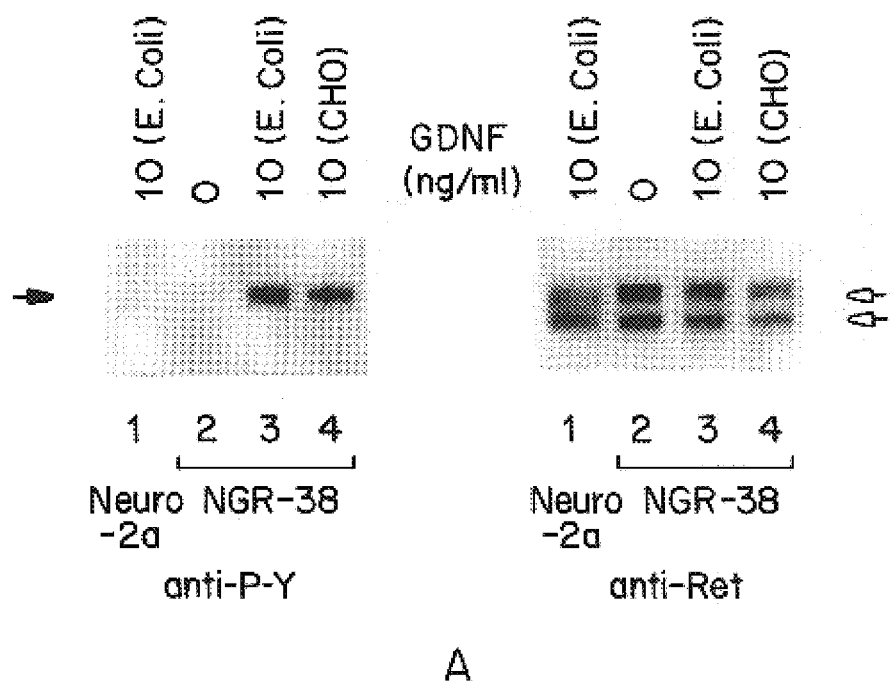

The ability of the Ret protein tyrosine kinase receptor to associate with GDNF in the presence of GDNFR-α led to the study of GDNF stimulation of the autophosphorylation of Ret. NGR-38 cells were treated with GDNF, lysed, and the lysates immunoprecipitated with anti-Ret antibody. The immunoprecipitates were analyzed by Western blot using an anti-phosphotyrosine antibody as described in the Experimental Procedures. When NGR-38 cells (FIG. 9A, lanes 2–4) were treated with purified recombinant GDNF produced in either mammalian (CHO cells; FIG. 9A, lanes 4) or E. coli cells (FIG. 9A, lanes 1, 3), a strong band was observed at 170 kD, indicating autophosphorylation of tyrosine residues on the mature form of Ret. A much weaker corresponding band was observed in GDNF-treated Neuro-2a cells (FIG. 9A, lane 1). No phosphorylation was observed on the alternatively glycosylated 150 kD precursor form of Ret (FIG. 9A). The induction of Ret autophosphorylation by GDNF was dosage dependent. The dose response and kinetics of GDNF-induced Ret tyrosine phosphorylation in NGR-38 cells are shown in panels B and C. In all panels, the tyrosine phosphorylated 170 kD Ret bands are indicated by solid arrows. The amount of Ret protein loaded in each lane as determined by reprobing of the immunoblot with anti-Ret antibody (Santa Cruz, C-19, Cat. #sc-167) is shown on the right side of panel A. The band at ~150 kD represents an alternately glycosylated immature form of Ret that does not autophosphorylate. As shown in FIG. 9B, stimulation of Ret autophosphorylation in NGR-38 cells could be detected with 50 pg/mL of GDNF and the response was saturated at 20–50 ng/mL GDNF. The stimulation of Ret autophosphorylation by purified recombinant GDNF in NGR-38 cells over times of 0–20 minutes following treatment is shown in FIG. 9C. Increased levels of Ret autophosphorylation could be observed within one minute of GDNF treatment and was maximal at 10 minutes following treatment (FIG. 9C).

GDNF and Soluble GDNFR-α Induce Ret Autophosphorylation in Neuro-2A Cells

As discussed above, GDNFR-α is anchored to the cytoplasmic membrane through a GPI linkage and can be released by treatment with phosphatidylinositol-specific phospholipase C (PI-PLC). When NGR-38 cells were incubated with PI-PLC, GDNF-induced receptor autophosphorylation of Ret in these cells was abolished (FIG. 10A; PI-PLC treated (lane 1) or untreated (lanes 2 and 3) NGR-38 cells were incubated with (lanes 1 and 3) or without (lane 2) GDNF and analyzed for Ret autophosphorylation by immunoblotting as described in the Experimental Procedures).

FIG. 10B depicts parental Neuro-2a cells treated with (lanes 2,4,6,8) or without (lanes 1,3,5,7) GDNF in the presence (lanes 5–8) or absence (lanes 1–4) of PI-PLC/CM obtained from Neuro-2a or NGR-38 cells, as analyzed for Ret autophosphorylation by immunoblotting as described in the Experimental Procedures. NGR-38 cells treated with GDNF were used as a positive control. In both panels A and B, the autophosphorylated 170 kD Ret bands are marked by solid arrows. When conditioned medium containing soluble GDNFR-α released by PI-PLC treatment (PI-PLCICM) of NGR-38 cells was added to parental Neuro-2a cells along with GDNF, autophosphorylation of the Ret receptor comparable to that obtained with GDNF treatment of NOR-38 cells was observed (FIG. 10B, lanes 2 and 8). Only background levels of Ret autophosphorylation were observed when no GDNF was added, or when conditioned media derived from PI-PLC treatment of Neuro-2a cells was tested (FIG. 10B, lanes 3–7).

Ret-Fc Fusion Protein Blocks Ret Phosphorylation Induced by GDNF and Soluble GDNFR-α

Figure 11:
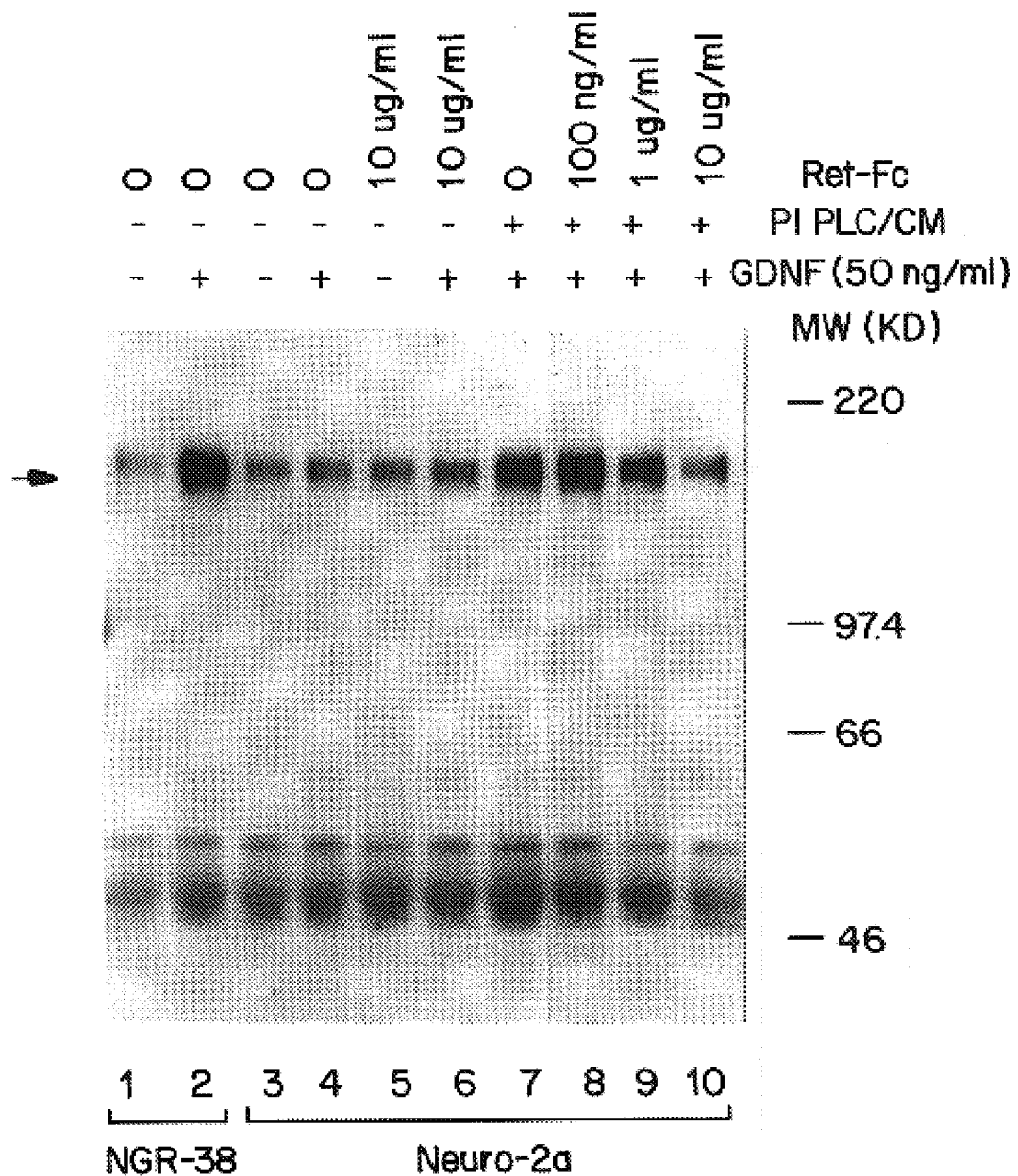
FIG. 11 depicts the results of the blocking of c-Ret autophosphorylation by a Ret-Fc fusion protein.

To confirm that Ret phosphorylation induced by GDNF in the presence of GDNFR-α is the result of receptor autophosphorylation, a study was performed to determine whether a Ret extracellular domain immunoglobulin Fc (Ret-Fc) fusion protein could block Ret activation. Because of the technical difficulty of blocking the large number of GDNF alpha receptors expressed on NGR-38 cells, Ret phosphorylation assays were performed using Neuro-2a as the target cell and culture media removed from NGR-38 cells treated with PI-PLC as a source of GDNFR-α. Cells were treated with mixtures including various combinations of GDNF (50 ng/mL), media containing soluble GDNFR (e.g., PI-PLC/CM derived from NGR-38 cells), and different concentrations of Ret-Fc fusion protein either alone or in various combinations as indicated in FIG. 11. Neuro-2a cells were treated with GDNF, media containing soluble GDNFR-α, Ret-Fc, or the pre-incubated mixtures. The cells were then lysed, and the lysates were analyzed for c-Ret autophosphorylation by immunoprecipitation using anti-Ret antibody as described in the Experimental Procedures. The immunoprecipitates were analyzed by Western blot using an anti-phosphotyrosine antibody.

The pre-incubated mixture of GDNF and media containing soluble GDNFR-α induced tyrosine phosphorylation of Ret receptors expressed in Neuro-2a at a level comparable to GDNF-treated NGR-38 control cells (FIG. 11, lanes 7 and 2). The position of the autophosphorylated 170 kD Ret bands are marked by a solid arrow. When Ret-Fc fusion protein was included in the pre-incubated GDNF/GDNFR-α mixture, Ret phosphorylation was inhibited in a dose dependent manner (FIG. 11, lanes 8–10). This indicated that Ret phosphorylation is a result of a GDNF/Ret interaction mediated by GDNFR-α. In untreated Neuro-2a cells or in cells treated with any combination of GDNF or Ret-Fc fusion protein in the absence of GDNFR-α, only background levels of Ret phosphorylation were observed (FIG. 11, lanes 3–6).

GDNF Induces Autophosphorylation of c-RET Expressed in Embryonic Motor Neurons

Figure 12:
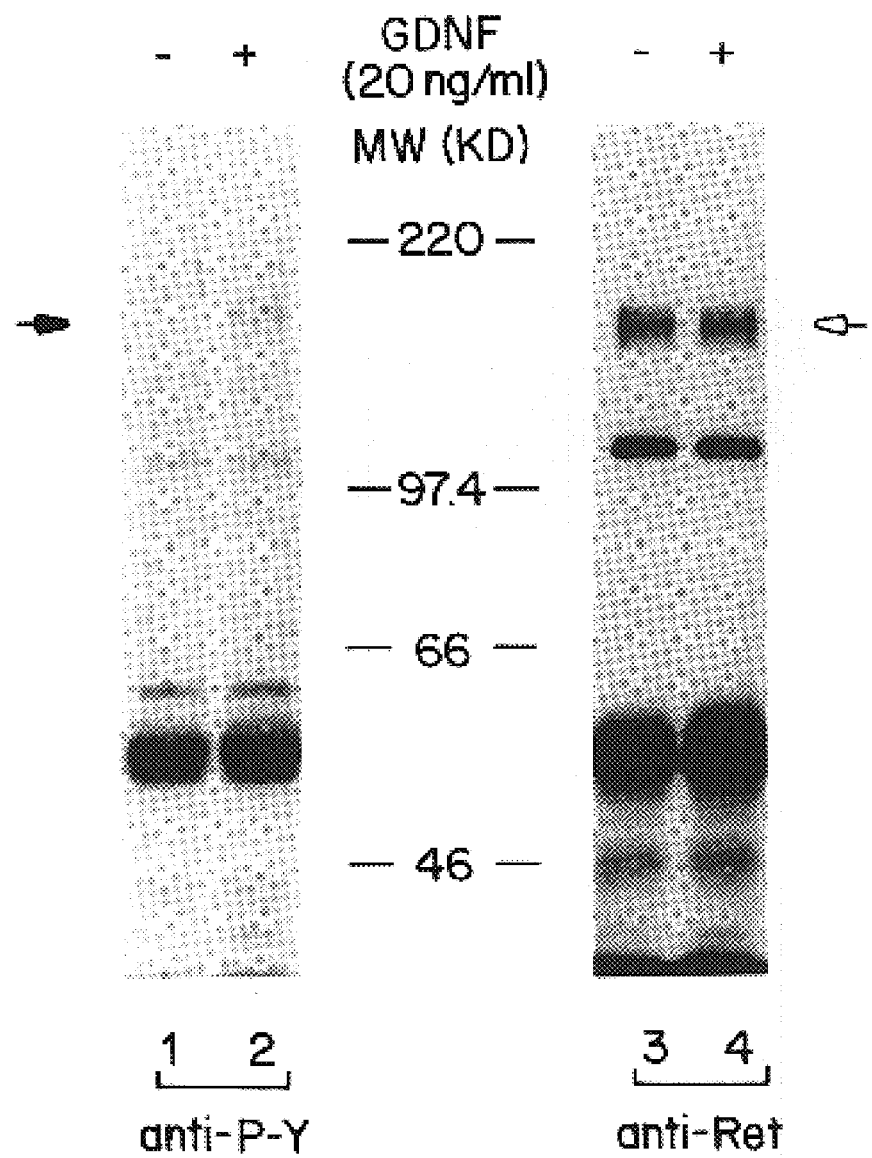
FIG. 12 depicts the results of the induction of c-Ret autophosphorylation by GDNF in motor neurons.

Spinal cord motor neurons are one of the major targets of GDNF action in vivo (Henderson et al., Science. 266, 1062–1064, 1994; Li et al., Proceedings Of The National Academy Of Sciences, U.S.A. 92, 9771–9775, 1995; Oppenheim et al., Nature. 373, 344–346, 1995; Yan et al., Nature. 373, 341–344, 1995; Zurn et al., Neuroreport. 6, 113–118, 1995). To test the ability of GDNF to induce Ret autophosphorylation in these cells, embryonic rat spinal cord motor neurons were treated with (lanes 2 and 4) or without (lanes 1 and 3) 20 ng/mL GDNF followed by lysis of the cells, immunoprecipitation with anti-Ret antibody, and analysis by Western blotting with anti-phosphotyrosine antibody as described in the Experimental Procedures. In lysates of cells treated with GDNF, a band of tyrosine phosphorylated protein with a molecular mass of ~170 kD was observed (FIG. 12, lane 2). No such signal was observed with cells treated with binding buffer alone (FIG. 12, lane 1). When the same Western blot filter was stripped and re-probed with anti-Ret antibody (i.e., the amount of c-Ret protein loaded in each lane was determined by reprobing the immunoblot with the anti-Ret antibody), bands with the same molecular mass and similar intensities appeared in both samples (FIG. 12, lanes 3 and 4). The phosphotyrosine band in GDNF-treated cells co-migrates with the Ret protein band, indicating GDNF stimulated autophosphorylation of Ret. The autophosphorylated Ret bands (lanes 1 and 2) and the corresponding protein bands (lanes 3 and 4) were marked by a solid arrow.

Discussion

Polypeptide growth factors elicit biological effects through binding to their cognate cell surface receptors. Receptors can be grouped into several classes based on their structure and mechanism of action. These classifications include the protein tyrosine kinases (PTKs), the serine/threonine kinases, and the cytokine receptors. Receptor PTK signaling is initiated by a direct interaction with ligand, which induces receptor dimerization or oligomerization that in turn leads to receptor autophosphorylation. The activated receptor then recruits and phosphorylates intracellular substrates, initiating a cascade of events which culminates in a biological response (Schlessinger and Ullrich, Neuron 9, 383–391, 1992). In contrast, signal transduction by serine/threonine kinase or cytokine receptors often involves formation of multi-component receptor complexes in which the ligand binding and signal transducing components are distinct. Examples are the TGF-receptor complex, a serine/threonine kinase receptor consisting of separate binding (Type II) and signaling (Type I) components and the CNTF family. CNTF, interleukin-6 (IL-6) and leukocyte inhibitory factor (LIF) share the common signaling components, gp130 and/or LIFR, in their respective receptor complexes. While the ligand specificity of these complexes is determined by a specific binding subunit to each individual ligand, signal transduction requires association of the initial complex of ligand and ligand binding subunit with other receptor subunits which cannot bind ligand directly (Ip et al., Cell. 69, 1121–1132, 1992). In the CNTF receptor complex, the ligand binding component is CNTF receptor (CNTFR), which like GDNFR, is a GPI-anchored membrane protein. The present invention involves the description of the first example of a receptor PTK whose autophosphorylation is dependent upon association with a separate ligand-specific binding component.

The present study confirms that GDNFR-α, a GPI-linked membrane protein that binds to GDNF with high affinity, is required for the efficient association of GDNF with the Ret receptor PTK. In the absence of GDNFR-α, GDNF is unable to bind to Ret or stimulate Ret receptor autophosphorylation. In the presence of GDNFR-α, GDNF associates with Ret and rapidly induces Ret autophosphorylation in a dose-dependent manner. GDNFR-α is able to function in either membrane bound or soluble forms (FIG. 11), as discussed above. GDNF concentrations of 50 pg/mL (1.7 pM) are able activate the Ret tyrosine kinase in cells expressing GDNFR-α. This is consistent with the dissociation constant (1.5 pM) found for the high affinity GDNF binding sites on NGR-38 cells. The rapid induction of Ret phosphorylation by GDNF (detectable one minute after treatment) and the ability of Ret-Fc to block autophosphorylation suggest that Ret is being activated directly rather than as a downstream consequence of the phosphorylation of some other receptor.

Cross-linking studies support the hypothesis that efficient association of Ret with GDNF depends on GDNFR-α. Cross-linking of GDNF to Ret in NGR-38 cells which express high levels of GDNFR-α is robust, but in parental Neuro-2a cells cross-linked products are barely detectable. Although conclusive identification of all the cross-linked complexes is difficult, the data clearly demonstrates an association of Ret with GDNF that is dependent on the presence of GDNFR-α, and demonstrates that GDNFR-α is included in some of the cross-linked products. The reason for the presence of minor cross-linked species in Neuro-2a cells is not clear. While the expression of GDNFR-α mRNA in Neuro-2a cells could not be detected by Northern blot, it is possible that GDNFR-α is expressed at very low levels in these cells.

The fact that Ret can be activated by GDNF in cultured rat embryonic spinal cord motor neurons further demonstrates the biological relevance of the Ret/GDNF interaction. These cells are a primary target of GDNF in vivo, and have been shown to respond to low doses of GDNF in vitro (Henderson et al., 1994). Stimulation of Ret phosphorylation was abolished when the motor neuron cells were pre-treated with PI-PLC (data not shown), suggesting that the activation of Ret by GDNF requires GDNFR-α.

Figure 13:
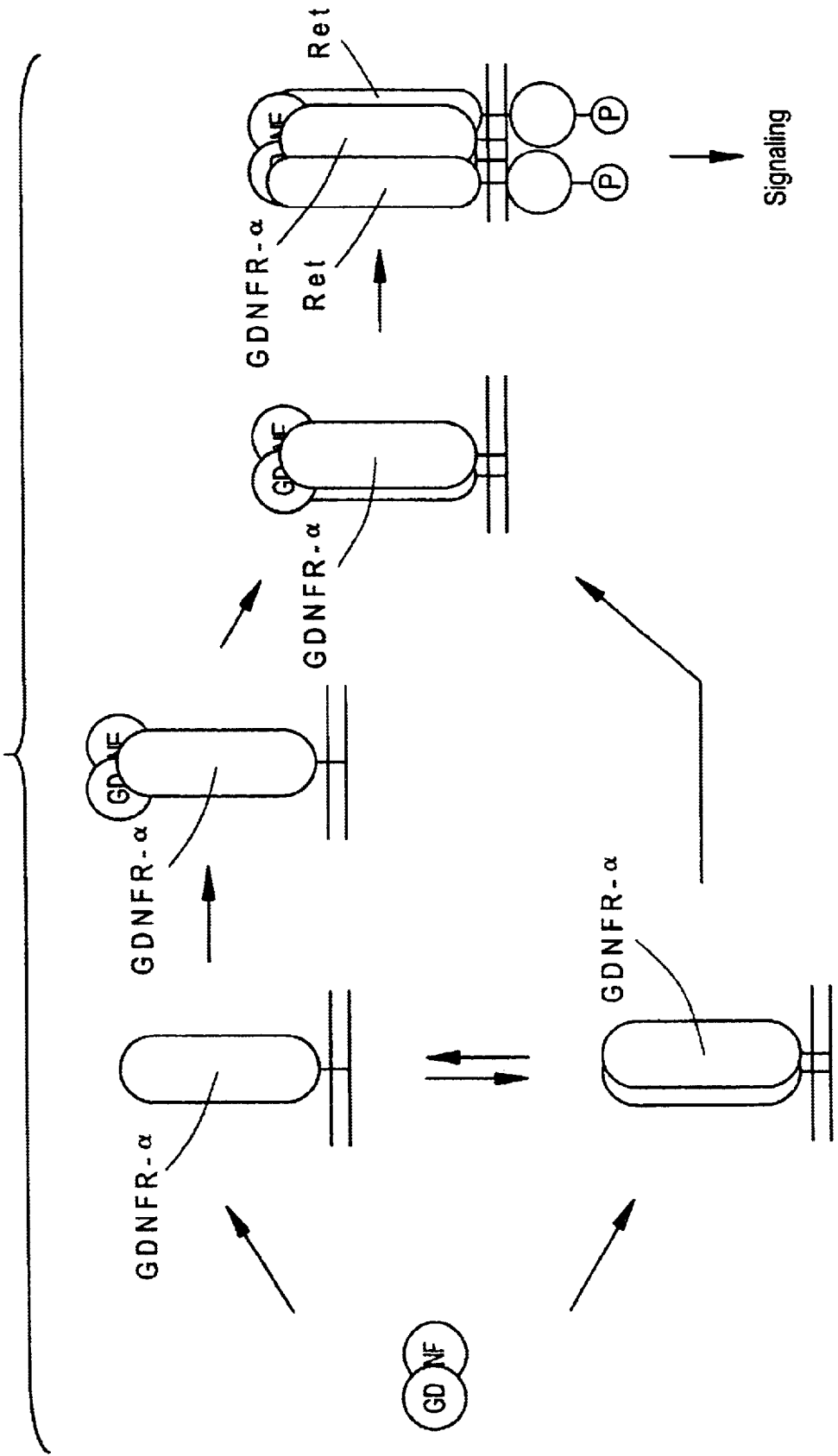
FIG. 13 depicts a model for GDNF signaling mediated by GDNFR-α and Ret.

Although binding of ligand to the receptor extracellular domain is the first step in the activation of other known receptor PTKs, the present data has shown that this is not the case for GDNF and Ret. FIG. 13 depicts a model for the binding of GDNF to GDNFR-α and Ret, and the consequent activation of the Ret PTK in response to GDNF. The initial event in this process is the binding of disulfide-linked dimeric GDNF to GDNFR-α in either monomeric or dimeric form. Although there is currently no direct evidence for the existence of dimeric GDNFR-α, when 293T cells were transfected with GDNFR-α cDNA, two classes of binding sites appeared. The simplest explanation for this observation is the existence of monomeric and dimeric GDNFR-α, each with its own ligand binding affinity. This is consistent with the finding that GDNF binding affinities are apparently unaffected by the presence of Ret. Since the present experiments do not address the question of whether dimeric GDNFR-α is in equilibrium with its monomer in the absence of GDNF or if dimerization is induced by GDNF binding, these possibilities are presented as alternate pathways. The complex consisting of dimeric GDNFR-α and dimeric GDNF can bind two molecules of Ret, forming the active signaling complex. As for other PTKs, close contact between the intracellular catalytic domains of two Ret molecules is likely to result in receptor autophosphorylation. This notion that Ret functions by this mechanism is supported by the fact that the MEN2A mutation which causes steady state dimerization of Ret results in constitutive activation of the Ret kinase (Santoro et al., 1995).

Motor neurons have been reported to respond to GDNF with an $ED_{50}$ of as low as 5 fM (Henderson et al., 1994). Although it is difficult to compare binding affinity with the $ED_{50}$ for a biological response, it is possible that very high affinity GDNF binding sites exist on these cells. Other cells, such as embryonic chick sympathetic neurons, have been reported to bind GDNF with a Kd of 1–5 nM (Trupp et al., Journal Of Cell Biology. 130, 137–148, 1995). It is unlikely that GDNFR is involved in a receptor complex for such low affinity sites, but a weak direct interaction between GDNF and Ret may be present.

Expression of c-ret has been observed during embryogenesis in many cell lineages of the developing central and peripheral nervous systems, including cells of the enteric nervous system (Pachnis, et al., Development, 119, 1005–1017, 1993; Tsuzuki et al., 1995). Outside the nervous system, c-ret expression has been detected in the Wolffian duct, ureteric bud epithelium and collecting ducts of the kidney (Pachnis, et al., supra; Tsuzuki et al., 1995). Ret expression has also been detected in all neuroblastoma cell lines derived from the neural crest (Ikeda et al., 1990) and from surgically resected neuroblastomas (Nagao et al., 1990; Takahashi & Cooper, 1987). GDNF expression has been observed in both CNS and PNS, as well as in non-neuronal tissues during embryonic development. The levels of GDNF expression found in many non-neuronal tissues were higher than in the nervous system (Choi-Lundberg and Bohn, Brain Res. Dev. Brain Res. 85, 80–88, 1995). Although expression of GDNFR-α has not been extensively studied, primary Northern blot analysis detected the presence of high levels of the GDNFR-α mRNA in the liver, brain, and kidney of adult rat and mouse. The similarity of the expression patterns of ret, GDNF, and GDNFR-α in developing nervous system and kidney is consistent with their combined action during development.

Mammalian kidney development has been postulated to result from reciprocal interactions between the metanephron and the developing ureter, a branch developed from the caudal part of the Wolffian duct (Saxen, Organogenesis of the kidney. Development and Cell Biology series, Cambridge University Press, Cambridge, England, 1987). While the expression of Ret has been found at the ureteric bud but not in the surrounding mesenchyme in developing embryos, the expression of GDNF was detected in the undifferentiated but not adult metanephric cap of the kidney. These observations suggest that an interaction between GDNF and Ret is responsible for initiating the development of the ureteric structure. Further support for this hypothesis is provided by targeted disruptions of the GDNF and ret genes, which result in very similar phenotypic defects in kidney (Schuchardt et al., Nature. 367, 380–383, 1994; Sanchez, in press). Another major phenotypic defect observed in both GDNF (−/−) and ret (−/−) knockout animals is a complete loss of the enteric neurons throughout the digestive tract. Hirschsprung's disease, a genetic disorder characterized by the congenital absence of parasympathetic innervation in the lower intestinal tract, has also been linked to "loss-of-function" mutations in ret (Romeo et al., Nature. 367, 377–378, 1994. Edery et al., 1994). A later report (Angrist et al., Hum. Mol.Genet. 4, 821–830, 1995) indicated that, contrary to earlier observations, some Hirschsprung's patients do not carry mutations in ret. It is now envisioned that such patients may carry mutations in GDNF, GDNFR-α or some other critical component of this signaling pathway.

Experimental Procedures

[$^{125}$I]GDNF Binding to Neuro-2a Cells Expressing GDNFR-α

Neuro-2a cells (ATCC #CCL 131) were transfected with an expression plasmid, as described above, using the Calcium Phosphate Transfection System (GIBCO/BRL) according to the manufacturer's directions. Transfected cells were selected for expression of the plasmid by growth in 400 µg/mL G418 antibiotic (Sigma). G418 resistant clones were expanded and assayed for GDNFR-α expression by binding to [$^{125}$I]GDNF (Amersham, Inc., custom iodination, catalog #IMQ1057). Cells from each clone were seeded at a density of 3×10$^4$ cells/cm$^2$ in duplicate wells of 24-well tissue culture plates (Becton Dickinson) pre-coated with polyomithine. Cells were washed once with ice-cold washing buffer (DMEM containing 25 mM HEPES, pH 7.5) and were then incubated with 50 pM [$^{125}$I]GDNF in binding buffer (washing buffer plus 0.2% BSA) at 4° C. for four hours either in the presence or absence of 500 mM unlabeled GDNF. Cells were then washed four times with ice-cold washing buffer, lysed in 1 M NaOH, and the cell-associated radiolabel quantitated in a 1470 Wizard Automated Gamma Counter (Wallac Inc.). The amount of GDNFR-α expressed by individual clones was estimated by the ratio of [$^{125}$I] GDNF bound to cells in the absence and presence of unlabeled GDNF. Three clones were chosen as representatives of high, moderate, and low level expressors of GDNFR-α for use in binding experiments. The ratios [$^{125}$I] GDNF bound in the absence and presence of unlabeled GDNF for these clones were: NGR-38) 16:1, NGR-16) 12.8:1, and NGR-33) 8:1. Equilibrium binding of [$^{125}$I] GDNF to NGR-38 cells was carried out as described above except that concentrations of labeled GDNF ranged from 0.5 pM to 1 nM. In all assays, nonspecific binding as estimated by the amount of radiolabel binding to cells in the presence of 500 nM unlabeled GDNF was subtracted from binding in the absence of unlabeled GDNF. Binding data was analyzed by Scatchard plot.

Chemical Cross-linking

Neuro-2a or NGR-38 cells were washed once with phosphate-buffered saline (PBS, pH 7.1), then treated for four hours at 4° C. with 1 or 3 nM [$^{125}$I]GDNF in binding buffer in the presence or absence of 500 nM unlabeled GDNF. Following binding, cells were washed four times with ice-cold washing buffer and incubated at room temperature for 45 minutes with 1 mM his suberate (BS$^3$, Pierce) in washing buffer. The cross-linking reaction was quenched by washing the cells three times with Tris-buffered saline (TBS, pH 7.5). The cells were then either lysed directly in SDS-PAGE sample buffer (80 mM Tris HCl [pH 6.8], 10% glycerol, 1% SDS, 0.025% bromophenol blue) or in Triton X-100 lysis buffer (50 mM Hepes, pH 7.5, 1% Triton X-100, 50 mM NaCl, 50 mM NaF, 10 mM sodium pyrophosphate, 1% aprotinin (Sigma, Cat. #A-6279), 1 mM PMSF (Sigma, Cat. #P-7626), 0.5 mM Na$_3$VO$_4$ (Fisher Cat. #S454–50). The lysates were clarified by centrifugation, incubated with 5 µg/mL of anti-Ret antibody (Santa Cruz Antibody, C-19, Cat. #SC-167), and the resulting immunocomplexes were collected by precipitation with protein A-Sepharose CL-4B (Pharmacia). The immunoprecipitates were washed three times with the lysis buffer, once with 0.5% NP-40 containing 50 mM NaCl and 20 mM Tris-Cl, pH 7.5, and were then resuspended in SDS-PAGE sample buffer. Both the whole cell lysates and the immunoprecipitates were fractionated by 7.5% SDS-PAGE with a ratio of Bis:Acrylamide at 1:200.

Western Blot Analysis

The autophosphorylation of Ret receptor was examined by Western blot analysis. Briefly, cells were seeded 24 hours prior to the assay in 6-well tissue culture dishes at a density of 1.5×10$^6$ cells/well. Cells were washed once with binding buffer and treated with various concentrations of different reagents (including GDNF, PI-PLC, PI-PLC/CM, and Ret-Fc fusion protein), either alone or in combination, in binding buffer for various periods of times. Treated cells and untreated controls were lysed in Triton X-100 lysis buffer and immunoprecipitated with the anti-Ret antibody (Santa Cruz, C-19, Cat. #SC-167) and protein-A Sepharose as described above. Immunoprecipitates were fractionated by SDS-PAGE and transferred to nitrocellulose membranes as described by Harlow and Lane (Antibodies: A Laboratory Manual. Cold Spring Harbor Laboratory: Cold Spring Harbor, N.Y., 1988). The membranes were pre-blocked with 5% BSA (Sigma) and the level of tyrosine phosphorylation of the receptor was determined by blotting the membrane with an anti-phosphotyrosine monoclonal antibody 4G10 (UBI, Cat. #05–321) at room temperature for two hours. The amount of protein included in each lane was determined by stripping and re-probing the same membrane with the anti-Ret antibody. Finally, the membrane was treated with chemiluminescence reagents (ECL, Amersham) following the manufacturer's instructions and exposed to X-ray films (Hyperfilm-ELC, Amersham).

Treatment of Cells with PI-PLC and Generation of PI-PLC Treated Conditioned Media In order to release GPI-linked GDNFR from the cell surface, cells were washed once with washing buffer, then incubated with 1 U/mL phosphatidylinositol specific phospholipase C (PI-PLC, Boehringer Mannheim, Cat. #1143069) in binding buffer at 37° C. for 45 minutes. The cells were then washed three times with washing buffer and further processed for Ret autophosphorylation assay or cross-linking. For generation of PI-PLC treated conditioned media (PI-PLC/CM), $8 \times 10^6$ cells were removed from tissue culture dishes by treating the cells with PBS containing 2 mM of EDTA at 37° C. for 5 to 10 minutes. Cells were washed once with washing buffer, resuspended in 1 mL of binding buffer containing 1 U/mL of PI-PLC, and incubated at 37° C. for 45 minutes. The cells were pelleted, and the PI-PLC/CM was collected.

Preparation of the Ret-Fc Fusion Protein

A cDNA encompassing the entire coding region of c-Ret was isolated from a day 17 rat placenta cDNA library using an oligonucleotide probe corresponding to the first 20 amino acids of the mouse c-Ret (Iwamoto et al., 1993; van Heyningen, 1994). The region coding for the extracellular domain of the Ret receptor (ending with the last amino acid, R636) was fused in-frame with the DNA coding for the Fc region of human IgG (IgGI) and subcloned into the expression vector pDSR2 as previously described (Bartley et al., Nature. 368, 558–560, 1994). The ret-Fc/pDSRa2 plasmid was transfected into Chinese hamster ovary (CHO) cells and the recombinant Ret-Fc fusion protein was purified by affinity chromatography using a $Ni^{++}$ column (Qiagen).

Preparation of Embryonic Rat Spinal Cord Motor Neuron Cultures

Enriched embryonic rat spinal cord motor neuron cultures were prepared from entire spinal cords of E15 Sprague-Dawley rat fetuses 24 hours before the experiments. The spinal cords were dissected, and the meninges and dorsal root ganglia (DRGs) were removed. The spinal cords were cut into smaller fragments and digested with papain in L15 medium (Papain Kit, Worthington). The motor neurons, which are larger than other types of cells included in the dissociated cell suspension, were enriched using a 6.8% Metrizamide gradient (Camu and Henderson, J Neuroscience. 44, 59–70, 1992). Enriched motor neurons residing at the interface between the metrizamide cushion and the cell suspension were collected, washed, and seeded in tissue culture dishes pre-coated with poly-L-ornithine and laminin at a density of $9 \times 10^4$ cells/$cm^2$ and were cultured at 37° C.

Example 10

GRR2 Mediation of Neurturin and GDNF-induced Ret Activation

The present study demonstrates that neurturin binds to both GDNFR-α and GRR2, a novel receptor related to GDNFR-α Both GDNFR-α and GRR2 can mediate neurturin-induced autophosphorylation of the Ret protein tyrosine kinase. GDNF also binds both GDNFR-α and GRR2, and activates Ret in the presence of either binding receptor. However, neurturin binds GRR2 more effectively than GDNF, while GDNF binds GDNFR-α more efficiently than neurturin. These data indicate that, while there is crosstalk, GDNF is the primary ligand for GDNFR-α and neurturin appears to exhibit a preference for GRR2.

Introduction

Recently, Kotzbauer et al. (Nature, 384, 467–470, 1996) reported the cloning of neurturin, a novel neurotrophic factor that is approximately 42% identical in amino acid sequence to GDNF. Both GDNF and neurturin are synthesized in pre-pro forms and their precursor molecules are proteolytically processed to yield mature proteins of about 100 amino acids that assemble into disulfide-lined homodimers. All seven cysteine residues crucial for the structure of GDNF and their spacing patterns are conserved in neurturin (Kotzbauer et al., 1996). Although the biological activities of neurturin have not yet been thoroughly investigated, they appear to be very similar to those of GDNF. Both neurturin and GDNF have been shown to promote the survival of sympathetic neurons derived from the superior cervical ganglia (SCG) and of sensory neurons of both the nodose (NG) and dorsal root ganglia (DRG). Neurturin and GDNF mRNAs are widely distributed in a variety of both neuronal and non-neuronal tissues of embryos and adults. Both are found in brain, kidney, and lung, whereas neurturin mRNA is also expressed at high levels in neonatal blood.

The structural and biological similarities between GDNF and neurturin suggest that their action may be mediated by the same or related receptors. The receptor for GDNF consists of a complex of GDNF receptor α (GDNFR-α) and the Ret protein tyrosine kinase (PTK) (Jing et al., Cell, 85, 1113–1124, 1996; Treanor et al., Nature, 382, 80–83, 1996). GDNFR-α is a glycosyl-phosphodylinositol (GPI) anchored cell surface molecule that serves to bind GDNF but cannot signal independently since it lacks a cytoplasmic domain. GDNF signaling is accomplished via association of the complex of GDNF and GDNFR-α with Ret, resulting in activation of the Ret kinase.

GDNFR-α mRNA is widely distributed in neuronal and nonneuronal tissues and is expressed through embryonic development to adulthood, implying a broad spectrum of biological functions (Treanor et al., 1996; Fox et al., unpublished data). The other component of the GDNP receptor complex, Ret, is a receptor type PTK encoded by the ret proto-oncogene. Ret mRNA and protein are highly expressed in the CNS and PNS, as well as in the kidney. Various mutations in the ret gene are associated with inherited human diseases, including familial medullary thyroid carcinoma (FMFC), multiple endocrine neoplasia typ 2A (MEN2A) and 2B (MEN2B), and Hirschsprung's disease. Targeted disruption of the ret gene in knockout mice results in severe phenotypic defects, including renal agenesis or severe dysgenesis and lack of entire enteric nervous system. These defects are extremely similar to those caused by GDNF null mutations, implying that GDNF-mediated signaling through Ret is required for the development of these tissues. Much less severe defects, however, were detected in a number of neuronal structures in which both GDNFR-α and Ret are expressed, such as the trigeminal and vestibular ganglia, the facial motor nucleos, the substantial nigra, and the locus coeruleus (Schuchardt et al., Nature, 367, 380–383, 1994; Treanor et al., 1996). This suggests that either GDNF signaling is not required for the embryonic development of these structures, or that some unknown signaling molecules similar to GDNF or Ret may exist that can substitute for them. Alternatively, the embryonic development of these tissues may completely rely on another yet unknown signaling system.

This example describes the cloning of a novel GDNFR-α related receptor, GRR2 (SEQ ID NO:36), and provides evidence that GRR2 is a receptor for neurturin. Analogous to GDNF and GDNFR-α, neurturin effectively binds GRR2 and induces Ret activation. The data also show that both GDNF and neurturin can interact with either GDNFR-α or GRR2 and activate the Ret PTK in the presence of either binding receptor.

Results
Cloning and Sequence Analysis of GRR2

A human expressed sequence tag (EST) with significant homology to GDNFR-α was found by a FASTA search of the publicly available nucleic acid sequence databases (Marra et al., 1996, WashU-HHMI Mouse EST Project, unpublished). Oligonucleotides corresponding to the ends of this EST were synthesized and used in a reverse transcription-polymerase chain reaction (RT-PCR) with human fetal brain mRNA as the template. A fragment of the expected length was isolated and used as a hybridization probe to screen a human fetal brain cDNA library. Five positive clones were identified and the longest clone was sequenced. This clone contained a large open reading frame coding for a 464 amino acid protein related in sequence to GDNFR-α. We have named this protein GDNFR-α Related Receptor 2 (GRR2). The oligonucleotides described above were also used to screen pools from a rat photoreceptor cDNA library (Jing et al., 1996) by PCR and a product of the expected length was obtained from a single pool. An individual cDNA clone from this pool was identified by hybridization to the radiolabeled PCR product and sequenced. This clone contained a 2.2 kb insert with an open reading coding for a 460 amino acid peptide that is nearly identical to human GRR2.

A comparison of the amino acid sequences of human and rat GDNFR-α and GRR2 is shown in FIG. 20. Shaded areas indicate amino acid sequence conservation between all four receptors while boxes indicate conservation only between the same receptor from different species. The amino acid sequences of both GDNFR-α and GRR2 are extremely well-conserved between species, each human receptor being 92% identical to its rat counterpart. The overall amino acid sequence identity between human GDNFR-α (hGDNFR-α) and human GRR2 (hGRR2) is 48%. The sequence is most divergent in the C-terminal region—amino acids 350–465 of hGDNFR-α are only 22% identical to amino acids 361–464 of hGRR2. In the N-terminal region, hGDNFR-α and hGRR2 are more closely related, sharing 56% amino acid identity. The corresponding identities between the rat GDNFR-α and GRR2 (rGDNFR-α and rGRR2) are very similar: 48% overall, 26% in the C-terminal region, and 55% in the N-terminal region. The sequence comparison indicates that GDNFR-α and GRR2 are likely to be structurally very similar. The positions of 30 of the 31 cysteine residues (shown in boldface, FIG. 20) found in GDNFR-α are conserved in both human and rat GRR2 (one additional cysteine residue is present near the N-terminus of hGRR2). In addition, the hydrophobic C-terminus involved in GPI-linkage of GDNFR-α to the cell membrane (Jing et al., 1996; Treanor et al., 1996) is also present in GRR2.

FIG. 20. Comparison of GDNFR-α and GRR2 Peptide Sequences

The amino acid sequences of human GDNFR-α (SEQ ID NO:2), rat GDNFR-α (SEQ ID NO:4), human GRR2 (SEQ ID NO:36) and rat GRR2 (SEQ ID NO:40) are aligned. Shaded areas indicate amino acids that are identical in all four sequences. Boxes indicate conservation between rat and human orthologs of the same receptor, but not between GDNFR-α and GRR2.

Both Neurturin and GDNF Bind to LA-N-5 and NGR-38 Cells

LA-N-5 is a human neuroblastoma cell line (Sonnenfeld and Ishii, J. Neuroscience Research, 8:375–391, 1982) that expresses high levels of ret mRNA (Bunone et al., Exp. Cell. Res., 217:92–99, 1995). RT-PCR experiments using primers specific to GDNFR-α and GRR2 showed that these cells express GRR2 mRNA, but GDNFR-α mRNA was not detected (data not shown). NGR-38 is a cell line derived from mouse Neuro-2a cells (Jing et al., 1996). It expresses high levels of both GDNFR-α and Ret (Jing et al., 1996), but no detectable GRR2 (data not shown), and binds GDNF specifically. LA-N-5 and NGR-38 cells were incubated with [$^{125}$I]-labeled recombinant human neurturin (NTN) or GDNF in the absence or presence of excess unlabeled ligand. As shown in FIG. 21A, [$^{125}$I]NTN bound to LA-N-5 cells more strongly than [$^{125}$I]GDNF, although both bound at detectable levels. The binding of [$^{125}$I]NTN to LA-N-5 cells was significantly inhibited by unlabeled neurturin, but not by GDNF. [$^{125}$I]GDNF also bound to LA-N-5 cells, however, the binding was inhibited by either cold GDNF or neurturin.

FIG. 21B depicts the binding of [$^{125}$I]NTN and [$^{125}$I]GDNF to the GDNFR-α expressing cell line NGR-38. Although both [$^{125}$I]NTN and [$^{125}$I]GDNF bound to NGR-38 cells, [$^{125}$I]GDNF bound more strongly. As was observed for LA-N-5 cells, the binding of [$^{125}$I]GDNF to NGR-38 cells was inhibited by both unlabeled neurturin and GDNF, while binding of [$^{125}$I]NTN was only replaceable by neurturin (FIG. 21B).

FIG. 21. Binding of Neurturin and GDNF to LA-N-5 and NGR-38 Cells

LA-N-S (A) and NGR-38 (B) cells were incubated with 50 pM of either [$^{125}$I]NTN or [$^{125}$I]GDNF in the absence (light gray bars) or presence of unlabeled GDNF (dark gray bars) or neurturin (black bars) at 4° C. for 2 hours. The unbound ligands were removed at the end of the incubation and the radioactivity associated with the cells was determined as described.

Cross-linking of Neurturin and GDNF to GDNFR-α and GRR2

Figure 22:
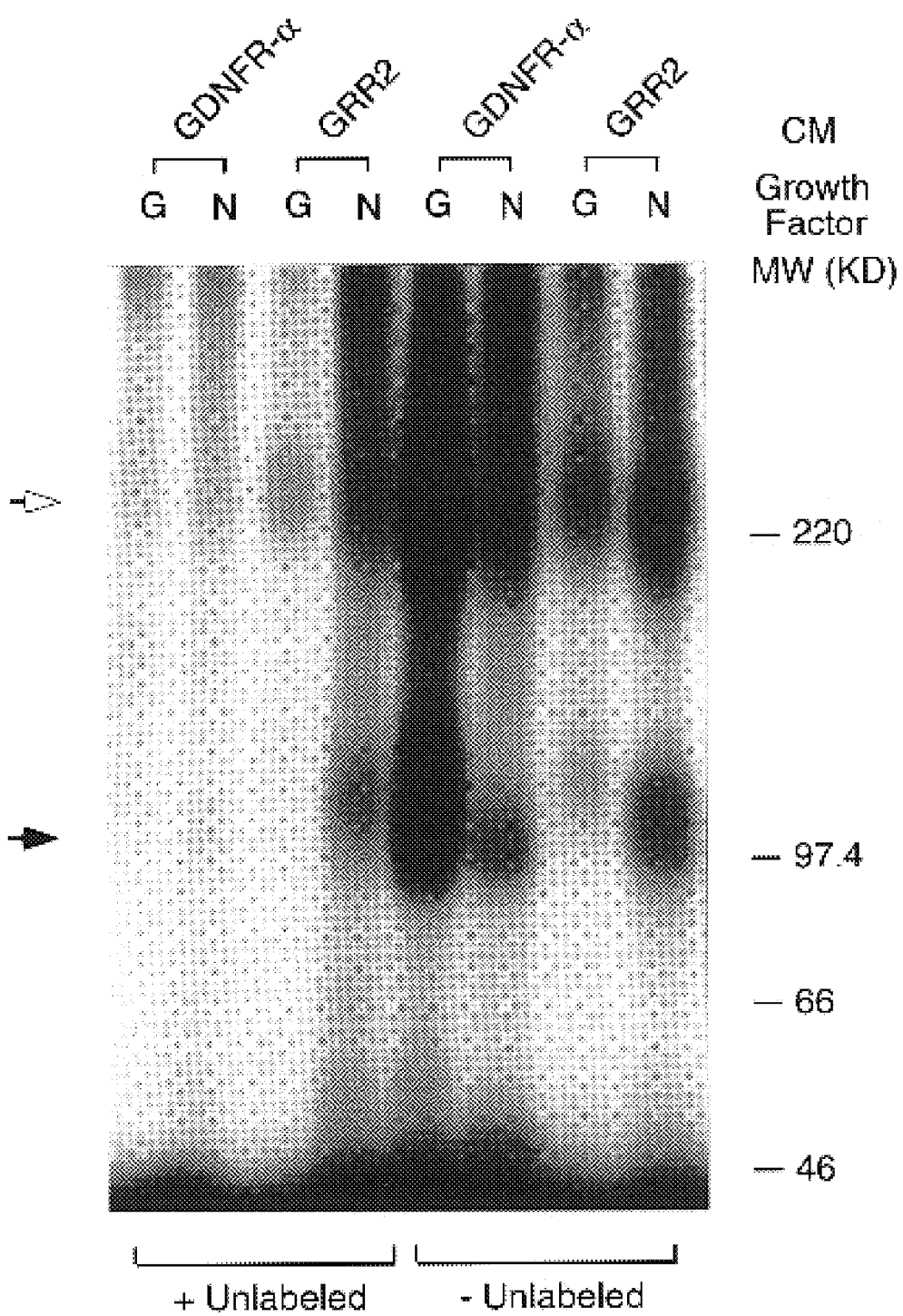
FIG. 22 depicts the results of the chemical cross-linking of neurturin and GDNF to GDNFR-α and GRR2.

The binding experiments suggest that both neurturin and GDNF interact with GDNFR-α and GRR2. However, lack of a GRR2 specific antibody made further study of these interactions difficult. To overcome this difficulty, plasmids were generated that transiently express GDNFR-α/Fc and GRR2/Fc fusion proteins when transfected into 293T cells. Conditioned medium (CM) containing either GDNFR-α/Fc or GRR2/Fc fusion proteins was incubated with [$^{125}$I]NTN or [$^{125}$I]GDNF, chemically cross-linked, and then precipitated directly using Protein-A Sepharose beads. The immunoprecipitates were analyzed by SDS-PAGE (FIG. 22). Major species of 100–120 kD and 90–110 kD were observed when [$^{125}$I]GDNF or [$^{125}$I]NTN were used, respectively (FIG. 22). Strong bands with higher molecular mass, ~300 kD for GDNFR-α/Fc and ~280 kD for GRR2/Fc, were also observed (FIG. 22). In addition, minor bands of ~15 kD, 35 kD, and 60 kD in the [$^{125}$I]GDNF lanes and ~12 kD, 26 kD, and 50 kD in the [$^{125}$I]NTN lanes, were visible (FIG. 22). When CM from mock transfected cells were used, no cross-linked band was precipitated by Protein-A Sepharose (data not shown). None or much weaker radio-labeled bands were detected when excess unlabeled ligands were added in the control samples (FIG. 22).

FIG. 22. Chemical Cross-linking of Neurturin and GDNF to GDNFR-α and GRR2 Receptors.

CM containing GDNFR-α/Fc (GDNFR-α) or GRR2/Fc (GRR2) fusion proteins were incubated with either 10 nM of

[$^{125}$I]NTN (N) or 5 nM of [$^{125}$I]GDNF (G) in the presence (+unlabeled) or absence (−unlabeled) neurturin (N) or GDNF (G). The bound receptor-ligand complexes were chemically cross-linked by 1 mM of BS$^3$, precipitated with Protein-A Sepharose and analyzed by SDS-PAGE as described. The solid arrow indicates the 90–110 kD and the 100–120 kD cross-linked species. The open arrow depicts the 280 kD and ~300 kD complexes.

Neurturin Induces Ret Autophosphorylation in Cells that Express GDNFR-α

Figure 23:
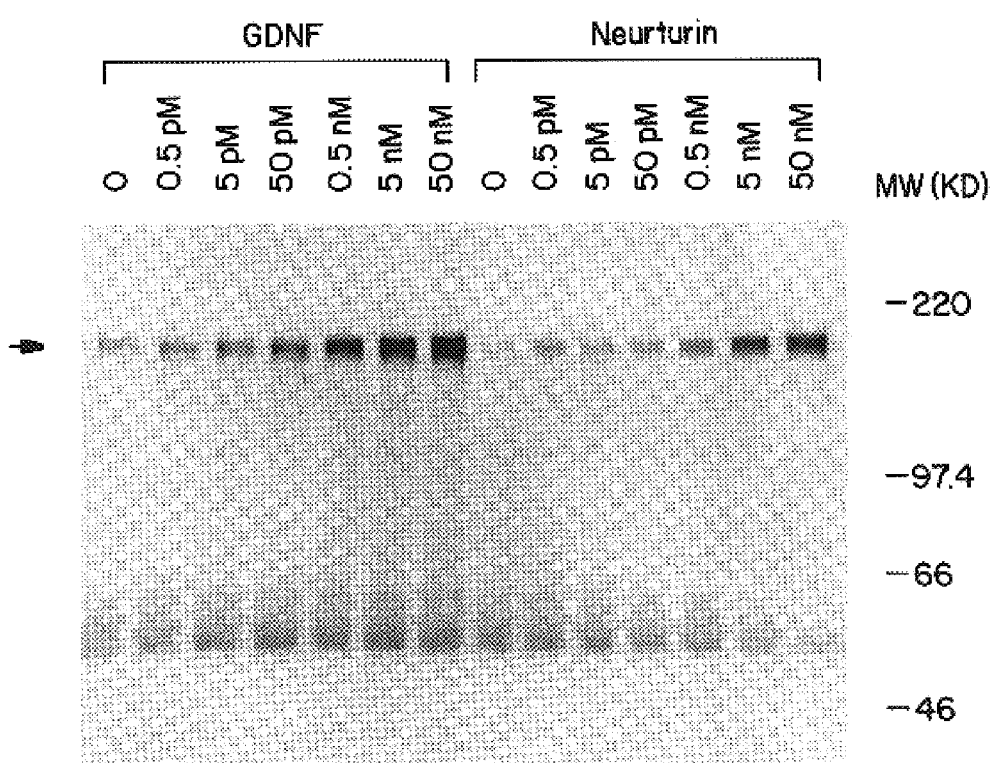
FIG. 23 depicts the results of neurturin induced ret autophosphorylation in NGR-38 cells.

The ability of neurturin to associate with GDNFR-α indicates that neurturin, like GDNF, may activate Ret through GDNFR-α. In order to examine this possibility, the ability of neurturin to induce Ret autophosphorylation in NGR-38 cells was tested. NGR-38 cells were treated with concentrations of neurturin ranging from 0 to 50 nM, lysed, and the lysates immunoprecipitated with anti-Ret antibody. The immunoprecipitates were analyzed by SDS-PAGE followed by immunoblotting using an anti-phosphotyrosine antibody. A 170 kD band, indicating autophosphorylation of tyrosine residues on the mature form of Ret, was observed in all lanes (FIG. 23, lanes 8–14 from left). A much weaker corresponding band was observed in neurturin-treated Neuro-2a cells (data not shown). The induction of Ret autophosphorylation by neurturin was dose-dependent. Stimulation of Ret autophosphorylation in NGR-38 cells could be detected with 500 pM neurturin (FIG. 23). In a parallel experiment using GDNF in place of neurturin, an increase in the level of phosphorylation of the 170 kD Ret band over background could be seen at a GDNF concentration of 5 pM (FIG. 23, lanes 1–7 from left). When the filters were stripped and re-probed with the anti-Ret antibody, the 170 kD Ret protein band appeared in all lanes with approximately equal intensity (data not shown).

FIG. 23. Neurturin and GDNF Induce Ret Autophosphorylation in NGR-38 Cells

NGR-38 cells were treated with various concentrations of GDNF or neurturin as described. The cells were lysed, immunoprecipitated with anti-Ret antibody, fractionated by SDS-PAGE, and blotted with anti-phosphotyrosine antibody for Ret phosphorylation. The bands of phosphorylated Ret are indicated by an arrow.

Neurturin and GDNF Induce Ret Autophosphorylation in LA-N-5 Cells

Figure 24:
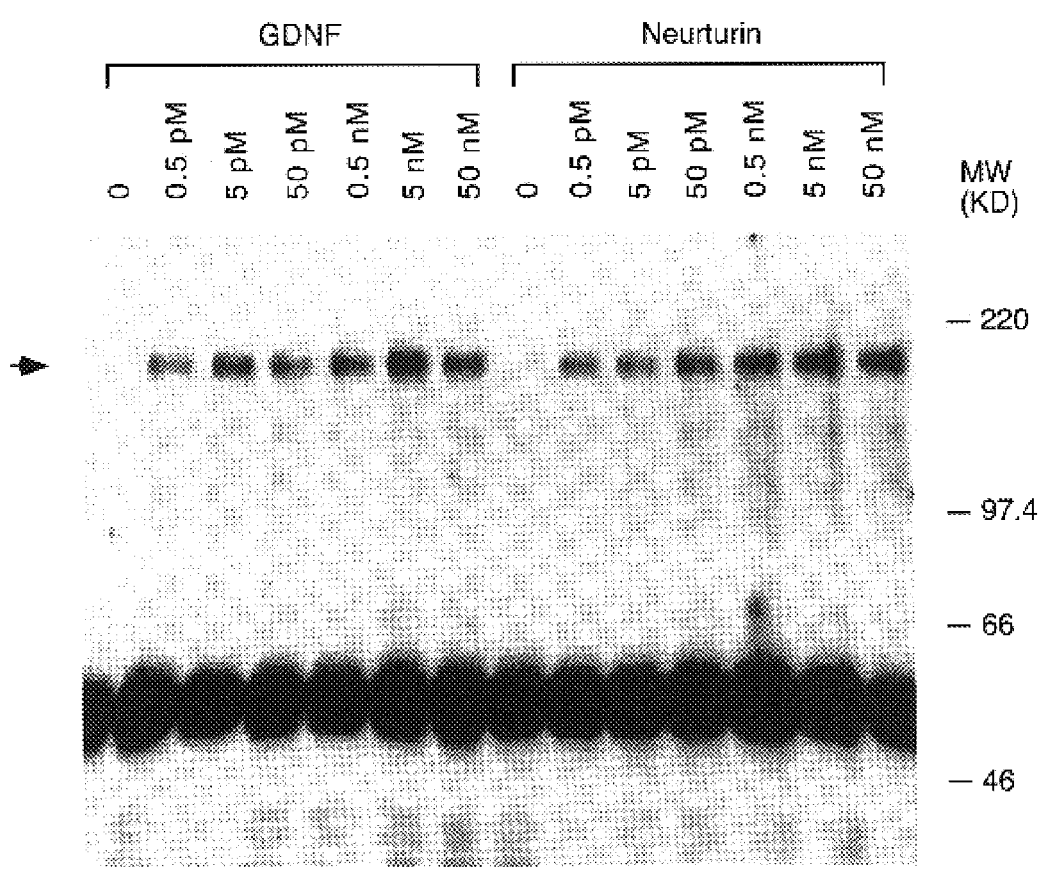
FIG. 24 depicts the results of neurturin induced ret autophosphorylation in LA-N-5 cells.

Both neurturin and GDNF bind to GRR2, and the Ret PTK can be activated by either neurturin or GDNF through GDNFR-α. These observations suggest that GRR2 may also be able to mediate neurturin and/or GDNF activation of Ret. To assess this possibility, human LA-N-5 neuroblastoma cells expressing GRR2 and Ret were treated with various concentrations of neurturin or GDNF and processed for immunoblotting as described in the previous section (FIG. 24). As shown, both neurturin and GDNF induced Ret autophosphorylation (FIG. 24).

FIG. 24. Neurturin and GDNF Induced Ret Autophosporulation in LA-N-5 Cells

LA-N-5 cells were treated with various concentrations of GDNF or neurturin as described. The cells were lysed, immunoprecipitated with anti-Ret antibody, fractionated by SDS-PAGE, and blotted with anti-phosphotyrosine antibody for Ret phosphorylation. The bands of phosphorylated Ret are indicated by an arrow.

Neurturin and GDNF Induce MAP Kinase activation in LA-N-5 and NGR-38 Cells

Figure 25:
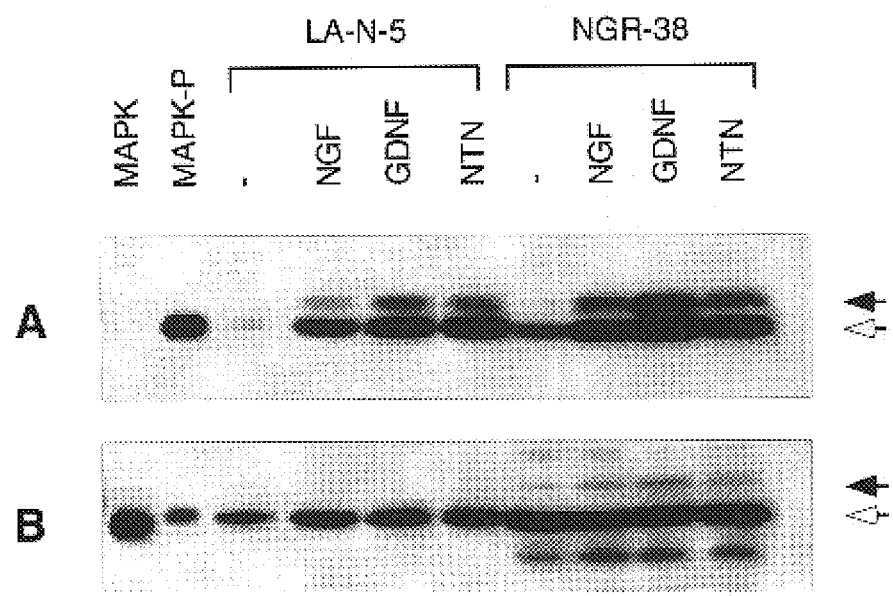
FIG. 25 (Panels A and B) depicts the results of neurturin and GDNF induced MAP kinase activation in LA-N-5 and NGR-38 cells.

We have demonstrated that both neurturin and GDNF can induce Ret autophosphorylation in cells expressing either GDNFR-α or GRR2. We then tested if the activation of Ret kinase by neurturin and/or GDNF could lead to activation of the downstream signaling molecule MAP kinase. Both LA-N-5 and NGR-38 cells were treated with either neurturin, GDNF, or NGF. Treated cells were lysed directly in SDS-PAGE sample buffer, fractionated by SDS-PAGE, and immunoblotted using an anti-phosphorylated MAP kinase antibody (New England Biolabs, Beverly, Mass.). As shown in FIG. 25, both p44 and p42 isoforms of MAP kinase are apparently activated by both neurturin and GDNF in either LA-N-5 or NGR-38 cells. MAP kinase activation by NGF (used as a positive control) was also observed.

FIG. 25 (Panels A and B). Neurturin and GDNF Induced MAP Kinase Activation in LA-N-5 and NGR-38 Cells 25A. LA-N-5 cells were treated with various concentrations of GDNF or neurturin as described. The cells were lysed directly in 2×SDS-PAGE sample buffer containing 0.5 mM NaVO$_4$, fractionated by SDS-PAGE, and blotted with an antibody against phosphorylated MAP kinase (MAPK-P). 25B. The membrane was stripped and reprobed with an anti-MAP kinase antibody for the amount of MAP kinase proteins loaded in each lane (MAPK).

Discussion

Signal transduction by most receptor PTKs starts by direct interaction with their ligands and consequent activation of the receptors. Cloning and characterization of GDNFR-α, an accessory molecule for ligand binding, revealed a novel mechanism by which Ret receptor PTK transduces the GDNF signal. GDNF does not bind Ret alone, instead, it first binds to GDNFR-α and then interacts with Ret as a part of the GDNF-GDNFR-α complex. The newly cloned GRR2 is related to GDNFR-α at both the amino acid level and the three dimensional structure. It shares 48% identical amino acid residues with GDNFR-α, among which are 30 of the 31 cysteines.

We have demonstrated that both neurturin and GDNF bind to GDNFR-α and GRR2. Binding of GDNF or neurturin to either GDNFR-α or GRR2 results in further association of the ligand with Ret and consequent activation of the Ret PTK and the MAP kinase, a downstream signaling molecule. However, each of the ligands appears to bind to one receptor preferentially. Neurturin binds GRR2 expressing LA-N-5 cells more efficiently than GDNF, and GDNF binds GDNFR-α expressing NGR-38 cells more efficiently than neurturin. It is not clear at this time why the binding of [$^{125}$I]GDNF to both GDNFR-α and GRR2 can be replaced by both unlabeled GDNF and neurturin, but that of [$^{125}$I]NTN can only be inhibited by cold neurturin.

Consistent with the binding study, GDNF is more effectively cross-linked to GDNFR-α/Fc fusion receptors than to GRR2/Fc, while neurturin cross-linking shows the opposite result.

Experimental Procedures cDNA Cloning of GRR2

A search of the GenBank database for sequences related to GDNFR-α resulted in the identification of EST, H12981.Gb__Est1. Primers corresponding to nucleotides 47 to 65 (5'-CTGCAAGAAGCTGCGCTCC-3') and 244 to 265 (5'-CTTGTCCTCATAGGAGCAGC-3') of H12981.Gb__Est1 (SEQ ID NOS: 59 and 60, respectively) were synthesized and used for RT-PCR with human fetal brain mRNA (Clontech, Cat. #64019-1) as the template. A 218 nt fragment was amplified, subcloned into pBlue-Script (Stratagene, La Jolla, Calif.), and sequenced to verify its correspondence with the original EST. The fragment was then radiolabeled with [$^{32}$P]-dCTP using a Random Primed DNA Labeling Kit (Stratagene, La Jolla, Calif.) according to the manufacturer's instructions. The radio-labeled probe was used to screen a human fetal brain cDNA library (Stratagene, La Jolla, Calif.). Two million clones were plated on 15 cm agarose plates and replicated on duplicate nitrocellulose filters. The filters were prehybridized at 55° C. for 3.5 hours in 200 ml of 6×SSC, 1×Denhardts, 0.5% SDS, and 50 µg/ml salmon sperm DNA. Following the addition of $2\times10^8$ cpm of the radiolabeled probe, hybridization was continued for 18 hours. Filters were then washed twice for 30 minutes each at 55° C. in 0.2×SSC, 0.1% SDS and exposed to X-ray film overnight with an intensifying screen. Five positive clones were identified and their DNA sequences were determined.

The oligonucleotide primers described above were also used for PCR screening of DNAs isolated from 27 pools (1500 clones each) of a rat photoreceptor cDNA library (Jing et al., 1996). A single positive pool was identified and screened by hybridization to the same radio-labeled probe as described above. An individual cDNA clone from this pool was identified and sequenced.

DNA Sequencing and Sequence Analysis

DNA sequencing was performed using an automated Applied Biosystems 373A DNA sequencer and Taq DyeDeoxy Terminator cycle sequencing kits (Applied Biosystems, Foster City Calif.). Comparison of the GDNFR-α and GRR2 sequences with public databases was carried out using the FASTA computer algorithm (Pearson and Lipman, Proceedings Of The National Academy Of Sciences Of The United States Of America. 85, 2444–2448, 1988). The peptide sequences of GDNFR-α and GRR2 were aligned using the Lineup program. All sequence analysis programs used were included in the Wisconsin sequence analysis package (Wisconsin Package Version 9.0, Genetics Computer Group, Madison, Wis.).

Binding of [$^{125}$I]GDNF and [$^{125}$I]NTN to NGR-38 and LA-N-5 Cells

Recombinant human neurturin was expressed in E. coli as insoluble protein. The inclusion bodies were solubilized, and the neurturin protein was re-folded and purified by ion exchange and hydrophobic interaction chromatography.

[$^{125}$I]NTN (~2000 Ci/mmole) was prepared using purified E. coli expressed protein (Amersham, Inc., Arlington Heights, Ill.; custom iodination, catalog #IMQ1057). Recombinant human GDNF was also radio-iodinated (Jing et al., 1996). Binding of [$^{125}$I]NTN and [$^{125}$I]GDNF to LA-N-5 and NGR-38 cells were carried out as previously described (Jing et al., 1990). Briefly, cells were seeded one day before the assay in 24-well Costar tissue culture plates pre-coated with polyomithine at a density of $3\times10^4$ cells/$cm^2$. Cells were placed on ice for 5 to 10 minutes, washed once with ice-cold buffer (DMEM containing 25 mM HEPES [pH 7.0]) and incubated at 4° C. in 0.2 ml binding buffer (washing buffer containing 2 mg/ml bovine serum albumin) containing various concentrations of [$^{125}$I]NTN or [$^{125}$I]GDNF in the absence or presence of 500 nM unlabeled ligands for 4 hours. Cells were washed 4 times with 0.5 ml ice-cold washing buffer and lysed with 0.5 ml of 1 M NaOH. The lysates were counted in a 1470 Wizard Automatic Gamma Counter (Wallac Inc., Gaithersburg, Md.).

Chemical Cross-linking

The coding regions of the first 455 amino acids of human GDNFR-α and the first 451 residues of human GRR2 cDNAs were fused in frame with a DNA fragment encoding the Fc region of human IgG1 tagged with 6 histidine residues at the carboxy terminus (Culouscou et al., J. Biochem., 270:12857–12863, 1995). This construct was then inserted into the expression vector pBK RSV (Stratagene, La Jolla, Calif.) as previously described (Jing et al., 1996). The GDNFR-α/Fc and GRR2/Fc fusion constructs were transfected into 293T cells, and conditioned media (CM, DMEM supplied with 0.5% fetal calf serum) containing the fusion proteins were collected 4 days after transfection. Aliquots of 1 ml CM plus 50 µl of 1 M HEPES, pH 7.5 were incubated at 4° C. with 10 nM of [$^{125}$I]NTN or 5 nM [$^{125}$I]GDNF in the presence or absence of 1 µM of unlabeled ligand for 4 hours. Bis suberate ($BS^3$ Pierce, Rockford, Ill.) stock solution in washing buffer (40 mM) was added to each binding mixture to a final concentration of 1 mM, mixed and incubated at room temperature for minutes. The reaction was quenched by adding 50 µl of 1 M glycine and incubating at room temperature for 15 minutes. Triton X-100 was added to a final concentration of 1%, and the cross-linked product was precipitated directly with 200 µl of Protein-A Sepharose CL-4B (Pharmacia). The cross-linked products were analyzed by 7.5% SDS-PAGE under reducing conditions.

Immunoblotting Analysis

Ret autophosphorylation was examined by immunoblot analysis as previously described (Jing et al., 1996). Briefly, cells were seeded 24 hours prior to the assay in 6-well tissue culture dishes at a density of $1.5\times10^6$ cells/well. Cells were washed once with binding buffer and treated with various concentrations of neurturin or GDNF (0.5 pM–50 nM) in binding buffer at 37° C. for 10 minutes. Treated cells and untreated controls were lysed in Triton X-100 lysis buffer (50 mM HEPES, pH 7.5, 1% Triton X-100, 50 mM NaCl, 50 mM NaF, 10 mM sodium pyrophosphate, 1% aprotinin (Sigma, Cat. #A-6279), 1 mM PMSF (Sigma, Cat. #P-7626), 0.5 mM $Na_3VO_4$ (Fisher Cat. #S454–50) and immunoprecipitated with an anti-Ret antibody (Santa Cruz Biotechnology) and protein-A Sepharose as described (Jing et al., 1996). Immunoprecipitates were fractionated by 7.5% SDS-PAGE and transferred to nitrocellulose membranes as described by Harlow and Lane (Antibodies LAboratory Manual, Spring Harbor Laboratory, Spring Harbor Press, 1988). The membranes were blocked with 5% BSA (Sigma) and tyrosine phosphorylation of the Ret receptor was detected by probing with an anti-phosphotyrosine monoclonal antibody 4G10 (UBI, Cat #05–321) at room temperature for 2 hours. The amount of Ret protein in each lane was determined by stripping and re-probing the same membrane with the anti-Ret antibody. Detection was accomplished using a sheep anti-mouse secondary antibody or protein-A conjugated to horseradish peroxidase (Amersham, cat. #NA931) in conjunction with chemiluminescence reagents (ECL, Amersham) following the manufacturer's instructions.

Activation of the MAP kinases was analyzed using a PhosphoPlus MAPK Antibody Kit (New England Biolabs, Beverly, Mass., Cat. #9100) following manufacturer's instructions. LA-N-5 and NGR-38 cells were seeded in 6-well dishes as described above. Cells were quiesced in DMEM containing 0.5% fetal calf serum (FCS) at 37° C. for 24 hours. The cells were then incubated with fresh media for 2 hours, treated with 50 ng/ml of NGF, GDNF, or neurturin at 37° C. for 5 minutes, and lysed directly in 150 µl of 2×SDS-PAGE sample buffer containing 0.5 mM NaVO4. The cell lysates were fractionated by 10% SDS-PAGE and transferred to a nitrocellulose filter. The filter was blocked with 5% non-fat dry milk at 4° C. overnight and then incubated overnight at 4° C. with a 1:1000 dilution of anti-phosphorylated MAP kinase antibody in the same buffer (New England Biolabs). Bands were detected using a horseradish peroxidase conjugated anti-rabbit antibody and the LumiGLO chemiluminescent reagents according to the manufacturer's recommendations. After exposure to X-ray film, the filter was stripped and reprobed by the anti-MAPK antibody.

FIG. 25 (Panels A and B). Neurturin and GDNF Induced MAP Kinase Activation in LA-N-5 and NGR-38 Cells 25A. LA-N-5 cells were treated with various concentrations of GDNF or neurturin as described. The cells were lysed directly in 2×SDS-PAGE sample buffer containing 0.5 mM NaVO$_4$, fractionated by SDS-PAGE, and blotted with an antibody against phosphorylated MAP kinase (MAPK-P). 25B. The membrane was stripped and reprobed with an anti-MAP kinase antibody for the amount of MAP kinase proteins loaded in each lane (MAPK).

Example 11

Cloning and Expression of GRR2 and GRR3

Signaling by glial cell line-derived neurotrophic factor (GDNF) is mediated by two receptor components. GDNF receptor-α (GDNFR-α) binds GDNF specifically, leading to the association of GDNF with Ret and the activation of the Ret kinase. Similarly, neurturin induces Ret activation through association with GRR2, a GDNFR-α-related receptor. Both GDNFR-α and GRR2 are capable of binding either GDNF or neurturin, but each exhibits a marked preference for its cognate ligand. A third molecule was cloned and is related in structure and primary amino acid sequence to GDNFR-α and GRR2. This molecule has been named GDNFR-α-related receptor 3 (GRR3). Analysis of the tissue distribution of GDNFR-α, GRR2, GRR3, and Ret by mRNA blot and in situ hybridization reveals overlapping but distinct patterns of expression. Consistent with their role in GDNF function, GDNFR and ret are co-expressed at known sites of GDNF action. GRR2 and GRR3 transcripts are also co-localized with those of ret in some cases, suggesting that GRR3 may also mediate Ret activation by GDNF or a related ligand.

Introduction

Glial cell line-derived neurotrophic factor (GDNF) is a potent survival factor for midbrain dopaminergic neurons, motor neurons, and several other types of neuronal cells. Targeted disruption of the GDNF gene in mice causes complete renal agenesis and the absence of enteric neurons (Moore et al., Nature, 382, 76–79, 1996; Pichel et al., Nature, 382, 73–76, 1996; Sanchez et al., Nature, 382, 7073, 1996; and Hudson et al., Brain Research Bulletin, 36, 425–32, 1995), indicating an essential role for GDNF in the development of the renal and the enteric nervous systems. The GDNF receptor was discovered to consist of a novel ligand binding component, GDNFR-α, and a signaling component, the Ret receptor protein tyrosine kinase.

GDNFR-α is attached to the cell membrane through a glycosyl-phosphatidylinositol (GPI) linkage but has no cytoplasmic domain. It binds GDNF specifically and with high affinity regardless of whether or not Ret is present. Ret is a receptor protein tyrosine kinase (PTK) originally discovered as a large open reading frame in the ret proto-oncogene. Its unique extracellular domain structure, which includes a signal peptide, a cadherin-like motif, and a cysteine-rich region, places it outside any other known receptor PTK sub-family. Ret alone does not bind GDNF, but was found to form a complex with GDNF and GDNFR-α that results in Ret activation. Activation of the Ret kinase appears to be associated with the biological effects of GDNF. Targeted disruption of the Ret PTK gene results in a phenotype nearly identical to that resulting from the disruption of GDNF (Schuchardt et al., Nature, 367, 380–383, 1994). In situ hybridization and immunohistochemical analysis detects high level expression of ret mRNA and protein in the developing central and peripheral nervous systems and in the excretory system of the mouse embryo. This expression pattern is similar to that of GDNF and is consistent with Ret's role in GDNF signaling.

The expression pattern of GDNFR-α is also consistent with its involvement in GDNF signaling. GDNFR-α mRNA has been found in a number of GDNF-responsive cell types and structures of the nervous system, often colocalized with ret. In the central nervous system, GDNFR-α mRNA has been observed in both developing and adult rat ventral midbrain, facial nucleus and ventral spinal cord. In addition, some specific cells in the superior colliculus, the lateral septum, the molecular layer of cerebellum adjacent to Purkinje cells, and some nuclei in cerebral cortex and the dorsomedial tegmental area have been shown to express GDNFR-α. In the peripheral nervous system, GDNFR-α mRNA expression has been found in subpopulations of neurons in dorsal root ganglia, in enteric neurons, and in neurons from sympathetic ganglia. High levels of GDNFR-α mRNA expression were also observed in other regions of the nervous system, including the retina, thalamus, pons, and medulla oblongata. Expression has also been seen in non-neuronal tissues such as the developing nephrons, pituitary, urogenital tract and pancreatic primordium.

Neurturin is a molecule which has similarities to GDNF in both amino acid sequence and biological activity. The GRR2 protein (GDNFR-α-Related Receptor 2), is a novel protein related in amino acid sequence to GDNFR-α. GRR2 is capable of binding both GDNF and neurturin, and like GDNFR-α, mediates the activation of the Ret PTK in response to these ligands. Although both GDNF and neurturin can bind both GDNFR-α and GRR2, GDNF exhibits a marked preference for GDNFR-α while neurturin interacts more strongly with GRR2. GDNFR-α-Related Receptor 3 (GRR3) a third member of this receptor family has also been found. The present study examines the tissue and cell-specific mRNA expression of GDNFR-α, GRR2, GRR3, and ret.

Results

Molecular Cloning and Sequence Comparison of GRR3 with GRR2 and GDNFR-α

Examination of publicly available sequence databases revealed the presence of a short expressed sequence tag (EST) with sequence homology to the GDNFR-α and GRR2 cDNA clones (WashU-HHMI Mouse EST Project). Oligonucleotides corresponding to the ends of this EST were used as primers in a reverse transcription-polymerase chain reaction (RT-PCR) with total rat embryo RNA as the template. A 225 nucleotide (nt) fragment was amplified, cloned into a plasmid vector, and sequenced to verify that it corresponded to the original GDNFR-α/GRR2-related EST. Plasmid DNAs isolated from pools of an E15 rat embryo cDNA library were screened by PCR and a single positive pool was found. Clones from this pool were screened by hybridization to the radiolabeled 225 nt PCR fragment and a single positive clone was isolated. Sequence analysis of the 1.8 kb insert from this clone revealed an open reading frame coding for a 397 amino acid peptide related to both GDNFR-α and GRR2. This protein was designated GDNFR-α-related receptor 3 (GRR3).

An alignment of the amino acid sequences of rat GDNFR-α, rat GRR2, and rat GRR3 (SEQ ID NOS:4, 40, and 42, respectively is shown in FIG. 26. The overall amino acid sequence identity among the three receptors is in the range of 30%–50%. GDNFR-α and GRR2 are somewhat more closely related to each other (48% identity) than they are to GRR3 (35% and 33% identity, respectively). Hydrophobic regions are found at both the amino and carboxy termini of all three molecules, except for the amino terminus of GRR2 (underlined, FIG. 26). The amino terminal regions of both GDNFR-α and GRR3 have the characteristics expected for signal peptide sequences. Although the GRR2 N-terminal sequence does not fit the criteria for a classical signal peptide, there is evidence that GRR2 is secreted. The carboxy terminal hydrophobic region of GDNFR-α is known to be involved in GPI-linkage to the cell membrane, and it is likely that the corresponding regions in GRR2 and GRR3 serve the same purpose. The most striking feature of the sequence alignment is the conservation of 28 cysteine residues among all three receptors (highlighted, FIG. 26), indicating that these proteins probably have similar three-dimensional structures. Several potential N-glycosylation sites are present in the receptors (shown in boldface, FIG. 26), but none are found at the same position in all three receptors. GDNFR-α and GRR2 share sites at positions 365 and 427 that are not found in GRR3, and GRR2 shares a possible site with GRR3 at positions 322–323 (FIG. 26).

Expression of GDNFR-α, GRR2, and GRR3 in Adult Rat

The expression of GDNFR-α, GRR2 and GRR3 mRNAs in adult rat tissues was examined by blot hybridization analysis. GDNFR-α mRNA is widely expressed, with high levels found in lung, brain, liver, kidney and spleen. Expression is also detectable in heart and among the tissues examined is absent only in muscle and testis. Two distinct size transcripts are observed and their relative amounts vary among the tissues. The 3.6 kb transcript is predominant in liver, lung, heart, and spleen while comparable amounts of the 3.6 kb and 8.5 kb transcripts are present in brain and kidney. The tissue distribution of GRR2 mRNA is similar to that of GDNFR-α. GRR2 expression is highest in lung, spleen and brain, with lesser amounts in kidney and heart. One difference is the lack of GRR2 expression in liver. The size of the GRR2 transcripts is approximately 3.6 kb, similar to the smaller of the two GDNFR-α transcripts. The expression of GRR3 mRNA is highest in kidney and is absent in brain. Detectable expression of GRR3 is also present in spleen, lung, liver, and heart. The transcript size for GRR3 is somewhat smaller (2.1 kb) than that observed for GDNFR-α and GRR2.

Expression of GDNFR-α, GRR2 and GRR3 in Mouse Embryo

Developmental expression of GDNFR-α, GRR2, and GRR3 mRNA was examined in the mouse on embryonic days 7, 11, 15, and 17. Expression of the 3.6 kb transcript of GDNFR-α is first apparent at E11, seems to decrease somewhat at E15, but then increases dramatically by E17. A minor amount of the 8.5 kb GDNFR-α mRNA can be detected on E11, but no expression of this transcript is detected thereafter. The expression of the 3.6 kb GRR2 transcript is barely detectable at E11, but increases gradually through E17. Expression of the 2.1 kb GRR3 mRNA is not detected at E7, but is quite strong by E11. After E11, expression decreases and remains constant from E15–E17.

In situ Hybridization Analysis of the Expression of GDNFR-α, GRR2, and GRR3

In order to provide clues to the potential roles and functional sites of GDNFR-α, GRR2 and GRR3, their expression was examined in regions where biological effects of GDNF have been demonstrated. In the E18 rat embryo, GDNF is highly expressed in the growing ureteric buds and maturing nephrons of the kidney as well as in the enteric neurons of the intestine. GDNFR-α is found in the same regions of the kidney and intestine as GDNF, but is also expressed at moderate levels in both the dorsal and ventral spinal cord. ret is expressed in the kidney and intestine as well, although its expression in the kidney seems to be confined to the ureteric buds. Expression of ret is high in the ventral motor neurons, but low in the dorsal region of the spinal cord. Like ret, expression of GRR2 in the kidney is restricted to the ureteric buds. GRR2 is expressed in both the dorsal and ventral regions of the spinal cord. A weak, diffuse hybridization signal was detected in the liver for GDNF, ret, and GDNFR-α.

In the postnatal day 7 rat, ret expression can be detected at substantial levels in the substantia nigra, trigeminal ganglia, and at a lower level in the reticular thalamic nucleus. GDNFR-α expression is high in both the reticular and ventromedial thalamic nuclei as well as in the medial habenular nucleus. Moderate expression of GDNFR-α is observed in the substantia nigra and lower but detectable levels are found in the hippocampus. GRR2 is expressed at moderate levels in the reticular thalanic nucleus, ventromedial thalamic nucleus, cerebral cortex (especially the cingulate cortex), and the substantia nigra. We could detect no expression of GRR3 in the P7 rat brain, but significant expression could be detected in the trigeminal ganglia.

Discussion

This study describes the isolation of GRR3, a novel molecule related to GDNFR-α and GRR2 and compares the tissue expression of ret with that of all three members of the GDNFR receptor family. GRR2 is 48% identical in amino acid sequence to GDNFR-α, while GRR3 is somewhat more distantly related at 35% identity. The position of 28 cysteine residues are conserved in all three molecules. Like GDNFR-α, both GRR2 and GRR3 have hydrophobic C-termini that are likely to be involved in GPI linkage to the cell membrane, and neither has a cytoplasmic domain. This strong conservation of sequence and structural features suggests that GDNFR-α, GRR2, and GRR3 define a new family of receptors for GDNF and related ligands. GDNF signaling is initiated by binding to GDNFR-α and accomplished by association and consequent activation of the Ret PTK. Based upon its sequence and structural similarities to GDNFR-α and GRR2, GRR3 is likely to function as a binding partner for GDNF, neurturin, and/or some other as yet undiscovered member of this ligand family.

The expression patterns of GDNFR-α, GRR2, and GRR3 in adult rat tissues are similar but distinct. All three mRNAs are found in lung, spleen, heart, and kidney while none of the three show significant expression in muscle or testis. Adult brain exhibits high expression of GDNFR-α and GRR2 mRNAs, but little or no GRR3 is detected. Expression of GDNFR-α mRNA is high in liver while GRR2 mRNA is almost nonexistent. If GDNF, neurturin and other as yet undiscovered GDNF-like ligands signal exclusively through Ret, differences in expression patterns of the ligand-specific binding receptors could provide a mechanism for ligand tissue specificity. Since the expression of c-ret can be detected throughout the period from E8.5 to E16.5, differences in the temporal expression of the receptor proteins could also define ligand specificity during development.

Expression of all the receptors and of c-ret is high in the adult kidney, the site of the most severe defects found in Ret knockout animals. In situ hybridization analyses indicate that ret, GDNFR-α, GRR2 and GRR3 are colocalized in several tissues, suggesting that GRR2 and GRR3 may also exert their in vivo effects through interaction with Ret (Table 5).

TABLE 5

Expression of ret, GDNFR-α, GRR2, and GRR3 in embryonic day 18 rat

|  | ret | GDNFR-α | GRR2 | GRR3 |
|---|---|---|---|---|
| Kidney/Intestine | +++ | +++ | ++ | −* |
| Brain: |  |  |  |  |
| Thalamic Nuclei: |  |  |  |  |
| Reticular | ++ | +++ | ++ | − |
| Ventral medial | + | +++ | ++ | − |
| Substantia Nigra | +++ | +++ | +++ | − |
| Habenular nucleus | − | +++ | − | − |
| Hippocampus | +/− | ++ | − | − |
| Spinal cord: |  |  |  |  |
| Dorsal | + | ++ | ++ | − |
| Ventral | ++ | +++ | ++ | − |
| Trigeminal Ganglia | +++ | +++ | − | +++ |

*High levels of expression were detected in the adult kidney.

Both GDNFR-α and GRR2 are transcribed along with ret in the kidney and intestine, in the substantia nigra, in the thalamus, and in ventral spinal motor neurons. This finding is consistent with GDNF's ability to promote the survival of dopaminergic and motor neurons and with the phenotypes of the Ret and GDNF knockout animals. Although little expression of GRR3 was found in the brain, it is co-expressed with ret and GDNFR-α in the trigeminal ganglia in E18 and P7 rats. These observations indicate that GDNF action may be regulated by association with different binding components depending on the tissue and developmental stage, while always signaling through Ret.

Although expression of ret is often co-localized with that of GDNFR-α, GRR2 and GRR3, there are several sites that express one or more of the binding receptors at high levels while ret expression is undetectable. Little or no ret is expressed in the spleen or lung where all three receptors are expressed at high levels. High levels of GDNFR-α mRNA are found in the liver, medial habenular nucleus, and the hippocampus, and GRR2 expression is prominent in the cortex. Little ret expression was observed in either of these regions. The lack of ret expression at some sites of substantial GDNFR expression suggests that either a signaling partner other than Ret may be employed by the GDNFRs in these tissues or that the receptors have an alternate mechanism of action. Two possibilities are that the receptors may act to sequester ligands of the GDNF family or that some fraction of the membrane bound receptors are released and mediate ligand function as soluble receptors.

Experimental Procedures

Cloning of GRR3

The GenBank database was searched for sequences related to GDNFR-α and GRR2 using the Wisconsin sequence analysis package (Wisconsin Package Version 9.0, Genetics Computer Group, Madison, Wis.). Oligonucleotide primers corresponding to regions near the ends of the EST AA238748.Gb_New2 were synthesized. Primers corresponding to AA238748.Gb_New2 were used for PCR screening of 83 pools of 1000 clones each from a rat E15 embryonic cDNA library. A single positive pool was identified by this method. The DNA fragment amplified from this pool was subcloned into a plasmid vector, and the insert was sequenced using an Applied Biosystems 373A automated DNA sequencer with Taq DyeDeoxy Terminator cycle sequencing kits (Applied Biosystems, Foster City, Calif.). The insert was then labeled with [$^{125}$I]-dCTP using a Random Primed DNA Labeling Kit (Stratagene, La Jolla, Calif.) according to the manufacturer's instructions. Clones from the cDNA library pool that had been identified as positive by PCR were plated on 15 cm agarose plates and replicated on duplicate nitrocellulose filters for screening by hybridization to the radiolabeled insert. Filters were prehybridized at 55° C. for 3.5 hours in 200 ml of 6×SSC, 1×Denhardts, 0.5% SDS, and 50 μg/ml salmon sperm DNA. Following the addition of 2×10$^8$ cpm of the radiolabeled probe, hybridization was continued for 18 hours. Filters were then washed twice for 30 minutes each at 55° C. in 0.2×SSC, 0.1% SDS and exposed to X-ray film overnight with an intensifying screen.

DNA Sequencing and Sequence Analysis

DNA from clones that screened positively by hybridization was prepared and sequenced using an automated Applied Biosystems 373A DNA sequencer and Taq DyeDeoxy Terminator cycle sequencing kits (Applied Biosystems, Foster City, Calif.). The peptide sequences of GDNFR-α, GRR2, and GRR3 were aligned using the Lineup program (Wisconsin Package Version 9.0, Genetics Computer Group, Madison, Wis.).

Blot Hybridization Analysis

For blot hybridization analysis, the cloned rat GRR3 cDNA was labeled using the Random Primed DNA Labeling Kit (Boehringer Mannheim, Indianapolis, Ind.) according to the manufacturer's instructions. Rat and mouse RNA blots (Clontech) were hybridized with the probe and washed at high stringency using the reagents of the ExpressHyb Kit (Clontech, Palo Alto, Calif.) according to the instructions of the manufacturer. Following exposure on X-ray film, the filters were stripped of probe by boiling in 0.5% SDS for 10 minutes and rehybridized with a β-actin probe (Clontech, Palo Alto, Calif.) as a control for total RNA loading.

In situ Hybridization

In situ hybridization using anti-sense riboprobes of GDNF, ret, GDNFR-α, GRR2, and GRR3, was done according to Zhou et al. (Journal of Neuroscience Research, 37, 129–143, 1994). The ret probe is a 316 nt fragment derived from the extracellular domain of the rat ret cDNA. GDNF mRNA was detected using a 303 nt fragment of a rat GDNF cDNA clone (nucleotide #50 to 352, Lin et al., 1993). GDNFR-α transcripts were detected with a 396 nt riboprobe (nucleotides 1072 to 1468). GRR2 transcripts were detected with a 205 nt antisense riboprobe corresponding to amino acids 339–413 of SEQ ID NO:40. GRR3 transcripts were detected with a 225 nt antisense riboprobe corresponding to amino acids 239–315 of SEQ ID NO:42.

While the present invention has been described in terms of preferred embodiments and exemplary nucleic acid and amino acid sequences, it is understood that variations and modifications will occur to those skilled in the art. Therefore, it is intended that the appended claims cover all such equivalent variations which come within the scope of the invention as claimed.

REFERENCES

Angrist, M., Bolk, S., Thiel, B., Puffenberger, E. G., Hofstra, R. M., Buys, C. H., Cass, D. T., and Chakravarti, A. (1995). Mutation analysis of the RET receptor tyrosine kinase in Hirschsprung disease. Hum. Mol. Genet.4, 821–830.

Arenas, E., Trupp, M., Akerud, P., and Ibanez, C. F. (1995). GDNF Prevents degeneration and promotes the phenotype of brain noradrenergic neurons in vivo. Neuron 15, 1465–1473.

Aruffo, A. and Seed, B. (1987). Molecular cloning of a CD28 cDNA by a high-efficiency COS cell expression system. Proceedings Of The National Academy Of Sciences Of The United States Of America. 84, 8573–8577.

Bartley, T. D., Hunt, R. W., Weicher, A. A., Boyle, W. J., Parker, V. P., Lindberg, R. A., Lu, H. S., Colombero, A. M., Elliott, R. L., Guthrie, B. A., Hoist, P. L., Skrine, J. D., Toso, R. J., Zhang, M., Fernandez, E., Trail, G., Varnum, B., Yarden, Y., Hunter, T., and Fox, G. M. (1994). B61 is a Ligand for the ECK Receptor protein-tyrosine kinase. Nature. 368, 558–560.

Beck, K. D., Valverde, J., Alexi, T., Poulsen, K., Moffat, B., Vandlen, R. A., Rosenthal, A., and Hefti, F. (1995). Mesencephalic dopaminergic neurons protected by GDNF from axotomy-induced degeneration in the adult brain. Nature. 373, 339–341.

Camu, W. and Henderson, C. (1992). Purification of embryonic rat motoneurons by panning on a monoclonal antibody to the low-affinity NGF receptor. J Neuroscience. 44, 59–70.

Choi-Lundberg, D. L. and Bohn, M. C. (1995). Ontogeny and distribution of glial cell line-derived neurotrophic factor (GDNF) mRNA in rat. Brain Res. Dev. Brain Res. 85, 80–88.

Davis, S., Aldrich, T. H., Valenzuela, D. M., Wong, V. V., Furth, M. E., Squinto, S. P., and Yancopoulos, G. D. (1991). The receptor for ciliary neurotrophic factor. Science. 253, 59–63.

Donis-Keller, H., Dou, S., Chi, D., Carlson, K., Toshima, K., Lairmore, T., Howe, J., Moley, J., Goodfellow, P. and Wells, S. (1993). Mutations in the ret proto-oncogene are associated with MEN 2A and FMTC. Hum. Molec. Genet. 2, 851–856.

Ebendal, T., Tomac, A., Hoffer, B. J., and Olson, L. (1995). Glial cell line-derived neurotrophic factor stimulates fiber formation and survival in cultured neurons from peripheral autonomic ganglia. Journal Of Neuroscience Research. 40, 276–284.

Economides, A. N., Ravetch, J. V., Yancopoulos, G. D., and Stahl, N. (1995). Designer cytokines: targeting actions to cells of choice. Science 270, 1351–1353.

Edery, P., Lyonnet, S., Mulligan, L., Pelet, A., Dow, E., Abel, L., Holder, S., Nihoul-Fekete, C., Ponder, B. and Munnich, A. (1994). Mutations of the ret proto-oncogene in Hirschsprug's disease. Nature. 367, 378–380.

Gearing, D. P., King, J. A., Gough, N. M., and Nicola, N. A. (1989). Expression cloning of a receptor for human granulocyte-macrophage colony-stimulating factor. EMBO Journal 8, 3667–3676.

Henderson, C. E., Phillips, H. S., Pollock, R. A., Davies, A. M., Lemeulle, C., Armanini, M., Simpson, L. C., Moffet, B., Vandlen, R. A., Koliatsos, V. E., and et al (1994). GDNF: a potent survival factor for motoneurons present in peripheral nerve and muscle. Science. 266, 1062–1064.

Hoffer, B. J., Hoffman, A., Bowenkamp, K., Huettl, P., Hudson, J., Martin, D., Lin, L. F., and Gerhardt, G. A. (1994). Glial cell line-derived neurotrophic factor reverses toxin-induced injury to midbrain dopaminergic neurons in vivo. Neuroscience Letters. 182, 107–111.

Hofstra, R., Landsvater, R., Ceccherini, I., Stulp, R., Stelwagen, T., Luo, Y., Pasini, B., Hoppener, J., van Amstel, H., Romeo, G., Lips, C. and Buys, C. (1994). A mutation in the ret proto-oncogene associated with multipleendocrine neoplasia type 2B and sporadic medullary thyroid carcinoma Nature. 367, 375–376.

Ikeda, I., Ishizaka, Y.; Tahira, T., Suzuki, T., Onda, M., Sugimura, T., and Nagao, M. (1990). Specific expression of the ret proto-oncogene in human neuroblastoma cell lines. Oncogene. 5, 1291–1296.

Ip, N. Y., Nye, S. H., Boulton, T. G., Davis, S., Yasukawa, K., Kishimoto, T., Anderson, D. J., and et al (1992). CNTF and LIF act on neuronal ceos via shared signaling pathways that involve the IL-6 signal transducing receptor component gp130. Cell. 69, 1121–1132.

Iwamoto, T., Taniguchi, M., Asia, N., Ohkusu, K., Nakashima, I. and Takahashi, M. (1993). cDNA cloning of mouse ret proto-oncongene and its sequence similarity to the cacherin superfamily. Oncogene. 8, 1087–1091.

Jing, S. Q., Spencer, T., Miller, K., Hopkins, C., and Trowbridge, I.S. (1990). Role of the human transferrin receptor cytoplasmic domain in endocytosis: localization of a specific signal sequence for internalization. Journal Of Cell Biology. 110, 283–294.

Kearns, C. M. and Gash, D. M. (1995). GDNF protects nigral dopacine neurons against 6-hydroxydopamine in vivo. Brain Research. 672, 104–111.

Kozak, M. (1987). An analysis of 5'-noncoding sequences from 699 vertebrate messenger RNAs. Nucleic Acids Research. 15, 8125–8148.

Li, L., Wu, W., Lin, L. F., Lei, M., Oppenheim, R. W., and Houenou, L. J. (1995). Rescue of adult mouse motoneurons from injury-induced cell death by glial cell line-derived neurotrophic factor. Proceedings Of The National Academy Of Sciences Of The United States Of America. 92, 9771–9775.

Lin, L-F. H., Doherty, D. H., Lile, J. D., Bektesh, S., and Collins, F. (1993). GDNF: a glial cell line-derived neurotrophic factor for midbrain dopaminergic neurons. Science. 260, 1130–1132.

Louis, J. C., Magal, E., and Varon, S. (1992). Receptor-mediated toxicity of norepinephrine on cultured catecholaminergic neurons of the rat brain stem. Journal Of Pharmacology And Experimental Therapeutics. 262, 127–1283.

Mount, H. T., Dean, D. O., Alberch, J., Dreyfus, C. F., and Black, I. B. (1995). Glial cell line-derived neurotrophic factor promotes the survival and morphologic differentiation of Purkinje cells. Proceedings Of The National Academy Of Sciences Of The United States Of America. 92, 9092–9096.

Mulligan, L., Kwok, J., Healey, C., Elsdon, M., Eng, C., Gardner, E., Love, D., Mole, S., Moore, J., Papi, L., Ponder, M., Telenius, H., Tunnacliffe, A. and Ponder, A . (1993). Gem-line mutations of the ret protoaoncongene in mutiple endocrine neoplasia type 2A. Nature. 363, 458–460.

Oppenheim, R. W., Houenou, L. J., Johnson, J. E., Lin, L. F., Li, L., Lo, A. C., Newsome, A. L., Prevette, D. M., and Wang, S. (1995). Developing motor neurons rescued from programmed and axotomy-induced cell death by GDNF. Nature. 373, 344–346.

Pachnis, V., Mankoo, B., and Costantini, F. (1993). Expression of the c-ret proto-oncogene during mouse embryogenesis. Development, 119, 1005–1017.

Pearson, W. R. and Lipman, D. J. (1988). Improved tools for biological sequence comparison. Proceedings Of The National Academy Of Sciences Of The United States Of America. 85, 2444–2448.

Poulsen, K. T., Armanini, M. P., Klein, R. D., Hynes, M. A., Phillips, H. S., and Rosenthal, A. (1994). TGF beta 2 and TGF beta 3 are potent survival factors for midbrain dopaminergic neurons. Neuron. 13, 1245–1252.

Romeo, G., Patrizia, R, Luo, Y., Barone, V., Seri, M., Ceceherini, I., Pasini, B., Bocciardi, R., Lerone, M., Kaariainen, H. and Maartucciello, G. (1994). Point mutations affecting the tyrosine kinase domain of the ret protooncogene in Hirscusprung's disease. Nature. 367, 377–378.

Santoro, M., Carlomagno, F., Romeo, A., Bottaro, D., Dathan, N., Grieco, M., Fusco, A., Vecchio, G., Matoskova, B., Kraus, M. and Di Fiore, P. (1995). Activation of ret as a dominant transforming gene by germline mutations of MEN2A and MEN2B. Science. 267, 381–383.

Sauer, H., Rosenblad, C., and Bjoerklund, A. (1995). Glial cell line-derived neurotrophic factor but not transforming growth factor beta 3 prevents delayed degeneration of nigral dopaminergic neurons following striatal 6-hydroxydopamine lesion. Proceedings Of The National Academy Of Sciences Of The United States Of America. 92, 8 935–8939.

Saxen, L. (1987). Organogenesis of the kidney. Development and Cell Biology series, Cambridge University Press, Cambridge, England.

Schaar, D. G., Sieber, B. A., Dreyfus, C. F., and Black, I. B. (1993). Regional and cell-specific expression of GDNF in rat brain. Experimental Neurology. 124, 368–371.

Schaar, D. G., Sieber, B. A., Sherwood, A. C., Dean, D., Mendoza, G., Ramakrishnan, L., Dreyfus, C. F., and Black, I. B. (1994). Multiple astrocyte transcripts encode nigral trophic factors in rat and human. Experimental Neurology. 130, 387–393.

Schiessinger, J. and Ullrich, A. (1992). Growth factor signaling by receptor tyrosine kinases. Neuron 9, 383–391.

Schuchardt, A., D'Agati, V., Laarsson-Blomberg, L., Costantini, F. and Pachnis, V. (1994). Defects in the kidney and enteric nervous system of mice lacking the tyrosine kinase receptor ret. Nature. 367, 380–383.

Segarini, P. R., Ziman, J. M., Kane, C. J., and Dasch, J. R. (1992). Two novel patterns of transforming growth factor beta (TGF-beta) binding to cell surface proteins are dependent upon the binding of TGF-beta 1 and indicate a mechanism of positive cooperativity. Journal Of Biological Chemistry. 267, 1048–1053.

Springer, J. E., Mu, X., Bergmann, L. W., and Trojanowski, J. Q. (1994). Expression of GDNF mRNA in rat and human nervous tissue. Experimental Neurology. 127, 167–170.

Stroemberg, I., Bjoerklund, L., Johansson, M., Tomac, A., Collins, F., Olson, L., Hoffer, B., and Humpel, C. (1993). Glial cell line-derived neurotrophic factor is expressed in the developing but not adult striatum and stimulates developing dopamine neurons in vivo. Experimental Neurology. 124, 401–412.

Takahashi, M., Ritz, J. and Cooper, G. (1985). Activation of a novel human tranforming gene, ret, by DNA rearrangement. Cell. 42, 581–588.

Takahashi, M. and Cooper, G. (1987). Ret transforming gene encodes a fusion protein homologous to tyrosine kinases. Mol. Cell. Biol., 7, 1378–1385.

Takebe, Y., Seiki, M., Fujisawa, J., Hoy, P., Yokota, K., Arai, K., Yoshida, M., and Arai, N. (1988). SRa promoter: an efficient and versatile mammalian cDNA expression system composed of the simian virus 40 early promoter and the R-U5 segment of human T-cell leukemia virus type 1 long terminal repeat. Mol. Cell. Biol. 8, 466–472.

Tomac, A., Lindqvist, E., Lin, L. F., Ogren, S. O., Young, D., Hoffer, B. J., and Olson, L. (1995a). Protection and repair of the nigrostriatal dopaminergic system by GDNF in vivo. Nature. 373, 335–339.

Tomac, A., Widenfalk, J., Lin, L. F., Kohno, T., Ebendal, T., Hoffer, B. J., and Olson, L. (1995b). Retrograde axonal transport of glial cell line-derived neurotrophic factor in the adult nigrostriatal system suggests a trophic role in the adult. Proceedings Of The National Academy Of Sciences Of The United States Of America 92, 8274–8278.

Trupp, M., Ryden, M., Joernvall, H., Funakoshi, H., Timmusk, T., Arenas, E., and Ibanez, C. F. (1995). Peripheral expression and biological activities of GDNF, a new neurotrophic factor for avian and mammalian peripheral neurons. Journal Of Cell Biology. 130, 137–148.

Tsuzuki, T., Takahashi, M., Asai, N., Iwashita, T., Matsuyama, M. and Asai, J. (1995). Spatial and temporal expression of the ret proto-oncogene product in embryonic, infant and adult rat tissues. Oncogene, 10, 191–198.

Ullrich, A and Schlessinger, J. (1990). Signal transduction by receptors with tyrosine kinase activity. Cell, 61, 203–211.

van der Geer, P., Hunter, T., and Lindberg, R. A. (1994). Receptor protein-tyrosine kinases and their signal transduction pathways. 10, 251–337.

van Heyningen, V. (1994). One gene-four syndromes. Nature, 367, 319–320. von Heijne, G. (1986). A new method for predicting signal sequence cleavage sites. Nucleic Acids Research. 14, 4683–4690.

Yan, Q., Matheson, C., and Lopez, O. T. (1995). In vivo neurotrophic effects of GDNF on neonatal and adult facial motor neurons. Nature. 373, 341–344.

Zurn, A. D., Baetge, E. E., Hammang, J. P., Tan, S. A., and Aebischer, P. (1994). Glial cell line-derived neurotrophic factor (GDNF), a new neurotrophic factor for motoneurones. Neuroreport. 6, 113–118.

What is claimed is:

1. An isolated polynucleic acid molecule encoding a protein comprising an amino acid sequence selected from the group consisting of SEQ ID NO: 38 and SEQ ID NO:42.

2. An isolated polynucleic acid molecule encoding a protein comprising an amino acid sequence selected from the group consisting of $Cys^{44}$ through $Cys^{389}$ of SEQ ID NO:38 and $Cys^{41}$ through $Cys^{337}$ of SEQ ID NO:42, wherein said protein is capable of binding to a glial cell line-derived neurotrophic factor or a neurturin neurotrophic factor such that the resulting protein/neurotrophic factor complex can bind to and induce phosphorylation of ret receptor protein tyrosine kinase.

3. An isolated polynucleic acid molecule comprising a nucleic acid sequence selected from the group consisting of:
   a) nucleotides of SEQ ID NO:37 encoding SEQ ID NO:38, and
   b) nucleotides of SEQ ID NO:41 encoding SEQ ID NO:42.

4. A vector comprising a polynucleic acid molecule of claim 1, 2 or 3 operatively linked to one or more operational elements effecting the amplification or expression of said polynucleic acid molecule.

5. A vector comprising a polynucleic acid molecule encoding a protein comprising the amino acid sequence of SEQ ID NOs: 38 or 42 operatively linked to one or more operational elements effecting the amplification or expression of said polynucleic acid molecule, wherein said protein is capable of binding to a neurotrophic factor such that the resulting protein/neurotrophic factor complex can bind to and induce phosphorylation of ret receptor protein tyrosine kinase.

6. An isolated host cell comprising a vector of claim 4.

7. An isolated host cell comprising a vector of claim 4 wherein said host cell is selected from the group consisting of a mammalian cell and a bacterial cell.

8. A host cell of claim 7 which is a COS-7 cell or *E. coli*.

9. An isolated host cell comprising a vector of claim 5.

10. A method for the production of a neurotrophic factor receptor protein comprising the steps of:
    (a) culturing an isolated host cell containing a polynucleic acid molecule of claim 1, 2 or 3, under conditions suitable for the expression of said neurotrophic factor receptor protein by said host cell; and
    (b) optionally, isolating said neurotrophic factor receptor protein expressed by said host cell.

11. A method for the production of a neurotrophic factor receptor protein, said method comprising the steps of:
    (a) culturing an isolated host cell, containing a polynucleic acid molecule encoding a protein comprising an amino acid sequence selected from the group consisting of
       (i) SEQ ID NO:38, and
       (ii) SEQ ID NO:42,
    under conditions suitable for the expression of said neurotrophic factor receptor protein by said host cell; and
    (b) optionally, isolating said neurotrophic factor receptor protein expressed by said host cell.

* * * * *

SEQUENCE LISTING

```
<160> NUMBER OF SEQ ID NOS: 61

<210> SEQ ID NO 1
<211> LENGTH: 2568
<212> TYPE: DNA
<213> ORGANISM: HUMAN
<220> FEATURE:
<221> NAME/KEY: CDS
<222> LOCATION: (540)..(1934)
<220> FEATURE:
```

-continued

```
<221> NAME/KEY: misc_feature
<222> LOCATION: (2078)..(2078)
<223> OTHER INFORMATION: N in position 2078 indicates a position of
      divergence between different receptor clones
<220> FEATURE:
<221> NAME/KEY: misc_feature
<222> LOCATION: (2107)..(2107)
<223> OTHER INFORMATION: N in position 2107 indicates a position of
      divergence between different receptor clones
<220> FEATURE:
<221> NAME/KEY: misc_feature
<222> LOCATION: (2241)..(2241)
<223> OTHER INFORMATION: N in position 2241 indicates a position of
      divergence between different receptor clones
<220> FEATURE:
<221> NAME/KEY: misc_feature
<222> LOCATION: (2250)..(2250)
<223> OTHER INFORMATION: N in position 2250  indicates a position of
      divergence between different receptor clones
<220> FEATURE:
<221> NAME/KEY: misc_feature
<222> LOCATION: (2256)..(2294)
<223> OTHER INFORMATION: N in positions 2256 to 2294  indicates
      positions of divergence between different receptor clones

<400> SEQUENCE: 1
aatctggcct cggaacacgc cattctccgc gccgcttcca ataaccacta acatccctaa      60
cgagcatccg agccgagggc tctgctcgga aatcgtcctg gcccaactcg gcccttcgag     120
ctctcgaaga ttaccgcatc tatttttttt ttctttttttt tcttttccta gcgcagataa    180
agtgagcccg gaaagggaag gaggggggcgg ggacaccatt gccctgaaag aataaataag    240
taaataaaca aactggctcc tcgccgcagc tggacgcggt cggttgagtc caggttgggt    300
cggacctgaa cccctaaaag cggaaccgcc tcccgccctc gccatcccgg agctgagtcg    360 ccggcggcg tggctgctgc cagacccgga gtttcctctt tcactggatg gagctgaact    420
ttgggcggcc agagcagcac agctgtccgg ggatcgctgc acgctgagct ccctcggcaa    480
gacccagcgg cggctcggga ttttttttggg ggggcgggga ccagccccgc gccggcacc   539 atg ttc ctg gcg acc ctg tac ttc gcg ctg ccg ctc ttg gac ttg ctc    587
Met Phe Leu Ala Thr Leu Tyr Phe Ala Leu Pro Leu Leu Asp Leu Leu
1               5                  10                  15 ctg tcg gcc gaa gtg agc ggc gga gac cgc ctg gat tgc gtg aaa gcc    635
Leu Ser Ala Glu Val Ser Gly Gly Asp Arg Leu Asp Cys Val Lys Ala
            20                  25                  30 agt gat cag tgc ctg aag gag cag agc tgc agc acc aag tac cgc acg    683
Ser Asp Gln Cys Leu Lys Glu Gln Ser Cys Ser Thr Lys Tyr Arg Thr
        35                  40                  45 cta agg cag tgc gtg gcg ggc aag gag acc aac ttc agc ctg gca tcc    731
Leu Arg Gln Cys Val Ala Gly Lys Glu Thr Asn Phe Ser Leu Ala Ser
    50                  55                  60 ggc ctg gag gcc aag gat gag tgc cgc agc gcc atg gag gcc ctg aag    779
Gly Leu Glu Ala Lys Asp Glu Cys Arg Ser Ala Met Glu Ala Leu Lys
65                  70                  75                  80 cag aag tcg ctc tac aac tgc cgc tgc aag cgg ggt atg aag aag gag    827
Gln Lys Ser Leu Tyr Asn Cys Arg Cys Lys Arg Gly Met Lys Lys Glu
                85                  90                  95 aag aac tgc ctg cgc att tac tgg agc atg tac cag agc ctg cag gga    875
Lys Asn Cys Leu Arg Ile Tyr Trp Ser Met Tyr Gln Ser Leu Gln Gly
            100                 105                 110 aat gat ctg ctg gag gat tcc cca tat gaa cca gtt aac agc aga ttg    923
Asn Asp Leu Leu Glu Asp Ser Pro Tyr Glu Pro Val Asn Ser Arg Leu
        115                 120                 125 tca gat ata ttc cgg gtg gtc cca ttc ata tca gat gtt ttt cag caa    971
Ser Asp Ile Phe Arg Val Val Pro Phe Ile Ser Asp Val Phe Gln Gln
```

```
                130                    135                    140
gtg gag cac att ccc aaa ggg aac aac tgc ctg gat gca gcg aag gcc    1019
Val Glu His Ile Pro Lys Gly Asn Asn Cys Leu Asp Ala Ala Lys Ala
145                 150                 155                 160 tgc aac ctc gac gac att tgc aag aag tac agg tcg gcg tac atc acc    1067
Cys Asn Leu Asp Asp Ile Cys Lys Lys Tyr Arg Ser Ala Tyr Ile Thr
                165                 170                 175 ccg tgc acc acc agc gtg tcc aac gat gtc tgc aac cgc cgc aag tgc    1115
Pro Cys Thr Thr Ser Val Ser Asn Asp Val Cys Asn Arg Arg Lys Cys
            180                 185                 190 cac aag gcc ctc cgg cag ttc ttt gac aag gtc ccg gcc aag cac agc    1163
His Lys Ala Leu Arg Gln Phe Phe Asp Lys Val Pro Ala Lys His Ser
        195                 200                 205 tac gga atg ctc ttc tgc tcc tgc cgg gac atc gcc tgc aca gag cgg    1211
Tyr Gly Met Leu Phe Cys Ser Cys Arg Asp Ile Ala Cys Thr Glu Arg
    210                 215                 220 agg cga cag acc atc gtg cct gtg tgc tcc tat gaa gag agg gag aag    1259
Arg Arg Gln Thr Ile Val Pro Val Cys Ser Tyr Glu Glu Arg Glu Lys
225                 230                 235                 240 ccc aac tgt ttg aat ttg cag gac tcc tgc aag acg aat tac atc tgc    1307
Pro Asn Cys Leu Asn Leu Gln Asp Ser Cys Lys Thr Asn Tyr Ile Cys
                245                 250                 255 aga tct cgc ctt gcg gat ttt ttt acc aac tgc cag cca gag tca agg    1355
Arg Ser Arg Leu Ala Asp Phe Phe Thr Asn Cys Gln Pro Glu Ser Arg
            260                 265                 270 tct gtc agc agc tgt cta aag gaa aac tac gct gac tgc ctc ctc gcc    1403
Ser Val Ser Ser Cys Leu Lys Glu Asn Tyr Ala Asp Cys Leu Leu Ala
        275                 280                 285 tac tcg ggg ctt att ggc aca gtc atg acc ccc aac tac ata gac tcc    1451
Tyr Ser Gly Leu Ile Gly Thr Val Met Thr Pro Asn Tyr Ile Asp Ser
    290                 295                 300 agt agc ctc agt gtg gcc cca tgg tgt gac tgc agc aac agt ggg aac    1499
Ser Ser Leu Ser Val Ala Pro Trp Cys Asp Cys Ser Asn Ser Gly Asn
305                 310                 315                 320 gac cta gaa gag tgc ttg aaa ttt ttg aat ttc ttc aag gac aat aca    1547
Asp Leu Glu Glu Cys Leu Lys Phe Leu Asn Phe Phe Lys Asp Asn Thr
                325                 330                 335 tgt ctt aaa aat gca att caa gcc ttt ggc aat ggc tcc gat gtg acc    1595
Cys Leu Lys Asn Ala Ile Gln Ala Phe Gly Asn Gly Ser Asp Val Thr
            340                 345                 350 gtg tgg cag cca gcc ttc cca gta cag acc acc act gcc act acc acc    1643
Val Trp Gln Pro Ala Phe Pro Val Gln Thr Thr Thr Ala Thr Thr Thr
        355                 360                 365 act gcc ctc cgg gtt aag aac aag ccc ctg ggg cca gca ggg tct gag    1691
Thr Ala Leu Arg Val Lys Asn Lys Pro Leu Gly Pro Ala Gly Ser Glu
    370                 375                 380 aat gaa att ccc act cat gtt ttg cca ccg tgt gca aat tta cag gca    1739
Asn Glu Ile Pro Thr His Val Leu Pro Pro Cys Ala Asn Leu Gln Ala
385                 390                 395                 400 cag aag ctg aaa tcc aat gtg tcg ggc aat aca cac ctc tgt att tcc    1787
Gln Lys Leu Lys Ser Asn Val Ser Gly Asn Thr His Leu Cys Ile Ser
                405                 410                 415 aat ggt aat tat gaa aaa gaa ggt ctc ggt gct tcc agc cac ata acc    1835
Asn Gly Asn Tyr Glu Lys Glu Gly Leu Gly Ala Ser Ser His Ile Thr
            420                 425                 430 aca aaa tca atg gct gct cct cca agc tgt ggt ctg agc cca ctg ctg    1883
Thr Lys Ser Met Ala Ala Pro Pro Ser Cys Gly Leu Ser Pro Leu Leu
        435                 440                 445 gtc ctg gtg gta acc gct ctg tcc acc cta tta tct tta aca gaa aca    1931
```

```
                Val Leu Val Val Thr Ala Leu Ser Thr Leu Leu Ser Leu Thr Glu Thr
                    450                 455                 460 tca tagctgcatt aaaaaaatac aatatggaca tgtaaaaaga caaaaaccaa            1984
Ser
465 gttatctgtt tcctgttctc ttgtatagct gaaattccag tttaggagct cagttgagaa    2044 acagttccat tcaactggaa cattttttt tttnccttt aagaaagctt cttgtgatcc      2104 ttngggctt ctgtgaaaaa cctgatgcag tgctccatcc aaactcagaa ggctttggga    2164 tatgctgtat tttaaaggga cagtttgtaa cttgggctgt aaagcaaact ggggctgtgt    2224 tttcgatgat gatgatnatc atgatnatga tnnnnnnnnn nnnnnnnnn nnnnnnnnn     2284 nnnnnnnnnn gattttaaca gttttacttc tggccttcc tagctagaga aggagttaat    2344 atttctaagg taactcccat atctcctta atgacattga tttctaatga tataaatttc    2404 agcctacatt gatgccaagc ttttttgcca caaagaagat tcttaccaag agtgggcttt   2464 gtggaaacag ctggtactga tgttcacctt tatatatgta ctagcatttt ccacgctgat   2524 gtttatgtac tgtaaacagt tctgcactct tgtacaaaag aaaa                    2568

<210> SEQ ID NO 2
<211> LENGTH: 465
<212> TYPE: PRT
<213> ORGANISM: HUMAN

<400> SEQUENCE: 2

Met Phe Leu Ala Thr Leu Tyr Phe Ala Leu Pro Leu Leu Asp Leu Leu
1               5                   10                  15

Leu Ser Ala Glu Val Ser Gly Gly Asp Arg Leu Asp Cys Val Lys Ala
                20                  25                  30

Ser Asp Gln Cys Leu Lys Glu Gln Ser Cys Ser Thr Lys Tyr Arg Thr
            35                  40                  45

Leu Arg Gln Cys Val Ala Gly Lys Glu Thr Asn Phe Ser Leu Ala Ser
        50                  55                  60

Gly Leu Glu Ala Lys Asp Glu Cys Arg Ser Ala Met Glu Ala Leu Lys
65                  70                  75                  80

Gln Lys Ser Leu Tyr Asn Cys Arg Cys Lys Arg Gly Met Lys Lys Glu
                85                  90                  95

Lys Asn Cys Leu Arg Ile Tyr Trp Ser Met Tyr Gln Ser Leu Gln Gly
                100                 105                 110

Asn Asp Leu Leu Glu Asp Ser Pro Tyr Glu Pro Val Asn Ser Arg Leu
            115                 120                 125

Ser Asp Ile Phe Arg Val Val Pro Phe Ile Ser Asp Val Phe Gln Gln
        130                 135                 140

Val Glu His Ile Pro Lys Gly Asn Asn Cys Leu Asp Ala Ala Lys Ala
145                 150                 155                 160

Cys Asn Leu Asp Asp Ile Cys Lys Lys Tyr Arg Ser Ala Tyr Ile Thr
                165                 170                 175

Pro Cys Thr Thr Ser Val Ser Asn Asp Val Cys Asn Arg Arg Lys Cys
            180                 185                 190

His Lys Ala Leu Arg Gln Phe Phe Asp Lys Val Pro Ala Lys His Ser
        195                 200                 205

Tyr Gly Met Leu Phe Cys Ser Cys Arg Asp Ile Ala Cys Thr Glu Arg
    210                 215                 220

Arg Arg Gln Thr Ile Val Pro Val Cys Ser Tyr Glu Glu Arg Glu Lys
225                 230                 235                 240
```

-continued

```
Pro Asn Cys Leu Asn Leu Gln Asp Ser Cys Lys Thr Asn Tyr Ile Cys
                245                 250                 255
Arg Ser Arg Leu Ala Asp Phe Phe Thr Asn Cys Gln Pro Glu Ser Arg
                260                 265                 270
Ser Val Ser Ser Cys Leu Lys Glu Asn Tyr Ala Asp Cys Leu Leu Ala
                275                 280                 285
Tyr Ser Gly Leu Ile Gly Thr Val Met Thr Pro Asn Tyr Ile Asp Ser
                290                 295                 300
Ser Ser Leu Ser Val Ala Pro Trp Cys Asp Cys Ser Asn Ser Gly Asn
305                 310                 315                 320
Asp Leu Glu Glu Cys Leu Lys Phe Leu Asn Phe Lys Asp Asn Thr
                325                 330                 335
Cys Leu Lys Asn Ala Ile Gln Ala Phe Gly Asn Gly Ser Asp Val Thr
                340                 345                 350
Val Trp Gln Pro Ala Phe Pro Val Gln Thr Thr Thr Ala Thr Thr Thr
                355                 360                 365
Thr Ala Leu Arg Val Lys Asn Lys Pro Leu Gly Pro Ala Gly Ser Glu
                370                 375                 380
Asn Glu Ile Pro Thr His Val Leu Pro Pro Cys Ala Asn Leu Gln Ala
385                 390                 395                 400
Gln Lys Leu Lys Ser Asn Val Ser Gly Asn Thr His Leu Cys Ile Ser
                405                 410                 415
Asn Gly Asn Tyr Glu Lys Glu Gly Leu Gly Ala Ser Ser His Ile Thr
                420                 425                 430
Thr Lys Ser Met Ala Ala Pro Pro Ser Cys Gly Leu Ser Pro Leu Leu
                435                 440                 445
Val Leu Val Val Thr Ala Leu Ser Thr Leu Leu Ser Leu Thr Glu Thr
                450                 455                 460
Ser
465

<210> SEQ ID NO 3
<211> LENGTH: 2138
<212> TYPE: DNA
<213> ORGANISM: RAT
<220> FEATURE:
<221> NAME/KEY: CDS
<222> LOCATION: (302)..(1705)

<400> SEQUENCE: 3
agctcgctct cccggggcag tggtgtggat gcaccggagt tcgggcgctg ggcaagttgg     60
gtcggaactg aaccccctgaa agcgggtccg cctcccgccc tcgcgcccgc ccggatctga    120
gtcgctggcg gcggtgggcg gcagagcgac ggggagtctg ctctcaccct ggatggagct    180
gaactttgag tggccagagg agcgcagtcg cccggggatc gctgcacgct gagctctctc    240
cccgagaccg ggcggcggct ttggattttg gggggcggg gaccagctgc gcggcggcac     300 c atg ttc cta gcc act ctg tac ttc gcg ctg cca ctc ctg gat ttg ctg    349
  Met Phe Leu Ala Thr Leu Tyr Phe Ala Leu Pro Leu Leu Asp Leu Leu
  1               5                   10                  15 atg tcc gcc gag gtg agt ggt gga gac cgt ctg gac tgt gtg aaa gcc    397
Met Ser Ala Glu Val Ser Gly Gly Asp Arg Leu Asp Cys Val Lys Ala
                20                  25                  30 agc gat cag tgc ctg aag gaa cag agc tgc agc acc aag tac cgc aca    445
Ser Asp Gln Cys Leu Lys Glu Gln Ser Cys Ser Thr Lys Tyr Arg Thr
            35                  40                  45
```

-continued

| | | | | | | | | | | | | | | | | |
|---|---|---|---|---|---|---|---|---|---|---|---|---|---|---|---|---|
| cta | agg | cag | tgc | gtg | gcg | ggc | aag | gaa | acc | aac | ttc | agc | ctg | aca | tcc | 493 |
| Leu | Arg | Gln | Cys | Val | Ala | Gly | Lys | Glu | Thr | Asn | Phe | Ser | Leu | Thr | Ser | |
| | 50 | | | | 55 | | | | 60 | | | | | | | |

```
cta agg cag tgc gtg gcg ggc aag gaa acc aac ttc agc ctg aca tcc    493
Leu Arg Gln Cys Val Ala Gly Lys Glu Thr Asn Phe Ser Leu Thr Ser
     50              55                  60 ggc ctt gag gcc aag gat gag tgc cgt agc gcc atg gag gcc ttg aag    541
Gly Leu Glu Ala Lys Asp Glu Cys Arg Ser Ala Met Glu Ala Leu Lys
 65          70                  75                  80 cag aag tct ctg tac aac tgc cgc tgc aag cgg ggc atg aag aaa gag    589
Gln Lys Ser Leu Tyr Asn Cys Arg Cys Lys Arg Gly Met Lys Lys Glu
                 85                  90                  95 aag aat tgt ctg cgt atc tac tgg agc atg tac cag agc ctg cag gga    637
Lys Asn Cys Leu Arg Ile Tyr Trp Ser Met Tyr Gln Ser Leu Gln Gly
             100                 105                 110 aat gac ctc ctg gaa gat tcc ccg tat gag ccg gtt aac agc agg ttg    685
Asn Asp Leu Leu Glu Asp Ser Pro Tyr Glu Pro Val Asn Ser Arg Leu
         115                 120                 125 tca gat ata ttc cgg gca gtc ccg ttc ata tca gat gtt ttc cag caa    733
Ser Asp Ile Phe Arg Ala Val Pro Phe Ile Ser Asp Val Phe Gln Gln
130             135                 140 gtg gaa cac att tcc aaa ggg aac aac tgc ctg gac gca gcc aag gcc    781
Val Glu His Ile Ser Lys Gly Asn Asn Cys Leu Asp Ala Ala Lys Ala
145             150                 155                 160 tgc aac ctg gac gac acc tgt aag aag tac agg tcg gcc tac atc acc    829
Cys Asn Leu Asp Asp Thr Cys Lys Lys Tyr Arg Ser Ala Tyr Ile Thr
                 165                 170                 175 ccc tgc acc acc agc atg tcc aac gag gtc tgc aac cgc cgt aag tgc    877
Pro Cys Thr Thr Ser Met Ser Asn Glu Val Cys Asn Arg Arg Lys Cys
                 180                 185                 190 cac aag gcc ctc agg cag ttc ttc gac aag gtt ccg gcc aag cac agc    925
His Lys Ala Leu Arg Gln Phe Phe Asp Lys Val Pro Ala Lys His Ser
                 195                 200                 205 tac ggg atg ctc ttc tgc tcc tgc cgg gac atc gcc tgc acc gag cgg    973
Tyr Gly Met Leu Phe Cys Ser Cys Arg Asp Ile Ala Cys Thr Glu Arg
     210                 215                 220 cgg cga cag act atc gtc ccc gtg tgc tcc tat gaa gaa cga gag agg   1021
Arg Arg Gln Thr Ile Val Pro Val Cys Ser Tyr Glu Glu Arg Glu Arg
225             230                 235                 240 ccc aac tgc ctg agt ctg caa gac tcc tgc aag acc aat tac atc tgc   1069
Pro Asn Cys Leu Ser Leu Gln Asp Ser Cys Lys Thr Asn Tyr Ile Cys
                 245                 250                 255 aga tct cgc ctt gca gat ttt ttt acc aac tgc cag cca gag tca agg   1117
Arg Ser Arg Leu Ala Asp Phe Phe Thr Asn Cys Gln Pro Glu Ser Arg
             260                 265                 270 tct gtc agc aac tgt ctt aag gag aac tac gca gac tgc ctc ctg gcc   1165
Ser Val Ser Asn Cys Leu Lys Glu Asn Tyr Ala Asp Cys Leu Leu Ala
         275                 280                 285 tac tcg gga ctg att ggc aca gtc atg act ccc aac tac gta gac tcc   1213
Tyr Ser Gly Leu Ile Gly Thr Val Met Thr Pro Asn Tyr Val Asp Ser
     290                 295                 300 agc agc ctc agc gtg gca cca tgg tgt gac tgc agc aac agc ggc aat   1261
Ser Ser Leu Ser Val Ala Pro Trp Cys Asp Cys Ser Asn Ser Gly Asn
305             310                 315                 320 gac ctg gaa gac tgc ttg aaa ttt ctg aat ttt ttt aag gac aat act   1309
Asp Leu Glu Asp Cys Leu Lys Phe Leu Asn Phe Phe Lys Asp Asn Thr
                 325                 330                 335 tgt ctc aaa aat gca att caa gcc ttt ggc aat ggc tca gat gtg acc   1357
Cys Leu Lys Asn Ala Ile Gln Ala Phe Gly Asn Gly Ser Asp Val Thr
                 340                 345                 350 atg tgg cag cca gcc cct cca gtc cag acc acc act gcc acc act acc   1405
Met Trp Gln Pro Ala Pro Pro Val Gln Thr Thr Thr Ala Thr Thr Thr
             355                 360                 365
```

-continued

```
act gcc ttc cgg gtc aag aac aag cct ctg ggg cca gca ggg tct gag    1453
Thr Ala Phe Arg Val Lys Asn Lys Pro Leu Gly Pro Ala Gly Ser Glu
    370                 375                 380 aat gag atc ccc aca cac gtt tta cca ccc tgt gcg aat ttg cag gct    1501
Asn Glu Ile Pro Thr His Val Leu Pro Pro Cys Ala Asn Leu Gln Ala
385                 390                 395                 400 cag aag ctg aaa tcc aat gtg tcg ggt agc aca cac ctc tgt ctt tct    1549
Gln Lys Leu Lys Ser Asn Val Ser Gly Ser Thr His Leu Cys Leu Ser
                405                 410                 415 gat agt gat ttc gga aag gat ggt ctc gct ggt gcc tcc agc cac ata    1597
Asp Ser Asp Phe Gly Lys Asp Gly Leu Ala Gly Ala Ser Ser His Ile
            420                 425                 430 acc aca aaa tca atg gct gct cct ccc agc tgc agt ctg agc tca ctg    1645
Thr Thr Lys Ser Met Ala Ala Pro Pro Ser Cys Ser Leu Ser Ser Leu
        435                 440                 445 ccg gtg ctg atg ctc acc gcc ctt gct gcc ctg tta tct gta tcg ttg    1693
Pro Val Leu Met Leu Thr Ala Leu Ala Ala Leu Leu Ser Val Ser Leu
    450                 455                 460 gca gaa acg tcg tagctgcatc cgggaaaaca gtatgaaaag acaaaagaga        1745
Ala Glu Thr Ser
465 accaagtatt ctgtccctgt cctcttgtat atctgaaaat ccagttttaa aagctccgtt  1805 gagaagcagt ttcacccaac tggaactctt tccttgtttt taagaaagct tgtggccctc  1865 agggcttct gttgaagaac tgctacaggg ctaattccaa acccataagg ctctggggcg   1925 tggtgcggct taaggggacc atttgcacca tgtaaagcaa gctggcttaa tcatgtgttt  1985 gatggtgagg atggtagtgg tgatgatgat ggtaatttta acagcttgaa ccctgttctc  2045 tctactggtt aggaacagga gatactattg ataaagattc ttccatgtct tactcagcag  2105 cattgccttc tgaagacagg cccgcagccg tcg                               2138
```

<210> SEQ ID NO 4
<211> LENGTH: 468
<212> TYPE: PRT
<213> ORGANISM: RAT

<400> SEQUENCE: 4

```
Met Phe Leu Ala Thr Leu Tyr Phe Ala Leu Pro Leu Leu Asp Leu Leu
1               5                   10                  15

Met Ser Ala Glu Val Ser Gly Gly Asp Arg Leu Asp Cys Val Lys Ala
            20                  25                  30

Ser Asp Gln Cys Leu Lys Glu Gln Ser Cys Ser Thr Lys Tyr Arg Thr
        35                  40                  45

Leu Arg Gln Cys Val Ala Gly Lys Glu Thr Asn Phe Ser Leu Thr Ser
    50                  55                  60

Gly Leu Glu Ala Lys Asp Glu Cys Arg Ser Ala Met Glu Ala Leu Lys
65                  70                  75                  80

Gln Lys Ser Leu Tyr Asn Cys Arg Cys Lys Arg Gly Met Lys Lys Glu
                85                  90                  95

Lys Asn Cys Leu Arg Ile Tyr Trp Ser Met Tyr Gln Ser Leu Gln Gly
            100                 105                 110

Asn Asp Leu Leu Glu Asp Ser Pro Tyr Glu Pro Val Asn Ser Arg Leu
        115                 120                 125

Ser Asp Ile Phe Arg Ala Val Pro Phe Ile Ser Asp Val Phe Gln Gln
    130                 135                 140

Val Glu His Ile Ser Lys Gly Asn Asn Cys Leu Asp Ala Ala Lys Ala
```

```
                145                 150                 155                 160
Cys Asn Leu Asp Asp Thr Cys Lys Lys Tyr Arg Ser Ala Tyr Ile Thr
                    165                 170                 175
Pro Cys Thr Thr Ser Met Ser Asn Glu Val Cys Asn Arg Arg Lys Cys
                180                 185                 190
His Lys Ala Leu Arg Gln Phe Phe Asp Lys Val Pro Ala Lys His Ser
            195                 200                 205
Tyr Gly Met Leu Phe Cys Ser Cys Arg Asp Ile Ala Cys Thr Glu Arg
        210                 215                 220
Arg Arg Gln Thr Ile Val Pro Val Cys Ser Tyr Glu Glu Arg Glu Arg
225                 230                 235                 240
Pro Asn Cys Leu Ser Leu Gln Asp Ser Cys Lys Thr Asn Tyr Ile Cys
                245                 250                 255
Arg Ser Arg Leu Ala Asp Phe Phe Thr Asn Cys Gln Pro Glu Ser Arg
                260                 265                 270
Ser Val Ser Asn Cys Leu Lys Glu Asn Tyr Ala Asp Cys Leu Leu Ala
            275                 280                 285
Tyr Ser Gly Leu Ile Gly Thr Val Met Thr Pro Asn Tyr Val Asp Ser
        290                 295                 300
Ser Ser Leu Ser Val Ala Pro Trp Cys Asp Cys Ser Asn Ser Gly Asn
305                 310                 315                 320
Asp Leu Glu Asp Cys Leu Lys Phe Leu Asn Phe Phe Lys Asp Asn Thr
                325                 330                 335
Cys Leu Lys Asn Ala Ile Gln Ala Phe Gly Asn Gly Ser Asp Val Thr
                340                 345                 350
Met Trp Gln Pro Ala Pro Val Gln Thr Thr Thr Ala Thr Thr Thr
            355                 360                 365
Thr Ala Phe Arg Val Lys Asn Lys Pro Leu Gly Pro Ala Gly Ser Glu
        370                 375                 380
Asn Glu Ile Pro Thr His Val Leu Pro Pro Cys Ala Asn Leu Gln Ala
385                 390                 395                 400
Gln Lys Leu Lys Ser Asn Val Ser Gly Ser Thr His Leu Cys Leu Ser
                405                 410                 415
Asp Ser Asp Phe Gly Lys Asp Gly Leu Ala Gly Ala Ser Ser His Ile
                420                 425                 430
Thr Thr Lys Ser Met Ala Ala Pro Pro Ser Cys Ser Leu Ser Ser Leu
            435                 440                 445
Pro Val Leu Met Leu Thr Ala Leu Ala Ala Leu Leu Ser Val Ser Leu
        450                 455                 460
Ala Glu Thr Ser
465

<210> SEQ ID NO 5
<211> LENGTH: 3209
<212> TYPE: DNA
<213> ORGANISM: HUMAN
<220> FEATURE:
<221> NAME/KEY: misc_feature
<222> LOCATION: (1)..(510)
<223> OTHER INFORMATION: note="1 to 510 is -237 to 272 of Fig 5
      Hsgr-21bf"
<220> FEATURE:
<221> NAME/KEY: misc_feature
<222> LOCATION: (1)..(539)
<223> OTHER INFORMATION: note="1 to 539 is -237 to 301 of Fig 5 Gdnfr"
<220> FEATURE:
<221> NAME/KEY: CDS
<222> LOCATION: (540)..(1937)
```

-continued

```
<220> FEATURE:
<221> NAME/KEY: misc_feature
<222> LOCATION: (1091)..(1091)
<223> OTHER INFORMATION: N in position 1091 indicates any nucleic acid
<220> FEATURE:
<221> NAME/KEY: misc_feature
<222> LOCATION: (2078)..(2078)
<223> OTHER INFORMATION: N in position 2078 indicates a position of
      divergence between different receptor clones
<220> FEATURE:
<221> NAME/KEY: misc_feature
<222> LOCATION: (2256)..(2294)
<223> OTHER INFORMATION: N in positions 2256 to 2294 indicates positions
      of divergence between different receptor clones

<400> SEQUENCE: 5
aatctggcct cggaacacgc cattctccgc gccgcttcca ataaccacta acatccctaa      60
cgagcatccg agccgagggc tctgctcgga aatcgtcctg gcccaactcg gcccttcgag     120
ctctcgaaga ttaccgcatc tattttttt ttctttttt tcttttccta gcgcagataa      180
agtgagcccg gaaagggaag gaggggggcgg ggacaccatt gccctgaaag aataaataag   240
taaataaaca aactggctcc tcgccgcagc tggacgcggt cggttgagtc caggttgggt    300
cggacctgaa ccctaaaag cggaaccgcc tcccgccctc gccatcccgg agctgagtcg     360
ccggcggcgg tggctgctgc cagacccgga gtttcctctt tcactggatg gagctgaact    420
ttgggcggcc agagcagcac agctgtccgg ggatcgctgc acgctgagct ccctcggcaa    480 gaccagcgg cggctcggga ttttttggg ggggcgggga ccagccccgc gccggcacc       539 atg ttc ctg gcg acc ctg tac ttc gcg ctg ccg ctc ttg gac ttg ctc      587
Met Phe Leu Ala Thr Leu Tyr Phe Ala Leu Pro Leu Leu Asp Leu Leu
1               5                   10                  15 ctg tcg gcc gaa gtg agc ggc gga gac cgc ctg gat tgc gtg aaa gcc      635
Leu Ser Ala Glu Val Ser Gly Gly Asp Arg Leu Asp Cys Val Lys Ala
            20                  25                  30 agt gat cag tgc ctg aag gag cag agc tgc agc acc aag tac cgc acg      683
Ser Asp Gln Cys Leu Lys Glu Gln Ser Cys Ser Thr Lys Tyr Arg Thr
        35                  40                  45 cta agg cag tgc gtg gcg ggc aag gag acc aac ttc agc ctg gca tcc      731
Leu Arg Gln Cys Val Ala Gly Lys Glu Thr Asn Phe Ser Leu Ala Ser
    50                  55                  60 ggc ctg gag gcc aag gat gag tgc cgc agc gcc atg gag gcc ctg aag      779
Gly Leu Glu Ala Lys Asp Glu Cys Arg Ser Ala Met Glu Ala Leu Lys
65                  70                  75                  80 cag aag tcg ctc tac aac tgc cgc tgc aag cgg ggt atg aag aag gag      827
Gln Lys Ser Leu Tyr Asn Cys Arg Cys Lys Arg Gly Met Lys Lys Glu
                85                  90                  95 aag aac tgc ctg cgc att tac tgg agc atg tac cag agc ctg cag gga      875
Lys Asn Cys Leu Arg Ile Tyr Trp Ser Met Tyr Gln Ser Leu Gln Gly
            100                 105                 110 aat gat ctg ctg gag gat tcc cca tat gaa cca gtt aac agc aga ttg      923
Asn Asp Leu Leu Glu Asp Ser Pro Tyr Glu Pro Val Asn Ser Arg Leu
        115                 120                 125 tca gat ata ttc cgg gtg gtc cca ttc ata tca gat gtt ttt cag caa      971
Ser Asp Ile Phe Arg Val Val Pro Phe Ile Ser Asp Val Phe Gln Gln
    130                 135                 140 gtg gag cac att ccc aaa ggg aac aac tgc ctg gat gca gcg aag gcc     1019
Val Glu His Ile Pro Lys Gly Asn Asn Cys Leu Asp Ala Ala Lys Ala
145                 150                 155                 160 tgc aac ctc gac gac att tgc aag aag tac agg tcg gcg tac atc acc     1067
Cys Asn Leu Asp Asp Ile Cys Lys Lys Tyr Arg Ser Ala Tyr Ile Thr
                165                 170                 175
```

-continued

| | |
|---|---|
| ccg tgc acc acc agc gtg tcc aan gat gtc tgc aac cgc cgc aag tgc<br>Pro Cys Thr Thr Ser Val Ser Xaa Asp Val Cys Asn Arg Arg Lys Cys<br>            180                  185                  190 | 1115 |
| cac aag gcc ctc cgg cag ttc ttt gac aag gtc ccg gcc aag cac agc<br>His Lys Ala Leu Arg Gln Phe Phe Asp Lys Val Pro Ala Lys His Ser<br>            195                  200                  205 | 1163 |
| tac gga atg ctc ttc tgc tcc tgc cgg gac atc gcc tgc aca gag cgg<br>Tyr Gly Met Leu Phe Cys Ser Cys Arg Asp Ile Ala Cys Thr Glu Arg<br>210                  215                  220 | 1211 |
| agg cga cag acc atc gtg cct gtg tgc tcc tat gaa gag agg gag aag<br>Arg Arg Gln Thr Ile Val Pro Val Cys Ser Tyr Glu Glu Arg Glu Lys<br>225                  230                  235                  240 | 1259 |
| ccc aac tgt ttg aat ttg cag gac tcc tgc aag acg aat tac atc tgc<br>Pro Asn Cys Leu Asn Leu Gln Asp Ser Cys Lys Thr Asn Tyr Ile Cys<br>            245                  250                  255 | 1307 |
| aga tct cgc ctt gcg gat ttt ttt acc aac tgc cag cca gag tca agg<br>Arg Ser Arg Leu Ala Asp Phe Phe Thr Asn Cys Gln Pro Glu Ser Arg<br>            260                  265                  270 | 1355 |
| tct gtc agc agc tgt cta aag gaa aac tac gct gac tgc ctc ctc gcc<br>Ser Val Ser Ser Cys Leu Lys Glu Asn Tyr Ala Asp Cys Leu Leu Ala<br>            275                  280                  285 | 1403 |
| tac tcg ggg ctt att ggc aca gtc atg acc ccc aac tac ata gac tcc<br>Tyr Ser Gly Leu Ile Gly Thr Val Met Thr Pro Asn Tyr Ile Asp Ser<br>290                  295                  300 | 1451 |
| agt agc ctc agt gtg gcc cca tgg tgt gac tgc agc aac agt ggg aac<br>Ser Ser Leu Ser Val Ala Pro Trp Cys Asp Cys Ser Asn Ser Gly Asn<br>305                  310                  315                  320 | 1499 |
| gac cta gaa gag tgc ttg aaa ttt ttg aat ttc ttc aag gac aat aca<br>Asp Leu Glu Glu Cys Leu Lys Phe Leu Asn Phe Phe Lys Asp Asn Thr<br>                  325                  330                  335 | 1547 |
| tgt ctt aaa aat gca att caa gcc ttt ggc aat ggc tcc gat gtg acc<br>Cys Leu Lys Asn Ala Ile Gln Ala Phe Gly Asn Gly Ser Asp Val Thr<br>            340                  345                  350 | 1595 |
| gtg tgg cag cca gcc ttc cca gta cag acc acc act gcc act acc acc<br>Val Trp Gln Pro Ala Phe Pro Val Gln Thr Thr Thr Ala Thr Thr Thr<br>            355                  360                  365 | 1643 |
| act gcc ctc cgg gtt aag aac aag ccc ctg ggg cca gca ggg tct gag<br>Thr Ala Leu Arg Val Lys Asn Lys Pro Leu Gly Pro Ala Gly Ser Glu<br>370                  375                  380 | 1691 |
| aat gaa att ccc act cat gtt ttg cca ccg tgt gca aat tta cag gca<br>Asn Glu Ile Pro Thr His Val Leu Pro Pro Cys Ala Asn Leu Gln Ala<br>385                  390                  395                  400 | 1739 |
| cag aag ctg aaa tcc aat gtg tcg ggc aat aca cac ctc tgt att tcc<br>Gln Lys Leu Lys Ser Asn Val Ser Gly Asn Thr His Leu Cys Ile Ser<br>            405                  410                  415 | 1787 |
| aat ggt aat tat gaa aaa gaa ggt ctc ggt gct tcc agc cac ata acc<br>Asn Gly Asn Tyr Glu Lys Glu Gly Leu Gly Ala Ser Ser His Ile Thr<br>                  420                  425                  430 | 1835 |
| aca aaa tca atg gct gct cct cca agc tgt ggt ctg agc cca ctg ctg<br>Thr Lys Ser Met Ala Ala Pro Pro Ser Cys Gly Leu Ser Pro Leu Leu<br>            435                  440                  445 | 1883 |
| gtc ctg gtg gta acc gct ctg tcc acc cta tta tct tta aca gaa aca<br>Val Leu Val Val Thr Ala Leu Ser Thr Leu Leu Ser Leu Thr Glu Thr<br>450                  455                  460 | 1931 |
| tca tag ctgcattaaa aaatacaat atggacatgt aaaagacaa aaccaagtt<br>Ser<br>465 | 1987 |
| atctgtttcc tgttctcttg tatagctgaa attccagttt aggagctcag ttgagaaaca | 2047 |
| gttccattca actggaacat ttttttttt nccttttaag aaagcttctt gtgatccttc | 2107 |

```
ggggcttctg tgaaaaacct gatgcagtgc tccatccaaa ctcagaaggc tttgggatat    2167
gctgtatttt aaagggacag tttgtaactt gggctgtaaa gcaaactggg gctgtgtttt    2227
cgatgatgat gatcatcatg atcatgatnn nnnnnnnnnn nnnnnnnnnn nnnnnnnnnn    2287
nnnnnnngat tttaacagtt ttacttctgg cctttcctag ctagagaagg agttaatatt    2347
tctaaggtaa ctcccatatc tcctttaatg acattgattt ctaatgatat aaatttcagc    2407
ctacattgat gccaagcttt tttgccacaa agaagattct taccaagagt gggctttgtg    2467
gaaacagctg gtactgatgt tcacctttat atatgtacta gcattttcca cgctgatgtt    2527
tatgtactgt aaacagttct gcactcttgt acaaagaaa aacacctgt cacatccaaa    2587 tatagtatct gtcttttcgt caaaatagag agtggggaat gagtgtgccg attcaatacc    2647
tcaatccctg aacgacactc tcctaatcct aagccttacc tgagtgagaa gccctttacc    2707
taacaaaagt ccaatatagc tgaaatgtcg ctctaatact ctttacacat atgaggttat    2767
atgtagaaaa aaattttact actaaatgat ttcaactatt ggctttctat attttgaaag    2827
taatgatatt gtctcatttt tttactgatg gtttaataca aaatacacag agcttgtttc    2887
ccctcataag tagtgttcgc tctgatatga acttcacaaa tacagctcat caaaagcaga    2947
ctctgagaag cctcgtgctg tagcagaaag ttctgcatca tgtgactgtg gacaggcagg    3007
aggaaacaga acagacaagc attgtctttt gtcattgctc gaagtgcaag cgtgcatacc    3067
tgtggaggga actggtggct gcttgtaaat gttctgcagc atctcttgac acacttgtca    3127
tgacacaatc cagtaccttg gttttcaggt tatctgacaa aggcagcttt gattgggaca    3187
tggaggcatg ggcaggccgg aa                                             3209
```

<210> SEQ ID NO 6
<211> LENGTH: 465
<212> TYPE: PRT
<213> ORGANISM: HUMAN
<220> FEATURE:
<221> NAME/KEY: misc_feature
<222> LOCATION: (184)..(184)
<223> OTHER INFORMATION: The 'Xaa' at location 184 stands for Lys, or
      Asn.

<400> SEQUENCE: 6

```
Met Phe Leu Ala Thr Leu Tyr Phe Ala Leu Pro Leu Leu Asp Leu Leu
1               5                   10                  15

Leu Ser Ala Glu Val Ser Gly Gly Asp Arg Leu Asp Cys Val Lys Ala
            20                  25                  30

Ser Asp Gln Cys Leu Lys Glu Gln Ser Cys Ser Thr Lys Tyr Arg Thr
        35                  40                  45

Leu Arg Gln Cys Val Ala Gly Lys Glu Thr Asn Phe Ser Leu Ala Ser
    50                  55                  60

Gly Leu Glu Ala Lys Asp Glu Cys Arg Ser Ala Met Glu Ala Leu Lys
65                  70                  75                  80

Gln Lys Ser Leu Tyr Asn Cys Arg Cys Lys Arg Gly Met Lys Lys Glu
                85                  90                  95

Lys Asn Cys Leu Arg Ile Tyr Trp Ser Met Tyr Gln Ser Leu Gln Gly
            100                 105                 110

Asn Asp Leu Leu Glu Asp Ser Pro Tyr Glu Pro Val Asn Ser Arg Leu
        115                 120                 125

Ser Asp Ile Phe Arg Val Val Pro Phe Ile Ser Asp Val Phe Gln Gln
    130                 135                 140
```

| | | | | | | | | | | | | | | |
|---|---|---|---|---|---|---|---|---|---|---|---|---|---|---|
| Val | Glu | His | Ile | Pro | Lys | Gly | Asn | Asn | Cys | Leu | Asp | Ala | Ala | Lys | Ala |
| 145 | | | | | 150 | | | | | 155 | | | | | 160 |

Val Glu His Ile Pro Lys Gly Asn Asn Cys Leu Asp Ala Ala Lys Ala
145                 150                 155                 160

Cys Asn Leu Asp Asp Ile Cys Lys Lys Tyr Arg Ser Ala Tyr Ile Thr
                165                 170                 175

Pro Cys Thr Thr Ser Val Ser Xaa Asp Val Cys Asn Arg Arg Lys Cys
            180                 185                 190

His Lys Ala Leu Arg Gln Phe Phe Asp Lys Val Pro Ala Lys His Ser
        195                 200                 205

Tyr Gly Met Leu Phe Cys Ser Cys Arg Asp Ile Ala Cys Thr Glu Arg
    210                 215                 220

Arg Arg Gln Thr Ile Val Pro Val Cys Ser Tyr Glu Glu Arg Glu Lys
225                 230                 235                 240

Pro Asn Cys Leu Asn Leu Gln Asp Ser Cys Lys Thr Asn Tyr Ile Cys
                245                 250                 255

Arg Ser Arg Leu Ala Asp Phe Phe Thr Asn Cys Gln Pro Glu Ser Arg
            260                 265                 270

Ser Val Ser Ser Cys Leu Lys Glu Asn Tyr Ala Asp Cys Leu Leu Ala
        275                 280                 285

Tyr Ser Gly Leu Ile Gly Thr Val Met Thr Pro Asn Tyr Ile Asp Ser
    290                 295                 300

Ser Ser Leu Ser Val Ala Pro Trp Cys Asp Cys Ser Asn Ser Gly Asn
305                 310                 315                 320

Asp Leu Glu Glu Cys Leu Lys Phe Leu Asn Phe Phe Lys Asp Asn Thr
                325                 330                 335

Cys Leu Lys Asn Ala Ile Gln Ala Phe Gly Asn Gly Ser Asp Val Thr
            340                 345                 350

Val Trp Gln Pro Ala Phe Pro Val Gln Thr Thr Thr Ala Thr Thr Thr
        355                 360                 365

Thr Ala Leu Arg Val Lys Asn Lys Pro Leu Gly Pro Ala Gly Ser Glu
    370                 375                 380

Asn Glu Ile Pro Thr His Val Leu Pro Pro Cys Ala Asn Leu Gln Ala
385                 390                 395                 400

Gln Lys Leu Lys Ser Asn Val Ser Gly Asn Thr His Leu Cys Ile Ser
                405                 410                 415

Asn Gly Asn Tyr Glu Lys Glu Gly Leu Gly Ala Ser Ser His Ile Thr
            420                 425                 430

Thr Lys Ser Met Ala Ala Pro Pro Ser Cys Gly Leu Ser Pro Leu Leu
        435                 440                 445

Val Leu Val Val Thr Ala Leu Ser Thr Leu Leu Ser Leu Thr Glu Thr
    450                 455                 460

Ser
465

<210> SEQ ID NO 7
<211> LENGTH: 508
<212> TYPE: DNA
<213> ORGANISM: HUMAN
<220> FEATURE:
<221> NAME/KEY: misc_feature
<222> LOCATION: (1)..(508)
<223> OTHER INFORMATION: Note="1 to 508 is -235 to 272 of Figure 5
      Hsgr-21af"

<400> SEQUENCE: 7
tctggcctcg gaacacgcca ttctccgcgc cgcttccaat aaccactaac atccctaacg    60
agcatccgag ccgagggctc tgctcggaaa tcgtcctggc ccaactcggc ccttcgagct   120

-continued

| ctcgaagatt accgcatcta tttttttttt cttttttttc ttttcctagc gcagataaag | 180 |
| tgagcccgga aagggaagga gggggcgggg acaccattgc cctgaaagaa taaataagta | 240 |
| aataaacaaa ctggctcctc gccgcagctg acgcggtcg gttgagtcca ggttgggtcg | 300 |
| gacctgaacc cctaaaagcg gaaccgcctc ccgccctcgc catcccggag ctgagtcgcc | 360 |
| ggcggcggtg gctgctgcca gacccggagt ttcctctttc actggatgga gctgaacttt | 420 |
| gggcggccag agcagcacag ctgtccgggg atcgctgcac gctgagctcc ctcggcaaga | 480 |
| cccagcggcg gctcgggatt tttttggg | 508 |

<210> SEQ ID NO 8
<211> LENGTH: 510
<212> TYPE: DNA
<213> ORGANISM: HUMAN
<220> FEATURE:
<221> NAME/KEY: misc_feature
<222> LOCATION: (1)..(510)
<223> OTHER INFORMATION: Note="1 to 510 is -237 to 272 of Figure 5
    Hsgr-21bf"

<400> SEQUENCE: 8

| aatctggcct cggaacacgc cattctccgc gccgcttcca ataaccacta acatccctaa | 60 |
| cgagcatccg agccgagggc tctgctcgga atcgtcctg gcccaactcg gcccttcgag | 120 |
| ctctcgaaga ttaccgcatc tatttttttt ttcttttttt tcttttccta gcgcagataa | 180 |
| agtgagcccg gaaagggaag gagggggcgg ggacaccatt gccctgaaag aataaataag | 240 |
| taaataaaca aactggctcc tcgccgcagc tggacgcggt cggttgagtc caggttgggt | 300 |
| cggacctgaa cccctaaaag cggaaccgcc tcccgccctc gccatcccgg agctgagtcg | 360 |
| ccggcggcgg tggctgctgc cagacccgga gtttcctctt tcactggatg gagctgaact | 420 |
| ttgggcggcc agagcagcac agctgtccgg ggatcgctgc acgctgagct ccctcggcaa | 480 |
| gacccagcgg cggctcggga ttttttttggg | 510 |

<210> SEQ ID NO 9
<211> LENGTH: 1927
<212> TYPE: DNA
<213> ORGANISM: HUMAN
<220> FEATURE:
<221> NAME/KEY: misc_feature
<222> LOCATION: (1)..(537)
<223> OTHER INFORMATION: Note= "1 to 537 is -235 to 301 of Figure 5
    21acon"
<220> FEATURE:
<221> NAME/KEY: CDS
<222> LOCATION: (538)..(1926)
<220> FEATURE:
<221> NAME/KEY: misc_feature
<222> LOCATION: (550)..(550)
<223> OTHER INFORMATION: N in position 550 indicates any nucleic acid

<400> SEQUENCE: 9

| tctggcctcg gaacacgcca ttctccgcgc gcttccaat aaccactaac atccctaacg | 60 |
| agcatccgag ccgagggctc tgctcggaaa tcgtcctggc ccaactcggc ccttcgagct | 120 |
| ctcgaagatt accgcatcta tttttttttt cttttttttc ttttcctagc gcagataaag | 180 |
| tgagcccgga aagggaagga gggggcgggg acaccattgc cctgaaagaa taaataagta | 240 |
| aataaacaaa ctggctcctc gccgcagctg acgcggtcg gttgagtcca ggttgggtcg | 300 |
| gacctgaacc cctaaaagcg gaaccgcctc ccgccctcgc catcccggag ctgagtcgcc | 360 |
| ggcggcggtg gctgctgcca gacccggagt ttcctctttc actggatgga gctgaacttt | 420 |

```
gggcggccag agcagcacag ctgtccgggg atcgctgcac gctgagctcc ctcggcaaga    480
cccagcggcg gctcgggatt tttttggggg ggcggggacc agccccgcgc cggcacc       537 atg ttc ctg gcg ncc ctg tac ttc gcg ctg ccg ctc ttg gac ttg ctc    585
Met Phe Leu Ala Xaa Leu Tyr Phe Ala Leu Pro Leu Leu Asp Leu Leu
1               5                   10                  15 ctg tcg gcc gaa gtg agc ggc gga gac cgc ctg gat tgc gtg aaa gcc    633
Leu Ser Ala Glu Val Ser Gly Gly Asp Arg Leu Asp Cys Val Lys Ala
            20                  25                  30 agt gat cag tgc ctg aag gag cag agc tgc agc acc aag tac cgc acg    681
Ser Asp Gln Cys Leu Lys Glu Gln Ser Cys Ser Thr Lys Tyr Arg Thr
        35                  40                  45 cta agg cag tgc gtg gcg ggc aag gag acc aac ttc agc ctg gca tcc    729
Leu Arg Gln Cys Val Ala Gly Lys Glu Thr Asn Phe Ser Leu Ala Ser
    50                  55                  60 ggc ctg gag gcc aag gat gag tgc cgc agc gcc atg gag gcc ctg aag    777
Gly Leu Glu Ala Lys Asp Glu Cys Arg Ser Ala Met Glu Ala Leu Lys
65                  70                  75                  80 cag aag tcg ctc tac aac tgc cgc tgc aag cgg ggt atg aag aag gag    825
Gln Lys Ser Leu Tyr Asn Cys Arg Cys Lys Arg Gly Met Lys Lys Glu
                85                  90                  95 aag aac tgc ctg cgc att tac tgg agc atg tac cag agc ctg cag gga    873
Lys Asn Cys Leu Arg Ile Tyr Trp Ser Met Tyr Gln Ser Leu Gln Gly
            100                 105                 110 aat gat ctg ctg gag gat tcc cca tat gaa cca gtt aac agc aga ttg    921
Asn Asp Leu Leu Glu Asp Ser Pro Tyr Glu Pro Val Asn Ser Arg Leu
        115                 120                 125 tca gat ata ttc cgg gtg gtc cca ttc ata tca gat gtt ttt cag caa    969
Ser Asp Ile Phe Arg Val Val Pro Phe Ile Ser Asp Val Phe Gln Gln
    130                 135                 140 gtg gag cac att ccc aaa ggg aac aac tgc ctg gat gca gcg aag gcc    1017
Val Glu His Ile Pro Lys Gly Asn Asn Cys Leu Asp Ala Ala Lys Ala
145                 150                 155                 160 tgc aac ctc gac gac att tgc aag aag tac agg tcg gcg tac atc acc    1065
Cys Asn Leu Asp Asp Ile Cys Lys Lys Tyr Arg Ser Ala Tyr Ile Thr
                165                 170                 175 ccg tgc acc acc agc gtg tcc aac gat gtc tgc aac cgc cgc aag tgc    1113
Pro Cys Thr Thr Ser Val Ser Asn Asp Val Cys Asn Arg Arg Lys Cys
            180                 185                 190 cac aag gcc ctc cgg cag ttc ttt gac aag gtc ccg gcc aag cac agc    1161
His Lys Ala Leu Arg Gln Phe Phe Asp Lys Val Pro Ala Lys His Ser
        195                 200                 205 tac gga atg ctc ttc tgc tcc tgc cgg gac atc gcc tgc aca gag cgg    1209
Tyr Gly Met Leu Phe Cys Ser Cys Arg Asp Ile Ala Cys Thr Glu Arg
    210                 215                 220 agg cga cag acc atc gtg cct gtg tgc tcc tat gaa gag agg gag aag    1257
Arg Arg Gln Thr Ile Val Pro Val Cys Ser Tyr Glu Glu Arg Glu Lys
225                 230                 235                 240 ccc aac tgt ttg aat ttg cag gac tcc tgc aag acg aat tac atc tgc    1305
Pro Asn Cys Leu Asn Leu Gln Asp Ser Cys Lys Thr Asn Tyr Ile Cys
                245                 250                 255 aga tct cgc ctt gcg gat ttt ttt acc aac tgc cag cca gag tca agg    1353
Arg Ser Arg Leu Ala Asp Phe Phe Thr Asn Cys Gln Pro Glu Ser Arg
            260                 265                 270 tct gtc agc agc tgt cta aag gaa aac tac gct gac tgc ctc ctc gcc    1401
Ser Val Ser Ser Cys Leu Lys Glu Asn Tyr Ala Asp Cys Leu Leu Ala
        275                 280                 285 tac tcg ggg ctt att ggc aca gtc atg acc ccc aac tac ata gac tcc    1449
Tyr Ser Gly Leu Ile Gly Thr Val Met Thr Pro Asn Tyr Ile Asp Ser
```

-continued

```
              290                 295                 300
agt agc ctc agt gtg gcc cca tgg tgt gac tgc agc aac agt ggg aac        1497
Ser Ser Leu Ser Val Ala Pro Trp Cys Asp Cys Ser Asn Ser Gly Asn
305                 310                 315                 320 gac cta gaa gag tgc ttg aaa ttt ttg aat ttc ttc aag gac aat aca        1545
Asp Leu Glu Glu Cys Leu Lys Phe Leu Asn Phe Phe Lys Asp Asn Thr
                    325                 330                 335 tgt ctt aaa aat gca att caa gcc ttt ggc aat ggc tcc gat gtg acc        1593
Cys Leu Lys Asn Ala Ile Gln Ala Phe Gly Asn Gly Ser Asp Val Thr
                340                 345                 350 gtg tgg cag cca gcc ttc cca gta cag acc acc act gcc act acc acc        1641
Val Trp Gln Pro Ala Phe Pro Val Gln Thr Thr Thr Ala Thr Thr Thr
            355                 360                 365 act gcc ctc cgg gtt aag aac aag ccc ctg ggg cca gca ggg tct gag        1689
Thr Ala Leu Arg Val Lys Asn Lys Pro Leu Gly Pro Ala Gly Ser Glu
        370                 375                 380 aat gaa att ccc act cat gtt ttg cca ccg tgt gca aat tta cag gca        1737
Asn Glu Ile Pro Thr His Val Leu Pro Pro Cys Ala Asn Leu Gln Ala
385                 390                 395                 400 cag aag ctg aaa tcc aat gtg tcg ggc aat aca cac ctc tgt att tcc        1785
Gln Lys Leu Lys Ser Asn Val Ser Gly Asn Thr His Leu Cys Ile Ser
                    405                 410                 415 aat ggt aat tat gaa aaa gaa ggt ctc ggt gct tcc agc cac ata acc        1833
Asn Gly Asn Tyr Glu Lys Glu Gly Leu Gly Ala Ser Ser His Ile Thr
                420                 425                 430 aca aaa tca atg gct gct cct cca agc tgt ggt ctg agc cca ctg ctg        1881
Thr Lys Ser Met Ala Ala Pro Pro Ser Cys Gly Leu Ser Pro Leu Leu
            435                 440                 445 gtc ctg gtg gta acc gct ctg tcc acc cta tta tct tta aca gaa a          1927
Val Leu Val Val Thr Ala Leu Ser Thr Leu Leu Ser Leu Thr Glu
        450                 455                 460

<210> SEQ ID NO 10
<211> LENGTH: 463
<212> TYPE: PRT
<213> ORGANISM: HUMAN
<220> FEATURE:
<221> NAME/KEY: misc_feature
<222> LOCATION: (5)..(5)
<223> OTHER INFORMATION: The 'Xaa' at location 5 stands for Thr, Ala,
      Pro, or Ser.

<400> SEQUENCE: 10

Met Phe Leu Ala Xaa Leu Tyr Phe Ala Leu Pro Leu Leu Asp Leu Leu
1               5                   10                  15

Leu Ser Ala Glu Val Ser Gly Gly Asp Arg Leu Asp Cys Val Lys Ala
            20                  25                  30

Ser Asp Gln Cys Leu Lys Glu Gln Ser Cys Ser Thr Lys Tyr Arg Thr
        35                  40                  45

Leu Arg Gln Cys Val Ala Gly Lys Glu Thr Asn Phe Ser Leu Ala Ser
    50                  55                  60

Gly Leu Glu Ala Lys Asp Glu Cys Arg Ser Ala Met Glu Ala Leu Lys
65                  70                  75                  80

Gln Lys Ser Leu Tyr Asn Cys Arg Cys Lys Arg Gly Met Lys Lys Glu
                85                  90                  95

Lys Asn Cys Leu Arg Ile Tyr Trp Ser Met Tyr Gln Ser Leu Gln Gly
            100                 105                 110

Asn Asp Leu Leu Glu Asp Ser Pro Tyr Glu Pro Val Asn Ser Arg Leu
        115                 120                 125
```

```
Ser Asp Ile Phe Arg Val Val Pro Phe Ile Ser Asp Val Phe Gln Gln
130                 135                 140
Val Glu His Ile Pro Lys Gly Asn Asn Cys Leu Asp Ala Ala Lys Ala
145                 150                 155                 160
Cys Asn Leu Asp Asp Ile Cys Lys Lys Tyr Arg Ser Ala Tyr Ile Thr
                165                 170                 175
Pro Cys Thr Thr Ser Val Ser Asn Asp Val Cys Asn Arg Arg Lys Cys
            180                 185                 190
His Lys Ala Leu Arg Gln Phe Phe Asp Lys Val Pro Ala Lys His Ser
        195                 200                 205
Tyr Gly Met Leu Phe Cys Ser Cys Arg Asp Ile Ala Cys Thr Glu Arg
    210                 215                 220
Arg Arg Gln Thr Ile Val Pro Val Cys Ser Tyr Glu Glu Arg Glu Lys
225                 230                 235                 240
Pro Asn Cys Leu Asn Leu Gln Asp Ser Cys Lys Thr Asn Tyr Ile Cys
                245                 250                 255
Arg Ser Arg Leu Ala Asp Phe Phe Thr Asn Cys Gln Pro Glu Ser Arg
            260                 265                 270
Ser Val Ser Ser Cys Leu Lys Glu Asn Tyr Ala Asp Cys Leu Leu Ala
        275                 280                 285
Tyr Ser Gly Leu Ile Gly Thr Val Met Thr Pro Asn Tyr Ile Asp Ser
    290                 295                 300
Ser Ser Leu Ser Val Ala Pro Trp Cys Asp Cys Ser Asn Ser Gly Asn
305                 310                 315                 320
Asp Leu Glu Glu Cys Leu Lys Phe Leu Asn Phe Lys Asp Asn Thr
                325                 330                 335
Cys Leu Lys Asn Ala Ile Gln Ala Phe Gly Asn Gly Ser Asp Val Thr
            340                 345                 350
Val Trp Gln Pro Ala Phe Pro Val Gln Thr Thr Ala Thr Thr Thr
        355                 360                 365
Thr Ala Leu Arg Val Lys Asn Lys Pro Leu Gly Pro Ala Gly Ser Glu
370                 375                 380
Asn Glu Ile Pro Thr His Val Leu Pro Pro Cys Ala Asn Leu Gln Ala
385                 390                 395                 400
Gln Lys Leu Lys Ser Asn Val Ser Gly Asn Thr His Leu Cys Ile Ser
            405                 410                 415
Asn Gly Asn Tyr Glu Lys Glu Gly Leu Gly Ala Ser Ser His Ile Thr
        420                 425                 430
Thr Lys Ser Met Ala Ala Pro Pro Ser Cys Gly Leu Ser Pro Leu Leu
    435                 440                 445
Val Leu Val Val Thr Ala Leu Ser Thr Leu Leu Ser Leu Thr Glu
450                 455                 460
```

<210> SEQ ID NO 11
<211> LENGTH: 1929
<212> TYPE: DNA
<213> ORGANISM: HUMAN
<220> FEATURE:
<221> NAME/KEY: misc_feature
<222> LOCATION: (1)..(539)
<223> OTHER INFORMATION: Note= "1 to 539 is -237 to 301 of Figure 5 21bcon"
<220> FEATURE:
<221> NAME/KEY: CDS
<222> LOCATION: (540)..(1928)

<400> SEQUENCE: 11

-continued

```
aatctggcct cggaacacgc cattctccgc gccgcttcca ataaccacta acatccctaa      60
cgagcatccg agccgagggc tctgctcgga aatcgtcctg cccaactcg gcccttcgag      120 ctctcgaaga ttaccgcatc tattttttt ttcttttttt tcttttccta gcgcagataa      180
agtgagcccg gaaagggaag gaggggcgg ggacaccatt gccctgaaag aataaataag      240
taaataaaca aactggctcc tcgccgcagc tggacgcggt cggttgagtc caggttgggt      300
cggacctgaa cccctaaaag cggaaccgcc tcccgccctc gccatcccgg agctgagtcg      360
ccggcggcgg tggctgctgc cagacccgga gtttcctctt tcactggatg gagctgaact      420 tgggcggcc agagcagcac agctgtccgg ggatcgctgc acgctgagct ccctcggcaa      480
gacccagcgg cggctcggga ttttttggg gggcgggga ccagccccgc gccggcacc       539
```

| | | | | | | | | | | | | | | | | |
|---|---|---|---|---|---|---|---|---|---|---|---|---|---|---|---|---|
| atg | ttc | ctg | gcg | acc | ctg | tac | ttc | gcg | ctg | ccg | ctc | ttg | gac | ttg | ctc | 587 |
| Met | Phe | Leu | Ala | Thr | Leu | Tyr | Phe | Ala | Leu | Pro | Leu | Leu | Asp | Leu | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ctg | tcg | gcc | gaa | gtg | agc | ggc | gga | gac | cgc | ctg | gat | tgc | gtg | aaa | gcc | 635 |
| Leu | Ser | Ala | Glu | Val | Ser | Gly | Gly | Asp | Arg | Leu | Asp | Cys | Val | Lys | Ala | |
| | | 20 | | | | | 25 | | | | | 30 | | | | |

| | | | | | | | | | | | | | | | | |
|---|---|---|---|---|---|---|---|---|---|---|---|---|---|---|---|---|
| agt | gat | cag | tgc | ctg | aag | gag | cag | agc | tgc | agc | acc | aag | tac | cgc | acg | 683 |
| Ser | Asp | Gln | Cys | Leu | Lys | Glu | Gln | Ser | Cys | Ser | Thr | Lys | Tyr | Arg | Thr | |
| | | 35 | | | | | 40 | | | | | 45 | | | | |

| | | | | | | | | | | | | | | | | |
|---|---|---|---|---|---|---|---|---|---|---|---|---|---|---|---|---|
| cta | agg | cag | tgc | gtg | gcg | ggc | aag | gag | acc | aac | ttc | agc | ctg | gca | tcc | 731 |
| Leu | Arg | Gln | Cys | Val | Ala | Gly | Lys | Glu | Thr | Asn | Phe | Ser | Leu | Ala | Ser | |
| 50 | | | | | 55 | | | | | 60 | | | | | | |

| | | | | | | | | | | | | | | | | |
|---|---|---|---|---|---|---|---|---|---|---|---|---|---|---|---|---|
| ggc | ctg | gag | gcc | aag | gat | gag | tgc | cgc | agc | gcc | atg | gag | gcc | ctg | aag | 779 |
| Gly | Leu | Glu | Ala | Lys | Asp | Glu | Cys | Arg | Ser | Ala | Met | Glu | Ala | Leu | Lys | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| cag | aag | tcg | ctc | tac | aac | tgc | cgc | tgc | aag | cgg | ggt | atg | aag | aag | gag | 827 |
| Gln | Lys | Ser | Leu | Tyr | Asn | Cys | Arg | Cys | Lys | Arg | Gly | Met | Lys | Lys | Glu | |
| | | | | 85 | | | | | 90 | | | | | 95 | | |

| | | | | | | | | | | | | | | | | |
|---|---|---|---|---|---|---|---|---|---|---|---|---|---|---|---|---|
| aag | aac | tgc | ctg | cgc | att | tac | tgg | agc | atg | tac | cag | agc | ctg | cag | gga | 875 |
| Lys | Asn | Cys | Leu | Arg | Ile | Tyr | Trp | Ser | Met | Tyr | Gln | Ser | Leu | Gln | Gly | |
| | | | 100 | | | | | 105 | | | | | 110 | | | |

| | | | | | | | | | | | | | | | | |
|---|---|---|---|---|---|---|---|---|---|---|---|---|---|---|---|---|
| aat | gat | ctg | ctg | gag | gat | tcc | cca | tat | gaa | cca | gtt | aac | agc | aga | ttg | 923 |
| Asn | Asp | Leu | Leu | Glu | Asp | Ser | Pro | Tyr | Glu | Pro | Val | Asn | Ser | Arg | Leu | |
| | | | | 115 | | | | | 120 | | | | | 125 | | |

| | | | | | | | | | | | | | | | | |
|---|---|---|---|---|---|---|---|---|---|---|---|---|---|---|---|---|
| tca | gat | ata | ttc | cgg | gtg | gtc | cca | ttc | ata | tca | gat | gtt | ttt | cag | caa | 971 |
| Ser | Asp | Ile | Phe | Arg | Val | Val | Pro | Phe | Ile | Ser | Asp | Val | Phe | Gln | Gln | |
| 130 | | | | | 135 | | | | | 140 | | | | | | |

| | | | | | | | | | | | | | | | | |
|---|---|---|---|---|---|---|---|---|---|---|---|---|---|---|---|---|
| gtg | gag | cac | att | ccc | aaa | ggg | aac | aac | tgc | ctg | gat | gca | gcg | aag | gcc | 1019 |
| Val | Glu | His | Ile | Pro | Lys | Gly | Asn | Asn | Cys | Leu | Asp | Ala | Ala | Lys | Ala | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tgc | aac | ctc | gac | gac | att | tgc | aag | aag | tac | agg | tcg | gcg | tac | atc | acc | 1067 |
| Cys | Asn | Leu | Asp | Asp | Ile | Cys | Lys | Lys | Tyr | Arg | Ser | Ala | Tyr | Ile | Thr | |
| | | | | 165 | | | | | 170 | | | | | 175 | | |

| | | | | | | | | | | | | | | | | |
|---|---|---|---|---|---|---|---|---|---|---|---|---|---|---|---|---|
| ccg | tgc | acc | acc | agc | gtg | tcc | aac | gat | gtc | tgc | aac | cgc | cgc | aag | tgc | 1115 |
| Pro | Cys | Thr | Thr | Ser | Val | Ser | Asn | Asp | Val | Cys | Asn | Arg | Arg | Lys | Cys | |
| | | | | 180 | | | | | 185 | | | | | 190 | | |

| | | | | | | | | | | | | | | | | |
|---|---|---|---|---|---|---|---|---|---|---|---|---|---|---|---|---|
| cac | aag | gcc | ctc | cgg | cag | ttc | ttt | gac | aag | gtc | ccg | gcc | aag | cac | agc | 1163 |
| His | Lys | Ala | Leu | Arg | Gln | Phe | Phe | Asp | Lys | Val | Pro | Ala | Lys | His | Ser | |
| | | | 195 | | | | | 200 | | | | | 205 | | | |

| | | | | | | | | | | | | | | | | |
|---|---|---|---|---|---|---|---|---|---|---|---|---|---|---|---|---|
| tac | gga | atg | ctc | ttc | tgc | tcc | tgc | cgg | gac | atc | gcc | tgc | aca | gag | cgg | 1211 |
| Tyr | Gly | Met | Leu | Phe | Cys | Ser | Cys | Arg | Asp | Ile | Ala | Cys | Thr | Glu | Arg | |
| | | 210 | | | | | 215 | | | | | 220 | | | | |

| | | | | | | | | | | | | | | | | |
|---|---|---|---|---|---|---|---|---|---|---|---|---|---|---|---|---|
| agg | cga | cag | acc | atc | gtg | cct | gtg | tgc | tcc | tat | gaa | gag | agg | gag | aag | 1259 |
| Arg | Arg | Gln | Thr | Ile | Val | Pro | Val | Cys | Ser | Tyr | Glu | Glu | Arg | Glu | Lys | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ccc | aac | tgt | ttg | aat | ttg | cag | gac | tcc | tgc | aag | acg | aat | tac | atc | tgc | 1307 |

```
Pro Asn Cys Leu Asn Leu Gln Asp Ser Cys Lys Thr Asn Tyr Ile Cys
                245                 250                 255 aga tct cgc ctt gcg gat ttt ttt acc aac tgc cag cca gag tca agg    1355
Arg Ser Arg Leu Ala Asp Phe Phe Thr Asn Cys Gln Pro Glu Ser Arg
            260                 265                 270 tct gtc agc agc tgt cta aag gaa aac tac gct gac tgc ctc ctc gcc    1403
Ser Val Ser Ser Cys Leu Lys Glu Asn Tyr Ala Asp Cys Leu Leu Ala
        275                 280                 285 tac tcg ggg ctt att ggc aca gtc atg acc ccc aac tac ata gac tcc    1451
Tyr Ser Gly Leu Ile Gly Thr Val Met Thr Pro Asn Tyr Ile Asp Ser
    290                 295                 300 agt agc ctc agt gtg gcc cca tgg tgt gac tgc agc aac agt ggg aac    1499
Ser Ser Leu Ser Val Ala Pro Trp Cys Asp Cys Ser Asn Ser Gly Asn
305                 310                 315                 320 gac cta gaa gag tgc ttg aaa ttt ttg aat ttc ttc aag gac aat aca    1547
Asp Leu Glu Glu Cys Leu Lys Phe Leu Asn Phe Phe Lys Asp Asn Thr
                325                 330                 335 tgt ctt aaa aat gca att caa gcc ttt ggc aat ggc tcc gat gtg acc    1595
Cys Leu Lys Asn Ala Ile Gln Ala Phe Gly Asn Gly Ser Asp Val Thr
            340                 345                 350 gtg tgg cag cca gcc ttc cca gta cag acc acc act gcc act acc acc    1643
Val Trp Gln Pro Ala Phe Pro Val Gln Thr Thr Thr Ala Thr Thr Thr
        355                 360                 365 act gcc ctc cgg gtt aag aac aag ccc ctg ggg cca gca ggg tct gag    1691
Thr Ala Leu Arg Val Lys Asn Lys Pro Leu Gly Pro Ala Gly Ser Glu
    370                 375                 380 aat gaa att ccc act cat gtt ttg cca ccg tgt gca aat tta cag gca    1739
Asn Glu Ile Pro Thr His Val Leu Pro Pro Cys Ala Asn Leu Gln Ala
385                 390                 395                 400 cag aag ctg aaa tcc aat gtg tcg ggc aat aca cac ctc tgt att tcc    1787
Gln Lys Leu Lys Ser Asn Val Ser Gly Asn Thr His Leu Cys Ile Ser
                405                 410                 415 aat ggt aat tat gaa aaa gaa ggt ctc ggt gct tcc agc cac ata acc    1835
Asn Gly Asn Tyr Glu Lys Glu Gly Leu Gly Ala Ser Ser His Ile Thr
            420                 425                 430 aca aaa tca atg gct gct cct cca agc tgt ggt ctg agc cca ctg ctg    1883
Thr Lys Ser Met Ala Ala Pro Pro Ser Cys Gly Leu Ser Pro Leu Leu
        435                 440                 445 gtc ctg gtg gta acc gct ctg tcc acc cta tta tct tta aca gaa a     1929
Val Leu Val Val Thr Ala Leu Ser Thr Leu Leu Ser Leu Thr Glu
    450                 455                 460

<210> SEQ ID NO 12
<211> LENGTH: 463
<212> TYPE: PRT
<213> ORGANISM: HUMAN

<400> SEQUENCE: 12

Met Phe Leu Ala Thr Leu Tyr Phe Ala Leu Pro Leu Leu Asp Leu Leu
1               5                   10                  15

Leu Ser Ala Glu Val Ser Gly Gly Asp Arg Leu Asp Cys Val Lys Ala
            20                  25                  30

Ser Asp Gln Cys Leu Lys Glu Gln Ser Cys Ser Thr Lys Tyr Arg Thr
        35                  40                  45

Leu Arg Gln Cys Val Ala Gly Lys Glu Thr Asn Phe Ser Leu Ala Ser
    50                  55                  60

Gly Leu Glu Ala Lys Asp Glu Cys Arg Ser Ala Met Glu Ala Leu Lys
65                  70                  75                  80

Gln Lys Ser Leu Tyr Asn Cys Arg Cys Lys Arg Gly Met Lys Lys Glu
```

```
                        85                  90                  95
Lys Asn Cys Leu Arg Ile Tyr Trp Ser Met Tyr Gln Ser Leu Gln Gly
            100                 105                 110

Asn Asp Leu Leu Glu Asp Ser Pro Tyr Glu Pro Val Asn Ser Arg Leu
            115                 120                 125

Ser Asp Ile Phe Arg Val Val Pro Phe Ile Ser Asp Val Phe Gln Gln
        130                 135                 140

Val Glu His Ile Pro Lys Gly Asn Asn Cys Leu Asp Ala Ala Lys Ala
145                 150                 155                 160

Cys Asn Leu Asp Asp Ile Cys Lys Lys Tyr Arg Ser Ala Tyr Ile Thr
                165                 170                 175

Pro Cys Thr Thr Ser Val Ser Asn Asp Val Cys Asn Arg Arg Lys Cys
            180                 185                 190

His Lys Ala Leu Arg Gln Phe Phe Asp Lys Val Pro Ala Lys His Ser
        195                 200                 205

Tyr Gly Met Leu Phe Cys Ser Cys Arg Asp Ile Ala Cys Thr Glu Arg
    210                 215                 220

Arg Arg Gln Thr Ile Val Pro Val Cys Ser Tyr Glu Glu Arg Glu Lys
225                 230                 235                 240

Pro Asn Cys Leu Asn Leu Gln Asp Ser Cys Lys Thr Asn Tyr Ile Cys
                245                 250                 255

Arg Ser Arg Leu Ala Asp Phe Phe Thr Asn Cys Gln Pro Glu Ser Arg
            260                 265                 270

Ser Val Ser Ser Cys Leu Lys Glu Asn Tyr Ala Asp Cys Leu Leu Ala
        275                 280                 285

Tyr Ser Gly Leu Ile Gly Thr Val Met Thr Pro Asn Tyr Ile Asp Ser
    290                 295                 300

Ser Ser Leu Ser Val Ala Pro Trp Cys Asp Cys Ser Asn Ser Gly Asn
305                 310                 315                 320

Asp Leu Glu Glu Cys Leu Lys Phe Leu Asn Phe Phe Lys Asp Asn Thr
                325                 330                 335

Cys Leu Lys Asn Ala Ile Gln Ala Phe Gly Asn Gly Ser Asp Val Thr
            340                 345                 350

Val Trp Gln Pro Ala Phe Pro Val Gln Thr Thr Thr Ala Thr Thr Thr
        355                 360                 365

Thr Ala Leu Arg Val Lys Asn Lys Pro Leu Gly Pro Ala Gly Ser Glu
    370                 375                 380

Asn Glu Ile Pro Thr His Val Leu Pro Pro Cys Ala Asn Leu Gln Ala
385                 390                 395                 400

Gln Lys Leu Lys Ser Asn Val Ser Gly Asn Thr His Leu Cys Ile Ser
                405                 410                 415

Asn Gly Asn Tyr Glu Lys Glu Gly Leu Gly Ala Ser Ser His Ile Thr
            420                 425                 430

Thr Lys Ser Met Ala Ala Pro Pro Ser Cys Gly Leu Ser Pro Leu Leu
        435                 440                 445

Val Leu Val Val Thr Ala Leu Ser Thr Leu Leu Ser Leu Thr Glu
    450                 455                 460

<210> SEQ ID NO 13
<211> LENGTH: 699
<212> TYPE: DNA
<213> ORGANISM: HUMAN
<220> FEATURE:
<221> NAME/KEY: misc_feature
<222> LOCATION: (1)..(699)
```

```
<223> OTHER INFORMATION: Note= "1 to 699 is 814 to 1512 of Figure 5
      Hsgr-29a"
<220> FEATURE:
<221> NAME/KEY: CDS
<222> LOCATION: (2)..(697)

<400> SEQUENCE: 13 g tcg gcg tac atc acc ccg tgc acc acc agc gtg tcc aat gat gtc tgc       49
    Ser Ala Tyr Ile Thr Pro Cys Thr Thr Ser Val Ser Asn Asp Val Cys
    1               5                  10                  15 aac cgc cgc aag tgc cac aag gcc ctc cgg cag ttc ttt gac aag gtc           97
Asn Arg Arg Lys Cys His Lys Ala Leu Arg Gln Phe Phe Asp Lys Val
            20                  25                  30 ccg gcc aag cac agc tac gga atg ctc ttc tgc tcc tgc cgg gac atc          145
Pro Ala Lys His Ser Tyr Gly Met Leu Phe Cys Ser Cys Arg Asp Ile
        35                  40                  45 gcc tgc aca gag cgg agg cga cag acc atc gtg cct gtg tgc tcc tat          193
Ala Cys Thr Glu Arg Arg Arg Gln Thr Ile Val Pro Val Cys Ser Tyr
50                  55                  60 gaa gag agg gag aag ccc aac tgt ttg aat ttg cag gac tcc tgc aag          241
Glu Glu Arg Glu Lys Pro Asn Cys Leu Asn Leu Gln Asp Ser Cys Lys
65                  70                  75                  80 acg aat tac atc tgc aga tct cgc ctt gcg gat ttt ttt acc aac tgc          289
Thr Asn Tyr Ile Cys Arg Ser Arg Leu Ala Asp Phe Phe Thr Asn Cys
                85                  90                  95 cag cca gag tca agg tct gtc agc agc tgt cta aag gaa aac tac gct          337
Gln Pro Glu Ser Arg Ser Val Ser Ser Cys Leu Lys Glu Asn Tyr Ala
            100                 105                 110 gac tgc ctc ctc gcc tac tcg ggg ctt att ggc aca gtc atg acc ccc          385
Asp Cys Leu Leu Ala Tyr Ser Gly Leu Ile Gly Thr Val Met Thr Pro
        115                 120                 125 aac tac ata gac tcc agt agc ctc agt gtg gcc cca tgg tgt gac tgc          433
Asn Tyr Ile Asp Ser Ser Ser Leu Ser Val Ala Pro Trp Cys Asp Cys
    130                 135                 140 agc aac agt ggg aac gac cta gaa gag tgc ttg aaa ttt ttg aat ttc          481
Ser Asn Ser Gly Asn Asp Leu Glu Glu Cys Leu Lys Phe Leu Asn Phe
145                 150                 155                 160 ttc aag gac aat aca tgt ctt aaa aat gca att caa gcc ttt ggc aat          529
Phe Lys Asp Asn Thr Cys Leu Lys Asn Ala Ile Gln Ala Phe Gly Asn
                165                 170                 175 ggc tcc gat gtg acc gtg tgg cag cca gcc ttc cca gta cag acc acc          577
Gly Ser Asp Val Thr Val Trp Gln Pro Ala Phe Pro Val Gln Thr Thr
            180                 185                 190 act gcc gct acc acc act gcc ctc cgg gtt aag aac aag ccc ctg ggg          625
Thr Ala Ala Thr Thr Thr Ala Leu Arg Val Lys Asn Lys Pro Leu Gly
        195                 200                 205 cca gca ggg tct gag aat gaa att ccc act cat gtt ttg cca ccg tgt          673
Pro Ala Gly Ser Glu Asn Glu Ile Pro Thr His Val Leu Pro Pro Cys
    210                 215                 220 gca aat tta cag gca cag aag ctg aa                                       699
Ala Asn Leu Gln Ala Gln Lys Leu
225                 230

<210> SEQ ID NO 14
<211> LENGTH: 232
<212> TYPE: PRT
<213> ORGANISM: HUMAN

<400> SEQUENCE: 14

Ser Ala Tyr Ile Thr Pro Cys Thr Thr Ser Val Ser Asn Asp Val Cys
1               5                  10                  15
```

-continued

```
Asn Arg Arg Lys Cys His Lys Ala Leu Arg Gln Phe Phe Asp Lys Val
         20                  25                  30

Pro Ala Lys His Ser Tyr Gly Met Leu Phe Cys Ser Cys Arg Asp Ile
         35                  40                  45

Ala Cys Thr Glu Arg Arg Arg Gln Thr Ile Val Pro Val Cys Ser Tyr
 50                  55                  60

Glu Glu Arg Glu Lys Pro Asn Cys Leu Asn Leu Gln Asp Ser Cys Lys
 65                  70                  75                  80

Thr Asn Tyr Ile Cys Arg Ser Arg Leu Ala Asp Phe Phe Thr Asn Cys
                 85                  90                  95

Gln Pro Glu Ser Arg Ser Val Ser Ser Cys Leu Lys Glu Asn Tyr Ala
                100                 105                 110

Asp Cys Leu Leu Ala Tyr Ser Gly Leu Ile Gly Thr Val Met Thr Pro
            115                 120                 125

Asn Tyr Ile Asp Ser Ser Ser Leu Ser Val Ala Pro Trp Cys Asp Cys
        130                 135                 140

Ser Asn Ser Gly Asn Asp Leu Glu Glu Cys Leu Lys Phe Leu Asn Phe
145                 150                 155                 160

Phe Lys Asp Asn Thr Cys Leu Lys Asn Ala Ile Gln Ala Phe Gly Asn
                165                 170                 175

Gly Ser Asp Val Thr Val Trp Gln Pro Ala Phe Pro Val Gln Thr Thr
            180                 185                 190

Thr Ala Ala Thr Thr Thr Ala Leu Arg Val Lys Asn Lys Pro Leu Gly
        195                 200                 205

Pro Ala Gly Ser Glu Asn Glu Ile Pro Thr His Val Leu Pro Pro Cys
    210                 215                 220

Ala Asn Leu Gln Ala Gln Lys Leu
225                 230
```

<210> SEQ ID NO 15
<211> LENGTH: 2157
<212> TYPE: DNA
<213> ORGANISM: HUMAN
<220> FEATURE:
<221> NAME/KEY: misc_feature
<222> LOCATION: (1)..(2157)
<223> OTHER INFORMATION: Note= "1 to 2157 is 814 to 2971 of Figure 5
      29brc"
<220> FEATURE:
<221> NAME/KEY: CDS
<222> LOCATION: (2)..(886)
<220> FEATURE:
<221> NAME/KEY: misc_feature
<222> LOCATION: (1204)..(1242)
<223> OTHER INFORMATION: N in positions 1204 to 1242 indicates positions
      of divergence between different receptor clones.

<400> SEQUENCE: 15

```
g tcg gcg tac atc acc ccg tgc acc acc agc gtg tcc aat gat gtc tgc       49
  Ser Ala Tyr Ile Thr Pro Cys Thr Thr Ser Val Ser Asn Asp Val Cys
  1               5                  10                  15 aac cgc cgc aag tgc cac aag gcc ctc cgg cag ttc ttt gac aag gtc        97
Asn Arg Arg Lys Cys His Lys Ala Leu Arg Gln Phe Phe Asp Lys Val
             20                  25                  30 ccg gcc aag cac agc tac gga atg ctc ttc tgc tcc tgc cgg gac atc       145
Pro Ala Lys His Ser Tyr Gly Met Leu Phe Cys Ser Cys Arg Asp Ile
         35                  40                  45 gcc tgc aca gag cgg agg cga cag acc atc gtg cct gtg tgc tcc tat       193
Ala Cys Thr Glu Arg Arg Arg Gln Thr Ile Val Pro Val Cys Ser Tyr
 50                  55                  60
```

```
gaa gag agg gag aag ccc aac tgt ttg aat ttg cag gac tcc tgc aag      241
Glu Glu Arg Glu Lys Pro Asn Cys Leu Asn Leu Gln Asp Ser Cys Lys
 65              70                  75                  80 acg aat tac atc tgc aga tct cgc ctt gcg gat ttt ttt acc aac tgc      289
Thr Asn Tyr Ile Cys Arg Ser Arg Leu Ala Asp Phe Phe Thr Asn Cys
                 85                  90                  95 cag cca gag tca agg tct gtc agc agc tgt cta aag gaa aac tac gct      337
Gln Pro Glu Ser Arg Ser Val Ser Ser Cys Leu Lys Glu Asn Tyr Ala
            100                 105                 110 gac tgc ctc ctc gcc tac tcg ggg ctt att ggc aca gtc atg acc ccc      385
Asp Cys Leu Leu Ala Tyr Ser Gly Leu Ile Gly Thr Val Met Thr Pro
        115                 120                 125 aac tac ata gac tcc agt agc ctc agt gtg gcc cca tgg tgt gac tgc      433
Asn Tyr Ile Asp Ser Ser Ser Leu Ser Val Ala Pro Trp Cys Asp Cys
    130                 135                 140 agc aac agt ggg aac gac cta gaa gag tgc ttg aaa ttt ttg aat ttc      481
Ser Asn Ser Gly Asn Asp Leu Glu Glu Cys Leu Lys Phe Leu Asn Phe
145                 150                 155                 160 ttc aag gac aat aca tgt ctt aaa aat gca att caa gcc ttt ggc aat      529
Phe Lys Asp Asn Thr Cys Leu Lys Asn Ala Ile Gln Ala Phe Gly Asn
                165                 170                 175 ggc tcc gat gtg acc gtg tgg cag cca gcc ttc cca gta cag acc acc      577
Gly Ser Asp Val Thr Val Trp Gln Pro Ala Phe Pro Val Gln Thr Thr
            180                 185                 190 act gcc gct acc acc act gcc ctc cgg gtt aag aac aag ccc ctg ggg      625
Thr Ala Ala Thr Thr Thr Ala Leu Arg Val Lys Asn Lys Pro Leu Gly
        195                 200                 205 cca gca ggg tct gag aat gaa att ccc act cat gtt ttg cca ccg tgt      673
Pro Ala Gly Ser Glu Asn Glu Ile Pro Thr His Val Leu Pro Pro Cys
    210                 215                 220 gca aat tta cag gca cag aag ctg aaa tcc aat gtg tcg ggc aat aca      721
Ala Asn Leu Gln Ala Gln Lys Leu Lys Ser Asn Val Ser Gly Asn Thr
225                 230                 235                 240 cac ctc tgt att tcc aat ggt aat tat gaa aaa gaa ggt ctc ggt gct      769
His Leu Cys Ile Ser Asn Gly Asn Tyr Glu Lys Glu Gly Leu Gly Ala
                245                 250                 255 tcc agc cac ata acc aca aaa tca atg gct gct cct cca agc tgt ggt      817
Ser Ser His Ile Thr Thr Lys Ser Met Ala Ala Pro Pro Ser Cys Gly
            260                 265                 270 ctg agc cca ctg ctg gtc ctg gtg gta acc gct ctg tcc acc cta tta      865
Leu Ser Pro Leu Leu Val Leu Val Val Thr Ala Leu Ser Thr Leu Leu
        275                 280                 285 tct tta aca gaa aca tca tag ctgcattaaa aaatacaat atggacatgt          916
Ser Leu Thr Glu Thr Ser
    290 aaaaagacaa aaaccaagtt atctgtttcc tgttctcttg tatagctgaa attccagttt    976 aggagctcag ttgagaaaca gttccattca actggaacat ttttttttt ccttttaaga   1036 aagcttcttg tgatccttcg gggcttctgt gaaaaacctg atgcagtgct ccatccaaac  1096 tcagaaggct ttgggatatg ctgtatttta aagggacagt ttgtaacttg ggctgtaaag  1156 caaactgggg ctgtgttttc gatgatgatg atcatcatga tcatgatnnn nnnnnnnnn   1216 nnnnnnnnnn nnnnnnnnnn nnnnngatt ttaacagttt tacttctggc ctttcctagc   1276 tagagaagga gttaatattt ctaaggtaac tcccatatct cctttaatga cattgatttc  1336 taatgatata aatttcagcc tacattgatg ccaagctttt ttgccacaaa gaagattctt  1396 accaagagtg ggctttgtgg aaacagctgg tactgatgtt caccttata tatgtactag   1456 cattttccac gctgatgttt atgtactgta aacagttctg cactcttgta caaaagaaaa  1516
```

-continued

| | |
|---|---|
| aacacctgtc acatccaaat atagtatctg tcttttcgtc aaaatagaga gtggggaatg | 1576 |
| agtgtgccga ttcaatacct caatccctga acgacactct cctaatccta agccttacct | 1636 |
| gagtgagaag cccttacct aacaaaagtc aatatagct gaaatgtcgc tctaatactc | 1696 |
| tttacacata tgaggttata tgtagaaaaa aattttacta ctaaatgatt tcaactattg | 1756 |
| gctttctata ttttgaaagt aatgatattg tctcattttt ttactgatgg tttaatacaa | 1816 |
| aatacacaga gcttgtttcc cctcataagt agtgttcgct ctgatatgaa cttcacaaat | 1876 |
| acagctcatc aaaagcagac tctgagaagc ctcgtgctgt agcagaaagt tctgcatcat | 1936 |
| gtgactgtgg acaggcagga ggaaacagaa cagacaagca ttgtcttttg tcattgctcg | 1996 |
| aagtgcaagc gtgcatacct gtggagggaa ctggtggctg cttgtaaatg ttctgcagca | 2056 |
| tctcttgaca cacttgtcat gacacaatcc agtaccttgg ttttcaggtt atctgacaaa | 2116 |
| ggcagctttg attgggacat ggaggcatgg gcaggccgga a | 2157 |

<210> SEQ ID NO 16
<211> LENGTH: 294
<212> TYPE: PRT
<213> ORGANISM: HUMAN

<400> SEQUENCE: 16

```
Ser Ala Tyr Ile Thr Pro Cys Thr Thr Ser Val Ser Asn Asp Val Cys
1               5                   10                  15

Asn Arg Arg Lys Cys His Lys Ala Leu Arg Gln Phe Phe Asp Lys Val
                20                  25                  30

Pro Ala Lys His Ser Tyr Gly Met Leu Phe Cys Ser Cys Arg Asp Ile
            35                  40                  45

Ala Cys Thr Glu Arg Arg Arg Gln Thr Ile Val Pro Val Cys Ser Tyr
        50                  55                  60

Glu Glu Arg Glu Lys Pro Asn Cys Leu Asn Leu Gln Asp Ser Cys Lys
65                  70                  75                  80

Thr Asn Tyr Ile Cys Arg Ser Arg Leu Ala Asp Phe Phe Thr Asn Cys
                85                  90                  95

Gln Pro Glu Ser Arg Ser Val Ser Cys Leu Lys Glu Asn Tyr Ala
            100                 105                 110

Asp Cys Leu Leu Ala Tyr Ser Gly Leu Ile Gly Thr Val Met Thr Pro
        115                 120                 125

Asn Tyr Ile Asp Ser Ser Leu Ser Val Ala Pro Trp Cys Asp Cys
130                 135                 140

Ser Asn Ser Gly Asn Asp Leu Glu Glu Cys Leu Lys Phe Leu Asn Phe
145                 150                 155                 160

Phe Lys Asp Asn Thr Cys Leu Lys Asn Ala Ile Gln Ala Phe Gly Asn
                165                 170                 175

Gly Ser Asp Val Thr Val Trp Gln Pro Ala Phe Pro Val Gln Thr Thr
            180                 185                 190

Thr Ala Ala Thr Thr Thr Ala Leu Arg Val Lys Asn Lys Pro Leu Gly
        195                 200                 205

Pro Ala Gly Ser Glu Asn Glu Ile Pro Thr His Val Leu Pro Pro Cys
    210                 215                 220

Ala Asn Leu Gln Ala Gln Lys Leu Lys Ser Asn Val Ser Gly Asn Thr
225                 230                 235                 240

His Leu Cys Ile Ser Asn Gly Asn Tyr Glu Lys Glu Gly Leu Gly Ala
                245                 250                 255
```

```
Ser Ser His Ile Thr Thr Lys Ser Met Ala Ala Pro Ser Cys Gly
        260                 265                 270
Leu Ser Pro Leu Leu Val Leu Val Thr Ala Leu Ser Thr Leu Leu
        275                 280                 285
Ser Leu Thr Glu Thr Ser
        290

<210> SEQ ID NO 17
<211> LENGTH: 659
<212> TYPE: DNA
<213> ORGANISM: HUMAN
<220> FEATURE:
<221> NAME/KEY: misc_feature
<222> LOCATION: (1)..(659)
<223> OTHER INFORMATION: Note= "1 to 659 is 1033 to 1691 of Figure 5
      Hsgr-21ar"
<220> FEATURE:
<221> NAME/KEY: CDS
<222> LOCATION: (2)..(658)

<400> SEQUENCE: 17 g aat ttg cag gac tcc tgc aag acg aat tac atc tgc aga tct cgc ctt        49
  Asn Leu Gln Asp Ser Cys Lys Thr Asn Tyr Ile Cys Arg Ser Arg Leu
  1               5                  10                  15 gcg gat ttt ttt acc aac tgc cag cca gag tca agg tct gtc agc agc        97
Ala Asp Phe Phe Thr Asn Cys Gln Pro Glu Ser Arg Ser Val Ser Ser
            20                  25                  30 tgt cta aag gaa aac tac gct gac tgc ctc ctc gcc tac tcg ggg ctt       145
Cys Leu Lys Glu Asn Tyr Ala Asp Cys Leu Leu Ala Tyr Ser Gly Leu
        35                  40                  45 att ggc aca gtc atg acc ccc aac tac ata gac tcc agt agc ctc agt       193
Ile Gly Thr Val Met Thr Pro Asn Tyr Ile Asp Ser Ser Ser Leu Ser
50                  55                  60 gtg gcc cca tgg tgt gac tgc agc aac agt ggg aac gac cta gaa gag       241
Val Ala Pro Trp Cys Asp Cys Ser Asn Ser Gly Asn Asp Leu Glu Glu
65                  70                  75                  80 tgc ttg aaa ttt ttg aat ttc ttc aag gac aat aca tgt ctt aaa aat       289
Cys Leu Lys Phe Leu Asn Phe Phe Lys Asp Asn Thr Cys Leu Lys Asn
                85                  90                  95 gca att caa gcc ttt ggc aat ggc tcc gat gtg acc gtg tgg cag cca       337
Ala Ile Gln Ala Phe Gly Asn Gly Ser Asp Val Thr Val Trp Gln Pro
            100                 105                 110 gcc ttc cca gta cag acc acc act gcc act acc acc act gcc ctc cgg       385
Ala Phe Pro Val Gln Thr Thr Thr Ala Thr Thr Thr Thr Ala Leu Arg
        115                 120                 125 gtt aag aac aag ccc ctg ggg cca gca ggg tct gag aat gaa att ccc       433
Val Lys Asn Lys Pro Leu Gly Pro Ala Gly Ser Glu Asn Glu Ile Pro
130                 135                 140 act cat gtt ttg cca ccg tgt gca aat tta cag gca cag aag ctg aaa       481
Thr His Val Leu Pro Pro Cys Ala Asn Leu Gln Ala Gln Lys Leu Lys
145                 150                 155                 160 tcc aat gtg tcg ggc aat aca cac ctc tgt att tcc aat ggt aat tat       529
Ser Asn Val Ser Gly Asn Thr His Leu Cys Ile Ser Asn Gly Asn Tyr
                165                 170                 175 gaa aaa gaa ggt ctc ggt gct tcc agc cac ata acc aca aaa tca atg       577
Glu Lys Glu Gly Leu Gly Ala Ser Ser His Ile Thr Thr Lys Ser Met
            180                 185                 190 gct gct cct cca agc tgt ggt ctg agc cca ctg ctg gtc ctg gtg gta       625
Ala Ala Pro Pro Ser Cys Gly Leu Ser Pro Leu Leu Val Leu Val Val
        195                 200                 205 acc gct ctg tcc acc cta tta tct tta aca gaa a                         659
Thr Ala Leu Ser Thr Leu Leu Ser Leu Thr Glu
```

210             215

<210> SEQ ID NO 18
<211> LENGTH: 219
<212> TYPE: PRT
<213> ORGANISM: HUMAN

<400> SEQUENCE: 18

Asn Leu Gln Asp Ser Cys Lys Thr Asn Tyr Ile Cys Arg Ser Arg Leu
1               5                   10                  15

Ala Asp Phe Phe Thr Asn Cys Gln Pro Glu Ser Arg Ser Val Ser Ser
            20                  25                  30

Cys Leu Lys Glu Asn Tyr Ala Asp Cys Leu Leu Ala Tyr Ser Gly Leu
        35                  40                  45

Ile Gly Thr Val Met Thr Pro Asn Tyr Ile Asp Ser Ser Leu Ser
    50                  55                  60

Val Ala Pro Trp Cys Asp Cys Ser Asn Ser Gly Asn Asp Leu Glu Glu
65              70                  75                  80

Cys Leu Lys Phe Leu Asn Phe Lys Asp Asn Thr Cys Leu Lys Asn
            85                  90                  95

Ala Ile Gln Ala Phe Gly Asn Gly Ser Asp Val Thr Val Trp Gln Pro
            100                 105                 110

Ala Phe Pro Val Gln Thr Thr Ala Thr Thr Thr Ala Leu Arg
            115                 120                 125

Val Lys Asn Lys Pro Leu Gly Pro Ala Gly Ser Glu Asn Glu Ile Pro
130                 135                 140

Thr His Val Leu Pro Pro Cys Ala Asn Leu Gln Ala Gln Lys Leu Lys
145                 150                 155                 160

Ser Asn Val Ser Gly Asn Thr His Leu Cys Ile Ser Asn Gly Asn Tyr
                165                 170                 175

Glu Lys Glu Gly Leu Gly Ala Ser Ser His Ile Thr Thr Lys Ser Met
            180                 185                 190

Ala Ala Pro Pro Ser Cys Gly Leu Ser Pro Leu Leu Val Leu Val Val
            195                 200                 205

Thr Ala Leu Ser Thr Leu Leu Ser Leu Thr Glu
    210                 215

<210> SEQ ID NO 19
<211> LENGTH: 630
<212> TYPE: DNA
<213> ORGANISM: HUMAN
<220> FEATURE:
<221> NAME/KEY: misc_feature
<222> LOCATION: (1)..(630)
<223> OTHER INFORMATION: Note= "1 to 630 is 1062 to 1691 of Figure 5
      Hsgr-21br"
<220> FEATURE:
<221> NAME/KEY: CDS
<222> LOCATION: (3)..(629)

<400> SEQUENCE: 19 ac atc tgc aga tct cgc ctt gcg gat ttt ttt acc aac tgc cag cca      47
   Ile Cys Arg Ser Arg Leu Ala Asp Phe Phe Thr Asn Cys Gln Pro
   1               5                   10                  15 gag tca agg tct gtc agc agc tgt cta aag gaa aac tac gct gac tgc     95
Glu Ser Arg Ser Val Ser Ser Cys Leu Lys Glu Asn Tyr Ala Asp Cys
                20                  25                  30 ctc ctc gcc tac tcg ggg ctt att ggc aca gtc atg acc ccc aac tac    143
Leu Leu Ala Tyr Ser Gly Leu Ile Gly Thr Val Met Thr Pro Asn Tyr
            35                  40                  45

```
ata gac tcc agt agc ctc agt gtg gcc cca tgg tgt gac tgc agc aac    191
Ile Asp Ser Ser Ser Leu Ser Val Ala Pro Trp Cys Asp Cys Ser Asn
        50                  55                  60 agt ggg aac gac cta gaa gag tgc ttg aaa ttt ttg aat ttc ttc aag    239
Ser Gly Asn Asp Leu Glu Glu Cys Leu Lys Phe Leu Asn Phe Phe Lys
 65                  70                  75 gac aat aca tgt ctt aaa aat gca att caa gcc ttt ggc aat ggc tcc    287
Asp Asn Thr Cys Leu Lys Asn Ala Ile Gln Ala Phe Gly Asn Gly Ser
 80                  85                  90                  95 gat gtg acc gtg tgg cag cca gcc ttc cca gta cag acc acc act gcc    335
Asp Val Thr Val Trp Gln Pro Ala Phe Pro Val Gln Thr Thr Thr Ala
            100                 105                 110 act acc acc act gcc ctc cgg gtt aag aac aag ccc ctg ggg cca gca    383
Thr Thr Thr Thr Ala Leu Arg Val Lys Asn Lys Pro Leu Gly Pro Ala
            115                 120                 125 ggg tct gag aat gaa att ccc act cat gtt ttg cca ccg tgt gca aat    431
Gly Ser Glu Asn Glu Ile Pro Thr His Val Leu Pro Pro Cys Ala Asn
        130                 135                 140 tta cag gca cag aag ctg aaa tcc aat gtg tcg ggc aat aca cac ctc    479
Leu Gln Ala Gln Lys Leu Lys Ser Asn Val Ser Gly Asn Thr His Leu
    145                 150                 155 tgt att tcc aat ggt aat tat gaa aaa gaa ggt ctc ggt gct tcc agc    527
Cys Ile Ser Asn Gly Asn Tyr Glu Lys Glu Gly Leu Gly Ala Ser Ser
160                 165                 170                 175 cac ata acc aca aaa tca atg gct gct cct cca agc tgt ggt ctg agc    575
His Ile Thr Thr Lys Ser Met Ala Ala Pro Pro Ser Cys Gly Leu Ser
                180                 185                 190 cca ctg ctg gtc ctg gtg gta acc gct ctg tcc acc cta tta tct tta    623
Pro Leu Leu Val Leu Val Val Thr Ala Leu Ser Thr Leu Leu Ser Leu
            195                 200                 205 aca gaa a                                                          630
Thr Glu

<210> SEQ ID NO 20
<211> LENGTH: 209
<212> TYPE: PRT
<213> ORGANISM: HUMAN

<400> SEQUENCE: 20

Ile Cys Arg Ser Arg Leu Ala Asp Phe Phe Thr Asn Cys Gln Pro Glu
 1               5                  10                  15

Ser Arg Ser Val Ser Ser Cys Leu Lys Glu Asn Tyr Ala Asp Cys Leu
                20                  25                  30

Leu Ala Tyr Ser Gly Leu Ile Gly Thr Val Met Thr Pro Asn Tyr Ile
            35                  40                  45

Asp Ser Ser Ser Leu Ser Val Ala Pro Trp Cys Asp Cys Ser Asn Ser
        50                  55                  60

Gly Asn Asp Leu Glu Glu Cys Leu Lys Phe Leu Asn Phe Phe Lys Asp
 65                  70                  75                  80

Asn Thr Cys Leu Lys Asn Ala Ile Gln Ala Phe Gly Asn Gly Ser Asp
                85                  90                  95

Val Thr Val Trp Gln Pro Ala Phe Pro Val Gln Thr Thr Thr Ala Thr
            100                 105                 110

Thr Thr Thr Ala Leu Arg Val Lys Asn Lys Pro Leu Gly Pro Ala Gly
        115                 120                 125

Ser Glu Asn Glu Ile Pro Thr His Val Leu Pro Pro Cys Ala Asn Leu
    130                 135                 140
```

```
Gln Ala Gln Lys Leu Lys Ser Asn Val Ser Gly Asn Thr His Leu Cys
145                 150                 155                 160

Ile Ser Asn Gly Asn Tyr Glu Lys Glu Gly Leu Gly Ala Ser Ser His
                165                 170                 175

Ile Thr Thr Lys Ser Met Ala Ala Pro Pro Ser Cys Gly Leu Ser Pro
            180                 185                 190

Leu Leu Val Leu Val Val Thr Ala Leu Ser Thr Leu Leu Ser Leu Thr
        195                 200                 205

Glu

<210> SEQ ID NO 21
<211> LENGTH: 1075
<212> TYPE: DNA
<213> ORGANISM: HUMAN
<220> FEATURE:
<221> NAME/KEY: misc_feature
<222> LOCATION: (1)..(1075)
<223> OTHER INFORMATION: Note= "1 to 1075 is 1255 to 2330 of Figure 5
      Hsgr-2"
<220> FEATURE:
<221> NAME/KEY: CDS
<222> LOCATION: (2)..(445)
<220> FEATURE:
<221> NAME/KEY: misc_feature
<222> LOCATION: (763)..(801)
<223> OTHER INFORMATION: N in position 763 to 801 indicates positions of
      divergence between different receptor clones.

<400> SEQUENCE: 21 t ggg aac gac cta gaa gag tgc ttg aaa ttt ttg aat ttc ttc aag gac      49
  Gly Asn Asp Leu Glu Glu Cys Leu Lys Phe Leu Asn Phe Phe Lys Asp
  1               5                   10                  15 aat aca tgt ctt aaa aat gca att caa gcc ttt ggc aat ggc tcc gat        97
Asn Thr Cys Leu Lys Asn Ala Ile Gln Ala Phe Gly Asn Gly Ser Asp
            20                  25                  30 gtg acc gtg tgg cag cca gcc ttc cca gta cag acc acc act gcc act       145
Val Thr Val Trp Gln Pro Ala Phe Pro Val Gln Thr Thr Thr Ala Thr
        35                  40                  45 acc acc act gcc ctc cgg gtt aag aac aag ccc ctg ggg cca gca ggg       193
Thr Thr Thr Ala Leu Arg Val Lys Asn Lys Pro Leu Gly Pro Ala Gly
    50                  55                  60 tct gag aat gaa att ccc act cat gtt ttg cca ccg tgt gca aat tta       241
Ser Glu Asn Glu Ile Pro Thr His Val Leu Pro Pro Cys Ala Asn Leu
65                  70                  75                  80 cag gca cag aag ctg aaa tcc aat gtg tcg ggc aat aca cac ctc tgt       289
Gln Ala Gln Lys Leu Lys Ser Asn Val Ser Gly Asn Thr His Leu Cys
                85                  90                  95 att tcc aat ggt aat tat gaa aaa gaa ggt ctc ggt gct tcc agc cac       337
Ile Ser Asn Gly Asn Tyr Glu Lys Glu Gly Leu Gly Ala Ser Ser His
                100                 105                 110 ata acc aca aaa tca atg gct gct cct cca agc tgt ggt ctg agc cca       385
Ile Thr Thr Lys Ser Met Ala Ala Pro Pro Ser Cys Gly Leu Ser Pro
            115                 120                 125 ctg ctg gtc ctg gtg gta acc gct ctg tcc acc cta tta tct tta aca       433
Leu Leu Val Leu Val Val Thr Ala Leu Ser Thr Leu Leu Ser Leu Thr
        130                 135                 140 gaa aca tca tag ctgcattaaa aaatacaat atggacatgt aaaaagacaa            485
Glu Thr Ser
145 aaaccaagtt atctgtttcc tgttctcttg tatagctgaa attccagttt aggagctcag     545 ttgagaaaca gttccattca actgaacat ttttttttt cctttttaaga aagcttcttg     605
```

-continued

| | |
|---|---|
| tgatccttcg gggcttctgt gaaaaacctg atgcagtgct ccatccaaac tcagaaggct | 665 |
| ttgggatatg ctgtatttta aagggacagt ttgtaacttg ggctgtaaag caaactgggg | 725 |
| ctgtgttttc gatgatgatg atcatcatga tcatgatnnn nnnnnnnnnn nnnnnnnnnn | 785 |
| nnnnnnnnnn nnnnnngatt ttaacagttt tacttctggc ctttcctagc tagagaagga | 845 |
| gttaatattt ctaaggtaac tcccatatct cctttaatga cattgatttc taatgatata | 905 |
| aatttcagcc tacattgatg ccaagctttt ttgccacaaa gaagattctt accaagagtg | 965 |
| ggctttgtgg aaacagctgg tactgatgtt cacctttata tatgtactag cattttccac | 1025 |
| gctgatgttt atgtactgta aacagttctg cactcttgta caaagaaaaa | 1075 |

<210> SEQ ID NO 22
<211> LENGTH: 147
<212> TYPE: PRT
<213> ORGANISM: HUMAN

<400> SEQUENCE: 22

```
Gly Asn Asp Leu Glu Glu Cys Leu Lys Phe Leu Asn Phe Phe Lys Asp
1               5                   10                  15

Asn Thr Cys Leu Lys Asn Ala Ile Gln Ala Phe Gly Asn Gly Ser Asp
            20                  25                  30

Val Thr Val Trp Gln Pro Ala Phe Pro Val Gln Thr Thr Thr Ala Thr
        35                  40                  45

Thr Thr Thr Ala Leu Arg Val Lys Asn Lys Pro Leu Gly Pro Ala Gly
    50                  55                  60

Ser Glu Asn Glu Ile Pro Thr His Val Leu Pro Pro Cys Ala Asn Leu
65                  70                  75                  80

Gln Ala Gln Lys Leu Lys Ser Asn Val Ser Gly Asn Thr His Leu Cys
                85                  90                  95

Ile Ser Asn Gly Asn Tyr Glu Lys Glu Gly Leu Gly Ala Ser Ser His
            100                 105                 110

Ile Thr Thr Lys Ser Met Ala Ala Pro Pro Ser Cys Gly Leu Ser Pro
        115                 120                 125

Leu Leu Val Leu Val Val Thr Ala Leu Ser Thr Leu Leu Ser Leu Thr
    130                 135                 140

Glu Thr Ser
145
```

<210> SEQ ID NO 23
<211> LENGTH: 1059
<212> TYPE: DNA
<213> ORGANISM: HUMAN
<220> FEATURE:
<221> NAME/KEY: misc_feature
<222> LOCATION: (1)..(1059)
<223> OTHER INFORMATION: Note= "1 to 1059 is 1272 to 2330 of Figure 5 Hsgr-9"
<220> FEATURE:
<221> NAME/KEY: CDS
<222> LOCATION: (3)..(428)

<400> SEQUENCE: 23

```
ag tgc ttg aaa ttt ttg aat ttc ttc aag gac aat aca tgt ctt aaa      47
   Cys Leu Lys Phe Leu Asn Phe Phe Lys Asp Asn Thr Cys Leu Lys
   1               5                   10                  15 aat gca att caa gcc ttt ggc aat ggc tcc gat gtg acc gtg tgg cag    95
Asn Ala Ile Gln Ala Phe Gly Asn Gly Ser Asp Val Thr Val Trp Gln
            20                  25                  30 cca gcc ttc cca gta cag acc acc act gcc act acc acc act gcc ctc   143
Pro Ala Phe Pro Val Gln Thr Thr Thr Ala Thr Thr Thr Thr Ala Leu
```

```
                                                                                   -continued Pro Ala Phe Pro Val Gln Thr Thr Ala Thr Thr Thr Ala Leu
            35                  40                  45 cgg gtt aag aac aag ccc ctg ggg cca gca ggg tct gag aat gaa att        191
Arg Val Lys Asn Lys Pro Leu Gly Pro Ala Gly Ser Glu Asn Glu Ile
        50                  55                  60 ccc act cat gtt ttg cca ccg tgt gca aat tta cag gca cag aag ctg        239
Pro Thr His Val Leu Pro Pro Cys Ala Asn Leu Gln Ala Gln Lys Leu
65                  70                  75 aaa tcc aat gtg tcg ggc aat aca cac ctc tgt att tcc aat ggt aat        287
Lys Ser Asn Val Ser Gly Asn Thr His Leu Cys Ile Ser Asn Gly Asn
80                  85                  90                  95 tat gaa aaa gaa ggt ctc ggt gct tcc agc cac ata acc aca aaa tca        335
Tyr Glu Lys Glu Gly Leu Gly Ala Ser Ser His Ile Thr Thr Lys Ser
                100                 105                 110 atg gct gct cct cca agc tgt ggt ctg agc cca ctg ctg gtc ctg gtg        383
Met Ala Ala Pro Pro Ser Cys Gly Leu Ser Pro Leu Leu Val Leu Val
            115                 120                 125 gta acc gct ctg tcc acc cta tta tct tta aca gaa aca tca tag            428
Val Thr Ala Leu Ser Thr Leu Leu Ser Leu Thr Glu Thr Ser
        130                 135                 140 ctgcattaaa aaatacaat  atggacatgt  aaaaagacaa  aaaccaagtt  atctgtttcc     488
tgttctcttg tatagctgaa attccagttt aggagctcag ttgagaaaca gttccattca       548
actggaacat tttttttttt tcctttaag  aaagcttctt  gtgatccttt  ggggcttctg     608
tgaaaaccct gatgcagtgc tccatccaaa ctcagaaggc tttgggatat gctgtatttt      668
aaagggacag tttgtaactt gggctgtaaa gcaaactggg gctgtgtttt cgatgatgat      728
gatgatcatg atgatgatca tcatgatcat gatgatgatc atcatgatca tgatgatgat      788
tttaacagtt ttacttctgg cctttcctag ctagagaagg agttaatatt tctaaggtaa      848
ctcccatatc tcctttaatg acattgattt ctaatgatat aaatttcagc ctacattgat      908
gccaagcttt tttgccacaa agaagattct taccaagagt gggctttgtg gaaacagctg      968
gtactgatgt tcacctttat atatgtacta gcattttcca cgctgatgtt tatgtactgt      1028
aaacagttct gcactcttgt acaaaagaaa a                                      1059

<210> SEQ ID NO 24
<211> LENGTH: 141
<212> TYPE: PRT
<213> ORGANISM: HUMAN

<400> SEQUENCE: 24

Cys Leu Lys Phe Leu Asn Phe Phe Lys Asp Asn Thr Cys Leu Lys Asn
1               5                   10                  15

Ala Ile Gln Ala Phe Gly Asn Gly Ser Asp Val Thr Val Trp Gln Pro
            20                  25                  30

Ala Phe Pro Val Gln Thr Thr Thr Ala Thr Thr Thr Ala Leu Arg
        35                  40                  45

Val Lys Asn Lys Pro Leu Gly Pro Ala Gly Ser Glu Asn Glu Ile Pro
    50                  55                  60

Thr His Val Leu Pro Pro Cys Ala Asn Leu Gln Ala Gln Lys Leu Lys
65                  70                  75                  80

Ser Asn Val Ser Gly Asn Thr His Leu Cys Ile Ser Asn Gly Asn Tyr
                85                  90                  95

Glu Lys Glu Gly Leu Gly Ala Ser Ser His Ile Thr Thr Lys Ser Met
            100                 105                 110

Ala Ala Pro Pro Ser Cys Gly Leu Ser Pro Leu Leu Val Leu Val Val
```

```
            115                 120                 125
Thr Ala Leu Ser Thr Leu Leu Ser Leu Thr Glu Thr Ser
    130                 135                 140

<210> SEQ ID NO 25
<211> LENGTH: 10
<212> TYPE: PRT
<213> ORGANISM: HUMAN

<400> SEQUENCE: 25

Gln Ser Cys Ser Thr Lys Tyr Arg Thr Leu
1               5                   10

<210> SEQ ID NO 26
<211> LENGTH: 10
<212> TYPE: PRT
<213> ORGANISM: HUMAN

<400> SEQUENCE: 26

Cys Lys Arg Gly Met Lys Lys Glu Lys Asn
1               5                   10

<210> SEQ ID NO 27
<211> LENGTH: 10
<212> TYPE: PRT
<213> ORGANISM: HUMAN

<400> SEQUENCE: 27

Leu Leu Glu Asp Ser Pro Tyr Glu Pro Val
1               5                   10

<210> SEQ ID NO 28
<211> LENGTH: 10
<212> TYPE: PRT
<213> ORGANISM: RAT

<400> SEQUENCE: 28

Cys Ser Tyr Glu Glu Arg Glu Arg Pro Asn
1               5                   10

<210> SEQ ID NO 29
<211> LENGTH: 14
<212> TYPE: PRT
<213> ORGANISM: RAT

<400> SEQUENCE: 29

Pro Ala Pro Pro Val Gln Thr Thr Thr Ala Thr Thr Thr Thr
1               5                   10

<210> SEQ ID NO 30
<211> LENGTH: 21
<212> TYPE: DNA
<213> ORGANISM: HUMAN

<400> SEQUENCE: 30
ctgtttgaat ttgcaggact c                                          21

<210> SEQ ID NO 31
<211> LENGTH: 36
<212> TYPE: DNA
<213> ORGANISM: HUMAN

<400> SEQUENCE: 31
ctcctctcta agcttctaac cacagcttgg aggagc                          36
```

-continued

<210> SEQ ID NO 32
<211> LENGTH: 37
<212> TYPE: DNA
<213> ORGANISM: HUMAN

<400> SEQUENCE: 32

```
ctcctctcta agcttctatg ggctcagacc acagctt                              37
```

<210> SEQ ID NO 33
<211> LENGTH: 60
<212> TYPE: DNA
<213> ORGANISM: HUMAN

<400> SEQUENCE: 33

```
ctcctctcta agcttctact tgtcatcgtc gtccttgtag tcaccacagc ttggaggagc     60
```

<210> SEQ ID NO 34
<211> LENGTH: 60
<212> TYPE: DNA
<213> ORGANISM: HUMAN

<400> SEQUENCE: 34

```
ctcctctcta agcttctact tgtcatcgtc gtccttgtag tctggctcag accacagctt    60
```

<210> SEQ ID NO 35
<211> LENGTH: 4232
<212> TYPE: DNA
<213> ORGANISM: HUMAN
<220> FEATURE:
<221> NAME/KEY: CDS
<222> LOCATION: (1587)..(2978)

<400> SEQUENCE: 35

```
catgaagaaa cctcagtaag tctcagactt ggcccaaagg agcccaacta gttactccct    60
ggtctgttac agaggatctg gctattacac tcaacagcaa aaattcaatt caatcccgct   120
aaagatataa gaatcactag gaakaataag ccagaactca agacagaaat agcattaagt   180
agttccttca gtacagtgag cagaagctgg ccactctacg actctawaag actcagaaaa   240
gcttactagg gaccwctggg catwccggtg tcctatgtgg ggatttcgta acgtctttga   300
gtcagaagct gccctcaaaa tagtttcttc tcaaaacggt ttcaggcttt gttagaaagg   360
gaagacttca ctgccacttt acccagatca tctaccccat ccttggaatg aatggggaag   420
cttcagccac cctaccaggc tcctaaaatc accaacttga gagaaaaact ataacgttgc   480
tctaccagta cttcaggagg ttaaagaaag tcacagaaga aaagaactct ggggaaaaca   540
gtcaaattcg gctattaaga cattagttac aggcccctgt acctctcctc tagaaaccct   600
gggagtacac ccgcagagga gagagagccc aagccaccaa gcaaagtcaa ccaatctggc   660 aaagggcgt cccactgcgg ctttcagtcc aagaagtgga tcctgctggt tcgcagtctc   720
tcttctatct cctcacttcc tatttaccct ttgaagtggg tactgaatag cccgttccca   780
agcagaggcc ctttgtatac ggggtgctac agtcgcctgg tggaaacacc ttggcagagt   840
tgtttggtgc caggatgggc cactgaaggc atctgctgtg gacacacaca cacacacaca   900
cacacacaca cacacacaca gagagaggag agagaaagac acacgcacgc agagacacac   960
ggtcactgga attccattag aaaaaagtga gccgagcaag ggttagcggg agaagatttt  1020
tttgaatctt gtcttcgtct tggtgcgaaa gaagcgactc cagtctctcg tcctcgaagc  1080
tccgactgga ttgttcttgg gcgctgacac ccgtctgtgg atttcttttc tatttgcatt  1140
```

-continued

```
ttattccgac cccctccctc gccgcttcct tccagcccct cactcgcaaa tcgcctctct     1200
ccccacctcc ccaggcccct cctgggaagc gcaggggaat tggacccgcg gggactcacg     1260
ccttcccgga cgattggagg ggagggctga cccaggact gggctgttgg cttagaaagc      1320
cgatacacag atacgcgtat atttgattgt agcgggcaag gggggcgtcg agaggcagca     1380
gcccatcgcc cgcctctcac cccaccccct ccagccagag gcgagaatcg caggactcgg     1440
gatcttcatc gggtggacta gctgggatct ccgcattgga tttggggctg attaccactg     1500
cttggctatt attattgttg ttgttactac tattattttt ttttacccaa gggagaaaga     1560
caaaaaaacg gtgggattta tttaac atg atc ttg gca aac gtc ttc tgc ctc     1613
                               Met Ile Leu Ala Asn Val Phe Cys Leu
                                 1                5 ttc ttc ttt cta gac gac acc ctc cgc tct ttg gcc agc cct tcc tcc     1661
Phe Phe Phe Leu Asp Asp Thr Leu Arg Ser Leu Ala Ser Pro Ser Ser
 10              15                  20                  25 ctg cag ggc ccc gag ctc cac ggc tgg cgc ccc cca gtg gac tgt gtc     1709
Leu Gln Gly Pro Glu Leu His Gly Trp Arg Pro Pro Val Asp Cys Val
             30                  35                  40 cgg gcc aat gag ctg tgt gcc gcc gaa tcc aac tgc agc tct cgc tac     1757
Arg Ala Asn Glu Leu Cys Ala Ala Glu Ser Asn Cys Ser Ser Arg Tyr
             45                  50                  55 cgc act ctg cgg cag tgc ctg gca ggc cgc gac cgc aac acc atg ctg     1805
Arg Thr Leu Arg Gln Cys Leu Ala Gly Arg Asp Arg Asn Thr Met Leu
             60                  65                  70 gcc aac aag gag tgc cag gcg gcc ttg gag gtc ttg cag gag agc ccg     1853
Ala Asn Lys Glu Cys Gln Ala Ala Leu Glu Val Leu Gln Glu Ser Pro
 75                  80                  85 ctg tac gac tgc cgc tgc aag cgg ggc atg aag aag gag ctg cag tgt     1901
Leu Tyr Asp Cys Arg Cys Lys Arg Gly Met Lys Lys Glu Leu Gln Cys
 90                  95                 100                 105 ctg cag atc tac tgg agc atc cac ctg ggg ctg acc gag ggt gag gag     1949
Leu Gln Ile Tyr Trp Ser Ile His Leu Gly Leu Thr Glu Gly Glu Glu
                110                 115                 120 ttc tac gaa gcc tcc ccc tat gag ccg gtg acc tcc cgc ctc tcg gac     1997
Phe Tyr Glu Ala Ser Pro Tyr Glu Pro Val Thr Ser Arg Leu Ser Asp
            125                 130                 135 atc ttc agg ctt gct tca atc ttc tca ggg aca ggg gca gac ccg gtg     2045
Ile Phe Arg Leu Ala Ser Ile Phe Ser Gly Thr Gly Ala Asp Pro Val
            140                 145                 150 gtc agc gcc aag agc aac cat tgc ctg gat gct gcc aag gcc tgc aac     2093
Val Ser Ala Lys Ser Asn His Cys Leu Asp Ala Ala Lys Ala Cys Asn
 155                 160                 165 ctg aat gac aac tgc aag aag ctg cgc tcc tcc tac atc tcc atc tgc     2141
Leu Asn Asp Asn Cys Lys Lys Leu Arg Ser Ser Tyr Ile Ser Ile Cys
170                 175                 180                 185 aac cgc gag atc tcg ccc acc gag cgc tgc aac cgc cgc aag tgc cac     2189
Asn Arg Glu Ile Ser Pro Thr Glu Arg Cys Asn Arg Arg Lys Cys His
                190                 195                 200 aag gcc ctg cgc cag ttc ttc gac cgg gtg ccc agc gag tac acc tac     2237
Lys Ala Leu Arg Gln Phe Phe Asp Arg Val Pro Ser Glu Tyr Thr Tyr
            205                 210                 215 cgc atg ctc ttc tgc tcc tgc caa gac cag gcg tgc gct gag cgc cgc     2285
Arg Met Leu Phe Cys Ser Cys Gln Asp Gln Ala Cys Ala Glu Arg Arg
            220                 225                 230 cgg caa acc atc ctg ccc agc tgc tcc tat gag gac aag gag aag ccc     2333
Arg Gln Thr Ile Leu Pro Ser Cys Ser Tyr Glu Asp Lys Glu Lys Pro
            235                 240                 245
```

```
aac tgc ctg gac ctg cgt ggc gtg tgc cgg act gac cac ctg tgt cgg    2381
Asn Cys Leu Asp Leu Arg Gly Val Cys Arg Thr Asp His Leu Cys Arg
250                 255                 260                 265 tcc cgg ctg gcc gac ttc cat gcc aat tgt cga gcc tcc tac cag acg    2429
Ser Arg Leu Ala Asp Phe His Ala Asn Cys Arg Ala Ser Tyr Gln Thr
            270                 275                 280 gtc acc agc tgc cct gcg gac aat tac cag gcg tgt ctg ggc tct tat    2477
Val Thr Ser Cys Pro Ala Asp Asn Tyr Gln Ala Cys Leu Gly Ser Tyr
        285                 290                 295 gct ggc atg att ggg ttt gac atg aca cct aac tat gtg gac tcc agc    2525
Ala Gly Met Ile Gly Phe Asp Met Thr Pro Asn Tyr Val Asp Ser Ser
    300                 305                 310 ccc act ggc atc gtg gtg tcc ccc tgg tgc agc tgt cgt ggc agc ggg    2573
Pro Thr Gly Ile Val Val Ser Pro Trp Cys Ser Cys Arg Gly Ser Gly
315                 320                 325 aac atg gag gag gag tgt gag aag ttc ctc agg gac ttc acc gag aac    2621
Asn Met Glu Glu Glu Cys Glu Lys Phe Leu Arg Asp Phe Thr Glu Asn
330                 335                 340                 345 cca tgc ctc cgg aac gcc atc cag gcc ttt ggc aac ggc acg aac gtg    2669
Pro Cys Leu Arg Asn Ala Ile Gln Ala Phe Gly Asn Gly Thr Asn Val
            350                 355                 360 aac gtg tcc cca aaa ggc ccc tcg ttc cag gcc acc cag gcc cct cgg    2717
Asn Val Ser Pro Lys Gly Pro Ser Phe Gln Ala Thr Gln Ala Pro Arg
        365                 370                 375 gtg gag aag acg cct tct ttg cca gat gac ctc agt gac agt acc agc    2765
Val Glu Lys Thr Pro Ser Leu Pro Asp Asp Leu Ser Asp Ser Thr Ser
    380                 385                 390 ttg ggg acc agt gtc atc acc acc tgc acg tct gtc cag gag cag ggg    2813
Leu Gly Thr Ser Val Ile Thr Thr Cys Thr Ser Val Gln Glu Gln Gly
395                 400                 405 ctg aag gcc aac aac tcc aaa gag tta agc atg tgc ttc aca gag ctc    2861
Leu Lys Ala Asn Asn Ser Lys Glu Leu Ser Met Cys Phe Thr Glu Leu
410                 415                 420                 425 acg aca aat atc atc cca ggg agt aac aag gtg atc aaa cct aac tca    2909
Thr Thr Asn Ile Ile Pro Gly Ser Asn Lys Val Ile Lys Pro Asn Ser
            430                 435                 440 ggc ccc agc aga gcc aga ccg tcg gct gcc ttg acc gtg ctg tct gtc    2957
Gly Pro Ser Arg Ala Arg Pro Ser Ala Ala Leu Thr Val Leu Ser Val
        445                 450                 455 ctg atg ctg aaa ctg gcc ttg taggctgtgg gaaccgagtc agaagatttt       3008
Leu Met Leu Lys Leu Ala Leu
460 tgaaagctac gcagacaaga acagccgcct gacgaaatgg aaacacacac agacacacac  3068 acaccttgca aaaaaaaaat tgttttccc accttgtcgc tgaacctgtc tcctcccagg   3128 tttcttctct ggagaagttt ttgtaaacca aacagacaag caggcaggca gcctgagagc  3188 tggcccaggg gtcccctggc agggaaaact ctggtgccgg ggagggcacg aggctctaga  3248 aatgcccttc actttctcct ggtgtttttc tctctggacc cttctgaagc agagaccgga  3308 caagagcctg cagcggaagg gactctgggc tgtgcctgag ctggctgggg gcaggacaa   3368 cacagctgct tccccaggct gcccactctg ggacccgct gggggctggc agagggcatc   3428 ggtcagcggg gcagcggggc tggccatgag ggtccacctt cagcccttg gcttcaagga   3488 tggagatggt tttgccctcc ctctctgccc tcggtgggg ctggtgggtc tgcagctggt   3548 gtgggaactt ccccacggat ggcggtggag ggggttcgca ccgtgctggg ctcccctga   3608 ctgtagcacg gagtgttggg gctggggcc agtccagga gggcttgaga gctcagcctg    3668 cctgggagag cccttgtggc gaggcattaa aacttgggca ccagcttctt tctcggtggc  3728
```

-continued

```
agaaattttg aagtcagaga gaaacggtcc tttgttggct tctttgcttt ctcgtgggtc      3788
ctttggcagg cctcccttg gggagaggga ggggagagac cacagccggg tgtgtgtctg       3848
cagcaccgtg ggccctcaag ctttcctgct gtcttctccc tcctcctcct ttccccttc       3908 tctttcctca tttcctagac gtacgtcaac tgtatgtaca taccggggct cctctcctaa      3968
catatatgta tatacacatc catatacata tattgtgtgg tttccccttt ctttcctttt      4028
tttaagcaac aaaactatgg aaataatacc ccaacagatg agcgaaaatg tattattgta      4088
aagtttattt ttttaatac tgttgtctat aatggggaaa aaggacattg ccccgcagt        4148 gccctgcccc agtcagcctg ctgggctct ggtgggggct cctgatccgc atccaagctt       4208
aaccaaggct ccaataaacg tgcg                                              4232
```

<210> SEQ ID NO 36
<211> LENGTH: 464
<212> TYPE: PRT
<213> ORGANISM: HUMAN

<400> SEQUENCE: 36

```
Met Ile Leu Ala Asn Val Phe Cys Leu Phe Phe Phe Leu Asp Asp Thr
1               5                   10                  15

Leu Arg Ser Leu Ala Ser Pro Ser Ser Leu Gln Gly Pro Glu Leu His
            20                  25                  30

Gly Trp Arg Pro Pro Val Asp Cys Val Arg Ala Asn Glu Leu Cys Ala
        35                  40                  45

Ala Glu Ser Asn Cys Ser Ser Arg Tyr Arg Thr Leu Arg Gln Cys Leu
    50                  55                  60

Ala Gly Arg Asp Arg Asn Thr Met Leu Ala Asn Lys Glu Cys Gln Ala
65                  70                  75                  80

Ala Leu Glu Val Leu Gln Glu Ser Pro Leu Tyr Asp Cys Arg Cys Lys
                85                  90                  95

Arg Gly Met Lys Lys Glu Leu Gln Cys Leu Gln Ile Tyr Trp Ser Ile
            100                 105                 110

His Leu Gly Leu Thr Glu Gly Glu Phe Tyr Glu Ala Ser Pro Tyr
        115                 120                 125

Glu Pro Val Thr Ser Arg Leu Ser Asp Ile Phe Arg Leu Ala Ser Ile
    130                 135                 140

Phe Ser Gly Thr Gly Ala Asp Pro Val Val Ser Ala Lys Ser Asn His
145                 150                 155                 160

Cys Leu Asp Ala Ala Lys Ala Cys Asn Leu Asn Asp Asn Cys Lys Lys
                165                 170                 175

Leu Arg Ser Ser Tyr Ile Ser Ile Cys Asn Arg Glu Ile Ser Pro Thr
            180                 185                 190

Glu Arg Cys Asn Arg Arg Lys Cys His Lys Ala Leu Arg Gln Phe Phe
        195                 200                 205

Asp Arg Val Pro Ser Glu Tyr Thr Tyr Arg Met Leu Phe Cys Ser Cys
    210                 215                 220

Gln Asp Gln Ala Cys Ala Glu Arg Arg Gln Thr Ile Leu Pro Ser
225                 230                 235                 240

Cys Ser Tyr Glu Asp Lys Glu Lys Pro Asn Cys Leu Asp Leu Arg Gly
                245                 250                 255

Val Cys Arg Thr Asp His Leu Cys Arg Ser Arg Leu Ala Asp Phe His
            260                 265                 270

Ala Asn Cys Arg Ala Ser Tyr Gln Thr Val Thr Ser Cys Pro Ala Asp
```

```
                  275                 280                 285
Asn Tyr Gln Ala Cys Leu Gly Ser Tyr Ala Gly Met Ile Gly Phe Asp
    290                 295                 300

Met Thr Pro Asn Tyr Val Asp Ser Ser Pro Thr Gly Ile Val Val Ser
305                 310                 315                 320

Pro Trp Cys Ser Cys Arg Gly Ser Gly Asn Met Glu Glu Cys Glu
                325                 330                 335

Lys Phe Leu Arg Asp Phe Thr Glu Asn Pro Cys Leu Arg Asn Ala Ile
            340                 345                 350

Gln Ala Phe Gly Asn Gly Thr Asn Val Asn Val Ser Pro Lys Gly Pro
        355                 360                 365

Ser Phe Gln Ala Thr Gln Ala Pro Arg Val Glu Lys Thr Pro Ser Leu
    370                 375                 380

Pro Asp Asp Leu Ser Asp Ser Thr Ser Leu Gly Thr Ser Val Ile Thr
385                 390                 395                 400

Thr Cys Thr Ser Val Gln Glu Gln Gly Leu Lys Ala Asn Asn Ser Lys
                405                 410                 415

Glu Leu Ser Met Cys Phe Thr Glu Leu Thr Thr Asn Ile Ile Pro Gly
            420                 425                 430

Ser Asn Lys Val Ile Lys Pro Asn Ser Gly Pro Ser Arg Ala Arg Pro
        435                 440                 445

Ser Ala Ala Leu Thr Val Leu Ser Val Leu Met Leu Lys Leu Ala Leu
    450                 455                 460

<210> SEQ ID NO 37
<211> LENGTH: 1991
<212> TYPE: DNA
<213> ORGANISM: HUMAN
<220> FEATURE:
<221> NAME/KEY: CDS
<222> LOCATION: (203)..(1402)

<400> SEQUENCE: 37
caagtcaaag gtttaatcat gatccaagag cccagagaga ctttaggaca ataataggaa      60
taaagcaagg cccacaggct ccagctcctg atgcccagat gttcggcagg atccggggac     120
agggcagtgc aggcagtagt tttccatcct ccatccaggg gaggagcgag gggagcgcgg     180
agcccggcgc ctacagctcg cc atg gtg cgc ccc ctg aac ccg cga ccg ctg      232
                         Met Val Arg Pro Leu Asn Pro Arg Pro Leu
                           1               5                  10 ccg ccc gta gtc ctg atg ttg ctg ctg ctg ccg ccg tcg ccg ctg            280
Pro Pro Val Val Leu Met Leu Leu Leu Leu Pro Pro Ser Pro Leu
                15                  20                  25 cct ctc gca gcc gga gac ccc ctt ccc aca gaa agc cga ctc atg aac        328
Pro Leu Ala Ala Gly Asp Pro Leu Pro Thr Glu Ser Arg Leu Met Asn
            30                  35                  40 agc tgt ctc cag gcc agg agg aag tgc cag gct gat ccc acc tgc agt        376
Ser Cys Leu Gln Ala Arg Arg Lys Cys Gln Ala Asp Pro Thr Cys Ser
        45                  50                  55 gct gcc tac cac cac ctg gat tcc tgc acc tct agc ata agc acc cca        424
Ala Ala Tyr His His Leu Asp Ser Cys Thr Ser Ser Ile Ser Thr Pro
    60                  65                  70 ctg ccc tca gag gag cct tcg gtc cct gct gac tgc ctg gag gca gca        472
Leu Pro Ser Glu Glu Pro Ser Val Pro Ala Asp Cys Leu Glu Ala Ala
75                  80                  85                  90 cag caa ctc agg aac agc tct ctg ata ggc tgc atg tgc cac cgg cgc        520
Gln Gln Leu Arg Asn Ser Ser Leu Ile Gly Cys Met Cys His Arg Arg
                95                  100                 105
```

```
atg aag aac cag gtt gcc tgc ttg gac atc tat tgg acc gtt cac cgt     568
Met Lys Asn Gln Val Ala Cys Leu Asp Ile Tyr Trp Thr Val His Arg
        110                 115                 120 gcc cgc agc ctt ggt aac tat gag ctg gat gtc tcc ccc tat gaa gac     616
Ala Arg Ser Leu Gly Asn Tyr Glu Leu Asp Val Ser Pro Tyr Glu Asp
            125                 130                 135 aca gtg acc agc aaa ccc tgg aaa atg aat ctc agc aaa ctg aac atg     664
Thr Val Thr Ser Lys Pro Trp Lys Met Asn Leu Ser Lys Leu Asn Met
140                 145                 150 ctc aaa cca gac tca gac ctc tgc ctc aag ttt gcc atg ctg tgt act     712
Leu Lys Pro Asp Ser Asp Leu Cys Leu Lys Phe Ala Met Leu Cys Thr
155                 160                 165                 170 ctc aat gac aag tgt gac cgg ctg cgc aag gcc tac ggg gag gcg tgc     760
Leu Asn Asp Lys Cys Asp Arg Leu Arg Lys Ala Tyr Gly Glu Ala Cys
                175                 180                 185 tcc ggg ccc cac tgc cag cgc cac gtc tgc ctc agg cag ctg ctc act     808
Ser Gly Pro His Cys Gln Arg His Val Cys Leu Arg Gln Leu Leu Thr
            190                 195                 200 ttc ttc gag aag gcc gcc gag ccc cac gcg cag ggc ctg cta ctg tgc     856
Phe Phe Glu Lys Ala Ala Glu Pro His Ala Gln Gly Leu Leu Leu Cys
        205                 210                 215 cca tgt gcc ccc aac gac cgg ggc tgc ggg gag cgc cgg cgc aac acc     904
Pro Cys Ala Pro Asn Asp Arg Gly Cys Gly Glu Arg Arg Arg Asn Thr
220                 225                 230 atc gcc ccc aac tgc gcg ctg ccg cct gtg gcc ccc aac tgc ctg gag     952
Ile Ala Pro Asn Cys Ala Leu Pro Pro Val Ala Pro Asn Cys Leu Glu
235                 240                 245                 250 ctg cgg cgc ctc tgc ttc tcc gac ccg ctt tgc aga tca cgc ctg gtg    1000
Leu Arg Arg Leu Cys Phe Ser Asp Pro Leu Cys Arg Ser Arg Leu Val
                255                 260                 265 gat ttc cag acc cac tgc cat ccc atg gac atc cta gga act tgt gca    1048
Asp Phe Gln Thr His Cys His Pro Met Asp Ile Leu Gly Thr Cys Ala
            270                 275                 280 aca gag cag tcc aga tgt cta cga gca tac ctg ggg ctg att ggg act    1096
Thr Glu Gln Ser Arg Cys Leu Arg Ala Tyr Leu Gly Leu Ile Gly Thr
        285                 290                 295 gcc atg acc ccc aac ttt gcc agc aat gtc aac acc agt gtt gcc tta    1144
Ala Met Thr Pro Asn Phe Ala Ser Asn Val Asn Thr Ser Val Ala Leu
300                 305                 310 agc tgc acc tgc cga ggc agt ggc aac ctg cag gag gag tgt gaa atg    1192
Ser Cys Thr Cys Arg Gly Ser Gly Asn Leu Gln Glu Glu Cys Glu Met
315                 320                 325                 330 ctg gaa ggg ttc ttc tcc cac aac ccc tgc ctc acg gag gcc att gca    1240
Leu Glu Gly Phe Phe Ser His Asn Pro Cys Leu Thr Glu Ala Ile Ala
                335                 340                 345 gct aag atg cgt ttt cac agc caa ctc ttc tcc cag gac tgg cca cac    1288
Ala Lys Met Arg Phe His Ser Gln Leu Phe Ser Gln Asp Trp Pro His
            350                 355                 360 cct acc ttt gct gtg atg gca cac cag aat gaa aac cct gct gtg agg    1336
Pro Thr Phe Ala Val Met Ala His Gln Asn Glu Asn Pro Ala Val Arg
        365                 370                 375 cca cag ccc tgg gtg ccc tct ctt ttc tcc tgc acg ctt ccc ttg att    1384
Pro Gln Pro Trp Val Pro Ser Leu Phe Ser Cys Thr Leu Pro Leu Ile
380                 385                 390 ctg ctc ctg agc cta tgg tagctggact tccccagggc cctcttcccc           1432
Leu Leu Leu Ser Leu Trp
395                 400 tccaccacac ccaggtggac ttgcagccca caaggggtga ggaaaggaca gcagcaggaa  1492
```

-continued

```
ggaggtgcag tgcgcagatg agggcacagg agaagctaag ggttatgacc tccagatcct    1552
tactggtcca gtcctcattc cctccacccc atctccactt ctgattcatg ctgcccctcc    1612
ttggtggcca caatttagcc atgtcatctg gtggtgacca gctccaccaa gccccttgt    1672 gagcccttcc tcttgactac caggatcacc agaatctaat aagttagcct ttctctattg    1732
cattccagat tagggttagg gtagggagga ctgggtgttc tgaggcagcc tagaaagtca    1792
ttctcctttg tgaagaaggc tcctgccccc tcgtctcctc ctctgagtgg aggatggaaa    1852
actactgcct gcactgccct gtccccggat cctgccgaac atctgggcat caggagctgg    1912
agcctgtggg ccttgcttta ttcctattat tgtcctaaag tctctctggg ctcttggatc    1972
atgattaaac ctttgactg                                                  1991
```

<210> SEQ ID NO 38
<211> LENGTH: 400
<212> TYPE: PRT
<213> ORGANISM: HUMAN

<400> SEQUENCE: 38

```
Met Val Arg Pro Leu Asn Pro Arg Pro Leu Pro Pro Val Val Leu Met
1               5                  10                  15

Leu Leu Leu Leu Pro Pro Ser Pro Leu Pro Leu Ala Ala Gly Asp
            20                  25                  30

Pro Leu Pro Thr Glu Ser Arg Leu Met Asn Ser Cys Leu Gln Ala Arg
        35                  40                  45

Arg Lys Cys Gln Ala Asp Pro Thr Cys Ser Ala Ala Tyr His His Leu
    50                  55                  60

Asp Ser Cys Thr Ser Ser Ile Ser Thr Pro Leu Pro Ser Glu Glu Pro
65                  70                  75                  80

Ser Val Pro Ala Asp Cys Leu Glu Ala Ala Gln Gln Leu Arg Asn Ser
                85                  90                  95

Ser Leu Ile Gly Cys Met Cys His Arg Met Lys Asn Gln Val Ala
            100                 105                 110

Cys Leu Asp Ile Tyr Trp Thr Val His Arg Ala Arg Ser Leu Gly Asn
        115                 120                 125

Tyr Glu Leu Asp Val Ser Pro Tyr Glu Asp Thr Val Thr Ser Lys Pro
    130                 135                 140

Trp Lys Met Asn Leu Ser Lys Leu Asn Met Leu Lys Pro Asp Ser Asp
145                 150                 155                 160

Leu Cys Leu Lys Phe Ala Met Leu Cys Thr Leu Asn Asp Lys Cys Asp
                165                 170                 175

Arg Leu Arg Lys Ala Tyr Gly Glu Ala Cys Ser Gly Pro His Cys Gln
            180                 185                 190

Arg His Val Cys Leu Arg Gln Leu Leu Thr Phe Phe Glu Lys Ala Ala
        195                 200                 205

Glu Pro His Ala Gln Gly Leu Leu Cys Pro Cys Ala Pro Asn Asp
    210                 215                 220

Arg Gly Cys Gly Glu Arg Arg Asn Thr Ile Ala Pro Asn Cys Ala
225                 230                 235                 240

Leu Pro Pro Val Ala Pro Asn Cys Leu Glu Leu Arg Arg Leu Cys Phe
                245                 250                 255

Ser Asp Pro Leu Cys Arg Ser Arg Leu Val Asp Phe Gln Thr His Cys
            260                 265                 270

His Pro Met Asp Ile Leu Gly Thr Cys Ala Thr Glu Gln Ser Arg Cys
        275                 280                 285
```

```
Leu Arg Ala Tyr Leu Gly Leu Ile Gly Thr Ala Met Thr Pro Asn Phe
    290                 295                 300
Ala Ser Asn Val Asn Thr Ser Val Ala Leu Ser Cys Thr Cys Arg Gly
305                 310                 315                 320
Ser Gly Asn Leu Gln Glu Glu Cys Glu Met Leu Glu Gly Phe Phe Ser
                325                 330                 335
His Asn Pro Cys Leu Thr Glu Ala Ile Ala Ala Lys Met Arg Phe His
            340                 345                 350
Ser Gln Leu Phe Ser Gln Asp Trp Pro His Pro Thr Phe Ala Val Met
        355                 360                 365
Ala His Gln Asn Glu Asn Pro Ala Val Arg Pro Gln Pro Trp Val Pro
    370                 375                 380
Ser Leu Phe Ser Cys Thr Leu Pro Leu Ile Leu Leu Ser Leu Trp
385                 390                 395                 400

<210> SEQ ID NO 39
<211> LENGTH: 2215
<212> TYPE: DNA
<213> ORGANISM: RAT
<220> FEATURE:
<221> NAME/KEY: CDS
<222> LOCATION: (684)..(2063)

<400> SEQUENCE: 39
```

| | | |
|---|---|---|
| gcggccgcgt cgaccttgac catgcagaca ctttttcagg cctctgtctg gtgtgaagtt | 60 |
| ggcagataca agcaaggccc gaaagggggtc tcagcttctc tctcctgggc ctcctggact | 120 |
| gagttaggct tgcttctggt tgtcttctaa aggcacggtg atacagaatg atgagactag | 180 |
| gctggagggg gctttctgct tctctgtgtg tgaccttgag ttatctccct tcgttggatc | 240 |
| cgagctttcc tggaatatga tgttgaatat gaatatgagt tctgcctaag gtccagacag | 300 |
| gctctgaggg ttaactgact tttggagcct tcaaatcaat accttggatg gagtgggggt | 360 |
| ttgtccaatg ggagttgagg caagatccct ttgcataagc cttgccacat catgttgaag | 420 |
| ccatgccatt ctgtctggac tattggcatc ttacctttcc agcagtttca gtgaaggcct | 480 |
| tcctggattt atcattctgt gttccactgc ctaggattgt gctcaagagg aaatgaatgt | 540 |
| gaaccatggt tgtaggggag tatggccaac caggttgggt ctgtgttgac cttggtcttg | 600 |
| gtgttctttt gtgtaaagtg ggtgagaagt tccttcaaac cttaggccta cattgggggtc | 660 |

```
agagactgtg gtggccctca ttc atg ctt gtc ttc cct tcc cac tac cca gac      713
                        Met Leu Val Phe Pro Ser His Tyr Pro Asp
                          1               5                  10 gaa acc ctc cgc tct ttg gcc agc cct tcc tcc ctg cag ggc tct gag        761
Glu Thr Leu Arg Ser Leu Ala Ser Pro Ser Ser Leu Gln Gly Ser Glu
             15                  20                  25 ctc cac ggc tgg cgc ccc caa gtg gac tgt gtc cgg gcc aat gag ctg        809
Leu His Gly Trp Arg Pro Gln Val Asp Cys Val Arg Ala Asn Glu Leu
         30                  35                  40 tgt gcg gct gaa tcc aac tgc agc tcc agg tac cgc acc ctt cgg cag        857
Cys Ala Ala Glu Ser Asn Cys Ser Ser Arg Tyr Arg Thr Leu Arg Gln
     45                  50                  55 tgc ctg gca ggc cgg gat cgc aat acc atg ctg gcc aat aag gag tgc        905
Cys Leu Ala Gly Arg Asp Arg Asn Thr Met Leu Ala Asn Lys Glu Cys
 60                  65                  70 cag gca gcc ctg gag gtc ttg cag gaa agc cca ctg tat gac tgc cgc        953
Gln Ala Ala Leu Glu Val Leu Gln Glu Ser Pro Leu Tyr Asp Cys Arg
 75                  80                  85                  90
```

```
tgc aag cgg ggc atg aag aag gag ctg cag tgt ctg cag atc tac tgg      1001
Cys Lys Arg Gly Met Lys Lys Glu Leu Gln Cys Leu Gln Ile Tyr Trp
            95                 100                 105 agc atc cat ctg ggg ctg aca gag ggt gag gag ttc tat gaa gct tcc      1049
Ser Ile His Leu Gly Leu Thr Glu Gly Glu Glu Phe Tyr Glu Ala Ser
        110                 115                 120 ccc tat gag cct gtg acc tcg cgc ctc tcg gac atc ttc agg ctc gct      1097
Pro Tyr Glu Pro Val Thr Ser Arg Leu Ser Asp Ile Phe Arg Leu Ala
    125                 130                 135 tca atc ttc tca ggg aca ggg aca gac ccg gcg gtc agt acc aaa agc      1145
Ser Ile Phe Ser Gly Thr Gly Thr Asp Pro Ala Val Ser Thr Lys Ser
140                 145                 150 aac cac tgc ctg gat gcc gcc aag gcc tgc aac ctg aat gac aac tgc      1193
Asn His Cys Leu Asp Ala Ala Lys Ala Cys Asn Leu Asn Asp Asn Cys
155                 160                 165                 170 aag aag ctt cgc tcc tct tat atc tcc atc tgc aac cgt gag atc tct      1241
Lys Lys Leu Arg Ser Ser Tyr Ile Ser Ile Cys Asn Arg Glu Ile Ser
                175                 180                 185 ccc acc gaa cgc tgc aac cgc cgc aag tgc cac aag gct ctg cgc cag      1289
Pro Thr Glu Arg Cys Asn Arg Arg Lys Cys His Lys Ala Leu Arg Gln
            190                 195                 200 ttc ttt gac cgt gtg ccc agc gag tat acc tac cgc atg ctc ttc tgc      1337
Phe Phe Asp Arg Val Pro Ser Glu Tyr Thr Tyr Arg Met Leu Phe Cys
        205                 210                 215 tcc tgt cag gac cag gca tgt gct gag cgt cgc cgg caa acc atc ctg      1385
Ser Cys Gln Asp Gln Ala Cys Ala Glu Arg Arg Arg Gln Thr Ile Leu
    220                 225                 230 ccc agt tgc tcc tat gag gac aag gag aag ccc aac tgc ctg gac ctg      1433
Pro Ser Cys Ser Tyr Glu Asp Lys Glu Lys Pro Asn Cys Leu Asp Leu
235                 240                 245                 250 cgc agc ctg tgt cgt aca gac cac ctg tgc cgg tcc cga ctg gca gat      1481
Arg Ser Leu Cys Arg Thr Asp His Leu Cys Arg Ser Arg Leu Ala Asp
                255                 260                 265 ttc cac gcc aac tgt cga gcc tcc tac cgg aca atc acc agc tgt cct      1529
Phe His Ala Asn Cys Arg Ala Ser Tyr Arg Thr Ile Thr Ser Cys Pro
            270                 275                 280 gcg gac aac tac cag gca tgt ctg ggc tcc tat gct ggc atg att ggg      1577
Ala Asp Asn Tyr Gln Ala Cys Leu Gly Ser Tyr Ala Gly Met Ile Gly
        285                 290                 295 ttt gat atg aca ccc aac tat gtg gac tcc aac ccc acg ggc atc gtg      1625
Phe Asp Met Thr Pro Asn Tyr Val Asp Ser Asn Pro Thr Gly Ile Val
    300                 305                 310 gtg tct ccc tgg tgc aat tgt cgt ggc agt ggg aac atg gaa gaa gag      1673
Val Ser Pro Trp Cys Asn Cys Arg Gly Ser Gly Asn Met Glu Glu Glu
315                 320                 325                 330 tgt gag aag ttc ctc agg gac ttc acg gaa aac cca tgc ctc cgg aat      1721
Cys Glu Lys Phe Leu Arg Asp Phe Thr Glu Asn Pro Cys Leu Arg Asn
                335                 340                 345 gcc att cag gcc ttt ggt aat ggc aca gat gtg aac atg tct ccc aaa      1769
Ala Ile Gln Ala Phe Gly Asn Gly Thr Asp Val Asn Met Ser Pro Lys
            350                 355                 360 ggc ccc tca ctc cca gct acc cag gcc cct cgg gtg gag aag act cct      1817
Gly Pro Ser Leu Pro Ala Thr Gln Ala Pro Arg Val Glu Lys Thr Pro
        365                 370                 375 tca ctg cca gat gac ctc agt gac agc acc agc ctg ggg acc agt gtc      1865
Ser Leu Pro Asp Asp Leu Ser Asp Ser Thr Ser Leu Gly Thr Ser Val
    380                 385                 390 atc acc acc tgc aca tct atc cag gag caa ggg ctg aag gcc aac aac      1913
Ile Thr Thr Cys Thr Ser Ile Gln Glu Gln Gly Leu Lys Ala Asn Asn
395                 400                 405                 410
```

```
tcc aaa gag tta agc atg tgc ttc aca gag ctc acg aca aac atc agt    1961
Ser Lys Glu Leu Ser Met Cys Phe Thr Glu Leu Thr Thr Asn Ile Ser
            415                 420                 425 cca ggg agt aaa aag gtg atc aaa ctt aac tca ggc tcc agc aga gcc    2009
Pro Gly Ser Lys Lys Val Ile Lys Leu Asn Ser Gly Ser Ser Arg Ala
        430                 435                 440 aga ctg tcg gct gcc ttg act gcc ctc cca ctc ctg atg ctg acc ttg    2057
Arg Leu Ser Ala Ala Leu Thr Ala Leu Pro Leu Leu Met Leu Thr Leu
            445                 450                 455 gcc ttg taggcctttg gaacccagca caaaagttct tcaagcaacc cagatatgaa     2113
Ala Leu
    460 ctcccgcctg acaaaatgga aacacacgca tacacacatg ccacacacag acacacacac  2173 agacacacac acacacacac atacagacgt cgacgcggcc gc                    2215
```

<210> SEQ ID NO 40
<211> LENGTH: 460
<212> TYPE: PRT
<213> ORGANISM: RAT

<400> SEQUENCE: 40

```
Met Leu Val Phe Pro Ser His Tyr Pro Asp Glu Thr Leu Arg Ser Leu
1               5                   10                  15

Ala Ser Pro Ser Ser Leu Gln Gly Ser Glu Leu His Gly Trp Arg Pro
            20                  25                  30

Gln Val Asp Cys Val Arg Ala Asn Glu Leu Cys Ala Ala Glu Ser Asn
        35                  40                  45

Cys Ser Ser Arg Tyr Arg Thr Leu Arg Gln Cys Leu Ala Gly Arg Asp
    50                  55                  60

Arg Asn Thr Met Leu Ala Asn Lys Glu Cys Gln Ala Ala Leu Glu Val
65                  70                  75                  80

Leu Gln Glu Ser Pro Leu Tyr Asp Cys Arg Cys Lys Arg Gly Met Lys
                85                  90                  95

Lys Glu Leu Gln Cys Leu Gln Ile Tyr Trp Ser Ile His Leu Gly Leu
            100                 105                 110

Thr Glu Gly Glu Glu Phe Tyr Glu Ala Ser Pro Tyr Glu Pro Val Thr
        115                 120                 125

Ser Arg Leu Ser Asp Ile Phe Arg Leu Ala Ser Ile Phe Ser Gly Thr
    130                 135                 140

Gly Thr Asp Pro Ala Val Ser Thr Lys Ser Asn His Cys Leu Asp Ala
145                 150                 155                 160

Ala Lys Ala Cys Asn Leu Asn Asp Asn Cys Lys Lys Leu Arg Ser Ser
                165                 170                 175

Tyr Ile Ser Ile Cys Asn Arg Glu Ile Ser Pro Thr Glu Arg Cys Asn
            180                 185                 190

Arg Arg Lys Cys His Lys Ala Leu Arg Gln Phe Phe Asp Arg Val Pro
        195                 200                 205

Ser Glu Tyr Thr Tyr Arg Met Leu Phe Cys Ser Cys Gln Asp Gln Ala
    210                 215                 220

Cys Ala Glu Arg Arg Arg Gln Thr Ile Leu Pro Ser Cys Ser Tyr Glu
225                 230                 235                 240

Asp Lys Glu Lys Pro Asn Cys Leu Asp Leu Arg Ser Leu Cys Arg Thr
                245                 250                 255

Asp His Leu Cys Arg Ser Arg Leu Ala Asp Phe His Ala Asn Cys Arg
            260                 265                 270
```

```
Ala Ser Tyr Arg Thr Ile Thr Ser Cys Pro Ala Asp Asn Tyr Gln Ala
        275                 280                 285

Cys Leu Gly Ser Tyr Ala Gly Met Ile Gly Phe Asp Met Thr Pro Asn
        290                 295                 300

Tyr Val Asp Ser Asn Pro Thr Gly Ile Val Val Ser Pro Trp Cys Asn
305                 310                 315                 320

Cys Arg Gly Ser Gly Asn Met Glu Glu Glu Cys Glu Lys Phe Leu Arg
                325                 330                 335

Asp Phe Thr Glu Asn Pro Cys Leu Arg Asn Ala Ile Gln Ala Phe Gly
        340                 345                 350

Asn Gly Thr Asp Val Asn Met Ser Pro Lys Gly Pro Ser Leu Pro Ala
        355                 360                 365

Thr Gln Ala Pro Arg Val Glu Lys Thr Pro Ser Leu Pro Asp Asp Leu
        370                 375                 380

Ser Asp Ser Thr Ser Leu Gly Thr Ser Val Ile Thr Thr Cys Thr Ser
385                 390                 395                 400

Ile Gln Glu Gln Gly Leu Lys Ala Asn Asn Ser Lys Glu Leu Ser Met
                405                 410                 415

Cys Phe Thr Glu Leu Thr Thr Asn Ile Ser Pro Gly Ser Lys Lys Val
        420                 425                 430

Ile Lys Leu Asn Ser Gly Ser Ser Arg Ala Arg Leu Ser Ala Ala Leu
        435                 440                 445

Thr Ala Leu Pro Leu Leu Met Leu Thr Leu Ala Leu
        450                 455                 460

<210> SEQ ID NO 41
<211> LENGTH: 1699
<212> TYPE: DNA
<213> ORGANISM: RAT
<220> FEATURE:
<221> NAME/KEY: CDS
<222> LOCATION: (67)..(1257)

<400> SEQUENCE: 41
gcggccgcgt cgaccgacgc ccagcacagg cagagcgctg ccgggtccgc ggcgtccaga        60 cccgcc atg ggg ctc tcc cgg agc ccg cga ccg ccg ccg cta gtg atc         108
       Met Gly Leu Ser Arg Ser Pro Arg Pro Pro Pro Leu Val Ile
       1               5                   10 ctg cta ctg gtg ctg tcg ctg tgg cta ccc ctt gga aca gga aac tcc        156
Leu Leu Leu Val Leu Ser Leu Trp Leu Pro Leu Gly Thr Gly Asn Ser
15                  20                  25                  30 ctt ccc aca gag aac agg ctt gtg aac agc tgt acc cag gcc aga aaa        204
Leu Pro Thr Glu Asn Arg Leu Val Asn Ser Cys Thr Gln Ala Arg Lys
                35                  40                  45 aaa tgc gag gct aat ccc gct tgc aag gct gcc tac cag cac ctg gac        252
Lys Cys Glu Ala Asn Pro Ala Cys Lys Ala Ala Tyr Gln His Leu Asp
            50                  55                  60 tcc tgc acc ccc agt ctc agc agt cca ctg ccc tca ggg gag tct gcc        300
Ser Cys Thr Pro Ser Leu Ser Ser Pro Leu Pro Ser Gly Glu Ser Ala
        65                  70                  75 aca tct gca gcg tgc ctt gaa gca gca cag caa ctc agg aac agc tct        348
Thr Ser Ala Ala Cys Leu Glu Ala Ala Gln Gln Leu Arg Asn Ser Ser
        80                  85                  90 ctc ata gac tgc agg tgc cac cgg cgc atg aag cac caa gct acc tgt        396
Leu Ile Asp Cys Arg Cys His Arg Arg Met Lys His Gln Ala Thr Cys
95                  100                 105                 110 ctg gac att tat tgg acc gtt cac cct gtc cga agc ctt ggt gac tac        444
```

```
Leu Asp Ile Tyr Trp Thr Val His Pro Val Arg Ser Leu Gly Asp Tyr
            115                 120                 125 gag ttg gac gtc tca ccc tat gaa gac aca gtg acc agc aaa ccc tgg     492
Glu Leu Asp Val Ser Pro Tyr Glu Asp Thr Val Thr Ser Lys Pro Trp
            130                 135                 140 aaa atg aat ctc agc aag ctg agc atg ctc aaa cca gac tcc gac ctc     540
Lys Met Asn Leu Ser Lys Leu Ser Met Leu Lys Pro Asp Ser Asp Leu
            145                 150                 155 tgc ctc aaa ttt gct atg ctg tgt act ctt aac gac aag tgc gac cgc     588
Cys Leu Lys Phe Ala Met Leu Cys Thr Leu Asn Asp Lys Cys Asp Arg
    160                 165                 170 ctc cga aag gcc tac ggg gag gcg tgc tca ggg atc cgc tgc cag cgc     636
Leu Arg Lys Ala Tyr Gly Glu Ala Cys Ser Gly Ile Arg Cys Gln Arg
175                 180                 185                 190 cac ctc tgc cta gct cag ctg cgc tcc ttc ttc gag aag gcg gca gag     684
His Leu Cys Leu Ala Gln Leu Arg Ser Phe Phe Glu Lys Ala Ala Glu
                195                 200                 205 tcc cac gct cag ggc ctg ctg ctg tgt ccc tgt gca ccc gaa gat gcg     732
Ser His Ala Gln Gly Leu Leu Leu Cys Pro Cys Ala Pro Glu Asp Ala
                210                 215                 220 ggc tgt ggg gag cgc cgg cgc aac acc atc gcc ccc agt tgc gcc ctc     780
Gly Cys Gly Glu Arg Arg Arg Asn Thr Ile Ala Pro Ser Cys Ala Leu
            225                 230                 235 ccg tct gtg gcc ccc aac tgc cta gat ctt cgg agc ttc tgc cgt gcg     828
Pro Ser Val Ala Pro Asn Cys Leu Asp Leu Arg Ser Phe Cys Arg Ala
    240                 245                 250 gac cct ctg tgc aga tca cgc ctg atg gac ttc cag acc cac tgc cac     876
Asp Pro Leu Cys Arg Ser Arg Leu Met Asp Phe Gln Thr His Cys His
255                 260                 265                 270 cct atg gac atc ctc ggg act tgt gca act gag cag tcc aga tgt ctg     924
Pro Met Asp Ile Leu Gly Thr Cys Ala Thr Glu Gln Ser Arg Cys Leu
                275                 280                 285 cgg gca tac ctg ggg cta att ggg act gcc atg acc cca aac ttc atc     972
Arg Ala Tyr Leu Gly Leu Ile Gly Thr Ala Met Thr Pro Asn Phe Ile
                290                 295                 300 agc aag gtc aac act act gtt gcc tta ggc tgt acc tgc cga ggc agt    1020
Ser Lys Val Asn Thr Thr Val Ala Leu Gly Cys Thr Cys Arg Gly Ser
            305                 310                 315 ggc aac ctg cag gac gag tgt gaa cag ctg gaa aag tcc ttc tcc cag    1068
Gly Asn Leu Gln Asp Glu Cys Glu Gln Leu Glu Lys Ser Phe Ser Gln
            320                 325                 330 aac ccc tgc ctc atg gag gcc att gcg gct aaa atg cgt ttc cac aga    1116
Asn Pro Cys Leu Met Glu Ala Ile Ala Ala Lys Met Arg Phe His Arg
335                 340                 345                 350 caa ctc ttc tcc cag gac tgg gcg gac tct act ttt tct gtg atg cag    1164
Gln Leu Phe Ser Gln Asp Trp Ala Asp Ser Thr Phe Ser Val Met Gln
                355                 360                 365 cag cag aac agc agc cct gct ctg agg ccc cag ctc agg cta ccc gtt    1212
Gln Gln Asn Ser Ser Pro Ala Leu Arg Pro Gln Leu Arg Leu Pro Val
                370                 375                 380 ctg tct ttc ttc atc ctt acc ttg att ctg ctg cag acc ctc tgg        1257
Leu Ser Phe Phe Ile Leu Thr Leu Ile Leu Leu Gln Thr Leu Trp
                385                 390                 395 taactgggct ccctcagggt cctttgtcct ctccaccaca cccagaccga cttgcagcct  1317
gtgatgggag agaaaatgct ggcctctgga agaagatgca accaggctca ctgcacatcc  1377
tgtctgctcc agatgaggtc ttggaagaag cgagggctgt gaccgttcag aatcctgagc  1437
ggccagcttt caaacctctc ctacttactc ctgcttgggc tgctcctccc taggaccttg  1497
```

```
tactccagtt tggctgtata ttgtggtggt gattagcttc ccacctccag cccttcttcc   1557
tgtttcccag gaccacccag ggctaatgac tcactcattc ctggttgcct tctccaggaa   1617
ggcaggctga gggttctgag gcagctgaga agatggtcc ctttgtgagg aaggctggtg   1677
gtccaaccgt cgacgcggcc gc                                            1699
```

<210> SEQ ID NO 42
<211> LENGTH: 397
<212> TYPE: PRT
<213> ORGANISM: RAT

<400> SEQUENCE: 42

```
Met Gly Leu Ser Arg Ser Pro Arg Pro Pro Leu Val Ile Leu Leu
1               5                   10                  15

Leu Val Leu Ser Leu Trp Leu Pro Leu Gly Thr Gly Asn Ser Leu Pro
            20                  25                  30

Thr Glu Asn Arg Leu Val Asn Ser Cys Thr Gln Ala Arg Lys Lys Cys
        35                  40                  45

Glu Ala Asn Pro Ala Cys Lys Ala Ala Tyr Gln His Leu Asp Ser Cys
    50                  55                  60

Thr Pro Ser Leu Ser Ser Pro Leu Pro Ser Gly Glu Ser Ala Thr Ser
65                  70                  75                  80

Ala Ala Cys Leu Glu Ala Ala Gln Gln Leu Arg Asn Ser Ser Leu Ile
                85                  90                  95

Asp Cys Arg Cys His Arg Arg Met Lys His Gln Ala Thr Cys Leu Asp
            100                 105                 110

Ile Tyr Trp Thr Val His Pro Val Arg Ser Leu Gly Asp Tyr Glu Leu
        115                 120                 125

Asp Val Ser Pro Tyr Glu Asp Thr Val Thr Ser Lys Pro Trp Lys Met
    130                 135                 140

Asn Leu Ser Lys Leu Ser Met Leu Lys Pro Asp Ser Asp Leu Cys Leu
145                 150                 155                 160

Lys Phe Ala Met Leu Cys Thr Leu Asn Asp Lys Cys Asp Arg Leu Arg
                165                 170                 175

Lys Ala Tyr Gly Glu Ala Cys Ser Gly Ile Arg Cys Gln Arg His Leu
            180                 185                 190

Cys Leu Ala Gln Leu Arg Ser Phe Phe Glu Lys Ala Ala Glu Ser His
        195                 200                 205

Ala Gln Gly Leu Leu Leu Cys Pro Cys Ala Pro Glu Asp Ala Gly Cys
    210                 215                 220

Gly Glu Arg Arg Arg Asn Thr Ile Ala Pro Ser Cys Ala Leu Pro Ser
225                 230                 235                 240

Val Ala Pro Asn Cys Leu Asp Leu Arg Ser Phe Cys Arg Ala Asp Pro
                245                 250                 255

Leu Cys Arg Ser Arg Leu Met Asp Phe Gln Thr His Cys His Pro Met
            260                 265                 270

Asp Ile Leu Gly Thr Cys Ala Thr Glu Gln Ser Arg Cys Leu Arg Ala
        275                 280                 285

Tyr Leu Gly Leu Ile Gly Thr Ala Met Thr Pro Asn Phe Ile Ser Lys
    290                 295                 300

Val Asn Thr Thr Val Ala Leu Gly Cys Thr Cys Arg Gly Ser Gly Asn
305                 310                 315                 320

Leu Gln Asp Glu Cys Glu Gln Leu Glu Lys Ser Phe Ser Gln Asn Pro
                325                 330                 335
```

```
Cys Leu Met Glu Ala Ile Ala Ala Lys Met Arg Phe His Arg Gln Leu
            340                 345                 350

Phe Ser Gln Asp Trp Ala Asp Ser Thr Phe Ser Val Met Gln Gln Gln
        355                 360                 365

Asn Ser Ser Pro Ala Leu Arg Pro Gln Leu Arg Leu Pro Val Leu Ser
    370                 375                 380

Phe Phe Ile Leu Thr Leu Ile Leu Leu Gln Thr Leu Trp
385                 390                 395

<210> SEQ ID NO 43
<211> LENGTH: 498
<212> TYPE: PRT
<213> ORGANISM: Artificial Sequence
<220> FEATURE:
<223> OTHER INFORMATION: Consensus GDNFR protein sequence
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (28)..(30)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(40)
<223> OTHER INFORMATION: Xaa can be any naturally occurring amino acid
<220> FEATURE:
<221> NAME/KEY: misc_feature
<222> LOCATION: (43)..(44)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (50)..(52)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (57)..(58)
<223> OTHER INFORMATION: Xaa can be any naturally occurring amino acid
<220> FEATURE:
<221> NAME/KEY: misc_feature
<222> LOCATION: (61)..(62)
<223> OTHER INFORMATION: Xaa can be any naturally occurring amino acid
```

```
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (73)..(75)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (85)..(90)
<223> OTHER INFORMATION: Xaa can be any naturally occurring amino acid
<220> FEATURE:
<221> NAME/KEY: misc_feature
<222> LOCATION: (92)..(93)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (99)..(100)
<223> OTHER INFORMATION: Xaa can be any naturally occurring amino acid
<220> FEATURE:
<221> NAME/KEY: misc_feature
<222> LOCATION: (116)..(117)
<223> OTHER INFORMATION: Xaa can be any naturally occurring amino acid
<220> FEATURE:
<221> NAME/KEY: misc_feature
<222> LOCATION: (120)..(120)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (127)..(128)
<223> OTHER INFORMATION: Xaa can be any naturally occurring amino acid
<220> FEATURE:
<221> NAME/KEY: misc_feature
<222> LOCATION: (130)..(131)
<223> OTHER INFORMATION: Xaa can be any naturally occurring amino acid
<220> FEATURE:
<221> NAME/KEY: misc_feature
<222> LOCATION: (134)..(135)
<223> OTHER INFORMATION: Xaa can be any naturally occurring amino acid
<220> FEATURE:
<221> NAME/KEY: misc_feature
<222> LOCATION: (138)..(138)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (155)..(156)
<223> OTHER INFORMATION: Xaa can be any naturally occurring amino acid
<220> FEATURE:
<221> NAME/KEY: misc_feature
<222> LOCATION: (158)..(159)
<223> OTHER INFORMATION: Xaa can be any naturally occurring amino acid
<220> FEATURE:
<221> NAME/KEY: misc_feature
<222> LOCATION: (161)..(164)
```

```
<223> OTHER INFORMATION: Xaa can be any naturally occurring amino acid
<220> FEATURE:
<221> NAME/KEY: misc_feature
<222> LOCATION: (166)..(170)
<223> OTHER INFORMATION: Xaa can be any naturally occurring amino acid
<220> FEATURE:
<221> NAME/KEY: misc_feature
<222> LOCATION: (174)..(174)
<223> OTHER INFORMATION: Xaa can be any naturally occurring amino acid
<220> FEATURE:
<221> NAME/KEY: misc_feature
<222> LOCATION: (187)..(187)
<223> OTHER INFORMATION: Xaa can be any naturally occurring amino acid
<220> FEATURE:
<221> NAME/KEY: misc_feature
<222> LOCATION: (197)..(198)
<223> OTHER INFORMATION: Xaa can be any naturally occurring amino acid
<220> FEATURE:
<221> NAME/KEY: misc_feature
<222> LOCATION: (200)..(203)
<223> OTHER INFORMATION: Xaa can be any naturally occurring amino acid
<220> FEATURE:
<221> NAME/KEY: misc_feature
<222> LOCATION: (205)..(206)
<223> OTHER INFORMATION: Xaa can be any naturally occurring amino acid
<220> FEATURE:
<221> NAME/KEY: misc_feature
<222> LOCATION: (227)..(228)
<223> OTHER INFORMATION: Xaa can be any naturally occurring amino acid
<220> FEATURE:
<221> NAME/KEY: misc_feature
<222> LOCATION: (230)..(230)
<223> OTHER INFORMATION: Xaa can be any naturally occurring amino acid
<220> FEATURE:
<221> NAME/KEY: misc_feature
<222> LOCATION: (239)..(241)
<223> OTHER INFORMATION: Xaa can be any naturally occurring amino acid
<220> FEATURE:
<221> NAME/KEY: misc_feature
<222> LOCATION: (243)..(243)
<223> OTHER INFORMATION: Xaa can be any naturally occurring amino acid
<220> FEATURE:
<221> NAME/KEY: misc_feature
<222> LOCATION: (246)..(246)
<223> OTHER INFORMATION: Xaa can be any naturally occurring amino acid
<220> FEATURE:
<221> NAME/KEY: misc_feature
<222> LOCATION: (254)..(254)
<223> OTHER INFORMATION: Xaa can be any naturally occurring amino acid
<220> FEATURE:
<221> NAME/KEY: misc_feature
<222> LOCATION: (261)..(262)
<223> OTHER INFORMATION: Xaa can be any naturally occurring amino acid
<220> FEATURE:
<221> NAME/KEY: misc_feature
<222> LOCATION: (272)..(273)
<223> OTHER INFORMATION: Xaa can be any naturally occurring amino acid
<220> FEATURE:
<221> NAME/KEY: misc_feature
<222> LOCATION: (278)..(278)
<223> OTHER INFORMATION: Xaa can be any naturally occurring amino acid
<220> FEATURE:
<221> NAME/KEY: misc_feature
<222> LOCATION: (288)..(288)
<223> OTHER INFORMATION: Xaa can be any naturally occurring amino acid
<220> FEATURE:
<221> NAME/KEY: misc_feature
<222> LOCATION: (292)..(295)
<223> OTHER INFORMATION: Xaa can be any naturally occurring amino acid
<220> FEATURE:
<221> NAME/KEY: misc_feature
<222> LOCATION: (297)..(297)
<223> OTHER INFORMATION: Xaa can be any naturally occurring amino acid
<220> FEATURE:
<221> NAME/KEY: misc_feature
<222> LOCATION: (299)..(299)
<223> OTHER INFORMATION: Xaa can be any naturally occurring amino acid
<220> FEATURE:
<221> NAME/KEY: misc_feature
```

-continued

```
<222> LOCATION: (302)..(302)
<223> OTHER INFORMATION: Xaa can be any naturally occurring amino acid
<220> FEATURE:
<221> NAME/KEY: misc_feature
<222> LOCATION: (304)..(304)
<223> OTHER INFORMATION: Xaa can be any naturally occurring amino acid
<220> FEATURE:
<221> NAME/KEY: misc_feature
<222> LOCATION: (307)..(308)
<223> OTHER INFORMATION: Xaa can be any naturally occurring amino acid
<220> FEATURE:
<221> NAME/KEY: misc_feature
<222> LOCATION: (311)..(311)
<223> OTHER INFORMATION: Xaa can be any naturally occurring amino acid
<220> FEATURE:
<221> NAME/KEY: misc_feature
<222> LOCATION: (314)..(314)
<223> OTHER INFORMATION: Xaa can be any naturally occurring amino acid
<220> FEATURE:
<221> NAME/KEY: misc_feature
<222> LOCATION: (320)..(320)
<223> OTHER INFORMATION: Xaa can be any naturally occurring amino acid
<220> FEATURE:
<221> NAME/KEY: misc_feature
<222> LOCATION: (330)..(330)
<223> OTHER INFORMATION: Xaa can be any naturally occurring amino acid
<220> FEATURE:
<221> NAME/KEY: misc_feature
<222> LOCATION: (332)..(334)
<223> OTHER INFORMATION: Xaa can be any naturally occurring amino acid
<220> FEATURE:
<221> NAME/KEY: misc_feature
<222> LOCATION: (340)..(340)
<223> OTHER INFORMATION: Xaa can be any naturally occurring amino acid
<220> FEATURE:
<221> NAME/KEY: misc_feature
<222> LOCATION: (347)..(348)
<223> OTHER INFORMATION: Xaa can be any naturally occurring amino acid
<220> FEATURE:
<221> NAME/KEY: misc_feature
<222> LOCATION: (356)..(356)
<223> OTHER INFORMATION: Xaa can be any naturally occurring amino acid
<220> FEATURE:
<221> NAME/KEY: misc_feature
<222> LOCATION: (359)..(360)
<223> OTHER INFORMATION: Xaa can be any naturally occurring amino acid
<220> FEATURE:
<221> NAME/KEY: misc_feature
<222> LOCATION: (365)..(365)
<223> OTHER INFORMATION: Xaa can be any naturally occurring amino acid
<220> FEATURE:
<221> NAME/KEY: misc_feature
<222> LOCATION: (375)..(385)
<223> OTHER INFORMATION: Xaa can be any naturally occurring amino acid
<220> FEATURE:
<221> NAME/KEY: misc_feature
<222> LOCATION: (387)..(387)
<223> OTHER INFORMATION: Xaa can be any naturally occurring amino acid
<220> FEATURE:
<221> NAME/KEY: misc_feature
<222> LOCATION: (391)..(395)
<223> OTHER INFORMATION: Xaa can be any naturally occurring amino acid
<220> FEATURE:
<221> NAME/KEY: misc_feature
<222> LOCATION: (397)..(397)
<223> OTHER INFORMATION: Xaa can be any naturally occurring amino acid
<220> FEATURE:
<221> NAME/KEY: misc_feature
<222> LOCATION: (399)..(399)
<223> OTHER INFORMATION: Xaa can be any naturally occurring amino acid
<220> FEATURE:
<221> NAME/KEY: misc_feature
<222> LOCATION: (401)..(401)
<223> OTHER INFORMATION: Xaa can be any naturally occurring amino acid
<220> FEATURE:
<221> NAME/KEY: misc_feature
<222> LOCATION: (404)..(406)
<223> OTHER INFORMATION: Xaa can be any naturally occurring amino acid
<220> FEATURE:
```

```
<221> NAME/KEY: misc_feature
<222> LOCATION: (410)..(413)
<223> OTHER INFORMATION: Xaa can be any naturally occurring amino acid
<220> FEATURE:
<221> NAME/KEY: misc_feature
<222> LOCATION: (415)..(418)
<223> OTHER INFORMATION: Xaa can be any naturally occurring amino acid
<220> FEATURE:
<221> NAME/KEY: misc_feature
<222> LOCATION: (420)..(420)
<223> OTHER INFORMATION: Xaa can be any naturally occurring amino acid
<220> FEATURE:
<221> NAME/KEY: misc_feature
<222> LOCATION: (422)..(422)
<223> OTHER INFORMATION: Xaa can be any naturally occurring amino acid
<220> FEATURE:
<221> NAME/KEY: misc_feature
<222> LOCATION: (424)..(426)
<223> OTHER INFORMATION: Xaa can be any naturally occurring amino acid
<220> FEATURE:
<221> NAME/KEY: misc_feature
<222> LOCATION: (428)..(429)
<223> OTHER INFORMATION: Xaa can be any naturally occurring amino acid
<220> FEATURE:
<221> NAME/KEY: misc_feature
<222> LOCATION: (432)..(432)
<223> OTHER INFORMATION: Xaa can be any naturally occurring amino acid
<220> FEATURE:
<221> NAME/KEY: misc_feature
<222> LOCATION: (434)..(434)
<223> OTHER INFORMATION: Xaa can be any naturally occurring amino acid
<220> FEATURE:
<221> NAME/KEY: misc_feature
<222> LOCATION: (437)..(437)
<223> OTHER INFORMATION: Xaa can be any naturally occurring amino acid
<220> FEATURE:
<221> NAME/KEY: misc_feature
<222> LOCATION: (439)..(439)
<223> OTHER INFORMATION: Xaa can be any naturally occurring amino acid
<220> FEATURE:
<221> NAME/KEY: misc_feature
<222> LOCATION: (441)..(441)
<223> OTHER INFORMATION: Xaa can be any naturally occurring amino acid
<220> FEATURE:
<221> NAME/KEY: misc_feature
<222> LOCATION: (443)..(445)
<223> OTHER INFORMATION: Xaa can be any naturally occurring amino acid
<220> FEATURE:
<221> NAME/KEY: misc_feature
<222> LOCATION: (448)..(448)
<223> OTHER INFORMATION: Xaa can be any naturally occurring amino acid
<220> FEATURE:
<221> NAME/KEY: misc_feature
<222> LOCATION: (454)..(457)
<223> OTHER INFORMATION: Xaa can be any naturally occurring amino acid
<220> FEATURE:
<221> NAME/KEY: misc_feature
<222> LOCATION: (460)..(463)
<223> OTHER INFORMATION: Xaa can be any naturally occurring amino acid
<220> FEATURE:
<221> NAME/KEY: misc_feature
<222> LOCATION: (465)..(467)
<223> OTHER INFORMATION: Xaa can be any naturally occurring amino acid
<220> FEATURE:
<221> NAME/KEY: misc_feature
<222> LOCATION: (469)..(470)
<223> OTHER INFORMATION: Xaa can be any naturally occurring amino acid
<220> FEATURE:
<221> NAME/KEY: misc_feature
<222> LOCATION: (472)..(472)
<223> OTHER INFORMATION: Xaa can be any naturally occurring amino acid
<220> FEATURE:
<221> NAME/KEY: misc_feature
<222> LOCATION: (475)..(475)
<223> OTHER INFORMATION: Xaa can be any naturally occurring amino acid
<220> FEATURE:
<221> NAME/KEY: misc_feature
<222> LOCATION: (478)..(479)
<223> OTHER INFORMATION: Xaa can be any naturally occurring amino acid
```

-continued

```
<220> FEATURE:
<221> NAME/KEY: misc_feature
<222> LOCATION: (490)..(490)
<223> OTHER INFORMATION: Xaa can be any naturally occurring amino acid
<220> FEATURE:
<221> NAME/KEY: misc_feature
<222> LOCATION: (494)..(497)
<223> OTHER INFORMATION: Xaa can be any naturally occurring amino acid

<400> SEQUENCE: 43

Met Val Xaa Xaa Leu Xaa Xaa Xaa Pro Xaa Pro Pro Xaa Xaa Xaa Met
1               5                   10                  15

Xaa Leu Xaa Leu Leu Ser Leu Ala Leu Pro Leu Xaa Xaa Xaa Leu Gln
            20                  25                  30

Gly Ala Glu Leu Xaa Gly Xaa Xaa Arg Leu Xaa Xaa Asp Cys Val Xaa
        35                  40                  45

Ala Xaa Xaa Xaa Cys Xaa Ala Glu Xaa Xaa Cys Ser Xaa Xaa Tyr Arg
    50                  55                  60

Thr Leu Arg Gln Cys Xaa Ala Gly Xaa Xaa Xaa Asn Thr Xaa Leu Ala
65                  70                  75                  80

Ser Gly Xaa Glu Xaa Xaa Xaa Xaa Xaa Cys Xaa Xaa Ala Xaa Glu
            85                  90                  95

Xaa Leu Xaa Xaa Ser Ser Leu Tyr Asp Cys Arg Cys Lys Arg Gly Met
        100                 105                 110

Lys Lys Glu Xaa Xaa Cys Leu Xaa Ile Tyr Trp Ser Xaa His Xaa Xaa
        115                 120                 125

Leu Xaa Xaa Gly Asn Xaa Xaa Leu Glu Xaa Ser Pro Tyr Glu Pro Xaa
        130                 135                 140

Val Thr Ser Arg Leu Ser Asp Ile Phe Arg Xaa Xaa Ser Xaa Xaa Ser
145                 150                 155                 160

Xaa Xaa Xaa Xaa Asp Xaa Xaa Xaa Xaa Lys Ser Asn Xaa Cys Leu
                165                 170                 175

Asp Ala Ala Lys Ala Cys Asn Leu Asn Asp Xaa Cys Lys Lys Leu Arg
                180                 185                 190

Ser Ala Tyr Ile Xaa Xaa Cys Xaa Xaa Xaa Ser Xaa Xaa Glu Arg
                195                 200                 205

Cys Asn Arg Arg Lys Cys His Lys Ala Leu Arg Gln Phe Phe Asp Lys
210                 215                 220

Val Pro Xaa Xaa His Xaa Tyr Gly Met Leu Phe Cys Ser Cys Xaa Xaa
225                 230                 235                 240

Xaa Asp Xaa Ala Cys Xaa Glu Arg Arg Gln Thr Ile Xaa Pro Ser
            245                 250                 255

Cys Ser Tyr Glu Xaa Xaa Glu Lys Pro Asn Cys Leu Asp Leu Arg Xaa
            260                 265                 270

Xaa Cys Arg Thr Asp Xaa Leu Cys Arg Ser Arg Leu Ala Asp Phe Xaa
    275                 280                 285

Thr Asn Cys Xaa Xaa Xaa Arg Xaa Val Xaa Ser Cys Xaa Ala Xaa
290                 295                 300

Asn Tyr Xaa Xaa Cys Leu Xaa Ala Tyr Xaa Gly Leu Ile Gly Thr Xaa
305                 310                 315                 320

Met Thr Pro Asn Tyr Val Asp Ser Ser Xaa Thr Xaa Xaa Xaa Val Ala
                325                 330                 335

Pro Trp Cys Xaa Cys Arg Gly Ser Gly Asn Xaa Xaa Glu Glu Cys Glu
                340                 345                 350

Lys Phe Leu Xaa Phe Phe Xaa Xaa Asn Pro Cys Leu Xaa Asn Ala Ile
                355                 360                 365
```

```
Gln Ala Phe Gly Asn Gly Xaa Xaa Xaa Xaa Xaa Xaa Xaa Xaa Xaa
        370                 375                 380

Xaa Pro Xaa Phe Ser Val Xaa Xaa Xaa Xaa Thr Xaa Thr Xaa Ala
385                 390                 395                 400

Xaa Arg Val Xaa Xaa Xaa Pro Ser Leu Xaa Xaa Xaa Ser Xaa Xaa
            405                 410                 415

Xaa Xaa Leu Xaa Thr Xaa Val Xaa Xaa Cys Xaa Xaa Leu Gln Xaa
        420                 425                 430

Gln Xaa Leu Lys Xaa Asn Xaa Ser Xaa Glu Xaa Xaa Xaa Cys Phe Xaa
        435                 440                 445

Glu Leu Thr Thr Asn Xaa Xaa Xaa Xaa Ser Gly Xaa Xaa Xaa Xaa Ile
    450                 455                 460

Xaa Xaa Xaa Ser Xaa Xaa Ala Xaa Pro Ser Xaa Ala Leu Xaa Xaa Leu
465             470                 475                 480

Pro Val Leu Met Leu Thr Ala Leu Ala Xaa Leu Leu Ser Xaa Xaa Xaa
            485                 490                 495

Xaa Ser

<210> SEQ ID NO 44
<211> LENGTH: 489
<212> TYPE: PRT
<213> ORGANISM: Artificial Sequence
<220> FEATURE:
<223> OTHER INFORMATION: Rat consensus sequence
<220> FEATURE:
<221> NAME/KEY: misc_feature
<222> LOCATION: (1)..(9)
<223> OTHER INFORMATION: Xaa can be any naturally occurring amino acid
<220> FEATURE:
<221> NAME/KEY: misc_feature
<222> LOCATION: (11)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (22)..(23)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(29)
<223> OTHER INFORMATION: Xaa can be any naturally occurring amino acid
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (37)..(39)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (45)..(47)
<223> OTHER INFORMATION: Xaa can be any naturally occurring amino acid
<220> FEATURE:
```

```
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (52)..(53)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (68)..(70)
<223> OTHER INFORMATION: Xaa can be any naturally occurring amino acid
<220> FEATURE:
<221> NAME/KEY: misc_feature
<222> LOCATION: (72)..(79)
<223> OTHER INFORMATION: Xaa can be any naturally occurring amino acid
<220> FEATURE:
<221> NAME/KEY: misc_feature
<222> LOCATION: (81)..(82)
<223> OTHER INFORMATION: Xaa can be any naturally occurring amino acid
<220> FEATURE:
<221> NAME/KEY: misc_feature
<222> LOCATION: (85)..(86)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (92)..(93)
<223> OTHER INFORMATION: Xaa can be any naturally occurring amino acid
<220> FEATURE:
<221> NAME/KEY: misc_feature
<222> LOCATION: (109)..(110)
<223> OTHER INFORMATION: Xaa can be any naturally occurring amino acid
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (118)..(118)
<223> OTHER INFORMATION: Xaa can be any naturally occurring amino acid
<220> FEATURE:
<221> NAME/KEY: misc_feature
<222> LOCATION: (120)..(121)
<223> OTHER INFORMATION: Xaa can be any naturally occurring amino acid
<220> FEATURE:
<221> NAME/KEY: misc_feature
<222> LOCATION: (123)..(124)
<223> OTHER INFORMATION: Xaa can be any naturally occurring amino acid
<220> FEATURE:
<221> NAME/KEY: misc_feature
<222> LOCATION: (126)..(128)
<223> OTHER INFORMATION: Xaa can be any naturally occurring amino acid
<220> FEATURE:
<221> NAME/KEY: misc_feature
<222> LOCATION: (131)..(131)
<223> OTHER INFORMATION: Xaa can be any naturally occurring amino acid
<220> FEATURE:
<221> NAME/KEY: misc_feature
<222> LOCATION: (136)..(136)
<223> OTHER INFORMATION: Xaa can be any naturally occurring amino acid
<220> FEATURE:
<221> NAME/KEY: misc_feature
<222> LOCATION: (148)..(149)
<223> OTHER INFORMATION: Xaa can be any naturally occurring amino acid
```

-continued

```
<220> FEATURE:
<221> NAME/KEY: misc_feature
<222> LOCATION: (151)..(152)
<223> OTHER INFORMATION: Xaa can be any naturally occurring amino acid
<220> FEATURE:
<221> NAME/KEY: misc_feature
<222> LOCATION: (154)..(157)
<223> OTHER INFORMATION: Xaa can be any naturally occurring amino acid
<220> FEATURE:
<221> NAME/KEY: misc_feature
<222> LOCATION: (159)..(163)
<223> OTHER INFORMATION: Xaa can be any naturally occurring amino acid
<220> FEATURE:
<221> NAME/KEY: misc_feature
<222> LOCATION: (167)..(167)
<223> OTHER INFORMATION: Xaa can be any naturally occurring amino acid
<220> FEATURE:
<221> NAME/KEY: misc_feature
<222> LOCATION: (180)..(180)
<223> OTHER INFORMATION: Xaa can be any naturally occurring amino acid
<220> FEATURE:
<221> NAME/KEY: misc_feature
<222> LOCATION: (190)..(191)
<223> OTHER INFORMATION: Xaa can be any naturally occurring amino acid
<220> FEATURE:
<221> NAME/KEY: misc_feature
<222> LOCATION: (193)..(196)
<223> OTHER INFORMATION: Xaa can be any naturally occurring amino acid
<220> FEATURE:
<221> NAME/KEY: misc_feature
<222> LOCATION: (198)..(199)
<223> OTHER INFORMATION: Xaa can be any naturally occurring amino acid
<220> FEATURE:
<221> NAME/KEY: misc_feature
<222> LOCATION: (220)..(221)
<223> OTHER INFORMATION: Xaa can be any naturally occurring amino acid
<220> FEATURE:
<221> NAME/KEY: misc_feature
<222> LOCATION: (223)..(223)
<223> OTHER INFORMATION: Xaa can be any naturally occurring amino acid
<220> FEATURE:
<221> NAME/KEY: misc_feature
<222> LOCATION: (232)..(234)
<223> OTHER INFORMATION: Xaa can be any naturally occurring amino acid
<220> FEATURE:
<221> NAME/KEY: misc_feature
<222> LOCATION: (236)..(236)
<223> OTHER INFORMATION: Xaa can be any naturally occurring amino acid
<220> FEATURE:
<221> NAME/KEY: misc_feature
<222> LOCATION: (239)..(239)
<223> OTHER INFORMATION: Xaa can be any naturally occurring amino acid
<220> FEATURE:
<221> NAME/KEY: misc_feature
<222> LOCATION: (247)..(247)
<223> OTHER INFORMATION: Xaa can be any naturally occurring amino acid
<220> FEATURE:
<221> NAME/KEY: misc_feature
<222> LOCATION: (254)..(255)
<223> OTHER INFORMATION: Xaa can be any naturally occurring amino acid
<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (266)..(266)
<223> OTHER INFORMATION: Xaa can be any naturally occurring amino acid
<220> FEATURE:
<221> NAME/KEY: misc_feature
<222> LOCATION: (271)..(271)
<223> OTHER INFORMATION: Xaa can be any naturally occurring amino acid
<220> FEATURE:
<221> NAME/KEY: misc_feature
<222> LOCATION: (281)..(281)
<223> OTHER INFORMATION: Xaa can be any naturally occurring amino acid
<220> FEATURE:
<221> NAME/KEY: misc_feature
<222> LOCATION: (285)..(285)
```

```
<223> OTHER INFORMATION: Xaa can be any naturally occurring amino acid
<220> FEATURE:
<221> NAME/KEY: misc_feature
<222> LOCATION: (287)..(288)
<223> OTHER INFORMATION: Xaa can be any naturally occurring amino acid
<220> FEATURE:
<221> NAME/KEY: misc_feature
<222> LOCATION: (290)..(291)
<223> OTHER INFORMATION: Xaa can be any naturally occurring amino acid
<220> FEATURE:
<221> NAME/KEY: misc_feature
<222> LOCATION: (293)..(293)
<223> OTHER INFORMATION: Xaa can be any naturally occurring amino acid
<220> FEATURE:
<221> NAME/KEY: misc_feature
<222> LOCATION: (295)..(295)
<223> OTHER INFORMATION: Xaa can be any naturally occurring amino acid
<220> FEATURE:
<221> NAME/KEY: misc_feature
<222> LOCATION: (297)..(297)
<223> OTHER INFORMATION: Xaa can be any naturally occurring amino acid
<220> FEATURE:
<221> NAME/KEY: misc_feature
<222> LOCATION: (300)..(301)
<223> OTHER INFORMATION: Xaa can be any naturally occurring amino acid
<220> FEATURE:
<221> NAME/KEY: misc_feature
<222> LOCATION: (304)..(304)
<223> OTHER INFORMATION: Xaa can be any naturally occurring amino acid
<220> FEATURE:
<221> NAME/KEY: misc_feature
<222> LOCATION: (307)..(307)
<223> OTHER INFORMATION: Xaa can be any naturally occurring amino acid
<220> FEATURE:
<221> NAME/KEY: misc_feature
<222> LOCATION: (313)..(313)
<223> OTHER INFORMATION: Xaa can be any naturally occurring amino acid
<220> FEATURE:
<221> NAME/KEY: misc_feature
<222> LOCATION: (322)..(323)
<223> OTHER INFORMATION: Xaa can be any naturally occurring amino acid
<220> FEATURE:
<221> NAME/KEY: misc_feature
<222> LOCATION: (325)..(327)
<223> OTHER INFORMATION: Xaa can be any naturally occurring amino acid
<220> FEATURE:
<221> NAME/KEY: misc_feature
<222> LOCATION: (333)..(333)
<223> OTHER INFORMATION: Xaa can be any naturally occurring amino acid
<220> FEATURE:
<221> NAME/KEY: misc_feature
<222> LOCATION: (340)..(341)
<223> OTHER INFORMATION: Xaa can be any naturally occurring amino acid
<220> FEATURE:
<221> NAME/KEY: misc_feature
<222> LOCATION: (349)..(350)
<223> OTHER INFORMATION: Xaa can be any naturally occurring amino acid
<220> FEATURE:
<221> NAME/KEY: misc_feature
<222> LOCATION: (352)..(353)
<223> OTHER INFORMATION: Xaa can be any naturally occurring amino acid
<220> FEATURE:
<221> NAME/KEY: misc_feature
<222> LOCATION: (358)..(358)
<223> OTHER INFORMATION: Xaa can be any naturally occurring amino acid
<220> FEATURE:
<221> NAME/KEY: misc_feature
<222> LOCATION: (368)..(368)
<223> OTHER INFORMATION: Xaa can be any naturally occurring amino acid
<220> FEATURE:
<221> NAME/KEY: misc_feature
<222> LOCATION: (371)..(371)
<223> OTHER INFORMATION: Xaa can be any naturally occurring amino acid
<220> FEATURE:
<221> NAME/KEY: misc_feature
<222> LOCATION: (375)..(376)
<223> OTHER INFORMATION: Xaa can be any naturally occurring amino acid
<220> FEATURE:
<221> NAME/KEY: misc_feature
```

-continued

```
<222> LOCATION: (378)..(381)
<223> OTHER INFORMATION: Xaa can be any naturally occurring amino acid
<220> FEATURE:
<221> NAME/KEY: misc_feature
<222> LOCATION: (383)..(383)
<223> OTHER INFORMATION: Xaa can be any naturally occurring amino acid
<220> FEATURE:
<221> NAME/KEY: misc_feature
<222> LOCATION: (385)..(390)
<223> OTHER INFORMATION: Xaa can be any naturally occurring amino acid
<220> FEATURE:
<221> NAME/KEY: misc_feature
<222> LOCATION: (393)..(395)
<223> OTHER INFORMATION: Xaa can be any naturally occurring amino acid
<220> FEATURE:
<221> NAME/KEY: misc_feature
<222> LOCATION: (397)..(397)
<223> OTHER INFORMATION: Xaa can be any naturally occurring amino acid
<220> FEATURE:
<221> NAME/KEY: misc_feature
<222> LOCATION: (399)..(402)
<223> OTHER INFORMATION: Xaa can be any naturally occurring amino acid
<220> FEATURE:
<221> NAME/KEY: misc_feature
<222> LOCATION: (404)..(409)
<223> OTHER INFORMATION: Xaa can be any naturally occurring amino acid
<220> FEATURE:
<221> NAME/KEY: misc_feature
<222> LOCATION: (411)..(411)
<223> OTHER INFORMATION: Xaa can be any naturally occurring amino acid
<220> FEATURE:
<221> NAME/KEY: misc_feature
<222> LOCATION: (413)..(415)
<223> OTHER INFORMATION: Xaa can be any naturally occurring amino acid
<220> FEATURE:
<221> NAME/KEY: misc_feature
<222> LOCATION: (417)..(419)
<223> OTHER INFORMATION: Xaa can be any naturally occurring amino acid
<220> FEATURE:
<221> NAME/KEY: misc_feature
<222> LOCATION: (421)..(421)
<223> OTHER INFORMATION: Xaa can be any naturally occurring amino acid
<220> FEATURE:
<221> NAME/KEY: misc_feature
<222> LOCATION: (423)..(423)
<223> OTHER INFORMATION: Xaa can be any naturally occurring amino acid
<220> FEATURE:
<221> NAME/KEY: misc_feature
<222> LOCATION: (426)..(426)
<223> OTHER INFORMATION: Xaa can be any naturally occurring amino acid
<220> FEATURE:
<221> NAME/KEY: misc_feature
<222> LOCATION: (428)..(428)
<223> OTHER INFORMATION: Xaa can be any naturally occurring amino acid
<220> FEATURE:
<221> NAME/KEY: misc_feature
<222> LOCATION: (430)..(434)
<223> OTHER INFORMATION: Xaa can be any naturally occurring amino acid
<220> FEATURE:
<221> NAME/KEY: misc_feature
<222> LOCATION: (436)..(456)
<223> OTHER INFORMATION: Xaa can be any naturally occurring amino acid
<220> FEATURE:
<221> NAME/KEY: misc_feature
<222> LOCATION: (458)..(459)
<223> OTHER INFORMATION: Xaa can be any naturally occurring amino acid
<220> FEATURE:
<221> NAME/KEY: misc_feature
<222> LOCATION: (461)..(462)
<223> OTHER INFORMATION: Xaa can be any naturally occurring amino acid
<220> FEATURE:
<221> NAME/KEY: misc_feature
<222> LOCATION: (464)..(465)
<223> OTHER INFORMATION: Xaa can be any naturally occurring amino acid
<220> FEATURE:
<221> NAME/KEY: misc_feature
<222> LOCATION: (467)..(468)
<223> OTHER INFORMATION: Xaa can be any naturally occurring amino acid
<220> FEATURE:
```

-continued

```
<221> NAME/KEY: misc_feature
<222> LOCATION: (476)..(476)
<223> OTHER INFORMATION: Xaa can be any naturally occurring amino acid
<220> FEATURE:
<221> NAME/KEY: misc_feature
<222> LOCATION: (478)..(480)
<223> OTHER INFORMATION: Xaa can be any naturally occurring amino acid
<220> FEATURE:
<221> NAME/KEY: misc_feature
<222> LOCATION: (482)..(484)
<223> OTHER INFORMATION: Xaa can be any naturally occurring amino acid
<220> FEATURE:
<221> NAME/KEY: misc_feature
<222> LOCATION: (486)..(486)
<223> OTHER INFORMATION: Xaa can be any naturally occurring amino acid

<400> SEQUENCE: 44
```

| | | | | | | | | | | | | | | |
|---|---|---|---|---|---|---|---|---|---|---|---|---|---|---|
| Xaa | Xaa | Xaa | Xaa | Xaa | Xaa | Xaa | Xaa | Xaa | Pro | Xaa | Xaa | Xaa | Xaa | Leu | Xaa |
| 1 | | | | 5 | | | | | 10 | | | | | 15 | |
| Thr | Leu | Xaa | Ser | Leu | Xaa | Xaa | Pro | Leu | Xaa | Leu | Xaa | Xaa | Ser | Xaa | Xaa |
| | | | 20 | | | | | 25 | | | | | 30 | | |
| Xaa | Xaa | Xaa | Arg | Xaa | Xaa | Xaa | Asp | Cys | Val | Xaa | Ala | Xaa | Xaa | Xaa | Cys |
| | | 35 | | | | | 40 | | | | | 45 | | | |
| Xaa | Ala | Glu | Xaa | Xaa | Cys | Ser | Xaa | Xaa | Tyr | Arg | Thr | Leu | Arg | Gln | Cys |
| 50 | | | | | 55 | | | | | 60 | | | | | |
| Xaa | Ala | Gly | Xaa | Xaa | Xaa | Asn | Xaa | Xaa | Xaa | Xaa | Xaa | Xaa | Xaa | Xaa | Ala |
| 65 | | | | 70 | | | | | 75 | | | | | 80 | |
| Xaa | Xaa | Glu | Cys | Xaa | Xaa | Ala | Xaa | Glu | Xaa | Leu | Xaa | Xaa | Ser | Ser | Leu |
| | | | | 85 | | | | | 90 | | | | | 95 | |
| Tyr | Asp | Cys | Arg | Cys | Lys | Arg | Gly | Met | Lys | Lys | Glu | Xaa | Xaa | Cys | Leu |
| | | | 100 | | | | | 105 | | | | | 110 | | |
| Xaa | Ile | Tyr | Trp | Ser | Xaa | His | Xaa | Xaa | Leu | Xaa | Xaa | Gly | Xaa | Xaa | Xaa |
| | | | 115 | | | | | 120 | | | | | 125 | | |
| Leu | Glu | Xaa | Ser | Pro | Tyr | Glu | Xaa | Pro | Val | Thr | Ser | Arg | Leu | Ser | Asp |
| 130 | | | | | 135 | | | | | 140 | | | | | |
| Ile | Phe | Arg | Xaa | Xaa | Ser | Xaa | Xaa | Ser | Xaa | Xaa | Xaa | Xaa | Asp | Xaa | Xaa |
| 145 | | | | 150 | | | | | 155 | | | | | 160 | |
| Xaa | Xaa | Xaa | Lys | Ser | Asn | Xaa | Cys | Leu | Asp | Ala | Ala | Lys | Ala | Cys | Asn |
| | | | 165 | | | | | 170 | | | | | 175 | | |
| Leu | Asn | Asp | Xaa | Cys | Lys | Lys | Leu | Arg | Ser | Ala | Tyr | Ile | Xaa | Xaa | Cys |
| | | | 180 | | | | | 185 | | | | | 190 | | |
| Xaa | Xaa | Xaa | Xaa | Ser | Xaa | Xaa | Xaa | Glu | Arg | Cys | Asn | Arg | Arg | Lys | Cys | His |
| | | | 195 | | | | | 200 | | | | | 205 | | |
| Lys | Ala | Leu | Arg | Gln | Phe | Phe | Asp | Lys | Val | Pro | Xaa | Xaa | His | Xaa | Tyr |
| 210 | | | | | 215 | | | | | 220 | | | | | |
| Gly | Met | Leu | Phe | Cys | Ser | Cys | Xaa | Xaa | Xaa | Asp | Xaa | Ala | Cys | Xaa | Glu |
| 225 | | | | | 230 | | | | | 235 | | | | | 240 |
| Arg | Arg | Arg | Gln | Thr | Ile | Xaa | Pro | Ser | Cys | Ser | Tyr | Glu | Xaa | Xaa | Glu |
| | | | | 245 | | | | | 250 | | | | | 255 | |
| Xaa | Pro | Asn | Cys | Leu | Asp | Leu | Arg | Ser | Xaa | Cys | Arg | Thr | Asp | Xaa | Leu |
| | | | 260 | | | | | 265 | | | | | 270 | | |
| Cys | Arg | Ser | Arg | Leu | Ala | Asp | Phe | Xaa | Thr | Asn | Cys | Xaa | Pro | Xaa | Xaa |
| | | | 275 | | | | | 280 | | | | | 285 | | |
| Arg | Xaa | Xaa | Thr | Xaa | Cys | Xaa | Ala | Xaa | Asn | Tyr | Xaa | Xaa | Cys | Leu | Xaa |
| | | 290 | | | | | 295 | | | | | 300 | | | |
| Ala | Tyr | Xaa | Gly | Leu | Ile | Gly | Thr | Xaa | Met | Thr | Pro | Asn | Tyr | Val | Asp |
| 305 | | | | | 310 | | | | | 315 | | | | | 320 |
| Ser | Xaa | Xaa | Thr | Xaa | Xaa | Xaa | Val | Ala | Pro | Trp | Cys | Xaa | Cys | Arg | Gly |

-continued

```
                    325                 330                 335
Ser Gly Asn Xaa Xaa Glu Glu Cys Glu Lys Phe Leu Xaa Xaa Phe Xaa
            340                 345                 350

Xaa Asn Pro Cys Leu Xaa Asn Ala Ile Gln Ala Phe Gly Asn Gly Xaa
        355                 360                 365

Asp Val Xaa Met Ser Gln Xaa Xaa Pro Xaa Xaa Xaa Xaa Thr Xaa Ala
    370                 375                 380

Xaa Xaa Xaa Xaa Xaa Xaa Arg Val Xaa Xaa Xaa Pro Xaa Leu Xaa Xaa
385                 390                 395                 400

Xaa Xaa Ser Xaa Xaa Xaa Xaa Xaa Thr Xaa Val Xaa Xaa Xaa Xaa Cys
            405                 410                 415

Xaa Xaa Xaa Gln Xaa Gln Xaa Leu Lys Xaa Asn Xaa Ser Xaa Xaa Xaa
        420                 425                 430

Xaa Xaa Cys Xaa Xaa Xaa Xaa Xaa Xaa Xaa Xaa Xaa Xaa Xaa Xaa Xaa
    435                 440                 445

Xaa Xaa Xaa Xaa Xaa Xaa Xaa Ser Xaa Xaa Ala Xaa Xaa Ser Xaa
    450                 455                 460

Xaa Leu Xaa Xaa Leu Pro Val Leu Met Leu Thr Xaa Leu Xaa Xaa Xaa
465                 470                 475                 480

Leu Xaa Xaa Xaa Leu Xaa Glu Thr Ser
            485
```

<210> SEQ ID NO 45
<211> LENGTH: 3209
<212> TYPE: DNA
<213> ORGANISM: HUMAN
<220> FEATURE:
<221> NAME/KEY: misc_feature
<222> LOCATION: (1091)..(1091)
<223> OTHER INFORMATION: N in position 1091 indicates any nucleic acid.
<220> FEATURE:
<221> NAME/KEY: misc_feature
<222> LOCATION: (2078)..(2078)
<223> OTHER INFORMATION: N in position 2078 indicates a position of
      divergence between different receptor clones.
<220> FEATURE:
<221> NAME/KEY: misc_feature
<222> LOCATION: (2256)..(2294)
<223> OTHER INFORMATION: N in positions 2256 to 2294 indicates positions
      of divergence between different receptor clones.

<400> SEQUENCE: 45

| | | | | | |
|---|---|---|---|---|---|
| aatctggcct | cggaacacgc | cattctccgc | gccgcttcca | ataaccacta | acatccctaa | 60 |
| cgagcatccg | agccgagggc | tctgctcgga | aatcgtcctg | gcccaactcg | gcccttcgag | 120 |
| ctctcgaaga | ttaccgcatc | tattttttt | ttctttttt | tcttttccta | gcgcagataa | 180 |
| agtgagcccg | gaaagggaag | gaggggggcgg | ggacaccatt | gccctgaaag | aataaataag | 240 |
| taaataaaca | aactggctcc | tcgccgcagc | tggacgcggt | cggttgagtc | caggttgggt | 300 |
| cggacctgaa | cccctaaaag | cggaaccgcc | tcccgccctc | gccatcccgg | agctgagtcg | 360 |
| ccggcggcgg | tggctgctgc | cagacccgga | gtttcctctt | tcactggatg | gagctgaact | 420 |
| ttgggcggcc | agagcagcac | agctgtccgg | ggatcgctgc | acgctgagct | ccctcggcaa | 480 |
| gacccagcgg | cggctcggga | ttttttttggg | ggggcgggga | ccagccccgc | gccggcacca | 540 |
| tgttcctggc | gaccctgtac | ttcgcgctgc | cgctcttgga | cttgctcctg | tcggccgaag | 600 |
| tgagcggcgg | agaccgcctg | gattgcgtga | agccagtga | tcagtgcctg | aaggagcaga | 660 |
| gctgcagcac | caagtaccgc | acgctaaggc | agtgcgtggc | gggcaaggag | accaacttca | 720 |
| gcctggcatc | cggcctggag | gccaaggatg | agtgccgcag | cgccatggag | gccctgaagc | 780 |

```
agaagtcgct ctacaactgc cgctgcaagc ggggtatgaa gaaggagaag aactgcctgc    840
gcatttactg gagcatgtac cagagcctgc agggaaatga tctgctggag gattccccat    900
atgaaccagt taacagcaga ttgtcagata tattccgggt ggtcccattc atatcagatg    960
tttttcagca agtggagcac attcccaaag ggaacaactg cctggatgca gcgaaggcct   1020
gcaacctcga cgacatttgc aagaagtaca ggtcggcgta catcacccog tgcaccacca   1080 gcgtgtccaa ngatgtctgc aaccgccgca agtgccacaa ggccctccgg cagttctttg   1140
acaaggtccc ggccaagcac agctacgaaa tgctcttctg ctcctgccgg acatcgcct    1200 gcacagagcg gaggcgacag accatcgtgc ctgtgtgctc ctatgaagag agggagaagc   1260
ccaactgttt gaatttgcag gactcctgca agacgaatta catctgcaga tctcgccttg   1320 cggattttt taccaactgc cagccagagt caaggtctgt cagcagctgt ctaaaggaaa    1380
actacgctga ctgcctcctc gcctactcgg ggcttattgg cacagtcatg acccccaact   1440
acatagactc cagtagcctc agtgtggccc catggtgtga ctgcagcaac agtgggaacg   1500
acctagaaga gtgcttgaaa ttttgaatt tcttcaagga caatacatgt cttaaaaatg    1560
caattcaagc ctttggcaat ggctccgatg tgaccgtgtg gcagccagcc ttcccagtac   1620
agaccaccac tgccactacc accactgccc tccgggttaa gaacaagccc ctggggccag   1680
cagggtctga gaatgaaatt cccactcatg ttttgccacc gtgtgcaaat ttacaggcac   1740
agaagctgaa atccaatgtg tcgggcaata cacacctctg tatttccaat ggtaattatg   1800
aaaaagaagg tctcggtgct tccagccaca taaccacaaa atcaatggct gctcctccaa   1860
gctgtggtct gagcccactg ctggtcctgg tggtaaccgc tctgtccacc ctattatctt   1920
taacagaaac atcatagctg cattaaaaaa atacaatatg gacatgtaaa aagacaaaaa   1980
ccaagttatc tgtttcctgt tctcttgtat agctgaaatt ccagtttagg agctcagttg   2040
agaaacagtt ccattcaact ggaacatttt tttttttncc ttttaagaaa gcttcttgtg   2100
atccttcggg gcttctgtga aaaacctgat gcagtgctcc atccaaactc agaaggcttt   2160
gggatatgct gtattttaaa gggacagttt gtaacttggg ctgtaaagca aactggggct   2220
gtgttttcga tgatgatgat catcatgatc atgatnnnnn nnnnnnnnnn nnnnnnnnn    2280 nnnnnnnnnn nnngattttt aacagttta cttctggcct ttcctagcta gagaaggagt    2340
taatatttct aaggtaactc ccatatctcc tttaatgaca ttgatttcta atgatataaa   2400
tttcagccta cattgatgcc aagcttttt gccacaaaga agattcttac caagagtggg   2460
ctttgtggaa acagctggta ctgatgttca cctttatata tgtactagca ttttccacgc   2520
tgatgtttat gtactgtaaa cagttctgca ctccttgtaca aagaaaaaa cacctgtcac   2580 atccaaatat agtatctgtc ttttcgtcaa aatagagagt ggggaatgag tgtgccgatt   2640
caatacctca atccctgaac gacactctcc taatcctaag ccttacctga gtgagaagcc   2700
ctttacctaa caaaagtcca atatagctga aatgtcgctc taatactctt tacacatatg   2760
aggttatatg tagaaaaaaa ttttactact aaatgatttc aactattggc tttctatatt   2820
ttgaaagtaa tgatattgtc tcattttttt actgatggtt taatacaaaa tacacagagc   2880
ttgtttcccc tcataagtag tgttcgctct gatatgaact tcacaaatac agctcatcaa   2940
aagcagactc tgagaagcct cgtgctgtag cagaaagttc tgcatcatgt gactgtggac   3000
aggcaggagg aaacagaaca gacaagcatt gtcttttgtc attgctcgaa gtgcaagcgt   3060
gcatacctgt ggagggaact ggtggctgct tgtaaatgtt ctgcagcatc tcttgacaca   3120
```

| cttgtcatga cacaatccag taccttggtt ttcaggttat ctgacaaagg cagctttgat | 3180 |
| tgggacatgg aggcatgggc aggccggaa | 3209 |

<210> SEQ ID NO 46
<211> LENGTH: 508
<212> TYPE: DNA
<213> ORGANISM: HUMAN

<400> SEQUENCE: 46

| tctggcctcg gaacacgcca ttctccgcgc cgcttccaat aaccactaac atccctaacg | 60 |
| agcatccgag ccgagggctc tgctcggaaa tcgtcctggc ccaactcggc ccttcgagct | 120 |
| ctcgaagatt accgcatcta tttttttttt cttttttttc ttttcctagc gcagataaag | 180 |
| tgagcccgga aagggaagga gggggcgggg acaccattgc cctgaaagaa taaataagta | 240 |
| aataaacaaa ctggctcctc gccgcagctg gacgcggtcg gttgagtcca ggttgggtcg | 300 |
| gacctgaacc cctaaaagcg gaaccgcctc ccgccctcgc catcccggag ctgagtcgcc | 360 |
| ggcggcggtg gctgctgcca gacccggagt ttcctctttc actggatgga gctgaacttt | 420 |
| gggcggccag agcagcacag ctgtccgggg atcgctgcac gctgagctcc ctcggcaaga | 480 |
| cccagcggcg gctcgggatt tttttggg | 508 |

<210> SEQ ID NO 47
<211> LENGTH: 510
<212> TYPE: DNA
<213> ORGANISM: HUMAN

<400> SEQUENCE: 47

| aatctggcct cggaacacgc cattctccgc gccgcttcca ataaccacta acatccctaa | 60 |
| cgagcatccg agccgagggc tctgctcgga aatcgtcctg gcccaactcg gcccttcgag | 120 |
| ctctcgaaga ttaccgcatc tattttttttt ttcttttttt tcttttccta gcgcagataa | 180 |
| agtgagcccg gaaagggaag gaggggggcgg ggacaccatt gccctgaaag aataaataag | 240 |
| taaataaaca aactggctcc tcgccgcagc tggacgcggt cggttgagtc caggttgggt | 300 |
| cggacctgaa cccctaaaag cggaaccgcc tcccgccctc gccatcccgg agctgagtcg | 360 |
| ccggcggcgg tggctgctgc cagacccgga gtttcctctt tcactggatg gagctgaact | 420 |
| ttgggcggcc agagcagcac agctgtccgg ggatcgctgc acgctgagct ccctcggcaa | 480 |
| gacccagcgg cggctcggga ttttttggg | 510 |

<210> SEQ ID NO 48
<211> LENGTH: 1927
<212> TYPE: DNA
<213> ORGANISM: HUMAN
<220> FEATURE:
<221> NAME/KEY: misc_feature
<222> LOCATION: (550)..(550)
<223> OTHER INFORMATION: N in position 550 indicates any nucleic acid

<400> SEQUENCE: 48

| tctggcctcg gaacacgcca ttctccgcgc cgcttccaat aaccactaac atccctaacg | 60 |
| agcatccgag ccgagggctc tgctcggaaa tcgtcctggc ccaactcggc ccttcgagct | 120 |
| ctcgaagatt accgcatcta tttttttttt cttttttttc tttcctagc gcagataaag | 180 |
| tgagcccgga aagggaagga gggggcgggg acaccattgc cctgaaagaa taaataagta | 240 |
| aataaacaaa ctggctcctc gccgcagctg gacgcggtcg gttgagtcca ggttgggtcg | 300 |
| gacctgaacc cctaaaagcg gaaccgcctc ccgccctcgc catcccggag ctgagtcgcc | 360 |

-continued

```
ggcggcggtg gctgctgcca gacccggagt ttcctctttc actggatgga gctgaacttt     420
gggcggccag agcagcacag ctgtccgggg atcgctgcac gctgagctcc ctcggcaaga     480
cccagcggcg gctcgggatt tttttggggg ggcggggacc agccccgcgc cggcaccatg     540
ttcctggcgn ccctgtactt cgcgctgccg ctcttggact tgctcctgtc ggccgaagtg     600
agcggcggag accgcctgga ttgcgtgaaa gccagtgatc agtgcctgaa ggagcagagc     660
tgcagcacca agtaccgcac gctaaggcag tgcgtggcgg gcaaggagac caacttcagc     720
ctggcatccg gcctggaggc caaggatgag tgccgcagcg ccatggaggc cctgaagcag     780
aagtcgctct acaactgccg ctgcaagcgg ggtatgaaga aggagaagaa ctgcctgcgc     840
atttactgga gcatgtacca gagcctgcag ggaaatgatc tgctggagga ttccccatat     900
gaaccagtta acagcagatt gtcagatata ttccgggtgg tcccattcat atcagatgtt     960
tttcagcaag tggagcacat tcccaaaggg aacaactgcc tggatgcagc gaaggcctgc    1020
aacctcgacg acatttgcaa gaagtacagg tcggcgtaca tcaccccgtg caccaccagc    1080
gtgtccaacg atgtctgcaa ccgccgcaag tgccacaagg ccctccggca gttctttgac    1140
aaggtcccgg ccaagcacag ctacggaatg ctcttctgct cctgccggga catcgcctgc    1200
acagagcgga ggcgacagac catcgtgcct gtgtgctcct atgaagagag ggagaagccc    1260
aactgtttga atttgcagga ctcctgcaag acgaattaca tctgcagatc tcgccttgcg    1320
gatttttta ccaactgcca gccagagtca aggtctgtca gcagctgtct aaaggaaaac    1380
tacgctgact gcctcctcgc ctactcgggg cttattggca cagtcatgac ccccaactac    1440
atagactcca gtagcctcag tgtggcccca tggtgtgact gcagcaacag tgggaacgac    1500
ctagaagagt gcttgaaatt tttgaatttc ttcaaggaca atacatgtct taaaaatgca    1560
attcaagcct ttggcaatgg ctccgatgtg accgtgtggc agccagcctt cccagtacag    1620
accaccactg ccactaccac cactgccctc cgggttaaga acaagcccct ggggccagca    1680
gggtctgaga atgaaattcc cactcatgtt ttgccaccgt gtgcaaattt acaggcacag    1740
aagctgaaat ccaatgtgtc gggcaataca cacctctgta tttccaatgg taattatgaa    1800
aaagaaggtc tcggtgcttc cagccacata accacaaaat caatggctgc tcctccaagc    1860
tgtggtctga gcccactgct ggtcctggtg gtaaccgctc tgtccaccct attatcttta    1920
acagaaa                                                              1927
```

<210> SEQ ID NO 49
<211> LENGTH: 1929
<212> TYPE: DNA
<213> ORGANISM: HUMAN

<400> SEQUENCE: 49

```
aatctggcct cggaacacgc cattctccgc gccgcttcca ataaccacta acatccctaa     60
cgagcatccg agccgagggc tctgctcgga aatcgtcctg gcccaactcg gcccttcgag    120
ctctcgaaga ttaccgcatc tattttttt ttctttttt tcttttccta gcgcagataa    180
agtgagcccg gaaagggaag gaggggggcgg ggacaccatt gccctgaaag aataaataag    240
taaataaaca aactggctcc tcgccgcagc tggacgcgt cggttgagtc caggttgggt    300
cggacctgaa ccccctaaaag cggaaccgcc tcccgcccct gccatcccgg agctgagtcg    360
ccggcggcgg tggctgctgc cagacccgga gtttcctctt tcactggatg gagctgaact    420
ttgggcggcc agagcagcac agctgtccgg ggatcgctgc acgctgagct ccctcggcaa    480
```

-continued

```
gacccagcgg cggctcggga ttttttttggg ggggcgggga ccagccccgc gccggcacca    540
tgttcctggc gaccctgtac ttcgcgctgc cgctcttgga cttgctcctg tcggccgaag    600
tgagcggcgg agaccgcctg gattgcgtga agccagtga tcagtgcctg aaggagcaga    660
gctgcagcac caagtaccgc acgctaaggc agtgcgtggc gggcaaggag accaacttca    720
gcctggcatc cggcctggag gccaaggatg agtgccgcag cgccatggag gccctgaagc    780
agaagtcgct ctacaactgc cgctgcaagc ggggtatgaa gaaggagaag aactgcctgc    840
gcatttactg gagcatgtac cagagcctgc agggaaatga tctgctggag gattccccat    900
atgaaccagt taacagcaga ttgtcagata tattccgggt ggtcccattc atatcagatg    960
tttttcagca agtggagcac attcccaaag gaacaactg cctggatgca gcgaaggcct   1020
gcaacctcga cgacatttgc aagaagtaca gtcggcgta catcaccccg tgcaccacca   1080
gcgtgtccaa cgatgtctgc aaccgccgca agtgccacaa ggccctccgg cagttctttg   1140
acaaggtccc ggccaagcac agctacgaa tgctcttctg ctcctgccgg acatcgcct   1200
gcacagagcg gaggcgacag accatcgtgc ctgtgtgctc ctatgaagag agggagaagc   1260
ccaactgttt gaatttgcag gactcctgca agacgaatta catctgcaga tctcgccttg   1320
cggattttttt taccaactgc cagccagagt caaggtctgt cagcagctgt ctaaaggaaa   1380
actacgctga ctgcctcctc gcctactcgg ggcttattgg cacagtcatg acccccaact   1440
acatagactc cagtagcctc agtgtggccc catggtgtga ctgcagcaac agtgggaacg   1500
acctagaaga gtgcttgaaa tttttgaatt tcttcaagga caatacatgt cttaaaaatg   1560
caattcaagc cttttggcaat ggctccgatg tgaccgtgtg gcagccagcc ttcccagtac   1620
agaccaccac tgccactacc accactgccc tccgggttaa gaacaagccc ctggggccag   1680
cagggtctga gaatgaaatt cccactcatg ttttgccacc gtgtgcaaat ttacaggcac   1740
agaagctgaa atccaatgtg tcgggcaata cacacctctg tatttccaat ggtaattatg   1800
aaaaagaagg tctcggtgct tccagccaca taaccacaaa atcaatggct gctcctccaa   1860
gctgtggtct gagcccactg ctggtcctgg tggtaaccgc tctgtccacc ctattatctt   1920
taacagaaa                                                           1929
```

<210> SEQ ID NO 50
<211> LENGTH: 699
<212> TYPE: DNA
<213> ORGANISM: HUMAN

<400> SEQUENCE: 50

```
gtcggcgtac atcacccccgt gcaccaccag cgtgtccaat gatgtctgca accgccgcaa     60
gtgccacaag gccctccggc agttctttga caaggtcccg gccaagcaca gctacggaat    120
gctcttctgc tcctgccggg acatcgcctg cacagagcgg aggcgacaga ccatcgtgcc    180
tgtgtgctcc tatgaagaga gggagaagcc caactgtttg aatttgcagg actcctgcaa    240
gacgaattac atctgcagat ctcgccttgc ggattttttt accaactgcc agccagagtc    300
aaggtctgtc agcagctgtc taaaggaaaa ctacgctgac tgcctcctcg cctactcggg    360
gcttattggc acagtcatga ccccccaacta catagactcc agtagcctca gtgtggcccc    420
atggtgtgac tgcagcaaca gtgggaacga cctagaagag tgcttgaaat ttttgaattt    480
cttcaaggac aatacatgtc ttaaaaatgc aattcaagcc ttttggcaatg gctccgatgt    540
gaccgtgtgg cagccagcct tcccagtaca gaccaccact gccgctacca ccactgccct    600
ccgggttaag aacaagcccc tggggccagc agggtctgag aatgaaattc ccactcatgt    660
```

-continued

| | |
|---|---|
| tttgccaccg tgtgcaaatt tacaggcaca gaagctgaa | 699 |

<210> SEQ ID NO 51
<211> LENGTH: 2158
<212> TYPE: DNA
<213> ORGANISM: HUMAN
<220> FEATURE:
<221> NAME/KEY: misc_feature
<222> LOCATION: (1027)..(1027)
<223> OTHER INFORMATION: N in position 1027 indicates a position of
      divergence between different receptor clones.
<220> FEATURE:
<221> NAME/KEY: misc_feature
<222> LOCATION: (1205)..(1243)
<223> OTHER INFORMATION: N in positions 1205 to 1243  indicates
      positions of divergence between different receptor clones.

<400> SEQUENCE: 51

| | |
|---|---|
| gtcggcgtac atcaccccgt gcaccaccag cgtgtccaat gatgtctgca accgccgcaa | 60 |
| gtgccacaag gccctccggc agttctttga caaggtcccg gccaagcaca gctacggaat | 120 |
| gctcttctgc tcctgccggg catcgcctgc acagagcgg aggcgacaga ccatcgtgcc | 180 |
| tgtgtgctcc tatgaagaga gggagaagcc caactgtttg aatttgcagg actcctgcaa | 240 |
| gacgaattac atctgcagat ctcgccttgc ggattttttt accaactgcc agccagagtc | 300 |
| aaggtctgtc agcagctgtc taaggaaaa ctacgctgac tgcctcctcg cctactcggg | 360 |
| gcttattggc acagtcatga ccccaacta catagactcc agtagcctca gtgtggcccc | 420 |
| atggtgtgac tgcagcaaca gtgggaacga cctagaagag tgcttgaaat ttttgaattt | 480 |
| cttcaaggac aatacatgtc ttaaaaatgc aattcaagcc tttggcaatg ctccgatgt | 540 |
| gaccgtgtgg cagccagcct tcccagtaca gaccaccact gccgctacca ccactgcccct | 600 |
| ccgggttaag aacaagcccc tggggccagc agggtctgag aatgaaattc ccactcatgt | 660 |
| tttgccaccg tgtgcaaatt tacaggcaca gaagctgaaa tccaatgtgt cgggcaatac | 720 |
| acacctctgt atttccaatg gtaattatga aaagaaggt ctcggtgctt ccagccacat | 780 |
| aaccacaaaa tcaatggctg ctcctccaag ctgtggtctg agcccactgc tggtcctggt | 840 |
| ggtaaccgct ctgtccaccc tattatcttt aacagaaaca tcatagctgc attaaaaaaa | 900 |
| tacaatatgg acatgtaaaa agacaaaaac caagttatct gtttcctgtt ctcttgtata | 960 |
| gctgaaattc cagtttagga gctcagttga gaaacagttc cattcaactg gaacattttt | 1020 |
| tttttttncct tttaagaaag cttcttgtga tccttcgggg cttctgtgaa aaacctgatg | 1080 |
| cagtgctcca tccaaactca gaaggctttg ggatatgctg tattttaaag ggacagtttg | 1140 |
| taacttgggc tgtaaagcaa actggggctg tgttttcgat gatgatgatc atcatgatca | 1200 |
| tgatnnnnnn nnnnnnnnnn nnnnnnnnnn nnngatttta acagttttac | 1260 |
| ttctggcctt tcctagctag agaaggagtt aatatttcta aggtaactcc catatctcct | 1320 |
| ttaatgacat tgatttctaa tgatataaat ttcagcctac attgatgcca agcttttttg | 1380 |
| ccacaaagaa gattcttacc aagagtgggc tttgtggaaa cagctggtac tgatgttcac | 1440 |
| ctttatatat gtactagcat tttccacgct gatgtttatg tactgtaaac agttctgcac | 1500 |
| tcttgtacaa agaaaaaaac acctgtcaca tccaaatata gtatctgtct tttcgtcaaa | 1560 |
| atagagagtg gggaatgagt gtgccgattc aatacctcaa tccctgaacg acactctcct | 1620 |
| aatcctaagc cttacctgag tgagaagccc tttacctaac aaaagtccaa tatagctgaa | 1680 |
| atgtcgctct aatactcttt acacatatga ggttatatgt agaaaaaat tttactacta | 1740 |

-continued

```
aatgatttca actattggct ttctatattt tgaaagtaat gatattgtct catttttta     1800 ctgatggttt aatacaaaat acacagagct tgtttcccct cataagtagt gttcgctctg    1860
atatgaactt cacaaataca gctcatcaaa agcagactct gagaagcctc gtgctgtagc    1920
agaaagttct gcatcatgtg actgtggaca ggcaggagga acagaacag acaagcattg     1980 tcttttgtca ttgctcgaag tgcaagcgtg catacctgtg gagggaactg gtggctgctt    2040
gtaaatgttc tgcagcatct cttgacacac ttgtcatgac acaatccagt accttggttt    2100
tcaggttatc tgacaaaggc agctttgatt gggacatgga ggcatgggca ggccggaa     2158
```

<210> SEQ ID NO 52
<211> LENGTH: 659
<212> TYPE: DNA
<213> ORGANISM: HUMAN

<400> SEQUENCE: 52

```
gaatttgcag gactcctgca agacgaatta catctgcaga tctcgccttg cggattttt     60 taccaactgc cagccagagt caaggtctgt cagcagctgt ctaaaggaaa actacgctga    120
ctgcctcctc gcctactcgg ggcttattgg cacagtcatg acccccaact acatagactc    180
cagtagcctc agtgtggccc catggtgtga ctgcagcaac agtgggaacg acctagaaga    240
gtgcttgaaa ttttttgaatt tcttcaagga caatacatgt cttaaaaatg caattcaagc    300 cttggcaat ggctccgatg tgaccgtgtg gcagccagcc ttcccagtac agaccaccac     360
tgccactacc accactgccc tccgggttaa gaacaagccc ctggggccag cagggtctga    420
gaatgaaatt cccactcatg ttttgccacc gtgtgcaaat ttacaggcac agaagctgaa    480
atccaatgtg tcgggcaata cacacctctg tatttccaat ggtaattatg aaaaagaagg    540
tctcggtgct tccagccaca taaccacaaa atcaatggct gctcctccaa gctgtggtct    600
gagcccactg ctggtcctgg tggtaaccgc tctgtccacc ctattatctt taacagaaa     659
```

<210> SEQ ID NO 53
<211> LENGTH: 630
<212> TYPE: DNA
<213> ORGANISM: HUMAN

<400> SEQUENCE: 53

```
acatctgcag atctcgcctt gcggattttt ttaccaactg ccagccagag tcaaggtctg    60
tcagcagctg tctaaaggaa aactacgctg actgcctcct cgcctactcg ggcttattg     120 gcacagtcat gacccccaac tacatagact ccagtagcct cagtgtggcc ccatggtgtg    180
actgcagcaa cagtgggaac gacctagaag agtgcttgaa attttttgaatt ttcttcaagg   240 acaatacatg tcttaaaaat gcaattcaag cctttggcaa tggctccgat gtgaccgtgt    300
ggcagccagc cttcccagta cagaccacca ctgccactac caccactgcc ctccgggtta    360
agaacaagcc cctggggcca gcagggtctg agaatgaaat tcccactcat gttttgccac    420
cgtgtgcaaa tttacaggca cagaagctga atccaatgt gtcgggcaat acacacctct     480
gtatttccaa tggtaattat gaaaaagaag gtctcggtgc ttccagccac ataaccacaa    540
aatcaatggc tgctcctcca agctgtggtc tgagcccact gctggtcctg gtggtaaccg    600
ctctgtccac cctattatct ttaacagaaa                                     630
```

<210> SEQ ID NO 54
<211> LENGTH: 1076
<212> TYPE: DNA
<213> ORGANISM: HUMAN

```
<220> FEATURE:
<221> NAME/KEY: misc_feature
<222> LOCATION: (586)..(586)
<223> OTHER INFORMATION: N in position 586 indicates a position of
      divergence between different receptor clones.
<220> FEATURE:
<221> NAME/KEY: misc_feature
<222> LOCATION: (764)..(802)
<223> OTHER INFORMATION: N in positions 764 to 802  indicates positions
      of divergence between different receptor clones.

<400> SEQUENCE: 54
tgggaacgac ctagaagagt gcttgaaatt tttgaatttc ttcaaggaca atacatgtct      60
taaaaatgca attcaagcct ttggcaatgg ctccgatgtg accgtgtggc agccagcctt    120
cccagtacag accaccactg ccactaccac cactgccctc cgggttaaga acaagcccct    180
ggggccagca gggtctgaga atgaaattcc cactcatgtt ttgccaccgt gtgcaaattt    240
acaggcacag aagctgaaat ccaatgtgtc gggcaataca cacctctgta tttccaatgg    300
taattatgaa aagaaggtc tcggtgcttc agccacata accacaaaat caatggctgc     360
tcctccaagc tgtggtctga gcccactgct ggtcctggtg gtaaccgctc tgtcccacct    420
attatcttta acagaaacat catagctgca ttaaaaaaat acaatatgga catgtaaaaa    480
gacaaaaacc aagttatctg tttcctgttc tcttgtatag ctgaaattcc agtttaggag    540
ctcagttgag aaacagttcc attcaactgg aacattttttt tttttncctt ttaagaaagc   600
ttcttgtgat ccttcggggc ttctgtgaaa aacctgatgc agtgctccat ccaaactcag    660
aaggctttgg gatatgctgt attttaaagg gacagtttgt aacttgggct gtaaagcaaa    720
ctggggctgt gttttcgatg atgatgatca tcatgatcat gatnnnnnnn nnnnnnnnnn    780
nnnnnnnnnn nnnnnnnnnn nngattttaa cagttttact tctggccttt cctagctaga    840
gaaggagtta atatttctaa ggtaactccc atatctcctt taatgacatt gatttctaat    900
gatataaatt tcagcctaca ttgatgccaa gcttttttgc cacaaagaag attcttacca    960
agagtgggct ttgtggaaac agctggtact gatgttcacc tttatatatg tactagcatt   1020
ttccacgctg atgtttatgt actgtaaaca gttctgcact cttgtacaaa agaaaa       1076

<210> SEQ ID NO 55
<211> LENGTH: 1059
<212> TYPE: DNA
<213> ORGANISM: HUMAN

<400> SEQUENCE: 55
agtgcttgaa attttgaat tccttcaagg acaatacatg tcttaaaaat gcaattcaag      60
cctttggcaa tggctccgat gtgaccgtgt ggcagccagc cttcccagta cagaccacca    120
ctgccactac caccactgcc ctccgggtta agaacaagcc cctggggcca gcagggtctg    180
agaatgaaat tcccactcat gttttgccac cgtgtgcaaa tttacaggca cagaagctga    240
aatccaatgt gtcgggcaat acacacctct gtatttccaa tggtaattat gaaaagaag    300 gtctcggtgc ttcagccac ataaccacaa atcaatggc tgctcctcca agctgtggtc     360
tgagcccact gctggtcctg gtggtaaccg ctctgtccac cctattatct ttaacagaaa    420
catcatagct gcattaaaaa aatacaatat ggacatgtaa aaagacaaaa accaagttat    480
ctgtttcctg ttctcttgta tagctgaaat tccagtttag gagctcagtt gagaaacagt    540
tccattcaac tggaacattt ttttttttc cttttaagaa agcttcttgt gatcctttgg    600
ggcttctgtg aaaaacctga tgcagtgctc catccaaact cagaaggctt tgggatatgc    660
```

```
tgtattttaa agggacagtt tgtaacttgg gctgtaaagc aaactggggc tgtgttttcg    720
atgatgatga tgatcatgat gatgatcatc atgatcatga tgatgatcat catgatcatg    780
atgatgattt taacagtttt acttctggcc tttcctagct agagaaggag ttaatatttc    840 taagtaact cccatatctc ctttaatgac attgatttct aatgatataa atttcagcct     900
acattgatgc caagcttttt tgccacaaag aagattctta ccaagagtgg gctttgtgga    960
aacagctggt actgatgttc acctttatat atgtactagc attttccacg ctgatgttta   1020
tgtactgtaa acagttctgc actcttgtac aaaagaaaa                          1059
```

<210> SEQ ID NO 56
<211> LENGTH: 468
<212> TYPE: PRT
<213> ORGANISM: Mus musculus

<400> SEQUENCE: 56

```
Met Phe Leu Ala Thr Leu Tyr Phe Val Leu Pro Leu Leu Asp Leu Leu
1               5                   10                  15

Met Ser Ala Glu Val Ser Gly Gly Asp Arg Leu Asp Cys Val Lys Ala
            20                  25                  30

Ser Asp Gln Cys Leu Lys Glu Gln Ser Cys Ser Thr Lys Tyr Arg Thr
        35                  40                  45

Leu Arg Gln Cys Val Ala Gly Lys Glu Thr Asn Phe Ser Leu Thr Ser
    50                  55                  60

Gly Leu Glu Ala Lys Asp Glu Cys Arg Ser Ala Met Glu Ala Leu Lys
65                  70                  75                  80

Gln Lys Ser Leu Tyr Asn Cys Arg Cys Lys Arg Gly Met Lys Lys Glu
                85                  90                  95

Lys Asn Cys Leu Arg Ile Tyr Trp Ser Met Tyr Gln Ser Leu Gln Gly
            100                 105                 110

Asn Asp Leu Leu Glu Asp Ser Pro Tyr Glu Pro Val Asn Ser Arg Leu
        115                 120                 125

Ser Asp Ile Phe Arg Ala Val Pro Phe Ile Ser Asp Val Phe Gln Gln
    130                 135                 140

Val Glu His Ile Ser Lys Gly Asn Asn Cys Leu Asp Ala Ala Lys Ala
145                 150                 155                 160

Cys Asn Leu Asp Asp Thr Cys Lys Lys Tyr Arg Ser Ala Tyr Ile Thr
                165                 170                 175

Pro Cys Thr Thr Ser Met Ser Asn Glu Val Cys Asn Arg Arg Lys Cys
            180                 185                 190

His Lys Ala Leu Arg Gln Phe Phe Asp Lys Val Pro Ala Lys His Ser
        195                 200                 205

Tyr Gly Met Leu Phe Cys Ser Cys Arg Asp Val Ala Cys Thr Glu Arg
    210                 215                 220

Arg Arg Gln Thr Ile Val Pro Val Cys Ser Tyr Glu Glu Arg Glu Arg
225                 230                 235                 240

Pro Asn Cys Leu Asn Leu Gln Asp Ser Cys Lys Thr Asn Tyr Ile Cys
                245                 250                 255

Arg Ser Arg Leu Ala Asp Phe Phe Thr Asn Cys Gln Pro Glu Ser Arg
            260                 265                 270

Ser Val Ser Asn Cys Leu Lys Glu Asn Tyr Ala Asp Cys Leu Leu Ala
        275                 280                 285

Tyr Ser Gly Leu Ile Gly Thr Val Met Thr Pro Asn Tyr Val Asp Ser
    290                 295                 300
```

-continued

```
Ser Ser Leu Ser Val Ala Pro Trp Cys Asp Cys Ser Asn Ser Gly Asn
305                 310                 315                 320

Asp Leu Glu Asp Cys Leu Lys Phe Leu Asn Phe Phe Lys Asp Asn Thr
            325                 330                 335

Cys Leu Lys Asn Ala Ile Gln Ala Phe Gly Asn Gly Ser Asp Val Thr
        340                 345                 350

Met Trp Gln Pro Ala Pro Pro Val Gln Thr Thr Thr Ala Thr Thr Thr
    355                 360                 365

Thr Ala Phe Arg Ile Lys Asn Lys Pro Ser Gly Pro Ala Cys Ser Glu
370                 375                 380

Asn Glu Ile Pro Thr His Val Leu Pro Pro Cys Ala Asn Leu Gln Ala
385                 390                 395                 400

Gln Lys Leu Lys Ser Asn Val Ser Gly Ser Thr His Leu Cys Leu Ser
            405                 410                 415

Asp Asn Asp Tyr Gly Lys Asp Gly Leu Ala Gly Ala Ser Ser His Ile
        420                 425                 430

Thr Thr Lys Ser Met Ala Ala Pro Pro Ser Cys Gly Leu Ser Ser Leu
    435                 440                 445

Pro Val Met Val Phe Thr Ala Leu Ala Ala Leu Leu Ser Val Ser Leu
450                 455                 460

Ala Glu Thr Ser
465

<210> SEQ ID NO 57
<211> LENGTH: 12
<212> TYPE: PRT
<213> ORGANISM: Unknown
<220> FEATURE:
<223> OTHER INFORMATION: Synthetic peptide sequence of arrestin

<400> SEQUENCE: 57

Val Phe Glu Glu Phe Ala Arg Gln Asn Leu Lys Cys
1               5                   10

<210> SEQ ID NO 58
<211> LENGTH: 8
<212> TYPE: PRT
<213> ORGANISM: Unknown
<220> FEATURE:
<223> OTHER INFORMATION: FLAG peptide sequence

<400> SEQUENCE: 58

Asp Tyr Lys Asp Asp Asp Asp Lys
1               5

<210> SEQ ID NO 59
<211> LENGTH: 19
<212> TYPE: DNA
<213> ORGANISM: Artificial Sequence
<220> FEATURE:
<223> OTHER INFORMATION: Primer sequence

<400> SEQUENCE: 59
ctgcaagaag ctgcgctcc                                                19

<210> SEQ ID NO 60
<211> LENGTH: 20
<212> TYPE: DNA
<213> ORGANISM: Artificial Sequence
<220> FEATURE:
<223> OTHER INFORMATION: Primer sequence
```

```
<400> SEQUENCE: 60
cttgtcctca taggagcagc                                              20

<210> SEQ ID NO 61
<211> LENGTH: 8
<212> TYPE: PRT
<213> ORGANISM: Artificial Sequence
<220> FEATURE:
<223> OTHER INFORMATION: Flag protein sequence

<400> SEQUENCE: 61

Asp Tyr Lys Asp Asp Asp Asp Lys
1               5
```